US009926568B2

(12) United States Patent
Scotcher et al.

(10) Patent No.: US 9,926,568 B2
(45) Date of Patent: Mar. 27, 2018

(54) COMPOSITIONS AND METHODS FOR CLOSTRIDIAL TRANSFORMATION

(71) Applicant: Danisco US Inc., Palo Alto, CA (US)

(72) Inventors: Miles C. Scotcher, Hayward, CA (US); Derek H. Wells, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 14/899,846

(22) PCT Filed: Jun. 20, 2014

(86) PCT No.: PCT/US2014/043424
§ 371 (c)(1),
(2) Date: Dec. 18, 2015

(87) PCT Pub. No.: WO2014/205355
PCT Pub. Date: Dec. 24, 2014

(65) Prior Publication Data
US 2016/0138030 A1 May 19, 2016

Related U.S. Application Data

(60) Provisional application No. 61/838,224, filed on Jun. 21, 2013.

(51) Int. Cl.
| | |
|---|---|
| *C12N 15/70* | (2006.01) |
| *C12N 15/74* | (2006.01) |
| *C12N 9/10* | (2006.01) |
| *C12P 5/00* | (2006.01) |
| *C12P 7/06* | (2006.01) |

(52) U.S. Cl.
CPC ........... *C12N 15/74* (2013.01); *C12N 9/1007* (2013.01); *C12N 15/70* (2013.01); *C12P 5/007* (2013.01); *C12P 7/065* (2013.01); *C12Y 201/01* (2013.01); *Y02E 50/17* (2013.01)

(58) Field of Classification Search
None
See application file for complete search history.

(56) References Cited

U.S. PATENT DOCUMENTS

| | | |
|---|---|---|
| 4,570,029 A | 2/1986 | Kulprathipanja et al. |
| 4,683,202 A | 7/1987 | Mullis |
| 4,703,007 A | 10/1987 | Mulholland et al. |
| 6,106,888 A | 8/2000 | Dale et al. |
| 6,176,176 B1 | 1/2001 | Dale et al. |
| 7,527,959 B2 | 5/2009 | Dunn-Coleman et al. |
| 7,541,026 B2 | 6/2009 | Power et al. |
| 7,604,974 B2 | 10/2009 | Jones et al. |
| 7,622,290 B2 | 11/2009 | Brunstedt et al. |
| 7,629,451 B2 | 12/2009 | Clarkson et al. |
| 8,420,360 B2 | 4/2013 | Calabria et al. |
| 2007/0259397 A1 | 11/2007 | Beekwilder et al. |
| 2009/0226569 A1 | 9/2009 | Ramer et al. |
| 2009/0252828 A1 | 10/2009 | Cascao-Pereira et al. |
| 2009/0275080 A1 | 11/2009 | Aehle et al. |
| 2009/0275103 A1 | 11/2009 | Stougaard et al. |
| 2009/0311764 A1 | 12/2009 | Shaw et al. |
| 2011/0178261 A1 | 7/2011 | Feher et al. |
| 2014/0234926 A1* | 8/2014 | Beck ................. C12N 1/20 435/146 |

FOREIGN PATENT DOCUMENTS

| | | |
|---|---|---|
| WO | WO 98/02550 A2 | 1/1998 |
| WO | WO 98/02550 A3 | 1/1998 |
| WO | WO 2004/033646 A2 | 4/2004 |
| WO | WO 2004/033646 A3 | 4/2004 |
| WO | WO 2009/076676 A2 | 6/2009 |
| WO | WO 2009/076676 A3 | 6/2009 |
| WO | WO 2009/132220 A2 | 10/2009 |
| WO | WO 2009/132220 A3 | 10/2009 |
| WO | WO 2009/132220 A9 | 10/2009 |
| WO | WO 2010/003007 A2 | 1/2010 |
| WO | WO 2010/003007 A3 | 1/2010 |
| WO | WO 2010/013077 A2 | 2/2010 |
| WO | WO 2010/031062 A1 | 3/2010 |
| WO | WO 2010/031068 A1 | 3/2010 |
| WO | WO 2010/031076 A2 | 3/2010 |
| WO | WO 2010/031076 A3 | 3/2010 |
| WO | WO 2010/031079 A1 | 3/2010 |
| WO | WO 2010/078457 A2 | 7/2010 |
| WO | WO 2010/078457 A3 | 7/2010 |
| WO | WO 2010/148150 A1 | 12/2010 |
| WO | WO 2010/148256 A1 | 12/2010 |
| WO | WO 2011/075534 A2 | 6/2011 |
| WO | WO 2011/075534 A3 | 6/2011 |

(Continued)

OTHER PUBLICATIONS

Mermelstein et al. 1993 (in vivo methylation in *Escherichia coli* by the *Bacillus subtilis* phage o3T I methyltransferase to protect plasmids from restriction upon transformation of *Clostridium acetobutylicum* ATCC 824; Applied and Environmental Microbiology, 59(4):1077-1081).*
Mermelstein et al. 1993 (In Vivo Methylation in *Escherichia coli* by the *Bacillus subtilis* phage f3Tl Methyltransferase to Protect Plasmids from Restriction upon Transformation of *Clostridium acetobutylicum* ATCC 824; Applied and Environmental Microbiology 59(4):1077-1081).*
Butkus et al. 1985 (Nucleic Acid Research 13(9):5727-5747).*
Heap et al. 2009 (A Modular System for Clostridium Shuttle Plasmids; Journal of Microbiological Methods 78:79-85).*
Heap et al. 2007 (The ClosTron: A Universal Gene Knock-out System for the Genus Clostridium; Journal of Microbiological Methods 70: 452-464; see p. 455, right column).*
Allcock, et al., "Clostridium Acetobutylicum Protoplast Formation and Regeneration," *Applied Environmental Microbiology*, 1982, vol. 43, No. 3, pp. 719-721.
Altschul, et al., "Gapped Blast and PSI-BLAST: A new Generation of Protein Database Search Programs," *Nucleic Acids Res.*, 1997, vol. 25, No. 17, pp. 3389-3402.
Andreesen, J. R., et al., "Introduction to the physiology and biochemistry of the genus Clostridium," *In Clostridia*, 1989, pp. 27-62.
Ausubel, F. M., et al., "Introduction of DNA into Mammalian Cells," Current Protocols in Molecular Biology (eds.) Chapter 9, 1987.

(Continued)

*Primary Examiner* — Mary Lyons
(74) *Attorney, Agent, or Firm* — Mintz Levin Cohn Ferris Glovsky and Popeo, P.C.

(57) ABSTRACT

The invention provides compositions and methods for clostridial bacteria that have been engineered to produce and/or to improve efficiency of production of industrial bioproducts.

4 Claims, 73 Drawing Sheets

(56) References Cited

FOREIGN PATENT DOCUMENTS

WO    WO 201318164 A2 * 12/2013    ............... C12N 1/20

OTHER PUBLICATIONS

Bart, et al., "Direct detection of methylation in genomic DNA," *Nucleic Acids Research*, 2005, vol. 33 pp. 51-85.
Bennett and Lasure, "More Gene Manipulations in Fungi," *Academic Press*, San Diego, 199, pp. 70-76, 1.
Bitinaite, et al., "Esp3I—type IIs methyltransferases modifying cytosine and adenine in complementary strands of the target DNA," *Nucleic Acids Research*, 1992, vol. 20, pp. 4981-4985.
Burkhardt, et al., "Relationship of group P1 plasmids revealed by heteroduplex experiments: RP1, RP4, R68 and RK2 are identical." *Journal of General Microbiology*, 1979, vol. 114, pp. 341-348.
Butkus, et al., "Investigation of Restriction-Modification Enzymes from M. Varians RFL19 With a New Type of Specificity Toward Modification of Substrate," *Nucl. Acids Res.*, 1985, vol. 13, No. 16, pp. 5727-5746.
Campbell, et al., "Improved Transformation Efficiency of Aspergillus niger Using the Homologus niaD Gene for Nitrate Reductase," *Current Genetics*, 1989, 16:53-56.
Cato, E. P., et al., "Genus Clostridium," in: *Bergey's Manual of Systematic Bacteriology*, 1986, 2:1141-1200.
Chang and Cohen, "High Frequency Transformation of *Bacillus subtilis* Protoplasts by Plasmid DNA," *Molecular Genes and Genetics*, 1979, 168(1):111-115
Chee, et al., "Accessing Genetic Information with High-Density DNA Arrays," *Science*, 1996; 274:610-614.
Clark, T. A. et al., "Characterization of DNA Methyltransferase Specificities Using DNA Sequencing," *Nucleic Acids Research*, 2012, 40(4) e29):1-12.
Davis et al., "Gene cloning in Clostridia" (P. Durre, P., ed. 2005), pp. 37-52.
Devereux, et al., "A Comprehensive Set of Sequence Analysis Programs for The VAX," *Nucl. Acid. Res.*, 1984, 12:387-395
Dong, et al., "Engineering Clostridium Strain to Accept Unmethylated DNA," *PLoS One*, 2010, 5(2):e9038, pp. 1-8.
Drmanac, et al., "DNA Sequence Determination by Hybridization: aStrategy for Efficient Large-Scale Sequencing." *Science*, 1993, 260:1649- 1652.
Drmanac, et al., "Accurate sequencing by hybridization for DNA diagnostics and individual genomics," *Nature Biotechnology*, 1998, 16:54-58.
Farzaneh, et al., "Optimization of the Ammonia Fiber Explosion (AFEX) Treatment Hydrolysis of Corn Stover," *Bioresource Technology*, 2005, 96 (18): 2014-2018.
Frunzke, et al., "Co-ordinated Regulation of Gluconate Catabolism and Glucose Glutamicurn by Two Functionally Equivalent Transcriptional Regulators, GntR1 and GntR2," *Mol. Microbiol.*, 2008, 67(2):305-22.
Fu, et al., Sequencing exons 5 to 8 of the p53 gene by MALDI-TOF mass spectrometry, *Nature Biotechnology*, 1998, 16:381-384
Genbank Accession No. AJ457070, last updated Apr. 15, 2005, located at https://www.ncbi.nlm.nih.gov/nuccore/AJ457070, printed on Apr. 26, 2017.
Genbank Accession No. AY279379, last updated Mar. 11, 2005, located at https://www.ncbi.nlm.nih.gov/nuccore/AY279379, printed on Apr. 26, 2017.
Genbank Accession No. AY316691, last updated Feb. 15, 2005, located at https://www.ncbi.nlm.nih.gov/nuccore/AY316691, printed on Apr. 26, 2017.
Genbank Accession No. AY341431, last updated Feb. 15, 2005, located at https://www.ncbi.nlm.nih.gov/nuccore/AY341431, printed on Apr. 26, 2017.
Guzman, et al., "Tight Regulation, Modulation, and High-Level Expression by Vectors PBAD Promoter," *Journal of Bacteriology*, 1995, 177(14): 4121-413.

Heap, et al., "A modular system for Clostridium shuttle plasmids," *Journal of Microbiological Methods* 78:79-85.
Hopwood, The Isolation of Mutants, Methods of Microbiology (J.R. Norris and D.W. Ribbons, eds., pp. 363-433.
Hunter, B.K. (1985). "Formaldehyde Metabolism by *Escherichia coli*. Carbon and Incoproration into Glycerol, 1,2-Propanediol, and 1,3-Propanediol," Biochemistry, 1985, 24(15):4148-4155.
International Search Report and the Written Opinion of the International Searching Application No. PCT/US2014/043424, dated Jan. 5, 2015.
Jennert K C B, et al., "Gene Transfer to Clostridium Cellulolyticum ATCC35319 Microbiology," Microbiology, 2000, 146:3071-3080.
Kola, Y. et al., "Biosynthesis of Ether-Type Polar Lipids in Archaea and Evolutionary Considerations," *Microbiology and Molecular Biology Reviews*, 2007, 71(1):97-120.
Kopke, et al., "Fermentative production of ethanol from carbon monoxide," *Current Opinion in Biotechnology*, 2011, 22:320-323.
Leang, C. et al., "A Genetic System for Clostridium Ljungdahii: a Chassis for Autotrophic Production of Biocommodities and a Model Homoacetogen," *Applied and Environmental Microbiology*, 2012, 79(4):1102-1109.
McFarlane, et al., A simplified method for conjugal gene transfer into the filamentous cyanobacterium *Anabaena* sp. ATCC 27893, *Journal of Microbiological Methods*, 1987, 6:301-305.
Mermelstein, L.D., et al., "In Vivo Methylation in *Escherichia coli* by the *Bacillus Subtilis* Phage.Phi.3T I Methyltransferase to Protect Plasmids from Restriction Upon Transformation of Clostridium Acetobutylicum ATCC 824," *Appl. Environ. Microbial*, 1993, pp. 1077-1081.
Metcalf, et al., "A genetic system for Archaea of the genus Methanosarcina: liposome-mediated transformation and construction of shuttle vectors," *Proceedings of the National Academy of Sciences*, 1997, 94:2626-2631.
Miller et al., "First Isolation of an Isoprene Synthase Gene From Poplar and Successful Expression of the Gene in *Escherichia coli*," *Planta*, 213: 483-487, 2001.
Misoph, et al., Effect of CO2 on the Fermentation Capacities of the Acetogen Peptostreptococcus productus U-1, *Journal of Bacteriology*, 1996, 178(11):3140-45.
Needleman and Wunsch, "A General Method Applicable to the Search for Similarities in the Amino Add Sequence of Two Proteins," *J. Mol. Biol.*, 1970, 48:443-453.
Parke, D., "Construction of Mobilizable Vectors Derived From Plasmids RP4, pUC18 and pUC19," *Gene*, 1990, 93:35-137.
Pearson and Lipman, "Improved Tools for Biological Sequence Comparison," *Proc. Natl. Acad. Sci.*, 1988, USA 85:2444.
Purdy D., et al:, "Conjugative Transfer of Clostridal Shuttle Vectors from *Escherichia coli* to Clostridium Difficile Through Circumvention of the Restriction Barrier," *Molecular Microbiology*, Wiley-Blackwell Publishing Ltd, Gb, 2002, 46(2):439-452.
Rimbault, A. et al., "Headspace Gas Chromatographic-Mass Spectrometric Analysis of Light Hydrocarbons and Volatile Organosulphur Compounds in Reduced-Pressure Cultures of Clostlridiilmn," *J. of Chromatography*, 1986, 375:11-25.
Romero, et al., "Transformation of undomesticated strains of *Bacillus subtilis* by protoplast electroporation," *Journal of Microbiological Methods*, 2006, vol. 66: 556-559.
Sears, L.E., et al. "Circumvent Thermal Cycle Sequencing and Alternative Manual and Automated DNA Sequencing Protocols Using the Highly Thermostable VentR (exo-) DNA polymerase," *Biotechniques*, 1992, 13(4):626-633.
Sharkey et al., "Evolution of the Isoprene Biosynthetic Pathway in Kudzu," *Plant Physiology*, 2005, 137: 700-712.
Shimada, "In Vitro Mutagenesis Protocols," *Methods in Molecular Biology*, 1996, 57:157-165.
Silver, et al., "Characterization of Aspen Isoprene Synthase, an Enzyme Responsible for Leaf Isoprene Emission to the Atmosphere." *J. Biol. Chem.*, 1995, 270:13010-13016.
Smith and Waterman, "Comparison of Biosciences," *Adv. Appl. Math.*, 1981, 2:482-489.

(56) References Cited

OTHER PUBLICATIONS

Takahashi, N., et al., "A DNA Methyltransferase Can Protect the Genome from Postdisturbance Attack by a Restriction-Modification Gene Complex," *Journal of Bacteriology*, 2002, 184(22):6100-6108.

Wilkins, et al., 2011, Microbial Production of Ethanol from Carbon Monxide, *Current Opinion in Biotechnology*, vol. 22:326-330.

William, et al., "Embryonic Stem Cells as Targets for Gene Transfer: A New Approach to Molecular Manipulation of the Murine Hematopoietic System," *Journal of General Microbiology*, 1990, 136: 819-826.

Yamada, K. et al. "Production of Glycerol from Methanol by a Mutant Strain of *Candida boidinii* No. 2201," Agric. Biol. Chem., 1989, 53(2):541-543.

Youngman, et al., "Genetic Transposition and Insertional Mutagenesis in *Bacillus subtilis* with Streptococcus Faecalis Transposon Tn917," *PNAS*, 1983, 80:2305-2309.

Zimmerman, et al., *Methods in Molecular and Cellular Biology*, 1992, 3(1):39-42.

\* cited by examiner

FIG. 1 atggccgtactccgcaatattgatgagcaactgaccgaggaatttaagaaactgccgatcgactattgggactttgaggg
tgaggacacgaaagaactgacgcacggcctgcacaactatccggcggtgatggtttatccgatctaccgtaacattatc
gacatcgtgaagcgtcacggtgaggtcgaaacctttctggacccgtttatgggtagcggtacgggcctggtggaaggca
agctggcgggtttcaacaaagtgtacggtacggatctgaatcctctggcagtgctgctgagcaaggttaagaccaccgtc
ttgaaagaggatagcgtggatattcaggacaagctgctgcgcgagaatattgagcaggcgttcgtgtccagcaaacag
ctgctggataacattgacaattacattgcggagaagggcctggacgtcagcgccaaagacggctggggctctgatgcg
catgtcattttgcgcgagtatctggatacctacaacagcggtctgaaaatcccagactttaagaatatgggttattggttcaa
accgcgcgttattctggagctgcaactgattaaggatatcattctgcagatcgagaatgaggacttccgtaacttctttctggt
ctgcttctctgaaactgcccgctacgtgagcaacacccgtaatggtgagttcaagctgttccgtatcaagaaagaaaaag
tggcagatttcaatccggacgttaagatcgagttttacaaatatctggatcgtaacatcgaaaagattaaagactttgacaa
acgttgtaacaacgattgcgaagttagcgttgcttttgaagatacccgcattctggactcggttccggacaatagcatcgat
ctgatgattaccagcccaccgtacggcgatagcaaaactacggtggcgtacggtcaatttagccgtccgtctttgtggtggt
tggatctggaattgatggacatcgaagagctgaatcaagttgacaacaatctgctgggtggtaagaaggtggacaaag
acttcgagtgtgaactgagctcccgtaccttggagaaggcgattaaagaaatcaaagaaaaggacctggaccgcgca
cgtgacgtttatagcttctacgaggatttggataaggctatggagtccattacgaaaaagatgcgtcataacagctaccag
ttctgggttgtcggtaaccgtaccgttaaagaagtcaaactgctgaccaacgaaatcattagcgaactgggcgagaaat
atggtttggttgaggtttacgatatcccgcgtaacatcccgaataaggtcatgccgagccgtaattccccgaccaatgaaa
ccggcaagacggtcagcaccatgacgaacgagcacatcgtcgtgctgcgcaaagatcgt

FIG. 2 atggctgtattgagaaatattgatgaacaattaacagaagaattcaaaaaactaccaatagattattgggattttgaaggtg
aagatacaaaagaattaacgcatggacttcacaattaccctgctgttatggtatatcctatatatagaaatataatagatatt
gtcaaaaggcatggtgaggtagaaacttttttagatcctttcatgggttctggtacaggacttgtagagggaaaattggcag
gctttaataaagtttatgggacagatttaaacccttttagcggtcttattaagtaaggttaaaacaactgtattaaaagaagatt
ctgtagatattcaagataaaattacttagagagaatattgaacaagcatttgttagcagcaaacaattacttgataatattgat
aattacattgcagaaaaaggtttagatgtatctgctaaagatggatggggttcagatgcacatgttattctgagagaatactt
agatacatataactcaggtttaaaaattccagacttcaaaaatatggggtactggtttaaaccacgtgtgatattagagcttc
aacttattaaggatataatactacaaatagaaaacgaagattttagaaatttcttcttagtatgttttagtgaaactgcaagat
atgttagtaatacaagaaatggtgagtttaaactatttagaattaaaaaggaaaaagtagcagatttcaatcctgatgttaa
aatcgagttctataagtatttagatagaaacatcgaaaaaataaaagactttgataaaagatgtaataacgactgcgaag
ttagtgttgcatttgaggatactaggattttagatagtgtacctgacaatagcatagatttaatgataactagtccaccatatgg
tgattctaaaactactgtagcatatggacagttcagtagaccctctttatggtggttagatctagagcttatggacatagaag
aattaaatcaagtagataacaacctactaggcggtaagaaagttgacaaggattttgaatgtgaattatcaagtagaactt
tagaaaaagcaataaaagagattaaggaaaaagaccttgatagagcaagagatgtttatagtttctatgaggacttaga
taaagcaatggaatcaataactaagaaaatgagacataatagttatcaattctgggttgttgggaacagaacagtaaaa
gaagttaagctattaactaatgaaattatttcagaattaggtgaaaagtacggtttagtggaagtatatgatatacctagaaa
tataccaaataaagttatgccaagcaggaattcaccaactaatgaaacaggaaaaactgtaagtacaatgacaaatga
acatatagtagtattaagaaaagatagggaa

FIG. 3

MAVLRNIDEQLTEEFKKLPIDYWDFEGEDTKELTHGLHNYPAVMVYPIYRNIIDIVKRHG
EVETFLDPFMGSGTGLVEGKLAGFNKVYGTDLNPLAVLLSKVKTTVLKEDSVDIQDKLL
RENIEQAFVSSKQLLDNIDNYIAEKGLDVSAKDGWGSDAHVILREYLDTYNSGLKIPDF
KNMGYWFKPRVILELQLIKDIILQIENEDFRNFFLVCFSETARYVSNTRNGEFKLFRIKKE
KVADFNPDVKIEFYKYLDRNIEKIKDFDKRCNNDCEVSVAFEDTRILDSVPDNSIDLMIT
SPPYGDSKTTVAYGQFSRPSLWWLDLELMDIEELNQVDNNLLGGKKVDKDFECELSS
RTLEKAIKEIKEKDLDRARDVYSFYEDLDKAMESITKKMRHNSYQFWVVGNRTVKEVK
LLTNEIISELGEKYGLVEVYDIPRNIPNKVMPSRNSPTNETGKTVSTMTNEHIVVLRKDR

FIG. 4A atgtataccctagagagattaaaaattaggttaagagaaataaatcaaatgggatatgttagaactcacaggagtggtcc
tactggaataggtaaaactcttgaagatttattaggaattgcagagaataatattgctggagcagatcttgaccatcttggcg
agttaaaatcatgtagaaacgggcaaattagcatggttacattgtttacaaaaagtcctagccctccacgagtaaacact
gcacttctagaatcctatggctatgttgaccctacaagaggcggacgaaaaatacttcacacaactttaaatggtgttaact
acaatactgtaaacggaaccccttatggattcaaagtcgaagttagaggaagtaggttatatttactttctaatttccctacgc
aagttaatgcttattgggaaagagaagatttacgttatgcttttgaaagtaaacttccacgtctaatatttgttaaagcaaattc
acgaggtgctggaagaaatgaagaatttcattttgtagaagcctatcatcttgaaggctttagttttgaacaatttgaagattt
actagaacaaggaattataaaaatcgacattcgtataggacaatatccagatggacgaacccatgaccatggtacagc
ttttagaattatgaatgacagaatagatgacttatttgaaaataaaataagattatta

FIG. 5

MYTLERLKIRLREINQMGYVRTHRSGPTGIGKTLEDLLGIAENNIAGADLDHLGELKS
CRNGQISMVTLFTKSPSPPRVNTALLESYGYVDPTRGGRKILHTTLNGVNYNTVNGT
PYGFKVEVRGSRLYLLSNFPTQVNAYWEREDLRYAFESKLPRLIFVKANSRGAGRN
EEFHFVEAYHLEGFSFEQFEDLLEQGIIKIDIRIGQYPDGRTHDHGTAFRIMNDRIDDL
FENKIRL

FIG. 7A ttgaagaacaaaaaacaaggggggtgaaacaatgcagataacagtaaaatttaatattattttgacaaaagaacaagta
caactaatagaatctatatcaaaagaatatatccatactgttaatagccttgtttcatctacgctccaatcagaagaaagagt
aaagctatcatctaaagatgttttgcaaatatgccaagtgcagtgaaaaatcaatctattagagatgccaaaagtatctgt
actaagtacaagaaagctatcaaggctaattccaaactgcctactgataaacaaaaagtaatcaatgtagctaccctaa
aaaacctgtctgtatatggaataatcaaaattattcacttaaagacggtattcttagttttcccgttattatagatgggaaatcg
cagcgtattcaaactagaactatcatgacagactatcagctaaaacaactagaaggtcatttgggagcattgcgtataact
aagaaaagcaataaatatatcgctcaaataagtgttgaaaaagtatctcatatagttaaaggtgatgttgtaatgggtgttg
acttaggcctaaaagttcctgctgtagctgtaaccgattcaggaaaaacgtttttttttggaaacggtaggcaaaataaata
cgtcaaacgtaaatataaagcgaaacgtaaaaaacttggaaaagccaagaagcttaaagtcattaaaaagcttgatg
ataaagaacaacgttggatgacagaccaagaccacaaagtaagtagagaaataattaattttgcagtaaataataatgt
ttctgatattcggcttgaaaaattaacgaatatcagaaacacggcaagaacaagccgtaaaaacgaaaaaaatctaca
tacatggtcattctatcgtctagctcaattcatagagtataaggcactattgaaggggataaaggttgaatatgttgatcctaa
atacacttctcaaatatgccctgaatgtaagaaactaaataaagcaagagatagaaaatataaatgctcctgtggttttaa
aacacatagggatagagtaggtgctataaatataattaatgcacctgtagtagatggtaaaagtctactagcctagggtac
tatatgtactgctctaggagggtaatggcatacccctaagcttgaggtcatactccgatagcagaaatgtacttcggtttaat
cactcaagaatcccactgctttagctgtgggagtgtcaaatgaagcatgatggtcatttatctgtaactagtgaaggaagat
tgtattatgctggtagtcaaaaaattagttttaatagtggtatacctttaaatacaggagatggagttgttgtttggaatgaaatt
caagatttaatttcaacttctgatgtttattccgatgttactttaacggatgaaattgcaaattcaaattatccaaatataaattttg
aatatgatggaaaagaaccgattagcaatccgttttgggattatgaaaacttacatacaggtactagaagtattgatatag
gtgcaaatccagatttatcagctctagtagggaaaacatatgaagatgttattagtgaaaatccaagtcaacaaaatccta
tggtgcctccgataccatttcctgattcatggtttggcaaatgaaagatatagttaacgatagtggaacatggcaagggg
aaggcatagatggaagtactggaactgcaatagatagtcctccattagatattcctggaacgtggcaaggcaaatggtct
tggacagcagacggtcaattagttttcgatggttcttttcaggttctgacggaacaacatggcaaggaacatatacgcata
caggaataggtgttcagaatcctgtactaaatccaccactaaccccggatttaacaggaataacaggttggttatcatctat
aagttcatggttaactagtttgtttgcgtttccaactgattttagtttgaatttagacccgttgaaaaatctacctatagcaacaa
aatttcctttctgtttgccatttgatttaaaaaatagcattgaatcattgcaatctcctgtcgttgtcccagttttacgactacttgg
aatttaccctttttatcaaggagatatagagattaatttagcagctatggaacgatttgcacaaataacacgttggggaacgtt
aattgtatttaatcttggtttaatacttgttacaaggaaggtgttatcatgatatggcaagcactagcatctttttattaatctacttat
taaagcattaggaacggttttagggggcaattatcggattattaccttcaagtccttttcaaactatttcaaattcagcagtaaca
gaatatttaggcatgttgaattggtttatatccgtagatgccatgataactatattaacttactggactactgcaattataagtta
ctatgtaatatcaactgcgatgagatggggaaaaacaattgaataggggggataatatgataagttttatagtggtactcca
ggaagtggaaaaagtcttaatatagctagatacatatggattaaagttcgacatgctaaacaaaatataatacttgttaata
tgacagttaatagagagtatcttattcatcaaaactgaagcaacttgttaataaaattagattgaaattaaaacttaaacct
attaatactaagttaaaagactatggcaaaatctattctataagactcgatcagctgaacacaaaatttctagaagattatg
ctatgaaatttcacatggtgggcattgaaggacaatcaaaaataataatagatgaggcacaactgatttggtccccaacg
gtgatgaaaaataaaaagcaggtagaccctaattatcgtgaacgctggatagagtttatgacactccatagacacttagg
ttttgacatgataattataagtcaatttgataggttgatagatgcacaaatacgttgtctatttgaatacaatcatattcatcgga
aagtcaataactttttgtataggttattggctaaacctattcaaaataaaagtatttgcagaagtgcaatattggtatggagtta
gagcaaggattggagttaattt

FIG. 7B cttcgctattactccatggacttcaaaacactataggaaaatttataacgcacataaaaggttctcagatttaaagggaa
agaaaaaagtagcgtagcgttggactttttcttcccttaaatcaagaaatataatgttcgtaaaaaaatgaatcctgatgt
catggatcacgtggcagcagtcaatatttagatctaaaaattgaataatatccaaacaaataggaggtgtgtaaaataa
atgttcgtgattatatggttaatgttaagtgctgcagctatagcagctactctttggtattattatcaaaatgcttaataaaatag
atttacaaaagtgtctatacatgatagtatatatttaatgatatataggggggtgtatagattgtttacaaggaaaccagaa
actaaaaataagtctttagttcttagaatgacagaaacgcaaaagaagatacttgagattatggctaatgagagaggttt
atcacaatcagaattaattatgatattattggagaatgaattcaagaagcctgtattagaaataaagcagcaagattaaa
cttgccgccttggatagcggagcaacggttttatccaagcggtaaacaatattctaaacagcggtgtttaaaattatcaac
tagaagtgtattaatggctgcggaaagaaatattaaaccagtactatcacaattcgcaccttaaaagtaaggtttttaatgt
ttaattttggcacggaacttgctctttcttgatatattacaaacaagtcggctaaaattgaaattttaacgttatcctgaaagg
ggggcaaaatttggatgagaagatacttaaagatgtaagggtttctaaaaatcatttacaatcggttcataataataatca
gtataataagttgattgtaggttattacaatcaatacatagaagattctagacctgtaaagaagaaaaagactattttggat
tatactagatttacttatgaagattatttgttgaaaaattagaacataaaagagataagttagctaattgtaataagaaatg
ggaagttgaagtttatgaaaaacttaaagtaaaagattatgtgtctactttattatgtaatgataagttttgtagtaattgtaag
aaagtaaagcaagcttcaaggatggcgaaaaatatgcctttgcttgaacagtataaagataaattatatcaaatgggtttt
aactacaccaaatattgtagatcatacaggggggaagaattgaaaaaagagattaaaaagcaatttaaagcattaactta
tttaacagaatatttaaaaggtaaaaaacaagtaaagggtttagattttgatattggatacttaggtgcaataaggtcgttg
gaggtaacttatagcggtgactattatcatccgcatttgcatttgatattagtattggataatcaaaatgaatttataacagat
aaaaaaaaatataaataactattcttatgattattataaaaaaagaccaactagattattttcagattttgaaatattgttacag
aaatcttggtatctttatataatgggaaagattgactaaggaaaatatagataaactggaaaaaggttatagttgcatg
atggataaggcaaaagaagatgatttttagaagttttaaatacatggtgaagaatgatccggcagaggagaatgtaa
aaggtagtaacaaaatgacttataaaaattttagagtattagaatatgcattgcatagtataagacagatacaaggttatg
gagtttttataatattaaagatatattaatggctgaagaagtaaatgaaatgtatgaatggataagagagtatttaatcaa
aaatgaaggagaagctcctgcatatcgtgttgagaagatacagaagcttctagatgatactgagtatactcttatatcaa
ggaaaaaaatatttacgtatttaagaaaaatatactctgaataataacattatagcataaagagggcttaattgctctctttt
ttaatttcttttaaagcttcatttgggtgtatgtttaatagattacagtaaattcgcctgaaagcccacggtttcaatcgtgggat
gaaaggcgtttcttttaatcttcttgttgcagtttcagtttaaaactgatactataaatatatgggacaagattatagaagaac
acaaacaacagtatcttaataaactatcatttttgttttctgtccaaggtacagacgtaaagttctagttggagaagttgaaa
taaaatttaaacagcttctcaatgagatttgtaaagacattgaaatagaaattttggcaatagaatgtgataaagaccact
gccatcttttgtcaatgcacttcctcatttaagtccagcagacataatggcaaaagtgaaaggagtgacttctcgattatta
aggcaggaatttaaacatctgcgacatttgccaagtcttggacaagaagctattttgtatctaccgcaggaaatgtatca
agtgaaactataaaacgatatg

FIG. 9 cctgcaggataaaaaaattgtagataaattttataaaatagttttatctacaatttttttatcaggaaacagctatgaccgcggccgctgt
atccatatgaccatgattacgaattcgagctcggtacccggggatcctctagagtcgacgtcacgcgtccatggagatctcgaggcctgc
agacatgcaagcttggcactggccgtcgttttacaacgtcgtgactgggaaaaccctggcgttacccaacttaatcgccttgcagcacat
cccccttcgccagctggcgtaatagcgaagaggcccgcaccgatcgcccttcccaacagttgcgcagcctgaatggcgaatggcgcta
gcataaaaataagaagcctgcatttgcaggcttcttatttttatggcgcgccgcattcacttcttttctatataaatatgagcgaagcgaat
aagcgtcggaaaagcagcaaaaagtttccttttttgctgttggagcatgggggttcaggggggtgcagtatctgacgtcaatgccgagcga
aagcgagccgaagggtagcatttacgttagataaccccctgatatgctccgacgctttatatagaaaagaagattcaactaggtaaaat
cttaatataggttgagatgataaggtttataaggaatttgtttgttctaattttttcactcattttgttctaatttcttttaacaaatgttcttttt
ttttagaacagttatgatatagttagaatagtttaaaataaggagtgagaaaaagatgaaagaaagatatggaacagtctataaaggct
ctcagaggctcatagacgaagaaagtggagaagtcatagaggtagacaagttataccgtaaacaaacgtctggtaacttcgtaaaggc
atatatagtgcaattaataagtatgttagatatgattggcggaaaaaaacttaaaatcgttaactatatcctagataatgtccacttaagt
aacaatacaatgatagctacaacaagagaaatagcaaaagctacaggaacaagtctacaaacagtaataacaacacttaaaatctta
gaagaaggaaatattataaaaagaaaaactggagtattaatgttaaaccctgaactactaatgagaggcgacgaccaaaaacaaaaa
tacctcttactcgaatttgggaactttgagcaagaggcaaatgaaatagattgacctcccaataacaccacgtagttattgggaggtcaa
tctatgaaatgcgattaagggccggccagtgggcaagttgaaaaattcacaaaaatgtggtataatatctttgttcattagagcgataaa
cttgaatttgagagggaacttagatggtatttgaaaaaattgataaaaaatagttggaacagaaaagagtattttgaccactactttgcaa
gtgtaccttgtacctacagcatgaccgttaaagtggatatcacacaaataaaggaaaagggaatgaaactatatcctgcaatgctttatt
atattgcaatgattgtaaaccgccattcagagtttaggacggcaatcaatcaagatggtgaattggggatatatgatgagatgataccaa
gctatacaatatttcacaatgatactgaaacattttccagcctttggactgagtgtaagtctgactttaaatcattttagcagattatgaaa
gtgatacgcaacggtatggaaacaatcatagaatggaaggaaagccaaatgctccggaaaacatttttaatgtatctatgataccgtgg
tcaaccttcgatggctttaatctgaatttgcagaaaggatatgattatttgattcctatttttactatggggaaatattataaagaagataa
caaaattatacttcctttggcaattcaagttcatcacgcagtatgtgacggatttcacatttgccgttttgtaaacgaattgcaggaattgat
aaatagttaacttcaggtttgtctgtaactaaaaacaagtatttaagcaaaaacatcgtagaaatacggtgttttttgttaccctaagttta
aactccttttttgataatctcatgaccaaaatcccttaacgtgagttttcgttccactgagcgtcagacccccgtagaaaagatcaaaggatc
ttcttgagatccttttttttctgcgcgtaatctgctgcttgcaaacaaaaaaaccaccgctaccagcggtggtttgtttgccggatcaagagc
taccaactcttttttccgaaggtaactggcttcagcagagcgcagataccaaatactgttcttctagtgtagccgtagttaggccaccacttc
aagaactctgtagcaccgcctacatacctcgctctgctaatcctgttaccagtggctgctgccagtggcgataagtcgtgtcttaccgggtt
ggactcaagacgatagttaccggataaggcgcagcggtcgggctgaacggggggttcgtgcacacagcccagcttggagcgaacgac
ctacaccgaactgagatacctacagcgtgagctatgagaaagcgccacgcttcccgaagggagaaaggcggacaggtatccggtaag
cggcagggtcggaacaggagagcgcacgagggagcttcaggggggaaacgcctggtatctttatagtcctgtcgggtttcgccacctct
gacttgagcgtcgatttttgtgatgctcgtcaggggggcggagcctatggaaaaacgccagcaacgcggccttttttacggttcctggcctt
ttgctggccttttgctcacatgttcttcctgcgttatcccctgattctgtggataaccgtattaccgcctttgagtgagctgataccgctcgcc
gcagccgaacgaccgagcgcagcgagtcagtgagcgaggaagcggaagagcgcccaatacgcagggcccctgcttcggggtcatta
tagcgatttttcggtatatccatcctttttcgcacgatatacaggattttgccaaagggttcgtgtagactttccttggtgtatccaacggcg
tcagccgggcaggataggtgaagtaggcccacccgcgagcgggtgttccttcttcactgtcccttattcgcacctggcggtgctcaacgg
gaatcctgctctgcgaggctggccggctaccgccggcgtaacagatgagggcaagcggatggctgatgaaaccaagccaaccaggaa
gggcagcccacctatcaaggtgtactgccttccagacgaacgaagagcgattgaggaaaaggcggcggcggccggcatgagcctgtc
ggcctacctgctggccgtcggccagggctacaaaatcacgggcgtcgtggactatgagcacgtccgcgagctggcccgcatcaatggcg
acctgggccgcctggcggcctgctgaaactctggctcaccgacgacccgcgcacggcgcggttcggtgatgccacgatcctcgccctg
ctggcgaagatcgaagagaagcaggacgagcttggcaaggtcatgatgggcgtggtccgcccgagggcagagccatgactttttagc
cgctaaaacggccgggggggtgcgcgtgattgccaagcacgtccccatgcgctccatcaagaagagcgacttcgcggagctggtgaagt
acatcaccgacgagcaaggcaagaccgatcgggccc (contains 4 *Cac*I sites)

Putative restriction sites

FIG. 11 cctgcaggataaaaaaattgtagataaattttataaaatagttttatctacaatttttttatcaggaaacagctatgaccgcgg
ccgcgtgtagtagcctgtgaaataagtaaggaaaaaaaagaagtaagtgttatatatgatgattattttgtagatgtagata
ggataatagaatccatagaaaatataggttatacagttatataaaaattactttaaaaattaataaaaacatggtaaaatat
aaatcgtataaagttgtgtaatttttaaggaggtgtgttacatatgaccatgattacgaattcgagctcggtacccggggatc
ctctagagtcgacgtcacgcgtccatggagatctcgaggcctgcagacatgcaagcttggcactggccgtcgttttacaa
cgtcgtgactgggaaaaccctggcgttacccaacttaatcgccttgcagcacatcccctttcgccagctggcgtaatagc
gaagaggcccgcaccgatcgcccttcccaacagttgcgcagcctgaatggcgaatggcgctagcataaaaataagaa
gcctgcatttgcaggcttcttattttatggcgcgccgcattcacttcttttctatataaatatgagcgaagcgaataagcgtcg
gaaaagcagcaaaaagtttccttttgctgttggagcatgggggttcaggggggtgcagtatctgacgtcaatgccgagcg
aaagcgagccgaagggtagcatttacgttagataacccccctgatatgctccgacgctttatatagaaaagaagattcaac
taggtaaaatcttaatataggttgagatgataaggtttataaggaatttgtttgttctaattttcactcattttgttctaatttcttttaa
caaatgttcttttttttttagaacagttatgatatagttagaatagtttaaaataaggagtgagaaaaagatgaaagaaagat
atggaacagtctataaaggctctcagaggctcatagacgaagaaagtggagaagtcatagaggtagacaagttatacc
gtaaacaaacgtctggtaacttcgtaaaggcatatatagtgcaattaataagtatgttagatatgattggcggaaaaaaac
ttaaaatcgttaactatatcctagataatgtccacttaagtaacaatacaatgatagctacaacaagagaaatagcaaaa
gctacaggaacaagtctacaaacagtaataacaacacttaaaatcttagaagaaggaaatattataaaaagaaaaac
tggagtattaatgttaaaccctgaactactaatgagaggcgacgaccaaaaacaaaaatacctcttactcgaatttggga
actttgagcaagaggcaaatgaaatagattgacctcccaataacaccacgtagttattgggaggtcaatctatgaaatgc
gattaagggccggccgaagcaaacttaagagtgtgttgatagtgcagtatcttaaaattttgtataataggaattgaagtta
aattagatgctaaaaatttgtaattaagaaggagtgattacatgaacaaaaatataaaatattctcaaaactttttaacgagt
gaaaaagtactcaaccaaataataaaacaattgaatttaaaagaaaccgataccgtttacgaaattggaacaggtaaa
gggcatttaacgacgaaactggctaaaataagtaaacaggtaacgtctattgaattagacagtcatctattcaacttatcgt
cagaaaaattaaaactgaatactcgtgtcactttaattcaccaagatattctacagtttcaattccctaacaaacagaggtat
aaaattgtgggagtattccttaccatttaagcacacaaattattaaaaaagtggttttgaaagccatgcgtctgacatctat
ctgattgttgaagaaggattctacaagcgtaccttggatattcaccgaacactagggttgctcttgcacactcaagtctcgat
tcagcaattgcttaagctgccagcggaatgctttcatcctaaaccaaaagtaaacagtgtcttaataaaacttacccgccat
accacagatgttccagataaatattggaagctatatacgtactttgtttcaaaatgggtcaatcgagaatatcgtcaactgttt
actaaaaatcagtttcatcaagcaatgaaacacgccaaagtaaacaatttaagtaccgttacttatgagcaagtattgtct
atttttaatagttatctattatttaacgggaggaaataattctatgagtcgcttttgtaaatttggaaagttacacgttactaaagg
gaatgtgtttaaactccttttgataatctcatgaccaaaatcccttaacgtgagttttcgttccactgagcgtcagacccccgta
gaaaagatcaaaggatcttcttgagatccttttttctgcgcgtaatctgctgcttgcaaacaaaaaaaccaccgctaccag
cggtggtttgtttgccggatcaagagctaccaactctttttccgaaggtaactggcttcagcagagcgcagataccaaata
ctgttcttctagtgtagccgtagttaggccaccacttcaagaactctgtagcaccgcctacatacctcgctctgctaatcctgtt
accagtggctgctgccagtggcgataagtcgtgtcttaccgggttggactcaagacgatagttaccggataaggcgcag
cggtcgggctgaacggggggttcgtgcacacagcccagcttggagcgaacgacctacaccgaactgagatacctaca
gcgtgagctatgagaaagcgccacgcttcccgaagggagaaaggcggacaggtatccggtaagcggcagggtcgg
aacaggagagcgcacgagggagcttccaggggggaaacgcctggtatctttatagtcctgtcgggtttcgccacctctga
cttgagcgtcgatttttgtgatgctcgtcaggggggcggagcctatgaaaaacgccagcaacgcggcctttttacggttc
ctggccttttgctggccttttgctcacatgttctttcctgcgttatccctgattctgtggataaccgtattaccgcctttgagtgagc
tgataccgctcgccgcagccgaacgaccgagcgcagcgagtcagtgagcgaggaagcggaagagcgcccaatac
gcagggccc

FIG. 15 cctgcaggataaaaaaattgtagataaattttataaaatagttttatctacaattttttatcaggaaacagctatgaccgcggcc
gcgtgtagtagcctgtgaaataagtaaggaaaaaaaagaagtaagtgttatatatgatgattattttgtagatgtagataggat
aatagaatccatagaaaatataggttatacagttatataaaaattactttaaaaattaataaaaacatggtaaaatataaatcg
tataaagttgtgtaattttaaggaggtgtgttacatatgaccatgattacgaattcgagctcggtacccggggatcctctagagt
cgacgtcacgcgtccatggagatctcgaggcctgcagacatgcaagcttggcactggccgtcgtttacaacgtcgtgactg
ggaaaaccctgacgttacccaacttaatcgccttgcagcacatcccccttttcgccagctggcgtaatagcgaagaggcccg
caccgatcgcccttcccaacagttgcgcagcctgaatggcgaatggcgctagcataaaaataagaagcctgcatttgcagg
cttcttattttatggcgcgccgcattcacttctttctatataaatatgagcgaagcgaataagcgtcggaaaagcagcaaaaa
gtttccttttgctgttggagcatgggggttcagggggtgcagtatctgacgtcaatgccgagcgaaagcgagccgaagggta
gcatttacgttagataaccccctgatatgctccgacgctttatatagaaaagaagattcaactaggtaaaatcttaatataggtt
gagatgataaggtttataaggaattgtttgttctaatttttcactcatttgttctaatttcttttaacaaatgttctttttttttagaacagtt
atgatatagttagaatagtttaaaataaggagtgagaaaaagatgaaagaaagatatggaacagtctataaaggctctcag
aggctcatagacgaagaaagtggagaagtcatagaggtagacaagttataccgtaaacaaacgtctggtaacttcgtaaa
ggcatatatagtgcaattaataagtatgttagatatgattggcggaaaaaaacttaaaatcgttaactatatcctagataatgtc
cacttaagtaacaatacaatgatagctacaacaagagaaatagcaaaagctacaggaacaagtctacaaacagtaataa
caacacttaaaatcttagaagaaggaaatattataaaaagaaaaactggagtattaatgttaaaccctgaactactaatgag
aggcgacgaccaaaaacaaaaatacctcttactcgaatttgggaactttgagcaagaggcaaatgaaatagattgacctcc
caataacaccacgtagttattgggaggtcaatctatgaaatgcgattaagggccggccgaagcaaacttaagagtgtgttga
tagtgcagtatcttaaaattttgtataataggaattgaagttaaattagatgctaaaaatttgtaattaagaaggagtgattacatg
aacaaaaatataaaatattctcaaaacttttttaacgagtgaaaaagtactcaaccaaataataaaaacaattgaatttaaaag
aaaccgataccgtttacgaaattggaacaggtaaagggcatttaacgacgaaactggctaaaataagtaaacaggtaacg
tctattgaattagacagtcatctattcaacttatcgtcagaaaaattaaaactgaatactcgtgtcactttaattcaccaagatattc
tacagtttcaattccctaacaaacagaggtataaaattgttgggagtattccttaccatttaagcacacaaattattaaaaaagt
ggttttgaaagccatgcgtctgacatctatctgattgttgaagaaggattctacaagcgtaccttggatattcaccgaacactag
ggttgctcttgcacactcaagtctcgattcagcaattgcttaagctgccagcggaatgcttcatcctaaaccaaaagtaaaca
gtgtcttaataaaacttacccgccataccacagatgttccagataaatattggaagctatatacgtactttgtttcaaaatgggtc
aatcgagaatatcgtcaactgtttactaaaaatcagtttcatcaagcaatgaaacacgccaaagtaaacaatttaagtaccgt
tacttatgagcaagtattgtctattttaatagttatctattatttaacgggaggaaataattctatgagtcgcttttgtaaatttggaaa
gttacacgttactaaagggaatgtgtttaaactccttttgataatctcatgaccaaaatcccttaacgtgagttttcgttccactga
gcgtcagaccccgtagaaaagatcaaaggatcttcttgagatcctttttttctgcgcgtaatctgctgcttgcaaacaaaaaaa
ccaccgctaccagcggtggtttgtttgccggatcaagagctaccaactctttttccgaaggtaactggcttcagcagagcgca
gataccaaatactgttcttctagtgtagccgtagttaggccaccacttcaagaactctgtagcaccgcctacatacctcgctctg
ctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatac
ctacagcgtgagctatgagaaagcgccacgcttcccgaagggagaaaggcggacaggtatccggtaagcggcagggtc
ggaacaggagagcgcacgagggagcttcaggggggaaacgcctgatatctttatagtcctgtcgggtttcgccacctctgac
ttgagcgtcgatttttgtgatgctcgtcaggggggcggagcctatgaaaaacgccagcaacgcggcctttttacggttcctga
ccttttgctggccttttgctcacatgttcttcctgcgttatcccctgattctgtggataaccgtattaccgcctttgagtgagctgatac
cgctcgccgcagccgaacgaccgagcgcagcgagtcagtgagcgaggaagcggaagagcgcccaatacgcagggc
cc 1 = Primers 418 & 419
2 = Primers 420 & 421
3 = Primers 422 & 423

FIG. 20A ttgaagaacaaaaaacaagggggtgaaacaatgcagataacagtaaaatttaatattattttgacaaaagaacaagta
caactaatagaatctatatcaaaagaatatatccatactgttaatagccttgtttcatctacgctccaatcagaagaaagagt
aaagctatcatctaaagatgttttgcaaatatgccaagtgcagtgaaaaatcaatctattagagatgccaaaagtatctgt
actaagtacaagaaagctatcaaggctaattccaaactgcctactgataaacaaaaagtaatcaatgtagctacccttaa
aaaacctgtctgtatatggaataatcaaaattattcacttaaagacggtattcttagttttcccgttattatagatgggaaatcg
cagcgtattcaaactagaactatcatgacagactatcagctaaaacaactagaaggtcatttgggagcattgcgtataac
taagaaaagcaataaatatatcgctcaaataagtgttgaaaaagtatctcatatagttaaaggtgatgttgtaatgggtgttg
acttaggcctaaaagttcctgctgtagctgtaaccgattcaggaaaaacgttttttttggaaacggtaggcaaaataaata
cgtcaaacgtaaatataaagcgaaacgtaaaaaacttggaaaagccaagaagcttaaagtcattaaaaagcttgatg
ataaagaacaacgttggatgacagaccaagaccacaaagtaagtagagaaataattaattttgcagtaaataataatgt
ttctgatattcggcttgaaaaattaacgaatatcagaaacacggcaagaacaagccgtaaaaacgaaaaaaatctaca
tacatggtcattctatcgtctagctcaattcatagagtataaggcactattgaaggggataaaggttgaatatgttgatcctaa
atacacttctcaaatatgccctgaatgtaagaaactaaataaagcaagagatagaaaatataaatgctcctgtggttttaa
aacacatagggatagagtaggtgctataaatataattaatgcacctgtagtagatggtaaaagtctactagcctagggta
ctatatgtactgctctaggagggtaatggcatacccctaagcttgaggtcatactccgatagcagaaatgtacttcggtttaa
tcactcaagaatcccactgctttagctgtgggagtgtcaaatgaagcatgatggtcatttatctgtaactagtgaaggaaga
ttgtattatgctggtagtcaaaaaattagttttaatagtggtataccctttaaatacaggagatggagttgttgtttggaatgaaatt
caagatttaatttcaacttctgatgtttattccgatgttactttaacggatgaaattgcaaattcaaattatccaaatataaattttg
aatatgatggaaaagaaccgattagcaatccgtttgggattatgaaaacttacatacaggtactagaagtattgatatag
gtgcaaatccagatttatcagctctagtagggaaaacatatgaagatgttattagtgaaaatccaagtcaacaaaatccta
tggtgcctccgataccatttcctgattcatggtttggcaaatggaaagatatagttaacgatagtggaacatggcaagggg
aaggcatagatggaagtactggaactgcaatagatagtcctccattagatattcctggaacgtggcaaggcaaatggtct
tggacagcagacggtcaattagttttcgatggttctttttcaggttctgacggaacaacatggcaaggaacatatacgcata
caggaataggtgttcagaatcctgtactaaatccaccactaaccccggatttaacaggaataacaggttggttatcatctat
aagttcatggttaactagtttgtttgcgtttccaactgattttagtttgaatttagacccgttgaaaaatctacctatagcaacaa
aatttcctttctgtttgccatttgatttaaaaaatagcattgaatcattgcaatctcctgtcgttgtcccagttttttacgactacttgg
aatttacccttttatcaaggagatatagagattaatttagcagctatggaacgatttgcacaaataacacgttggggaacgtt
aattgtatttaatcttggtttaatacttgttacaaggaaggtgttatcatgatatggcaagcactagcatcttttattaatctacttat
taaagcattaggaacggttttaggggcaattatcggattattaccttcaagtccttttcaaactatttcaaattcagcagtaac
agaatatttaggcatgttgaattggtttatatccgtagatgccatgataactatattaacttactggactactgcaattataagtt
actatgtaatatcaactgcgatgagatggggaaaaacaattgaataggggggataatatgataagtttttatagtggtactcc
aggaagtggaaaaagtcttaatatagctagatacatatggattaaagttcgacatgctaaacaaaatataatacttgttaat
atgacagttaatagagagtatcttattacatcaaaactgaagcaacttgttaataaaattagattgaaattaaaacttaaac
ctattaatactaagttaaaagactatggcaaaatctattctataagactcgatcagctgaacacaaaatttctagaagattat
gctatgaaatttcacatggtgggcattgaaggacaatcaaaaataataatagatgaggcacaactgatttggtccccaac
ggtgatgaaaataaaaagcaggtagaccctaattatcgtgaacgctggatagagtttatgacactccatagacacttag
gttttgacatgataattataagtcaatttgataggttgatagatgcacaaatacgttgtctatttgaatacaatcatattcatcgg
aaagtcaataactttgtataggttattggctaaacctattcaaaataaaagtatttgcagaagtgcaatattggtatggagtt
agagcaaggattggagttaatttcttcgctattactccatggacttcaaaacactataggaaaatttataacgcacat

FIG. 20B aaaaggttctcagatttaaagggaaagaaaaaagtagcgtagcgttggactttttcttccctttaaatcaagaaatataat
gttcgtaaaaaatgaatcctgatgtcatggatcacgtggcagcagtcaatatttagatctaaaaattgaataatatccaaa
caaataggaggtgtgtaaaataaatgttcgtgattatatggttaatgttaagtgctgcagctatagcagctactctttggtatta
ttatcaaaatgcttaataaaatagatttacaaaagtgtctatacatgatagtatatatttaatgatatataggggggtgtatag
attgtttacaaggaaaccagaaactaaaaataagtctttagttcttagaatgacagaaacgcaaaagaagatacttgag
attatggctaatgagagaggtttatcacaatcagaattaattatgatattattggagaatgaattcaagaagcctgtattaga
aataaagcagcaagattaaacttgccgccttggatagcggagcaacggtttatccaagcggtaaacaatattctaaac
agcggtgtttaaaattatcaactagaagtgtattaatggctgcggaaagaaatattaaaccagtactatcacaattcgcac
cttaaaagtaaggtttttaatgtttaattttggcacggaacttgctctttcttgatatattacaaacaagtcggctaaaattgaaat
tttaacgttatcctgaaaggggggcaaaatttggatgagaagatacttaaagatgtaagggtttctaaaaatcatttacaat
cggttcataataataatcagtataataagttgattgtaggttattacaatcaatacatagaagattctagacctgtaaagaag
aaaaagactattttggattatactagatttacttatgaagattattttgttgaaaaattagaacataaaagagataagttagct
aattgtaataagaaatgggaagttgaagtttatgaaaaacttaaagtaaaagattatgtgtcactttattatgtaatgataag
ttttgtagtaattgtaagaaagtaaagcaagcttcaaggatggcgaaaaatatgcctttgcttgaacagtataaagataaat
tatatcaaatggttttaactacaccaaatattgtagatcatacaggggaagaattgaaaaaagagattaaaaagcaattta
aagcattaacttatttaacagaatatttaaaaggtaaaaaacaagtaaagggtttagattttgatattggatacttaggtgca
ataaggtcgttggaggtaacttatagcggtgactattatcatccgcatttgcatttgatattagtattggataatcaaaatgaat
ttataacagataaaaaaaatataaataactattcttatgattattataaaaaaagaccaactagattatttcagattttgaaat
attgttacagaaatcttggtatcttttatataatggggaaagattgactaaggaaaatatagataaactggaaaaaggttat
agttgcatgatggataaggcaaaagaagatgattttttagaagtttttaaatacatggtgaagaatgatccggcagagga
gaatgtaaaaggtagtaacaaaatgacttataaaaaattttagagtattagaatatgcattgcatagtataagacagataca
aggttatggagttttttataatattaaagatatattaatggctgaagaagtaaatgaaatgtatgaatggataagagagtattt
aatcaaaaatgaaggagaagctcctgcatatcgtgttgagaagatacagaagcttctagatgatactgagtatactcttat
atcaaggaaaaaaatatttacgtatttaagaaaaatatactctgaataataaaggtcaatctatgaaatgcgattaagggc
cggccagtgggcaagttgaaaaattcacaaaaatgtggtataatatctttgttcattagagcgataaacttgaatttgagag
ggaacttagatggtatttgaaaaaattgataaaaatagttggaacagaaaagagtattttgaccactactttgcaagtgtac
cttgtacctacagcatgaccgttaaagtggatatcacacaaataaaggaaaagggaatgaaactatatcctgcaatgctt
tattatattgcaatgattgtaaaccgccattcagagtttaggacggcaatcaatcaagatggtgaattggggatatatgatg
agatgataccaagctatacaatatttcacaatgatactgaaacattttccagcctttggactgagtgtaagtctgactttaaat
cattttttagcagattatgaaagtgatacgcaacggtatggaaacaatcatagaatggaaggaaagccaaatgctccgga
aaacattttaatgtatctatgataccgtggtcaaccttcgatggctttaatctgaatttgcagaaaggatatgattatttgattcc
tatttttactatggggaaatattataaagaagataacaaaattatacttcctttggcaattcaagttcatcacgcagtatgtgac
ggatttcacatttgccgttttgtaaacgaattgcaggaattgataaatagttaacttcaggtttgtctgtaactaaaaacaagta
tttaagcaaaaacatcgtagaaatacggtgttttttgttaccctaagttaaactccttttttgataatctcatgaccaaaatcccctt
aacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactcttttttccgaa
ggtaactggcttcagcagagcgcagataccaaatactgttcttctagtgtagccgtagttaggccaccacttcaagaactct
gtagcaccgcctacatacctcgctctgctaatcctgttaccagtggctgctgccagtggcgataagtcgtgtcttaccgggtt
ggactcaagacgatagttac

FIG. 20C cggataaggcgcagcggtcgggctgaacgggggttcgtgcacacagcccagcttggagcgaacgacctacaccgaac
tgagatacctacagcgtgagctatgagaaagcgccacgcttcccgaagggagaaaggcggacaggtatccggtaagcg
gcagggtcggaacaggagagcgcacgagggagcttcaggggggaaacgcctggtatctttatagtcctgtcgggtttcgcc
acctctgacttgagcgtcgattttgtgatgctcgtcaggggggcggagcctatggaaaaacgccagcaacgcggcctttta
cggttcctggccttttgctggccttttgctcacatgttcttcctgcgttatccctgattctgtggataaccgtattaccgcctttgagtg
agctgataccgctcgccgcagccgaacgaccgagcgcagcgagtcagtgagcgaggaagcggaagagcgcccaata
cgcagggccccctgcttcggggtcattatagcgattttttcggtatatccatccttttcgcacgatatacaggattttgccaaagg
gttcgtgtagactttccttggtgtatccaacggcgtcagccgggcaggataggtgaagtaggcccacccgcgagcgggtgtt
ccttcttcactgtcccttattcgcacctggcggtgctcaacgggaatcctgctctgcgaggctggccggctaccgccggcgtaa
cagatgagggcaagcggatggctgatgaaaccaagccaaccaggaagggcagcccacctatcaaggtgtactgccttc
cagacgaacgaagagcgattgaggaaaaggcggcggcggccggcatgagcctgtcggcctacctgctggccgtcggcc
agggctacaaaatcacgggcgtcgtggactatgagcacgtccgcgagctggcccgcatcaatggcgacctgggccgcct
gggcggcctgctgaaactctggctcaccgacgacccgcgcacggcgcggttcggtgatgccacgatcctcgccctgctgg
cgaagatcgaagagaagcaggacgagcttggcaaggtcatgatgggcgtggtccgcccgagggcagagccatgacttt
ttagccgctaaaacggccgggggggtgcgcgtgattgccaagcacgtccccatgcgctccatcaagaagagcgacttcgcg
gagctggtgaagtacatcaccgacgagcaaggcaagaccgatcgggccccctgcaggataaaaaaattgtagataaatt
ttataaaatagttttatctacaattttttttatcaggaaacagctatgaccgcggccgccattatagcataaagagggcttaattgct
ctctttttaatttcttttaaagcttcatttgggtgtatgtttaatagattacagtaaattcgcctgaaagcccacggtttcaatcgtggg
atgaaaggcgtttctttaatcttcttgttgcagtttcagtttaaaactgatactataaatatatgggacaagattatagaagaacac
aaacaacagtatctttaataaactatcattttgttttctgtccaaggtacagacgtaaagttctagttggagaagttgaaataaaa
tttaaacagcttctcaatgagatttgtaaagacattgaaatagaaattttggcaatagaatgtgataaagaccactgccatcttttt
gtcaatgcacttcctcatttaagtccagcagacataatggcaaaagtgaaaggagtgacttctcgattattaaggcaggaattt
aaacatctgcgacatttgccaagtctttggacaagaagctattttgtatctaccgcaggaaatgtatcaagtgaaactataaaa
cgatatg

FIG. 22A ttgaagaacaaaaaacaagggggtgaaacaatgcagataacagtaaaatttaatattattttgacaaaagaacaagta
caactaatagaatctatatcaaaagaatatatccatactgttaatagccttgtttcatctacgctccaatcagaagaaagagt
aaagctatcatctaaagatgttttgcaaatatgccaagtgcagtgaaaaatcaatctattagagatgccaaaagtatcgt
actaagtacaagaaagctatcaaggctaattccaaactgcctactgataaacaaaaagtaatcaatgtagctacccttaa
aaaacctgtctgtatatggaataatcaaaattattcacttaaagacggtattcttagttttcccgttattatagatgggaaatcg
cagcgtattcaaactagaactatcatgacagactatcagctaaaacaactagaaggtcatttgggagcattgcgtataac
taagaaaagcaataaatatatcgctcaaataagtgttgaaaaagtatctcatatagttaaaggtgatgttgtaatgggtgttg
acttaggcctaaaagttcctgctgtagctgtaaccgattcaggaaaaacgttttttttggaaacggtaggcaaaataaata
cgtcaaacgtaaatataaagcgaaacgtaaaaaacttggaaaagccaagaagcttaaagtcattaaaaagcttgatg
ataaagaacaacgttggatgacagaccaagaccacaaagtaagtagagaaataattaattttgcagtaaataataatgt
ttctgatattcggcttgaaaaattaacgaatatcagaaacacggcaagaacaagccgtaaaaacgaaaaaaatctaca
tacatggtcattctatcgtctagctcaattcatagagtataaggcactattgaaggggataaaggttgaatatgttgatcctaa
atacacttctcaaatatgccctgaatgtaagaaactaaataaagcaagagatagaaaatataaatgctcctgtggttttaa
aacacatagggatagagtaggtgctataaatataattaatgcacctgtagtagatggtaaaagtctactagcctagggta
ctatatgtactgctctaggaggggtaatggcatacccctaagcttgaggtcatactccgatagcagaaatgtacttcggtttaa
tcactcaagaatcccactgctttagctgtgggagtgtcaaatgaagcatgatggtcatttatctgtaactagtgaaggaaga
ttgtattatgctggtagtcaaaaaattagttttaatagtggtataccctttaaatacaggagatggagttgttgtttggaatgaaatt
caagatttaatttcaacttctgatgtttattccgatgttactttaacgatgaaattgcaaattcaaattatccaaatataaattttg
aatatgatggaaaagaaccgattagcaatccgttttgggattatgaaaacttacatacaggtactagaagtattgatatag
gtgcaaatccagatttatcagctctagtagggaaaacatatgaagatgttattagtgaaaatccaagtcaacaaaatccta
tggtgcctccgataccatttcctgattcatggtttggcaaatggaaagatatagttaacgatagtggaacatggcaagggg
aaggcatagatggaagtactggaactgcaatagatagtcctccattagatattcctggaacgtggcaaggcaaatggtct
tggacagcagacggtcaattagttttcgatggtctttttcaggttctgacggaacaacatggcaaggaacatatacgcata
caggaataggtgttcagaatcctgtactaaatccaccactaaccccggatttaacaggaataacaggttggttatcatctat
aagttcatggttaactagtttgtttgcgttccaactgattttagtttgaatttagacccgttgaaaaatctacctatagcaacaa
aatttccttctgtttgccatttgatttaaaaaatagcattgaatcattgcaatctcctgtcgttgtcccagttttacgactacttgg
aatttacccttttatcaaggagatatagagattaatttagcagctatggaacgatttgcacaaataacacgttggggaacgtt
aattgtatttaatcttggtttaatacttgttacaaggaaggtgttatcatgatatggcaagcactagcatcttttattaatctacttat
taaagcattaggaacggttttaggggcaattatcggattattaccttcaagtccttttcaaactatttcaaattcagcagtaac
agaatatttaggcatgttgaattggtttatatccgtagatgccatgataactatattaacttactggactactgcaattataagtt
actatgtaatatcaactgcgatgagatggggaaaaacaattgaataggggggataatatgataagttttatagtggtactcc
aggaagtggaaaaagtcttaatatagctagatacatatggattaaagttcgacatgctaaacaaaatataatacttgttaat
atgacagttaatagagagtatcttattacatcaaaactgaagcaacttgttaataaaattagattgaaattaaaacttaaac
ctattaatactaagttaaaagactatggcaaaatctattctataagactcgatcagctgaacacaaaattctagaagattat
gctatgaaatttcacatggtgggcattgaaggacaatcaaaaataataatagatgaggcacaactgatttggtccccaac
ggtgatgaaaaataaaaagcaggtagaccctaattatcgtgaacgctggatagagtttatgacactccataga

FIG. 22B cacttaggttttgacatgataattataagtcaatttgataggttgatagatgcacaaatacgttgtctatttgaatacaatcatatt
catcggaaagtcaataacttttgtataggttattggctaaacctattcaaaataaaagtatttgcagaagtgcaatattggtat
ggagttagagcaaggattggagttaatttcttcgctattactccatggacttcaaaacactataggaaaatttataacgcac
ataaaaggttctcagatttaaagggaaagaaaaaagtagcgtagcgttggactttttcttcccttttaaatcaagaaatata
atgttcgtaaaaaaatgaatcctgatgtcatggatcacgtggcagcagtcaatatttagatctaaaaattgaataatatcca
aacaaataggaggtgtgtaaaataaatgttcgtgattatatggttaatgttaagtgctgaggtcaatctatgaaatgcgatta
agggccggccagtgggcaagttgaaaaattcacaaaaatgtggtataatatctttgttcattagagcgataaacttgaattt
gagagggaacttagatggtatttgaaaaaattgataaaaatagttggaacagaaaagagtattttgaccactacttttgcaa
gtgtaccttgtacctacagcatgaccgttaaagtggatatcacacaaataaaggaaaagggaatgaaactatatcctgc
aatgctttattatattgcaatgattgtaaaccgccattcagagtttaggacggcaatcaatcaagatggtgaattggggatat
atgatgagatgataccaagctatacaatatttcacaatgatactgaaacattttccagccttggactgagtgtaagtctgac
tttaaatcatttttagcagattatgaaagtgatacgcaacggtatggaaacaatcatagaatggaaggaaagccaaatgc
tccggaaaacatttttaatgtatctatgataccgtggtcaaccttcgatggctttaatctgaatttgcagaaaggatatgattatt
tgattcctattttactatggggaaatattataaagaagataacaaaattatacttcctttggcaattcaagttcatcacgcagt
atgtgacggatttcacatttgccgttttgtaaacgaattgcaggaattgataaaatagttaacttcaggtttgtctgtaactaaaa
acaagtatttaagcaaaaacatcgtagaaatacggtgttttttgttaccctaagtttaaactccttttgataatctcatgacca
aaatcccttaacgtgagttttcgttccactgagcgtcagaccccgtagaaaagatcaaaggatcttcttgagatccttttttct
gcgcgtaatctgctgcttgcaaacaaaaaaaccaccgctaccagcggtggtttgtttgccggatcaagagctaccaactc
tttttccgaaggtaactggcttcagcagagcgcagataccaaatactgttcttctagtgtagccgtagttaggccaccacttc
aagaactctgtagcaccgcctacatacctcgctctgctaatcctgttaccagtggctgctgccagtggcgataagtcgtgtc
ttaccgggttggactcaagacgatagttaccggataaggcgcagcggtcgggctgaacggggggttcgtgcacacagc
ccagcttggagcgaacgacctacaccgaactgagatacctacagcgtgagctatgagaaagcgccacgcttcccgaa
gggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcagggggggc
ggagcctatggaaaaacgccagcaacgcggcctttttacggttcctggccttttgctggccttttgctcacatgttctttcctgc
gttatcccctgattctgtggataaccgtattaccgcctttgagtgagctgataccgctcgccgcagccgaacgaccgagcg
cagcgagtcagtgagcgaggaagcggaagagcgcccaatacgcagggccccctgcttcggggtcattatagcgattt
ttcggtatatccatccttttcgcacgatatacaggattttgccaaaggggttcgtgtagactttccttggtgtatccaacggcgtc
agccgggcaggataggtgaagtaggcccaccccgcgagcggtgttccttcttcactgtcccttattcgcacctggcggtg
ctcaacgggaatcctgctctgcgaggctggccggctaccgccggcgtaacagatgagggcaagcggatggctgatga
aaccaagccaaccaggaagggcagcccacctatcaaggtgtactgccttccagacgaacgaagagcgattgagga
aaaggcggcggcggccggcatgagcctgtcggcctacctgctggccgtcggccagggctacaaaatcacgggcgtc
gtggactatgagcacgtccgcgagctggcccgcatcaatggcgacctgggccgcctgggcggcctgctgaaactctgg
ctcaccgacgacccgcgcacggcgcggttcggtgatgccacgatcctcgccctgctggcgaagatcgaagagaagca
ggacgagcttggcaaggtcatgatgggcgtggtccgcccgagggcagagccatgacttttttagccgctaaaacggcc
gggggtgcgcgtgattgccaagcacgtccccatgcgctccatcaagaagagcgacttcgcggagctggtgaag

FIG. 22C tacatcaccgacgagcaaggcaagaccgatcgggccccctgcaggataaaaaaattgtagataaattttataaaatagtttt
atctacaattttttatcaggaaacagctatgaccgcggccgccagctatagcagctactctttggtattattatcaaaatgcttaa
taaaatagatttacaaaagtgtctatacatgatagtatatatttaatgatatataggggggtgtatagattgtttacaaggaaacc
agaaactaaaaataagtctttagttcttagaatgacagaaacgcaaaagaagatacttgagattatggctaatgagagaggt
ttatcacaatcagaattaattatgatattattggagaatgaattcaagaagcctgtattagaaataaagcagcaagattaaactt
gccgccttggatagcggagcaacggttttatccaagcggtaaacaatattctaaacagcggtgtttaaaattatcaactagaa
gtgtattaatggctgcggaaagaaatattaaaccagtactatcacaattcgcaccttaaaagtaaggttttaatgtttaattttgg
cacggaacttgctctttcttgatatattacaaacaagtcggctaaaattgaaattttaacgttatcctgaaaggggggcaaaattt
ggatgagaagatacttaaagatgtaagggtttctaaaaatcatttacaatcggttcataataataatcagtataataagttgattg
taggttattacaatcaatacatagaagattctagacctgtaaagaagaaaaagactattttggattatactagatttacttatgaa
gattattttgttgaaaaattagaacataaaagagataagttagctaattgtaataagaaatgggaagttgaagtttatgaaaaa
cttaaagtaaaagattatgtgtctactttattatgtaatgataagttttgtagtaattgtaagaaagtaaagcaagcttcaaggatg
gcgaaaaatatgcctttgcttgaacagtataaagataaattatatcaaatggttttaactacaccaaatattgtagatcatacag
gggaagaattgaaaaaagagattaaaaagcaatttaaagcattaacttatttaacagaatatttaaaaggtaaaaaacaag
taaagggtttagattttgatattggatacttaggtgcaataaggtcgttggaggtaacttatagcggtgactattatcatccgcattt
gcatttgatattagtattggataatcaaaatgaatttataacagataaaaaaaatataaataactattcttatgattattataaaaa
aagaccaactagattattttcagattttgaaatattgttacagaaatcttggtatcttttatataatgggaaagattgactaagga
aaatatagataaactggaaaaaggttatagttgcatgatggataaggcaaaagaagatgattttttagaagttttaaatacat
ggtgaagaatgatccggcagaggagaatgtaaaaggtagtaacaaaatgacttataaaaattttagagtattagaatatgc
attgcatagtataagacagatacaaggttatgagttttttataatattaaagatatattaatggctgaagaagtaaatgaaatgt
atgaatggataagagagtatttaatcaaaaatgaaggagaagctcctgcatatcgtgttgagaagatacagaagcttctaga
tgatactgagtatactcttatatcaaggaaaaaaatatttacgtatttaagaaaaaatatactctgaataataacattatagcataa
agagggcttaattgctctctttttaatttcttttaaagcttcatttgggtgtatgtttaatagattacagtaaattcgcctgaaagccca
cggtttcaatcgtgggatgaaaggccgtttcttttaatcttcttgttgcagtttcagtttaaaactgatactataaatatatgggacaag
attatagaagaacacaaacaacagtatctttaataaactatcattttgttttctgtccaaggtacagacgtaaagttctagttgga
gaagttgaaataaaatttaaacagcttctcaatgagatttgtaaagacattgaaatagaaatttggcaatagaatgtgataaa
gaccactgccatctttttgtcaatgcacttcctcatttaagtccagcagacataatggcaaaagtgaaaggagtgacttctcgat
tattaaggcaggaatttaaacatctgcgacatttgccaagtctttggacaagaagctattttgtatctaccgcaggaaatgtatc
aagtgaaactataaaacgatatg

FIG. 24A gcaaactattaactggcgaactacttactctagcttcccggcaacaattaatagactggatggaggcggataaagttgca
ggaccacttctgcgctcggcccttccggctggctggtttattgctgataaatctggagccggtgagcgtgggtctcgcggtat
cattgcagcactggggccagatggtaagccctcccgtatcgtagttatctacacgacggggagtcaggcaactatggat
gaacgaaatagacagatcgctgagataggtgcctcactgattaagcattggtaactgtcagaccaagtttactcatatata
ctttagattgatttacgcgccctgtagcggcgcattaagcgcggcgggtgtggtggttacgcgcagcgtgaccgctacactt
gccagcgccctagcgcccgctcctttcgctttcttccttccttctcgccacgttcgccggctttccccgtcaagctctaaatc
gggggctcccttagggttccgatttagtgctttacggcacctcgaccccaaaaaacttgatttgggtgatggttcacgtagt
gggccatcgccctgatagacggttttcgccctttgacgttggagtccacgttctttaatagtggactcttgttccaaacttgaa
caacactcaaccctatctcgggctattctttgatttataagggatttgccgatttcggcctattggttaaaaaatgagctgattt
aacaaaatttaacgcgaattttaacaaaatattaacgtttacaatttaaaaggatctaggtgaagatccttttgataatctc
atgaccaaaatcccttaacgtgagttttcgttccactgagcgtcagacccgtagaaaagatcaaaggatcttcttgagat
cctttttttctgcgcgtaatctgctgcttgcaaacaaaaaaaccaccgctaccagcggtggtttgtttgccggatcaagagct
accaactcttttccgaaggtaactggcttcagcagagcgcagataccaaatactgtccttctagtgtagccgtagttaggc
caccacttcaagaactctgtagcaccgcctacatacctcgctctgctaatcctgttaccagtcaggcatttgagaagcaca
cggtcacactgcttccggtagtcaataaaccggtaaaccagcaatagacataagcggctatttaacgaccctgccctga
accgacgaccgggtcgaatttgcttcgaatttctgccattcatccgcttattatcacttattcaggcgtagcaccaggcgttta
agggcaccaataactgccttaaaaaaattacgccccgccctgccactcatcgcagtactgttgtaattcattaagcattctg
ccgacatggaagccatcacagacggcatgatgaacctgaatcgccagcggcatcagcaccttgtcgccttgcgtataat
atttgcccatggtgaaaacgggggcgaagaagttgtccatattggccacgtttaaatcaaaactggtgaaactcacccag
ggattggctgagacgaaaaacatattctcaataaaccctttagggaaataggccaggttttcaccgtaacacgccacatc
ttgcgaatatatgtgtagaaactgccggaaatcgtcgtggtattcactccagagcgatgaaaacgtttcagtttgctcatgg
aaaacggtgtaacaagggtgaacactatcccatatcaccagctcaccgtctttcattgccatacggaattccggatgagc
attcatcaggcgggcaagaatgtgaataaaggccggataaaacttgtgcttatttttctttacggtctttaaaaaggccgtaa
tatccagctgaacggtctggttataggtacattgagcaactgactgaaatgcctcaaaatgttctttacgatgccattgggat
atatcaacggtggtatatccagtgattttttctccattttagcttccttagctcctgaaaatctcgataactcaaaaaatacgcc
cggtagtgatcttatttcattatggtgaaagttggaacctcttacgtgccgatcaacgtctcatttcgccaaaagttggccca
gggcttcccggtatcaacagggacaccaggatttatttattctgcgaagtgatcttccgtcacaggtatttattcggcgcaaa
gtgcgtcggtgatgctgccaacttactgatttagtgtatgatggtgttttgaggtgctccagtggcttctgtttctatcagctgtc
cctcctgttcagctactgacggggtggtgcgtaacggcaaaagcaccgccggacatcagcgctagcggagtgtatactg
gcttactatgttggcactgatgagggtgtcagtgaagtgcttcatgtggcaggagaaaaaaggctgcaccggtgcgtcag
cagaatatgtgatacaggatatattccgcttcctcgctcactgactcgctacgctcggtcgttcgactgcggcgagcggaa
atggcttacgaacggggcggagattcctggaagatgccaggaagatacttaacagggaagtgagagggccgcggc
aaagccgttttccataggctccgccccctgacaagcatcacgaaatctgacgctcaaatcagtggtggcgaaacccg
acaggactataaagataccaggcgtttccccctggcggctccctcgtgcgctctcctgttcctgcctttcggtttaccggtgtc
attccgctgttatggccgcgtttgtctcattccacgcctgacactcagttccgggtaggcagttcgctccaagctggactgtat
gcacgaaccccccgttcagtccgaccgctgcgccttatccggtaactatcgtcttgagtccaacccggaaagacatgca
aaagcacc

FIG. 24B actggcagcagccactggtaattgatttagaggagttagtcttgaagtcatgcgccggttaaggctaaactgaaaggaca
agttttggtgactgcgctcctccaagccagttacctcggttcaaagagttggtagctcagagaaccttcgaaaaaccgccc
tgcaaggcggttttttcgttttcagagcaagagattacgcgcagaccaaaacgatctcaagaagatcatcttattaatcaga
taaaatatttgctcatgagcccgaagtggcgagcccgatcttccccatcggtgatgtcggcgatataggcgccagcaacc
gcacctgtggcgccggtgatgccggccacgatgcgtccggcgtagaggatctgctcatgtttgacagcttatcatcgatgc
ataatgtgcctgtcaaatggacgaagcagggattctgcaaaccctatgctactccgtcaagccgtcaattgtctgattcgtt
accaattatgacaacttgacggctacatcattcacttttcttcacaaccggcacggaactcgctcgggctggccccggtgc
attttttaaatacccgcgagaaatagagttgatcgtcaaaaccaacattgcgaccgacggtggcgataggcatccgggtg
gtgctcaaaagcagcttcgcctggctgatacgttggtcctcgcgccagcttaagacgctaatccctaactgctggcggaa
aagatgtgacagacgcgacggcgacaagcaaacatgctgtgcgacgctggcgatatcaaaattgctgtctgccaggtg
atcgctgatgtactgacaagcctcgcgtacccgattatccatcggtggatggagcgactcgttaatcgcttccatgcgccg
cagtaacaattgctcaagcagatttatcgccagcagctccgaatagcgcccttccccttgccggcgttaatgatttgccca
aacaggtcgctgaaatgcggctggtgcgcttcatccgggcgaaagaaccccgtattggcaaatattgacggccagttaa
gccattcatgccagtaggcgcgcggacgaaagtaaacccactggtgataccattcgcgagcctccggatgacgaccgt
agtgatgaatctctcctggcgggaacagcaaaatatcacccggtcggcaaacaaattctcgtccctgattttcaccaccc
cctgaccgcgaatggtgagattgagaatataacctttcattcccagcggtcggtcgataaaaaaatcgagataaccgttg
gcctcaatcggcgttaaacccgccaccagatgggcattaaacgagtatcccggcagcaggggatcattttgcgcttcag
ccatacttttcatactcccgccattcagagaagaaaccaattgtccatattgcatcagacattgccgtcactgcgtcttttact
ggctcttctcgctaaccaaaccggtaaccccgcttattaaaagcattctgtaacaaagcgggaccaaagccatgacaaa
aacgcgtaacaaaagtgtctataatcacggcagaaaagtccacattgattatttgcacggcgtcacactttgctatgccat
agcattttatccataagattagcggatcctacctgacgcttttatcgcaactctctactgttctccatacccgttttttgggcta
gcgaattcgagctcggtacccggggaggaataataaatggccgtactccgcaatattgatgagcaactgaccgaggaa
tttaagaaactgccgatcgactattgggactttgagggtgaggacacgaaagaactgacgcacggcctgcacaactatc
cggcggtgatggtttatccgatctaccgtaacattatcgacatcgtgaagcgtcacggtgaggtcgaaacctttctggaccc
gtttatgggtagcggtacgggcctggtggaaggcaagctggcgggtttcaacaaagtgtacggtacggatctgaatcctc
tggcagtgctgctgagcaaggttaagaccaccgtcttgaaagaggatagcgtggatattcaggacaagctgctgcgcg
agaatattgagcaggcgttcgtgtccagcaaacagctgctggataacattgacaattacattgcggagaagggcctgga
cgtcagcgccaaagacggctggggctctgatgcgcatgtcattttgcgcgagtatctggatacctacaacagcggtctga
aaatcccagactttaagaatatgggttattggttcaaaccgcgcgttattctggagctgcaactgattaaggatatcattctgc
agatcgagaatgaggacttccgtaacttctttctggtctgcttctctgaaactgcccgctacgtgagcaacacccgtaatggt
gagttcaagctgttccgtatcaagaaagaaaaagtggcagatttcaatccggacgttaagatcgagttttacaaatatctg
gatcgtaacatcgaaaagattaaagactttgacaaacgttgtaacaacgattgcgaagttagcgttgctttgaagatacc
cgcattctggactcggttccggacaatagcatcgatctgatgattaccagcccaccgtacggcgatagcaaaactacggt
ggcgtacggtcaatttagccgtccgtctttgtggtggttggatctggaattgatggacatcgaagagctgaatcaagttgac
aacaatctgctgggtggtaagaaggtggacaaagacttcgagtgtgaactgagctcccgtaccttggagaaggcgatta
aagaaatcaaagaaaaggacctggaccgcgcacgtgacgtttatagcttctacgaggatttggataaggctatggagtc
cattacgaaaaagatgc

FIG. 24C gtcataacagctaccagttctgggttgtcggtaaccgtaccgttaaagaagtcaaactgctgaccaacgaaat
cattagcgaactgggcgagaaatatggtttggttgaggtttacgatatcccgcgtaacatcccgaataaggtcat
gccgagccgtaattccccgaccaatgaaaccggcaagacggtcagcaccatgacgaacgagcacatcgtc
gtgctgcgcaaagatcgttgaggctgttttggcggatgagagaagattttcagcctgatacagattaaatcaga
acgcagaagcggtctgataaaacagaatttgcctggcggcagtagcgcggtggtcccacctgaccccatgc
cgaactcagaagtgaaacgccgtagcgccgatggtagtgtggggtctccccatgcgagagtagggaactgc
caggcatcaaataaaacgaaaggctcagtcgaaagactgggcctttcgttttatctgttgtttgtcggtgaacgct
ctcctgagtaggacaaatccgccgggagcggatttgaacgttgcgaagcaacggcccggagggtggcggg
caggacgcccgccataaactgccaggcatcaaattaagcagaaggccatcctgacggatggcctttttgcgtt
tctacaaactcttttgtttattttctaaatacattcaaatatgtatccgctcatgagacaataaccctgataaatgctt
caataatattgaaaaaggaagagtatgagtattcaacatttccgtgtcgcccttattcctttttgcggcattttgcc
ttcctgtttttgctcacccagaaacgctggtgaaagtaaaagatgctgaagatcagttgggtgca

FIG. 28A aaactcctttttgataatctcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgttt
gccggatcaagagctaccaactcttttccgaaggtaactggcttcagcagagcgcagataccaaatactgttcttctagtgt
agccgtagttaggccaccacttcaagaactctgtagcaccgcctacatacctcgctctgctaatcctgttaccagtggctgct
gccagtggcgataagtcgtgtcttaccgggttggactcaagacgatagttaccggataaggcgcagcggtcgggctgaac
gggggttcgtgcacacagcccagcttggagcgaacgacctacaccgaactgagatacctacagcgtgagctatgaga
aagcgccacgcttcccgaagggagaaaggcggacaggtatccggtaagcggcagggtcggaacaggagagcgcac
gagggagcttccaggggggaaacgcctggtatctttatagtcctgtcggtttcgccacctctgacttgagcgtcgattttgtga
tgctcgtcaggggggcggagcctatgaaaaacgccagcaacgcggccttttttacggttcctggccttttgctggccttttgct
cacatgttctttcctgcgttatccctgattctgtggataaccgtattaccgcctttgagtgagctgataccgctcgccgcagccg
aacgaccgagcgcagcgagtcagtgagcgaggaagcggaagagcgcccaatacgcagggcccctgcttcggggtc
attatagcgattttttcggtatatccatcctttttcgcacgatatacaggattttgccaaagggttcgtgtagactttccttggtgtatc
caacggcgtcagccgggcaggataggtgaagtagcccacccgcgagcgggtgttccttcttcactgtcccttattcgcac
ctggcggtgctcaacgggaatcctgctctgcgaggctggccggctaccgccggcgtaacagatgagggcaagcggatg
gctgatgaaaccaagccaaccaggaagggcagcccacctatcaaggtgtactgccttccagacgaacgaagagcgat
tgaggaaaaggcggcggcggccggcatgagcctgtcggcctacctgctggccgtcggccagggctacaaaatcacgg
gcgtcgtggactatgagcacgtccgcgagctggcccgcatcaatggcgacctgggccgcctgggcggcctgctgaaact
ctggctcaccgacgacccgcgcacggcgcggttcggtgatgccacgatcctcgccctgctggcgaagatcgaagagaa
gcaggacgagcttggcaaggtcatgatgggcgtggtccgcccgagggcagagccatgacttttttagccgctaaaacgg
ccggggggtgcgcgtgattgccaagcacgtccccatgcgctccatcaagaagagcgacttcgcggagctggtgaagtac
atcaccgacgagcaaggcaagaccgatcgggcccctgcaggataaaaaaattgtagataaatttataaaatagtttat
ctacaatttttatcaggaaacagctatgaccgcggccgccagctatagcagctactctttggtattattatcaaaatgcttaat
aaaatagatttacaaaagtgtctatacatgatagtatatatttaatgatatatagggggtgtatagattgtttacaaggaaacc
agaaactaaaaataagtctttagttcttagaatgacagaaacgcaaaagaagatacttgagattatggctaatgagagag
gtttatcacaatcagaattaattatgatattattggagaatgaattcaagaagcctgtattagaaataaagcagcaagattaa
acttgccgccttggatagcggagcaacggttttatccaagcggtaaacaatattctaaacagcggtgtttaaaattatcaact
agaagtgtattaatggctgcggaaagaaatattaaaccagtactatcacaattcgcaccttaaaagtaaggttttaatgttta
attttggcacggaacttgctctttcttgatatattacaaacaagtcggctaaaattgaaattttaacgttatcctgaaaggggg
caaaatttggatgagaagatacttaaagatgtaagggttctaaaaatcatttacaatcggttcataataataatcagtataat
aagttgattgtaggttattacaatcaatacatagaagattctagacctgtaaagaagaaaaagactattttggattatactaga
tttacttatgaagattatttgttgaaaaattagaacataaaagagataagttagctaattgtaataagaaatgggaagttgaa
gtttatgaaaaacttaaagtaaaagattatgtgtcactttattatgtaatgataagttttgtagtaattgtaagaaagtaaagca
agcttcaaggatggcgaaaaatatgcctttgcttgaacagtataaagataaattatatcaaatggttttaactacaccaaatat
tgtagatcatacaggggaagaattgaaaaaagagattaaaaagcaatttaaagcattaacttatttaacagaatatttaaa
aggtaaaaaacaagtaaagggtttagattttgatattggatacttaggtgcaataaggtcgttggaggtaacttatagcggtg
actattatcatccgcatttgcatttgatattagtattggataatcaaaatgaatttataacagataaaaaaaatataaataactat
tcttatgattattataaaaaagaccaactagattattttcagattttgaaatattgttacagaaatcttggtatcttttatataatgg
ggaaagattgactaaggaaaatatagataaactggaaaaaggttatagttgcatgatggataaggcaaaagaagatgat
ttttagaagttttaaatacatggtgaagaatgatccggcagaggagaatgtaaaaggtagtaacaaaatgacttataaaa
at

FIG. 28B tttagagtattagaatatgcattgcatagtataagacagatacaaggttatggagtttttataatattaaagatatattaatgg
ctgaagaagtaaatgaaatgtatgaatggataagagagtatttaatcaaaaatgaaggagaagctcctgcatatcgtgtt
gagaagatacagaagcttctagatgatactgagtatactcttatatcaaggaaaaaaatatttacgtatttaagaaaaatat
actctgaataataacattatagcataaagagggcttaattgctctcttttttaatttcttttaaagcttcatttgggtgtatgtttaata
gattacagtaaattcgcctgaaagcccacggtttcaatcgtgggatgaaaggcgtttcttttaatcttcttgttgcagtttcagttt
aaaactgatactataaatatatgggacaagattatagaagaacacaaacaacagtatctttaataaactatcattttgttttct
gtccaaggtacagacgtaaagttctagttggagaagttgaaataaaatttaaacagcttctcaatgagatttgtaaagaca
ttgaaatagaaattttggcaatagaatgtgataaagaccactgccatcttttgtcaatgcacttcctcatttaagtccagcag
acataatggcaaaagtgaaaggagtgacttctcgattattaaggcaggaatttaaacatctgcgacatttgccaagtctttg
gacaagaagctattttgtatctaccgcaggaaatgtatcaagtgaaactataaaacgatatgttgaagaacaaaaaaca
aggggtgaaacaatgcagataacagtaaaatttaatattattttgacaaaagaacaagtacaactaatagaatctatat
caaaagaatatatccatactgttaatagccttgtttcatctacgctccaatcagaagaaagagtaaagctatcatctaaaga
tgtttttgcaaatatgccaagtgcagtgaaaaatcaatctattagagatgccaaaagtatctgtactaagtacaagaaagct
atcaaggctaattccaaactgcctactgataaacaaaaagtaatcaatgtagctacccttaaaaaacctgtctgtatatgg
aataatcaaaattattcacttaaagacggtattcttagttttcccgttattatagatgggaaatcgcagcgtattcaaactaga
actatcatgacagactatcagctaaaacaactagaaggtcatttgggagcattgcgtataactaagaaaagcaataaat
atatcgctcaaataagtgttgaaaaagtatctcatatagttaaaggtgatgttgtaatgggtgttgacttaggcctaaaagttc
ctgctgtagctgtaaccgattcaggaaaaacgttttttttttggaaacggtaggcaaaataaatacgtcaaacgtaaatataa
agcgaaacgtaaaaaacttggaaaagccaagaagcttaaagtcattaaaaagcttgatgataaagaacaacgttgga
tgacagaccaagaccacaaagtaagtagagaaataattaattttgcagtaaataataatgttctgatattcggcttgaaa
aattaacgaatatcagaaacacggcaagaacaagccgtaaaaacgaaaaaaatctacatacatggtcattctatcgtc
tagctcaattcatagagtataaggcactattgaagggggataaaggttgaatatgttgatcctaaatacacttctcaaatatgc
cctgaatgtaagaaactaaataaagcaagagatagaaaatataaatgctcctgtggttttaaaacacatagggatagag
taggtgctataaatataattaatgcacctgtagtagatggtaaaagtctactagcctagggtactatatgtactgctctagga
ggggtaatggcatacccctaagcttgaggtcatactccgatagcagaaatgtacttcggtttaatcactcaagaatcccact
gctttagctgtgggagtgtcaaatgaagcatgatggtcatttatctgtaactagtgaaggaagattgtattatgctggtagtca
aaaaattagttttaatagtggtataccttaaatacaggagatggagttgttgtttggaatgaaattcaagatttaatttcaactt
ctgatgtttattccgatgttactttaacggatgaaattgcaaattcaaattatccaaatataaattttgaatatgatggaaaaga
accgattagcaatccgttttgggattatgaaaacttacatacaggtactagaagtattgatataggtgcaaatccagatttat
cagctctagtagggaaaacatatgaagatgttattagtgaaaatccaagtcaacaaaatcctatggtgcctccgatacca
tttcctgattcatggtttggcaaatggaaagatatagttaacgatagtggaacatggcaaggggaaggcatagatggaag
tactggaactgcaatagatagtcctccattagatattcctggaacgtggcaaggcaaatggtcttggacagcagacggtc
aattagttttcgatggttcttttttcaggttctgacggaacaacatggcaaggaacatatacgcatacaggaataggtgttcag
aatcctgtactaaatccaccactaaccccggatttaacaggaataacaggttggttatcatctataagttcatggttaactag
tttgtttgcgtttccaactgattttagtttgaatttagacccgttgaaaaatctacctatagcaacaaaatttcctttctgtttgccatt
tgatttaaaaaatagcattgaatcattgcaatctcctgtcgttgtcccagttttacgactacttggaatttaccccttttatcaagg
agatatagagattaatttagcagctatggaacgatttgcacaaataacacgttgggaacgttaattgtatttaatcttggttt
aatacttgttacaaggaaggtgttatcatgatatggcaagcactagcatcttttattaatctacttattaaagcattaggaacg
gttttaggggcaattatcggattattaccttcaagtccttttcaaactatttcaaattcagcagtaacagaatatttaggcatgtt
gaattggt

FIG. 28C ttatatccgtagatgccatgataactatattaacttactggactactgcaattataagttactatgtaatatcaactgcgatgag
atggggaaaaacaattgaataggggataatatgataagtttttatagtggtactccaggaagtggaaaaagtcttaatat
agctagatacatatggattaaagttcgacatgctaaacaaaatataatacttgttaatatgacagttaatagagagtatctta
ttacatcaaaactgaagcaacttgttaataaaattagattgaaattaaaacttaaacctattaatactaagttaaaagactat
ggcaaaatctattctataagactcgatcagctgaacacaaaatttctagaagattatgctatgaaatttcacatggtgggca
ttgaaggacaatcaaaaataataatagatgaggcacaactgatttggtccccaacggtgatgaaaaataaaaagcag
gtagaccctaattatcgtgaacgctggatagagtttatgacactccatagacacttaggttttgacatgataattataagtca
atttgataggttgatagatgcacaaatacgttgtctatttgaatacaatcatattcatcggaaagtcaataacttttgtataggtt
attggctaaacctattcaaaataaaagtatttgcagaagtgcaatattggtatggagttagagcaaggattggagttaatttc
ttcgctattactccatggacttcaaaacactataggaaaatttataacgcacataaaaggttctcagatttaaagggaaag
aaaaaagtagcgtagcgttggacttttttcttcccttttaaatcaagaaatataatgttcgtaaaaaaatgaatcctgatgtcat
ggatcacgtggcagcagtcaatatttagatctaaaaattgaataatatccaaacaaataggaggtgtgtaaaataaatgtt
cgtgattatatggttaatgttaagtgctgaggtcaatctatgaaatgcgattaagggccggccgaagcaaacttaagagtgt
gttgatagtgcagtatcttaaaattttgtataataggaattgaagttaaattagatgctaaaaatttgtaattaagaaggagtg
attacatgaacaaaaatataaaatattctcaaaacttttttaacgagtgaaaaagtactcaaccaaataataaaacaattg
aatttaaaagaaaccgataccgtttacgaaattggaacaggtaaagggcatttaacgacgaaactggctaaaataagt
aaacaggtaacgtctattgaattagacagtcatctattcaacttatcgtcagaaaaattaaaactgaatactcgtgtcacttt
aattcaccaagatattctacagtttcaattccctaacaaacagaggtataaaattgttgggagtattccttaccatttaagcac
acaaattattaaaaaagtggttttttgaaagccatgcgtctgacatctatctgattgttgaagaaggattctacaagcgtaccttt
ggatattcaccgaacactagggttgctcttgcacactcaagtctcgattcagcaattgcttaagctgccagcggaatgctttc
atcctaaaccaaaagtaaacagtgtcttaataaaaacttacccgccataccacagatgttccagataaatattggaagctat
atacgtactttgtttcaaaatgggtcaatcgagaatatcgtcaactgtttactaaaaatcagtttcatcaagcaatgaaacac
gccaaagtaaacaatttaagtaccgttacttatgagcaagtattgtctatttttaatagttatctattatttaacgggaggaaat
aattctatgagtcgcttttgtaaatttggaaagttacacgttactaaagggaatgtgttt

FIG. 31A aaactcctttttgataatctcatgaccaaaatcccttaacgtgagttttcgttccactgagcgtcagacccccgtagaaaagatca
aaggatcttcttgagatcctttttttctgcgcgtaatctgctgcttgcaaacaaaaaaaccaccgctaccagcggtggtttgtttgc
cggatcaagagctaccaactcttttccgaaggtaactggcttcagcagagcgcagataccaaatactgttcttctagtgtagc
cgtagttaggccaccacttcaagaactctgtagcaccgcctacatacctcgctctgctaatcctgttaccagtggctgctgcca
gtggcgataagtcgtgtcttaccgggttggactcaagacgatagttaccggataaggcgcagcggtcgggctgaacgggg
ggttcgtgcacacagcccagcttggagcgaacgacctacaccgaactgagatacctacagcgtgagctatgagaaagcg
ccacgcttcccgaagggagaaaggcggacaggtatccggtaagcggcagggtcggaacaggagagcgcacgaggga
gcttccaggggaaacgcctggtatctttatagtcctgtcgggtttcgccacctctgacttgagcgtcgatttttgtgatgctcgtca
ggggggcggagcctatggaaaaacgccagcaacgcggccttttacggttcctggccttttgctggccttttgctcacatgttctt
tcctgcgttatcccctgattctgtggataaccgtattaccgcctttgagtgagctgataccgctcgccgcagccgaacgaccga
gcgcagcgagtcagtgagcgaggaagcggaagagcgcccaatacgcagggcccctgcttcggggtcattatagcgatt
ttttcggtatatccatccttttcgcacgatatacaggatttgccaaagggtcgtgtagactttccttggtgtatccaacggcgtca
gccgggcaggataggtgaagtaggcccaccgcgagcgggtgttccttcttcactgtcccttattcgcacctggcggtgctca
acgggaatcctgctctgcgaggctggccggctaccgccggcgtaacagatgagggcaagcggatggctgatgaaacca
agccaaccaggaagggcagcccacctatcaaggtgtactgccttccagacgaacgaagagcgattgaggaaaaggcg
gcggcggccggcatgagcctgtcggcctacctgctggccgtcggccagggctacaaaatcacgggcgtcgtggactatga
gcacgtccgcgagctggcccgcatcaatggcgacctgggccgcctgggcggcctgctgaaactctggctcaccgacgac
ccgcgcacggcgcggttcggtgatgccacgatcctcgccctgctggcgaagatcgaagagaagcaggacgagcttggca
aggtcatgatgggcgtggtccgcccgagggcagagccatgactttttagccgctaaaacggccggggggtgcgcgtgatt
gccaagcacgtccccatgcgctccatcaagaagagcgacttcgcggagctggtgaagtacatcaccgacgagcaaggc
aagaccgatcgggcccctgcaggataaaaaattgtagataaattttataaaatagttttatctacaatttttttatcaggaaac
agctatgaccgcggccgccagctatagcagctactctttggtattattatcaaaatgcttaataaaatagatttacaaaagtgtct
atacatgatagtatatatttaatgatatataggggggtgtatagattgtttacaaggaaaccagaaactaaaaataagtctttagt
tcttagaatgacagaaacgcaaaagaagatacttgagattatggctaatgagagaggtttatcacaatcagaattaattatga
tattattggagaatgaattcaagaagcctgtattagaaataaagcagcaagattaaacttgccgccttggatagcggagcaa
cggttttatccaagcggtaaacaatattctaaacagcggtgtttaaaattatcaactagaagtgtattaatggctgcggaaaga
aatattaaaccagtactatcacaattcgcaccttaaaagtaaggtttttaatgtttaattttggcacggaacttgatatattacaaa
caagtcggctaaaattgaaattttaacgttatcctgaaaggggggcaaaatttggatgagaagatacttaaagatgtaagggt
ttctaaaaatcatttacaatcggttcataataataatcagtataataagttgattgtaggttattacaatcaatacatagaagattct
agacctgtaaagaagaaaaagactattttggattatactagatttacttatgaagattattttgttgaaaaattagaacataaaag
agataagttagctaattgtaataagaaatgggaagttgaagtttatgaaaaacttaaagtaaaagattatgtgtcactttattat
gtaatgataagttttgtagtaattgtaagaaagtaaagcaagcttcaaggatggcgaaaaatatgcctttgcttgaacagtata
aagataaattatatcaaatggttttaactacaccaaatattgtagatcatacaggggaagaattgaaaaaagagattaaaaa
gcaatttaaagcattaacttatttaacagaatatttaaaaggtaaaaaacaagtaaagggtttagattttgatattggatacttag
gtgcaataaggtcgttggaggtaacttatagcggtgactattatcatccgcatttgcatttgatattagtattggataatcaaatg
aatttataacagataaaaaaatataaataactattcttatgattattataaaaaaagaccaactagattattttcagattttgaaa
tattgttacagaaatcttggtatcttttatataatggggaaagattgactaaggaaaatatagataaactggaaaaaggttatag
ttgcatgatggataaggcaaagaagatgattttttagaagttttaaatacatggtgaagaatgatccggcagaggagaatg
taaaaggtagtaacaaaatgacttataaaaattttagagtattagaatatgcattgcatagtataagacagatacaaggttatg
gagtttttataatattaaagatatattaatggctgaagaagtaaatgaaatgtatgaatggataagagagtatttaatcaaaaat
gaaggagaagctcctgcatatcgtgttgagaagatacagaagcttctagatgatactgagtatactcttatatcaaggaaaaa
aatatttacgtatttaagaaaaatatactctgaataataacattatagcataagagggcttaattgctctctttttttaatttcttttaaa
gcttcatttgggtgtatgtttaatagattacagtaaattcgcctgaaagcccacggtttc

FIG. 31B aatcgtgggatgaaaggcgtttcttttaatcttcttgttgcagtttcagtttaaactgatactataaatattagcgttggacttttttcttcccttt
aaatcaagaaatataatgttcgtaaaaaaatgaatcctgatgtcatggatcacgtggcagcagtcaatatttagatctaaaaattga
ataatatccaaacaaataggaggtgtgtaaaataaatgttcgtgattatatggttaatgttaagtgctgaggtcaatctatgaaatgcg
attaagggccggccgaagcaaacttaagagtgtgttgatagtgcagtatcttaaaattttgtataataggaattgaagttaaattagat
gctaaaaatttgtaattaagaaggagtgattacatgaacaaaaatataaaatattctcaaaacttttttaacgagtgaaaaagtactc
aaccaaataataaaacaattgaatttaaaagaaaccgataccgtttacgaaattggaacaggtaaagggcatttaacgacgaa
actggctaaaataagtaaacaggtaacgtctattgaattagacagtcatctattcaacttatcgtcagaaaaattaaaactgaatact
cgtgtcactttaattcaccaagatattctacagtttcaattccctaacaaacagaggtataaaattgttgggagtattccttaccatttaa
gcacacaaattattaaaaaagtggttttttgaaagccatgcgtctgacatctatctgattgttgaagaaggattctacaagcgtaccttg
gatattcaccgaacactagggttgctcttgcacactcaagtctcgattcagcaattgcttaagctgccagcggaatgctttcatcctaa
accaaaagtaaacagtgtcttaataaaacttacccgccataccacagatgttccagataaatattggaagctatatacgtactttgttt
caaaatgggtcaatcgagaatatcgtcaactgtttactaaaaatcagtttcatcaagcaatgaaacacgccaaagtaaacaattta
agtaccgttacttatgagcaagtattgtctattttttaatagttatctattatttaacgggaggaaataattctatgagtcgcttttgtaaatttg
gaaagttacacgttactaaagggaatgtgttt

FIG. 33A cctgcaggataaaaaaattgtagataaatttttataaaatagtttatctacaatttttttatcaggaaacagctatgaccgcggccgct
gtatccatatgaccatgattacgaattcgagctcggtacccggggatcctctagagtcgacgtcacgcgtccatggagatctcga
ggcctgcagacatgcaagcttggcactggccgtcgttttacaacgtcgtgactgggaaaaccctggcgttacccaacttaatcgc
cttgcagcacatcccccttttcgccagctggcgtaatagcgaagaggcccgcaccgatcgcccttcccaacagttgcgcagcctg
aatggcgaatggcgctagcataaaaataagaagcctgcatttgcaggcttcttattttttatggcgcgccgttctgaatccttagctaa
tggttcaacaggtaactatgacgaagatagcaccctggataagtctgtaatggattctaaggcatttaatgaagacgtgtatataa
aatgtgctaatgaaaagaaaatgcgttaaaagagcctaaaatgagttcaaatggttttgaaattgattggtagtttaatttaatata
ttttttctattggctatctcgatacctatagaatcttctgttcacttttgttttgaaatataaaaggggcttttttagcccctttttttaaaactc
cggaggagttcttcattcttgatactatacgtaactatttcgatttgacttcattgtcaattaagctagtaaaatcaatggttaaaaaa
caaaaaacttgcatttttctacctagtaatttataattttaagtgtcgagtttaaaagtataatttaccaggaaaggagcaagtttttaa
taaggaaaaattttttccttttaaaattctatttcgttatatgactaattataatcaaaaaaatgaaaataaacaagaggtaaaaactg
ctttagagaaatgtactgataaaaaaagaaaaaatcctagatttacgtcatacatagcacctttaactactaagaaaaatattgaa
aggacttccacttgtggagattatttgtttatgttgagtgatgcagacttagaacatttaaattacataaaggtaatttttgcggtaata
gattttgtccaatgtgtagttggcgacttgcttgtaaggatagtttagaaatatctattcttatggagcatttaagaaaagaagaaaat
aaagagtttatattttaactcttacaactccaaatgtaaaaagttatgatcttaattattctattaaacaatataataaatcttttaaaaa
attaatggagcgtaaggaagttaaggatataactaaaggttatataagaaaattagaagtaacttaccaaaaggaaaaataca
taacaaaggatttatggaaaataaaaaaagattattatcaaaaaaaaggacttgaaattggtgatttagaacctaatttgatactt
ataatcctcattttcatgtagttattgcagttaataaaagttatttacagataaaaattattatataaatcgagaaagatggttggaatt
atggaagtttgctactaaggatgattctataactcaagttgatgttagaaaagcaaaaattaatgattataaagaggtttacgaactt
gcgaaatattcagctaaagacactgattatttaatatcgaggccagtatttgaaattttttataaagcattaaaaggcaagcaggta
ttagttttagtggatttttaaagatgcacacaaattgtacaagcaaggaaaacttgatgtttataaaaagaaagatgaaattaaat
atgtctatatagtttattataattggtgcaaaaaacaatatgaaaaaactagaataagggaacttacggaagatgaaaagaag
aattaaatcaagatttaatagatgaaatagaaatagattaaagtgtaactatactttatatatatatgattaaaaaaataaaaaaca
acagcctattaggttgttgtttttttattttcttattaattttttttaattttttagtttttagttctttttttaaaataagtttcagcctcttttttcaatattttta
aagaaggagtatttgcatgaattgcctttttctaacagacttaggaaatattttaacagtatcttcttgcgccggtgatttggaacttc
ataacttactaatttataattattatttctttttttaattgtaacagttgcaaaagaagctgaacctgttccttcaactagtttatcatcttcaat
ataatattcttgacctatatagtataaatatattttattatattttttactttttttctgaatctattatttttataatcataaaaagttttaccaccaa
aagaaggttgtactccttctggtccaacatatttttttactatattatctaaataattttttgggaactggtgttgtaatttgattaatcgaaca
accagttatacttaaaggaattataactataaaaatataggattatctttttaaatttcattattggcctccttttattaaatttatgttac
cataaaaaggacataacgggaatatgtagaatattttaatgtagacaaaattttacataaatataaagaaaggaagtgtttgtta
aattttatagcaaactatcaaaaattaggggggataaaaatttatgaaaaaaaggtttttcgatgttattttttatgtttaacttttaatagtttg
tggtttatttacaaattcggccggccagtgggcaagttgaaaaattcacaaaaatgtggtataatatctttgttcattagagcgataa
acttgaatttgagagggaacttagatggtatttgaaaaaattgataaaaatagttggaacagaaaagagtatttgaccactactttt
gcaagtgtaccttgtacctacagcatgaccgttaaagtggatatcacacaaataaaggaaaagggaatgaaactatatcctgc
aatgctttattatattgcaatgattgtaaaccgccattcagagtttaggacggcaatcaatcaagatggtgaattggggatatatgat
gagatgataccaagctatacaatatttcacaatgatactgaaacattttccagcctttggactgagtgtaagtctgactttaaatcattt
ttagcagattatgaaagtgatacgcaacggtatggaaacaatcatagaatggaaggaaagccaaatgctccggaaaacatttt
taatgtatctatgataccgtggtcaaccttcgatggctttaatctgaatttgcagaaaggatatgattatttgattcctattttttactatggg
gaaatattataaagaagataacaaaattatacttcctttggcaattcaagttcatcacgcagtatgtgacggatttcacatttgccgtt
ttgtaaacgaattgcaggaattgataaatagttaacttcaggtttgtctgtaactaaaaacaagtatttaagcaaaaacatcgtaga
aatacggtgtttttttgttacccctaagtttaaaactccttttttgataatctcatgaccaaaatcccttaacgtgagttttcgttccactgagcgt
cagaccccgtagaaaagatcaaaggatcttcttgagatccttttttctgcgcgtaatctgctgcttgcaaacaaaaaaaaccaccg
ctaccagcggtggtttgtttgccggatcaagagctaccaactcttttttccgaaggtaactggcttcagcagagcgcagataccaaa
tactgttcttctagtgtagccgtagttaggccaccacttcaagaactctgtagcaccgcctacatacctcgctctgctaatcctgttac
cagtggctgctgccagtggcgataagtcgtgtcttaccgggttggactcaagacgatagttaccggataaggcgcagcggtcgg
gctgaacggggggttcgtgcacacagcccagcttggagcgaacgacctacaccgaactgagatacctacagcgtgagctatg
agaaagcgccacgcttcccgaagggagaaaggcggacaggtatccgg

FIG. 33B taagcggcagggtcggaacaggagagcgcacgagggagcttccaggggggaaacgcctggtatctttatagtcctgtcgggtttcg
ccacctctgacttgagcgtcgattttgtgatgctcgtcagggggcggagcctatggaaaaacgccagcaacgcggccttttacgg
ttcctggccttttgctggccttttgctcacatgttctttcctgcgttatccctgattctgtggataaccgtattaccgcctttgagtgagctgata
ccgctcgccgcagccgaacgaccgagcgcagcgagtcagtgagcgaggaagcggaagagcgcccaatacgcagggccccc
tgcttcggggtcattatagcgattttttcggtatatccatccttttcgcacgatatacaggatttgccaaagggttcgtgtagactttccttg
gtgtatccaacggcgtcagccgggcaggataggtgaagtaggcccacccgcgagcgggtgttccttcttcactgtcccttattcgca
cctggcggtgctcaacgggaatcctgctctgcgaggctggccggctaccgccggcgtaacagatgagggcaagcggatggctga
tgaaaccaagccaaccaggaagggcagcccacctatcaaggtgtactgccttccagacgaacgaagagcgattgaggaaaag
gcggcggcggccggcatgagcctgtcggcctacctgctggccgtcggccagggctacaaaatcacgggcgtcgtggactatgag
cacgtccgcgagctggcccgcatcaatggcgacctggccgcctgggcggcctgctgaaactctggctcaccgacgacccgcgc
acggcgcggttcggtgatgccacgatcctcgccctgctggcgaagatcgaagagaagcaggacgagcttggcaaggtcatgatg
ggcgtggtccgcccgagggcagagccatgacttttttagccgctaaaacggccgggggggtgcgcgtgattgccaagcacgtcccc
atgcgctccatcaagaagagcgacttcgcggagctggtgaagtacatcaccgacgagcaaggcaagaccgatcgggccc

FIG. 35A

```
   1 ggataaaaaaattgtagataaatttttataaaatagtttttatctacaatttttttatcagg   60
  61 aaacagctatgaccgcggccgctgtatccatatgaccatgattacgaattcgagctcggt  120
 121 acccggggatcctctagagtcgacgtcacgcgtccatggagatctcgaggcctgcagaca  180
 181 tgcaagcttggcactggccgtcgttttacaacgtcgtgactgggaaaaccctggcgttac  240
 241 ccaacttaatcgccttgcagcacatccccctttcgccagctggcgtaatagcgaagaggc  300
 301 ccgcaccgatcgcccttcccaacagttgcgcagcctgaatggcgaatggcgctagcataa  360
 361 aaataagaagcctgcatttgcaggcttcttatttttatggcgcgccgccattattttttt  420
 421 gaacaattgacaattcatttcttattttttattaagtgatagtcaaaaggcataacagtg  480
 481 ctgaatagaaagaaatttacagaaaagaaaattatagaatttagtatgattaattatact  540
 541 catttatgaatgtttaattgaatacaaaaaaaaatacttgttatgtattcaattacgggt  600
 601 taaaatatagacaagttgaaaaatttaataaaaaaataagtcctcagctcttatatatta  660
 661 agctaccaacttagtatataagccaaaacttaaatgtgctaccaacacatcaagccgtta  720
 721 gagaactctatctatagcaatatttcaaatgtaccgacatacaagagaaacattaactat  780
 781 atatattcaatttatgagattatcttaacagatataaatgtaaattgcaataagtaagat  840
 841 ttagaagtttatagcctttgtgtattggaagcagtacgcaaaggcttttttatttgataa  900
 901 aaattagaagtatatttatttttcataattaatttatgaaaatgaaaggggggtgagcaa  960
 961 agtgacagaggaaagcagtatcttatcaaataacaaggtattagcaatatcattattgac 1020
1021 tttagcagtaaacattatgacttttatagtgcttgtagctaagtagtacgaaaggggggag 1080
1081 ctttaaaaagctccttggaatacatagaattcataaattaatttatgaaaagaagggcgt 1140
1141 atatgaaaacttgtaaaaattgcaaagagtttattaaagatactgaaatatgcaaaatac 1200
1201 attcgttgatgattcatgataaaacagtagcaacctattgcagtaaatacaatgagtcaa 1260
1261 gatgtttacataaagggaaagtccaatgtattaattgttcaaagatgaaccgatatggat 1320
1321 ggtgtgccataaaaatgagatgttttacagaggaagaacagaaaaagaacgtacatgca 1380
1381 ttaaatattatgcaaggagctttaaaaaagctcatgtaaagaagagtaaaagaaaaaat 1440
1441 aatttatttattaatttaatattgagagtgccgacacagtatgcactaaaaaatatatct 1500
1501 gtggtgtagtgagccgatacaaaaggatagtcactcgcatttttcataatacatcttatgt 1560
1561 tatgattatgtgtcggtgggacttcacgacgaaaacccacaataaaaaaagagttcgggg 1620
```

FIG. 35B

```
1621 tagggttaagcatagttgaggcaactaaacaatcaagctaggatatgcagtagcagaccg 1680
1681 taaggtcgttgtttaggtgtgttgtaatacatacgctattaagatgtaaaaatacggata 1740
1741 ccaatgaagggaaaagtataatttttggatgtagtttgtttgttcatctatgggcaaact 1800
1801 acgtccaaagccgtttccaaatctgctaaaaagtatatcctttctaaaatcaaagtcaag 1860
1861 tatgaaatcataaataaagtttaattttgaagttattatgatattatgttttctattaa 1920
1921 aataaattaagtatatagaatagtttaataatagtatatacttaatgtgataagtgtctg 1980
1981 acagtgtcacagaaaggatgattgttatggattataagcggccggccagtgggcaagttg 2040
2041 aaaaattcacaaaaatgtggtataatatctttgttcattagagcgataaacttgaatttg 2100
2101 agagggaacttagatggtatttgaaaaaattgataaaaatagttggaacagaaaagagta 2160
2161 ttttgaccactactttgcaagtgtaccttgtacctacagcatgaccgttaaagtggatat 2220
2221 cacacaaataaaggaaaagggaatgaaactatatcctgcaatgctttattatattgcaat 2280
2281 gattgtaaaccgccattcagagtttaggacggcaatcaatcaagatggtgaattgggggat 2340
2341 atatgatgagatgataccaagctatacaatatttcacaatgatactgaaacattttccag 2400
2401 cctttggactgagtgtaagtctgactttaaatcatttttagcagattatgaaagtgatac 2460
2461 gcaacggtatggaaacaatcatagaatggaaggaaagccaaatgctccggaaaacatttt 2520
2521 taatgtatctatgataccgtggtcaaccttcgatggctttaatctgaatttgcagaaagg 2580
2581 atatgattatttgattcctattttactatggggaaatattataaagaagataacaaaat 2640
2641 tatacttcctttggcaattcaagttcatcacgcagtatgtgacggatttcacatttgccg 2700
2701 ttttgtaaacgaattgcaggaattgataaatagttaacttcaggtttgtctgtaactaaa 2760
2761 aacaagtatttaagcaaaaacatcgtagaaatacggtgttttttgttaccctaagtttaa 2820
2821 actcctttttgataatctcatgaccaaaatcccttaacgtgagttttcgttccactgagc 2880
2881 gtcagacccgtagaaaagatcaaaggatcttcttgagatcctttttttctgcgcgtaat 2940
2941 ctgctgcttgcaaacaaaaaaaccaccgctaccagcggtggtttgtttgccggatcaaga 3000
3001 gctaccaactcttttccgaaggtaactggcttcagcagagcgcagataccaaatactgt 3060
3061 ccttctagtgtagccgtagttaggccaccacttcaagaactctgtagcaccgcctacata 3120
3121 cctcgctctgctaatcctgttaccagtggctgctgccagtggcgataagtcgtgtcttac 3180
3181 cgggttggactcaagacgatagttaccggataaggcgcagcggtcgggctgaacggggg 3240
3241 ttcgtgcacacagcccagcttggagcgaacgacctacaccgaactgagatacctacagcg 3300
3301 tgagcattgagaaagcgccacgcttcccgaagggagaaaggcggacaggtatccggtaag 3360
3361 cggcagggtcggaacaggagagcgcacgagggagcttccaggggaaacgcctggtatct 3420
3421 ttatagtcctgtcgggtttcgccacctctgacttgagcgtcgatttttgtgatgctcgtc 3480
3481 agggggggcggagcctatggaaaaacgccagcaacgcggcctttttacggttcctggcctt 3540
3541 ttgctggccttttgctcacatgttctttcctgcgttatcccctgattctgtggataaccg 3600
3601 tattaccgcctttgagtgagctgataccgctcgccgcagccgaacgaccgagcgcagcga 3660
3661 gtcagtgagcgaggaagcggaagagcgcccaatacgcagggccccctgcttcgggtcat 3720
3721 tatagcgattttttcggtatatccatccttttcgcacgatatacaggattttgccaaag 3780
3781 ggttcgtgtagactttccttggtgtatccaacggcgtcagccgggcaggataggtgaagt 3840
3841 aggcccaccgcgagcgggtgttccttcttcactgtcccttattcgcacctggcggtgct 3900
3901 caacgggaatcctgctctgcgaggctggccggctaccgccggcgtaacagatgagggcaa 3960
3961 gcggatggctgatgaaaccaagccaaccaggaagggcagcccacctatcaaggtgtactg 4020
4021 ccttccagacgaacgaagagcgattgaggaaaagcggcggcggccggcatgagcctgtc 4080
4081 ggcctacctgctggccgtcggccagggctacaaaatcacgggcgtcgtggactatgagca 4140
4141 cgtccgcgagctggcccgcatcaatggcgacctgggccgcctgggcggcctgctgaaact 4200
4201 ctggctcaccgacgacccgcgcacggcgcggtcggtgatgccacgatcctcgccctgct 4260
4261 ggcgaagatcgaagagaagcaggacgagcttggcaaggtcatgatgggcgtggtccgccc 4320
4321 gagggcagagccatgacttttttagccgctaaaacggccggggggtgcgcgtgattgcca 4380
4381 agcacgtccccatgcgctccatcaagaagagcgacttcgcggagctggtgaagtacatca 4440
4441 ccgacgagcaaggcaagaccgatcgggccccctgca 4476
```

FIG. 45 Redirect Carbon Flux Away From Acetate

FIG. 50 cctgcaggataaaaaaattgtagataaattttataaaatagttttatctacaattttttttatcaggaaacagctatgaccgcggccgctgtatccatatg
accatgattacgaattcgagctcggtacccggggatcctctagagtcgacgtcacgcgtccatggagatctcgaggcctgcagacatgcaagcttggc
actggccgtcgttttacaacgtcgtgactgggaaaaccctggcgttacccaacttaatcgccttgcagcacatcccccttcgccagctggcgtaatagc
gaagaggcccgcaccgatcgcccttcccaacagttgcgcagcctgaatggcgaatggcgctagcataaaaataagaagcctgcatttgcaggcttctt
attttttatggcgcgccgttctgaatccttagctaatggttcaacaggtaactatgacgaagatagcaccctggataagtctgtaatggattctaaggcat
ttaatgaagacgtgtatataaaatgtgctaatgaaaaagaaaatgcgttaaaagagcctaaaatgagttcaaatggttttgaaattgattggtagttta
atttaatatattttttctattggctatctcgatacctatagaatcttctgttcacttttgttttgaaatataaaaaggggcttttttagccccttttttttaaaa
ctccggaggagttcttcattcttgatactatacgtaactattttcgatttgacttcattgtcaattaagctagtaaaatcaatggttaaaaaacaaaaaa
cttgcattttctacctagtaatttataattttaagtgtcgagtttaaaagtataattaccaggaaaggagcaagttttttaataaggaaaaattttccctt
ttaaaattctatttcgttatatgactaattataatcaaaaaatgaaaataaacaagaggtaaaaactgctttagagaaatgtactgataaaaaaaga
aaaaatcctagatttacgtcatacatagcaccttaactactaagaaaaaatattgaaaggacttccacttgtggagattatttgtttatgttgagtgatgc
agacttagaacattttaaattacataaaggtaattttgtcggtaatagatttttgtccaatgtgtagttggcgacttgcttgtaaggatagtttagaaatat
ctattcttatggagcatttaagaaaagaagaaaaataaagagtttatattttaactcttacaactccaaatgtaaaaagttatgatcttaattattctatt
aaacaatataataaatcttttaaaaaattaatggagcgtaaggaagttaaggatataactaaaggttatataagaaaattagaagtaacttaccaaa
aggaaaaatacataacaaaggatttatggaaaataaaaaaagattattatcaaaaaaaaggacttgaaattggtgatttagaacctaattttgatact
tataatcctcattttcatgtagttattgcagttaataaaagttattttacagataaaaattattatataaatcgagaaagatggttgaaattatggaagtt
tgctactaaggatgattctataactcaagttgatgttagaaaagcaaaaattaatgattataaagaggtttacgaacttgcgaaatattcagctaaaga
cactgattatttaatatcgaggccagtatttgaaattttttataaagcattaaaaggcaagcaggtattagttttttagtggattttttaaagatgcacaca
aattgtacaagcaaggaaaacttgatgtttataaaaagaaagatgaaattaaatatgtctatatagtttattataattggtgcaaaaaacaatatgaa
aaaactagaataaggaaacttacggaagatgaaaaagaagaattaaatcaagatttaatagatgaaatagaaatagattaaagtgtaactatacttt
atatatatatgattaaaaaaataaaaaacaacagcctattaggttgttgttttttatttttctttattaatttttttaattttttagttttttagttctttttaaaat
aagtttcagcctctttttcaatattttttaaagaaggagtatttgcatgaattgccttttttctaacagacttaggaaatattttaacagtatcttcttgcgcc
ggtgattttggaacttcataacttactaatttataattattatttttcttttttaattgtaacagttgcaaaagaagctgaacctgttccttcaactagtttatc
atcttcaatataatattcttgacctatatagtataaatatattttttattatattttttactttttctgaatctattatttttataatcataaaaagttttaccacca
aaagaaggttgtactccttctggtccaacatatttttttactatattatctaaataattttttgggaactggtgttgtaatttgattaatcgaacaaccagtta
tacttaaaggaattataactataaaaatatataggattatcttttttaaatttcattattggcctccttttttattaaatttatgttaccataaaaaggacata
acgggaatatgtagaatatttttaatgtagacaaaattttacataaatataaagaaaggaagtgtttgtttaaatttttatagcaaactatcaaaaattag
ggggataaaaatttatgaaaaaaaggttttcgatgttattttttatgtttaactttaatagtttgtggtttatttacaaattcggccggccgaagcaaactta
agagtgtgttgatagtgcagtatcttaaaattttgtataataggaattgaagttaaattagatgctaaaaatttgtaattaagaaggagtgattacatga
acaaaaatataaaatattctcaaaacttttttaacgagtgaaaaagtactcaaccaaataataaaacaattgaatttaaaagaaaccgataccgtttac
gaaattggaacaggtaaagggcatttaacgacgaaactggctaaaataagtaaacaggtaacgtctattgaattagacagtcatctattcaacttatc
gtcagaaaaattaaaactgaatactcgtgtcactttaattcaccaagatattctacagtttcaattccctaacaaacagaggtataaaattgttgggagt
attccttaccatttaagcacacaaattattaaaaaagtggttttttgaaagccatgcgtctgacatctatctgattgttgaagaaggattctacaagcgta
ccttggatattcaccgaacactaggggttgctcttgcacactcaagtctcgattcagcaattgcttaagctgccagcggaatgctttcatcctaaaccaaa
agtaaacagtgtcttaataaaacttacccgccataccacagatgttccagataaatattggaagctatatacgtactttgttcaaaatgggtcaatcga
gaatatcgtcaactgtttactaaaaatcagtttcatcaagcaatgaaacacgccaaagtaaacaatttaagtaccgttacttatgagcaagtattgtct
attttttaatagttatctattatttaacgggaggaaataattctatgagtcgcttttgaaatttggaaagttacacgttactaaaggaatgtgtttaaact
ccttttgataatctcatgaccaaaatcccttaacgtgagttttcgttccactgagcgtcagaccccgtagaaaagatcaaaggatcttcttgagatcctt
ttttttctgcgcgtaatctgctgcttgcaaacaaaaaaaccaccgctaccagcggtggtttgtttgccggatcaagagctaccaactctttttccgaaggt
aactggcttcagcagagcgcagataccaaatactgttcttctagtgtagccgtagttaggccaccacttcaagaactctgtagcaccgcctacatacct
cgctctgctaatcctgttaccagtggctgctgccagtggcgataagtcgtgtcttaccgggttggactcaagacgatagttaccggataaggcgcagcg
gtcgggctgaacggggggttcgtgcacacagcccagcttggagcgaacgacctacaccgaactgagatacctacagcgtgagctatgagaaagcgc

FIG. 52 cctgcaggataaaaaaattgtagataaattttataaaatagttttatctacaattttttttatcaggaaacagctatgaccgcggccgctgtatccatatg
accatgattacgaattcgagctcggtacccggggatcctctagagtcgacgtcacgcgtccatggagatctcgaggcctgcagacatgcaagcttggc
actggccgtcgttttacaacgtcgtgactgggaaaaaccctggcgttacccaacttaatcgccttgcagcacatcccccttcgccagctggcgtaatagc
gaagaggcccgcaccgatcgcccttcccaacagttgcgcagcctgaatggcgaatggcgctagcataaaaataagaagcctgcatttgcaggcttctt
attttatggcgcgccgccattatttttttgaacaattgacaattcattcttatttttattaagtgatagtcaaaaggcataacagtgctgaatagaaag
aaatttacagaaaagaaaattatagaatttagtatgattaattatactcatttatgaatgtttaattgaatacaaaaaaaaatacttgttatgtattcaat
tacgggttaaaaatagacaagttgaaaaatttaataaaaaaaataagtcctcagctcttatatattaagctaccaacttagtatataagcaaaactta
aatgtgctaccaacacatcaagccgttagagaactctatctatagcaatatttcaaatgtaccgacatacaagagaaacattaactatatatattcaat
ttatgagattatcttaacagatataaatgtaaattgcaataagtaagatttagaagtttatagccttgtgtattggaagcagtacgcaaaggctttttta
tttgataaaaattagaagtatatttattttttcataattaatttatgaaaatgaaaggggggtgagcaaagtgacagaggaaagcagtatcttatcaaat
aacaaggtattagcaatatcattattgactttagcagtaaacattatgacttttatagtgcttgtagctaagtagtacgaaaggggggagctttaaaaag
ctccttggaatacatagaattcataaattaatttatgaaaagaagggcgtatatgaaaacttgtaaaaattgcaaagagtttattaaagatactgaaat
atgcaaaatacattcgttgatgattcatgataaaaacagtagcaacctattgcagtaaatacaatgagtcaagatgtttacataaagggaaagtccaat
gtattaattgttcaaagatgaaccgatatggatggtgtgccataaaaatgagatgttttacagaggaagaacagaaaaaagaacgtacatgcattaa
atattatgcaaggagctttaaaaaagctcatgtaaagaagagtaaaagaaaaaataatttatttattaatttaatattgagagtgccgacacagtat
gcactaaaaatatatctgtggtgtagtgagccgatacaaaaggatagtcactcgcattttcataatacatcttatgttatgattatgtgtcggtgggac
ttcacgacgaaaacccacaataaaaaaagagttcggggtagggttaagcatagttgaggcaactaaacaatcaagctaggatatgcagtagcagac
cgtaaggtcgttgtttaggtgtgttgtaatacatacgctattaagatgtaaaaatacggataccaatgaagggaaaagtataattttggatgtagtttg
tttgttcatctatgggcaaactacgtccaaagccgtttccaaatctgctaaaaagtatatcctttctaaaatcaaagtcaagtatgaaatcataaataaa
gtttaattttgaagttattatgatattatgtttttctattaaaataaattaagtatatagaatagtttaataatagtatatacttaatgtgataagtgtctga
cagtgtcacagaaaggatgattgttatggattataagcggccgccgaagcaaacttaagagtgtgttgatagtgcagtatcttaaaatttgtataat
aggaattgaagttaaattagatgctaaaaatttgtaattaagaaggagtgattacatgaacaaaaatataaaatattctcaaaactttttaacgagtg
aaaaagtactcaaccaataataaaacaattgaatttaaaagaaaccgataccgtttacgaaattggaacaggtaaagggcatttaacgacgaaac
tggctaaaataagtaaacaggtaacgtctattgaattagacagtcatctattcaacttatcgtcagaaaaattaaaactgaatactcgtgtcactttaat
tcaccaagatattctacagtttcaattccctaacaaacagaggtataaaattgttgggagtattccttaccatttaagcacacaaattattaaaaagtg
gttttgaaagccatgcgtctgacatctatctgattgttgaagaaggattctacaagcgtaccttggatattcaccgaacactagggttgctcttgcacac
tcaagtctcgattcagcaattgcttaagctgccagcggaatgctttcatcctaaaccaaaagtaaacagtgtcttaataaaacttacccgccataccac
agatgttccagataaatattggaagctatatacgtactttgtttcaaaatgggtcaatcgagaatatcgtcaactgtttactaaaaatcagtttcatcaa
gcaatgaaacacgccaaagtaaacaatttaagtaccgttacttatgagcaagtattgtctattttaatagttatctattatttaacgggaggaaataat
tctatgagtcgcttttgtaaatttggaaagttacacgttactaaagggaatgtgtttaaactccttttttgataatctcatgaccaaaatcccttaacgtga
gttttcgttccactgagcgtcagaccccgtagaaaagatcaaaggatcttcttgagatccttttttctgcgcgtaatctgctgcttgcaaacaaaaaaa
ccaccgctaccagcggtggtttgtttgccggatcaagagctaccaactctttttccgaaggtaactggcttcagcagagcgcagataccaaatactgttc
ttctagtgtagccgtagttaggccaccacttcaagaactctgtagcaccgcctacatacctcgctctgctaatcctgttaccagtggctgctgccagtggc
gataagtcgtgtcttaccgggttggactcaagacgatagttaccggataaggcgcagcggtcgggctgaacggggggttcgtgcacacagcccagctt
ggagcgaacgacctacaccgaactgagatacctacagcgtgagctatgagaaagcgccacgcttcccgaagggagaaaggcggacaggtatccgg
taagcggcagggtcggaacaggagagcgcacgagggagcttccaggggaaacgcctggtatctttatagtcctgtcgggtttcgccacctctgactt
gagcgtcgatttttgtgatgctcgtcaggggggcggagcctatggaaaaacgccagcaacgcggcctttttacggttcctggccttttgctggccttttgc
tcacatgttctttcctgcgttatcccctgattctgtggataaccgtattaccgcctttgagtgagctgataccgctcgccgcagccgaacgaccgagcgca
gcgagtcagtgagcgaggaagcggaagagcgcccaatacgcaggcccctgcttcggggtcattatagcgatttttcggtatatccatccttttttcg
cacgatatacaggattttgccaaaggggttcgtgtagactttccttggtgtatccaacggcgtcagccgggcaggataggtgaagtaggcccacccgcg
agcgggtgttccttcttcactgtcccttattcgcacctggcggtgctcaacgggaatcctgctctgcgaggctggccggctaccgccggcgtaacagatg
aggcgaaacggatggctgatgaaaccaagccaaccaggaagggcagcccacctatcaaggtgtactgccttccagacgaacgaagagcgattgag

FIG. 54 tcattccgctgttatggccgcgtttgtctcattccacgcctgacactcagttccgggtaggcagttcgctccaagctggactgtatgcacgaaccccccgttcagtccgaccgctgcgccttaccgg
taactatcgtcttgagtccaacccggaaagacatgcaaaagcaccactggcagcagccactggtaattgatttagaggagttagtcttgaagtcatgcgccggttaaggctaaactgaaaggac
aagttttggtgactgcgctcctccaagccagttacctcggttcaaagagttggtagctcagagaaccttcgaaaaaccgccctgcaaggcggttttttcgttttcagagcaagagattacgcgcag
accaaaacgatctcaagaagatcatcttattaatcagataaaatatttctagatttcagtgcaattatctcttcaaatgtagcacctgaagtcagccccatacgatataagttgtaattctcatgtt
tgacagcttatcatcgataagctttaatgcggtagtttatcacagttaaattgctaacgcagtcaggcaccgtgtatgaaatctaacaatgcgctcatcgtcatcctcggcaccgtcaccctggatg
ctgtaggcataggcttggttatgccggtactgccgggcctcttgcgggatatcgtccattccgacagcatcgccagtcactatggcgtgctgctagcgctatatgcgttgatgcaatttctatgcgca
cccgttctcggagcactgtccgaccgctttggccgccgcccagtcctgctcgcttcgctacttggagccactatcgactacgcgatcatggcgaccacacccgtcctgtggatcctctacgccggac
gcatcgtggccggcatcaccggcgccacaggtgcggttgctggcgcctatatcgccgacatcaccgatggggaagatcgggctcgccacttcgggctcatgagcgcttgtttcggcgtgggtatg
gtggcaggccccgtggccgggggactgttgggcgccatctccttgcatgcaccattccttgcggccggcggtgctcaacggcctcaacctactactgggctgcttcctaatgcaggagtcgcataag
gggagagcgtcgacagaaagtataatgagaaaatataaaatataaataattttctaaaaaacttgacatcatgtgaaaagtttgttataatataaatgagcacgttaatcatttaacatagataa
ttaaatagtaaaaggaggattagtcatgaggtcaaaaattgaggctaatgagtataaggatttttattcttggctttattttctacaaatatttatctgagaaagaggtggccttttttagaaaagaa
agattaaccgatgcagatattgaaaaagttacagaagatgatgttaagtacgcatcccatgtaagagaaaatttgggatattttattgcgtatgaaaatcttttttcaacttggcttaagaaaggt
aatgattttgatatatcgaatgttagggatgcattatctgcttttgatcgtaacattgatgatgtatatagaaaagtgtttgagaaaattttcaatacattgcagacaggcttatctaagcttggaga
aactgcacaagcacaaacaaaggctgtaaaaagtcttcttaaattgataagaaaaattccatggatggaaagcaagattatgatgttcttgggttcatttacgaatatctaattagtatgttcgc
tgccaacgcaggtaaaaaagcaggagaattttacactccgcatgaagtttctgtttttaatgtcagaaattattgcagaacattttgaaaaatagaaagcaaattaaaatatatgacccctacatctg
ggtcgggttcgttgctgataaatattggtaactcagctgcaaaatttatagatggagaaaacaagatagattattacgcacaggagcttaaggaaaatacttataacctcacaagaatgaactt
ggttatgcgtggcatcagtcctgcaaatataaatgtgagaaatggtgacacatataggatgattggcctttttttgaggataccgacaaggataaaacatataaatttataccagtagatgccg
ttgtttctaatccaccttactcacaaaaatgggatccatctgataaagaatttgacccacgatataagtattatgtggttgcaccaaagagtaaggctgattatgcattttattgcatgatttgtat
cacctaaaggacgatggtatcatgacaatcgttcttccccatggtgtacttttttagaggtggagaggaaggtaaaatcagagagaaacttatagaaaaaaaccgcatagatgcaattatcggat
taccaccaaatattttctttggtacaggtattcctactattataatggtccttaaaagaattcgccctacttcagacgtgttgattatagatgcatcaaagggttttgaaaagttggaaagaataa
caaattgagagcctgtgacattaaaaaaattgctgacactgttaagagcagagaatccattgaaaagtattcgactcttgtttctaaggaaaccatccgagaaaatggctataaccttaatatcc
ctcgctatgttaattccttagaacctgcagaaagttgggatattcatgcgactatgtttggtggaatacctgtaaaggaagtagaccaactattgagtattgggaggcttttcccgaactcaaag
atgcaattttctcggaaaatttctaatgaatatttagctgtgaaatgcgatgatattaaagcggctattacctctcatgagtcattgaaaatctataaacaggcattctcaaatgaatttggtaatttt
tatgaagaacttaaaaatgatttgattgaagaaattcttgatgtatctgctgagcatgagaaagaaaaggtaagcaaggatatttttataagaatagaaaatgtaaaacttgctgacaagtata
aagcgtaccagatactttcggataattgggatgtgatttcaacagatttggaaatgattcagtcagaaggttttgaggttatcaatcaagtggatcctaacatgattttaaagaagaaagaagct
aacgatgatgaggttccagaggtacaagtggggtggaagggtcatatactgccttttgatttgttcagagagagattcttactgaagattttagaagaacttcaggcaatagaaaaaagattaa
ctgaaatcacttctttgtatggtgaaattattgattcgcttgatgaagaagaaagagaaagcagtgtgttgaatgaagctaacgatgcttttgtagcaaaagaagttaagagttttgttgcagaag
ccctcagccgatgtggaaaatgatgaaattaaagcattaagaggatatcaagccttttcaaagaaaaaagaaaagctagattatgtaaataaatgtgatatagtttcgtggaatttaatggaac
aaggttctgatggagcatataagaaaggttctgttattagtagaataagcgaattgcaaaggatgtatgaattcccgaaagattccttgaacagaaagtgatgaccgtattatctcttatggaa
gaagaaagccaggctaaaaaagatctaaaacagaaatcggaagccctccatattaagaccaaagaaaccattgaaaatctggatgaagacgaatctttgcgtttgttagaattaaaatggat
aaagccattagtagattcccttttttgctattccagatgaaatcatcggagagctgattaacaagtaattcatcacacgataaatattgcactacattttccgatattgaacatgatatcgaaaac
acaagtgcgaaattatcaaatatgattgataagcttgttggcagtgtggcagatattgagggattagaagaattgaagaagattttggggggtatagtaaaaataagagttacctaaatggtaa
ctcttatttttttaatattgtttcatagtatttctttgtcgaccgatgcccttgagagccttcaacccagtcagctccttccggtgggcgcggggcatgactatcgtcgccgcacttatgactgtcttctt
atcatgcaactcgtaggacaggtgccggcagcgctctgggtcattttcggcgaggaccgctttcgctggagcgcgacgatgatcggcctgtcgcttgcggtattcggaatcttgcacgccctcgct
caagccttcgtcactggtcccgccaccaaacgtttcggcgagaagcaggccattatcgccggcatggcggccgacgcgctgggctacgtcttgctggcgttcgcgacgcgaggctggatggcctt
ccccattatgattcttctcgcttccggcggcatcggatgcccgcgttgcaggccatgctgtccaggcaggtagatgacgaccatcagggacagcttcaaggatcgctcgcggctcttaccagcct
aacttcgatcactggaccgctgatcgtcacggcgatttatgccgcctcggcgagcacatggaacgggttggcatggattgtaggcgccgccctataccttgtctgcctccccgcgttgcgtcgcgg
tgcatggagccgggccacctcgacctgaatggaagccggcggcacctcgctaacggattcaccactccaagaattggagccaatcaattcttgcggagaactgtgaatgcgcaaaccaaccct
tggcagaacatatccatcgcgtccgccatctccagcagccgcacgcggcgcatctcgggcagcgttgggtcctggccacggggtgcgcatgatcgtgctcctgtcgttgaggacccggctaggctg
gcggggttgccttactggttagcagaatgaatcaccgatacgcgagcgaacgtgaagcgactgctgctgcaaaacgtctgcgacctgagcaacaacatgaatggtcttcggtttccgtgttcgt
aaagtctggaaacgcggaagtccctactgctgctgaagttgcccgcaacagagagtggaaccaaccggtgataccacgatactgactgagagtcaacgccatgagcggcctcatttctt
attctgagttacaacagtccgcaccgctgccggtagctccttccggtgggcgcggggcatgactatcgtcgccgcacttatgactgtcttttttcatcatcatcgcaactcgtaggacaggtgccggcagc
gcccaacagtccccggccacggggcctgccaccataccacgccgaaacaagcgccctgcaccattatgttccggaacgggaaacgtcttgctcgagatctatcgattttcgttcgtgaataca
tgttataataactataactaataacgtaacgtgactggcaagagatattttaaaacaatgaataggtttacacttacttttagttttatggaaatgaaagatcatatcatatataatctagaataa
aattaactaaaataattattatctagataaaaaatttagaagccaatgaaatctataaatataaactaaattaagtttatttaattaacaactatggatataaaataggtactaatcaaaatagtga
ggaggatatatttgaatacatacgaacaaattaataaagtgaaaaaaaatacttcggaaacatttaaaaaataaccttattggtacttacatgtttggatcaggagttgagagtggactaaaacc
aaatagtgatcttgacttttttagtcgtcgtatctgaaccattgacagatcaaagtaaagaaaatacttatacaaaaaattagacctatttcaaaaaaaaataggagataaaagcaacttacgatat
attgaattaacaattattattcagcaagaaagtgtaccgtggaatcatcctcccaaacaagaatttatttatggagaatggttacaagagcttttatgaacaaggatacattcctcagaaggaatt
aaattcagatttaaccataatgctttaccaagcaaaacgaaaaaataaaagaatatacggaaatttatgacttagagggaattactacctgatattccattttctgatgtgagaagagcccattatgg
attcgtcagaggaattaatagataattatcaggatgatgaaaccaactctatattaactttatgccgtatgatttttaactatggacacgggtaaaatcataccaaaagatattgcgggaaatgca
gtggctgaatcttctccattagaacataggggagaattttgttagcagttcgtagtatcttggagagaatattgaatggactaatgaaaatgtaaatttaactataaactatttaaataacaga
ttaaaaaaattataaaaaaattgaaaaaatggtggaaacacttttttcaattttttttgttttattatttaatatttgggaaatattcattctaattggtaatcagattttagaaaacaataaacccttg
catatgatatcgatgtacagatccctggtatggcgtcagcaactccggatgagcattcatcaggcgggcaagaatgtgaataaggccgaagaatgtgaattttgttctttttttttacggtctttaaa
aaggccgtaatatccagctgaacggtctggttatagtacattgagcaactgactgaaatgcctcaaaatgttctttacgatgccattgggatatatcaacggtggtatatccagtgatttttttctc
catttttagcttccttagctcctgaaaatctcgataactcaaaaaatacgcccggtagtgatcttatttcattatggtgaaagtttggaacctcttacgtgccgatcaacgtctcattttcgccaaaagt
tggcccagggcttcccggtatcaacagggacaccaggattttatttattctgcgaagtgatcttccgtcacaggtatttattcggcgcaaagtgcgtcgggtgatgctgccaacttactgatttagtg
tatgatggtgtttttgaggtgctccagtggcttctgtttctcatcagctgtccctcctgttcagctactgacgggtggtgcgtaacggcaaaagcaccgccggacatcagcgctagcggagtgtata
ctggcttactatgttggcactgatgaggtgtcagtgaagtgcttcatgtggcaggagaaaaaaggctgcaccggtgcgtcagcagaatatgtgatacaggatatattccgcttcctcgctcacctg
actcgctacgctcggtcgttcgactgcggcgagcggaaatggcttacgaacggggcggagatttcctggaagatgccaggaagatacttaacagggaagtgagagggccgcggcaaagccgt
ttttccataggctccgcccccctgacaagcatcacgaaatctgacgctcaaatcagtggtggcgaaacccgacaggactataaagataccaggcgtttccccctggcggctccctcgtgcgctct
cctgttcctgccttcggtttaccggtg

FIG. 56 cttcattttttaatttaaaaggatctaggtgaagatcctttttgataatctcatgaccaaaatcccttaacgtgagttttcgttccactgagcgtcagacc
ccgtagaaaagatcaaaggatcttcttgagatccttttttctgcgcgtaatctgctgcttgcaaacaaaaaaaccaccgctaccagcggtggtttgt
ttgccggatcaagagctaccaactcttttccgaaggtaactggcttcagcagagcgcagataccaaatactgtccttctagtgtagccgtagttag
gccaccacttcaagaactctgtagcaccgcctacatacctcgctctgctaatcctgttaccagtggctgctgccagtggcgataagtcgtgtcttacc
gggttggactcaagacgatagttaccggataaggcgcagcggtcgggctgaacggggggttcgtgcacacagcccagcttggagcgaacgacct
acaccgaactgagatacctacagcgtgagctatgagaaagcgccacgcttcccgaagggagaaaggcggacaggtatccggtaagcggcaggg
tcggaacaggagagcgcacgagggagcttccaggggggaaacgcctggtatctttatagtcctgtcgggtttcgccacctctgacttgagcgtcgatt
tttgtgatgctcgtcagggggggcggagcctatggaaaaacgccagcaacgcggccttttacggttcctggccttttgctggccttttgctcacatgtt
cttttcctgcgttatccctgattctgtggataaccgtattaccgcctttgagtgagctgataccgctcgccgcagccgaacgaccgagcgcagcgagt
cagtgagcgaggaagcggaagagcgcctgatgcggtattttctccttacgcatctgtgcggctcgaggtcgacggtatcgataatcgcatttcatag
attgacctcccaataactacgtggtgttattgggaggtcaatctatttcatttgcctcttgctcaaagttcccaaattcgagtaagaggtattttgtttt
tggtcgtcgcctctcattagtagttcagggtttaacattaatactccagttttctttttataatatttccttcttctaagatttaagtgttgttattactgt
ttgtagacttgttcctgtagcttttgctatttctcttgttgtagctatcattgtattgttacttaagtggacattatctaggatatagttaacgattttaagt
ttttttccgccaatcatatctaacatacttattaattgcactatatatgcctttacgaagttaccagacgtttgtttacggtataacttgtctacctctatg
acttctccactttcttcgtctatgagcctctgagagcctttatagactgttccatatctttctttcatctttttctcactccttattttaaactattctaacta
tatcataactgttctaaaaaaaaagaacatttgttaaaagaaattagaacaaaatgagtgaaaaattagaacaaacaaattccttataaaccttg
tcatctcaacctatattaagattttacctagttgaatcttctttttctatataaagcgtcggagcatatcagggggttatctaacgtaaatgctacccttc
ggctcgctttcgctcggcattgacgtcagatactgcacccccctgaaccccatgctccaacagcaaaaaggaaacttttttgctgcttttccgacgctt
attcgcttcgctcatatttatatagaaaagaagtgaatgcgcaaaagacataatcgattcacaaaaaataggtacacgaaaaacaagttaaggga
tgcagtttatgcatcccttaacttacttattaaataatttatagctattgaaaagagataagaattgttcaaagctaatattgtttaaatcgtcaattcc
tgcatgttttaaggaattgttaaattgattttttgtaaatattttcttgtattctttgttaacccatttcataacgaaataattatacttctgtttatctttgt
gtgatattcttgatttttttctatttaatctgataagtgagctattcactttaggtttaggatgaaaatattctcttggaaccatacttaatatagaaata
tcaacttctgccattaaaaataatgccaatgagcgttttgtatttaataatctttttagcaaacccgtattccacgattaaataaatctcatcagctata
ctatcaaaaacaattttgcgtattatatccgtacttatgttataaggtatattaccaaatattttataggattggtttttaggaaatttaaactgcaata
tatccttgtttaaaacttggaaattatcgtgatcaacaagtttatttttctgtagttttgcataatttatggtctatttcaatggcagttacgaaattacac
ctctgtactaattcaagggtaaaatgcccttttcctgagccgatttcaaagatattatcatgttcatttaatcttatatttgtcattattttatctatattat
gttttgaagtaataaagttttgactgtgtttttatatttttctcgttcattataaccctctttattttttcctccttataaaattagtataattatagcacgag
ctctgataaatatgaacatgatgagtgatcgttaaatttatattcaataatcgcatcagattgcagtaaaagatatgagagatttatctagtttcttttt
ttacaagaaaaaagaaagttcttaaaggttttatactttggtcgtagagcacacggtttaacgacttaattacgaagtaaataagtctagtgtgtta
gactttaatgtttttttaaggcattagtgcatttaagcgtcagagcatggctttatgccgagaaaactattggttggaatggcgtgtgtgttagccaaa
gcttgatatcgaattcctgcagcccgcccatggacgcacaccgtggaaacggatgaaggcacgaacccagttgacataagcctgttcggttcgtaa
actgtaatgcaagtagcgtatgcgctcacgcaactggtccagaaccttgaccgaacgcagcggtggtaacggcgcagtggcggttttcatggcttg
ttatgactgtttttttgtacagtctatgcctcgggcatccaagcagcaagcgcgttacgccgtgggtcgatgtttgatgttatggagcagcaacgatg
ttacgcagcagcaacgatgttacgcagcagggcagtcgccctaaaacaaagttaggtggctcaagtatgggcatcattcgcacatgtaggctcgg
ccctgaccaagtcaaatccatgcgggctgctcttgatcttttcggtcgtgagttcggagacgtagccacctactcccaacatcagccggactccgatt
acctcgggaacttgctccgtagtaagacattcatcgcgcttgctgccttcgaccaagaagcggttgttggcgctctcgcggcttacgttctgcccaag
tttgagcagccgcgtagtgagatctatatctatgatctcgcagtctccggagagcaccggaggcagggcattgccaccgcgctcatcaatctcctca
agcatgaggccaacgcgcttggtgcttatgtgatctacgtgcaagcagattacggtgacgatcccgcagtggctctctatacaaagttgggcatac
gggaagaagtgatgcactttgatatcgacccaagtaccgccacctaacaattcgttcaagccgagatcggcttcccggccgcggagttgttcggta
aattgtcacaacgccgcgggggatccactagttctagagtcggtgaacgctctcctgagtaggacaaatccgccgggagcggatttgaacgttgcg
aagcaacggcccggagggtggcgggcaggacgcccgccataaactgccaggcatcaaattaagcagaaggccatcctgacggatggccttttg
cgtttctacaaactcttttgtttatttttctaaatacattcaaatatgtatccgctcatgagacaataaccctgataaatgcttcaataatattgaaaaa
ggaagagtatgagtattcaacatttccgtgtcgcccttattccctttttgcggcattttgccttcctgtttttgctcacccagaaacgctggtgaaagt
aaaagatgctgaagatcagttgggtgcacgagtgggttacatcgaactggatctcaacagcggtaagatccttgagagttttcgccccgaagaac
gttttccaatgatgagcacttttaaagttctgctatgtggcgcggtattatcccgtgttgacgccgggcaagagcaactcggtcgccgcatacactat
tctcagaatgacttggttgagtactcaccagtcacagaaaagcatcttacggatggcatgacagtaagagaattatgcagtgctgccataaccatg
agtgataacactgcggccaacttacttctgacaacgatcggaggaccgaaggagctaaccgcttttttgcacaacatgggggatcatgtaactcgc
cttgatcgttgggaaccggagctgaatgaagccataccaaacgacgagcgtgacaccacgatgcctgtagcaatggcaacaacgttgcgcaaact
attaactggcgaactacttactctagcttcccggcaacaattaatagactggatggaggcggataaagttgcaggaccacttctgcgctcggccctt
ccggctggctggtttattgctgataaatctggagccggtgagcgtgggtctcgcggtatcattgcagcactggggccagatggtaagccctcccgta
tcgtagttatctacacgacggggagtcaggcaactatggatgaacgaaatagacagatcgctgagataggtgcctcactgattaagcattggtaac
tgtcagaccaagtttactcatatatactttagattgatttaaaa

FIG. 58 tcattccgctgttatggccgcgtttgtctcattccacgcctgacactcagttccgggtaggcagttcgctccaagctggactgtatgcacgaacccccgttcagtccgaccgc
tgcgccttatccggtaactatcgtcttgagtccaacccggaaagacatgcaaaagcaccactggcagcagccactggtaattgatttagaggagttagtcttgaagtcatgc
gccggttaaggctaaactgaaaggacaagttttggtgactgcgctcctccaagccagttacctcggttcaaagagttggtagctcagagaaccttcgaaaaaccgccctgc
aaggcggttttttcgttttcagagcaagagattacgcgcagaccaaaacgatctcaagaagatcatcttattaatcagataaaatatttctagatttcagtgcaatttatctct
tcaaatgtagcacctgaagtcagccccatacgatataagttgtaattctcatgtttgacagcttatcatcgataagctttaatgcggtagtttatcacagttaaattgctaacg
cagtcaggcaccgtgtatgaaatctaacaatgcgctcatcgtcatcctcggcaccgtcaccctggatgctgtaggcataggcttggttatgccggtactgccgggcctcttgc
gggatatcgtccattccgacagcatcgccagtcactatggcgtgctgctagcgctatatgcgttgatgcaatttctatgcgcacccgttctcggagcactgtccgaccgctttg
gccgccgcccagtcctgctcgcttcgctacttggagccactatcgactacgcgatcatggcgaccacacccgtcctgtggatcctctacgccggacgcatcgtggccggcat
caccggcgccacaggtgcggttgctggcgcctatatcgccgacatcaccgatggggaagatcgggctcgccacttcgggctcatgagcgcttgtttcggcgtgggtatggt
ggcaggccccgtggccgggggactgttgggcgccatctccttgcatgcaccattccttgcggcggcggtgctcaacggcctcaacctactactgggctgcttcctaatgcag
gagtcgcataaggagagcgtcgacagaaagtataatgagaaaatataaaatataaataattttctaaaaaacttgacatcatgtgaaaagtttgttataatataaatga
gcacgttaatcatttaacatagataattaaatagtaaaaggaggattagtcatgaggtcaaaaattgaggctaatgagtataaggatttattcttggctttattttctacaa
atatttatctgagaaagaggtggccttttttagaaaagaaagattaaccgatgcagatattgaaaaagttacagaagatgatgttaagtacgcatcccatgtaagagaaaa
tttgggatattttattgcgtatgaaaatcttttttcaacttggcttaagaaaggtaatgattttgatatatcgaatgttagggatgcattatctgcttttgatcgtaacattgatg
atgtatatagaaaagtgtttgagaaaattttcaatacattgcagacaggcttatctaagcttggagaaactgcacaagcacaaacaaaggctgtaaaaagtcttcttaaatt
gataagaaaaattcctatggatggaaagcaagattatgatgttcttgggttcatttacgaatatctaattagtatgttcgctgccaacgcaggtaaaaaagcaggagaattt
tacactccgcatgaagtttctgttttaatgtcagaaattattgcagaacatttgaaaaatagaaagcaaattaaaatatatgaccctacatctgggtcgggttcgttgctgat
aaatattggtaactcagctgcaaaatttatagatgtgagaaaacaagatagattattacgcacaggagcttaaggaaaatacttataacctcacaagaatgaacttggttat
gcgtggcatcagtcctgcaaatataaatgtgagaaatggtgacacattagaggatgattggcctttttttgaggataccgacaaggataaaacatataaatttataccagta
gatgccgttgtttctaatccaccttactcacaaaaatgggatccatctgataaagaatttgacccacgatataagtattatggtgttgcaccaaagagtaaggctgattatgc
atttttattgcatgatttgtatcacctaaaggacgatggtatcatgacaatcgttcttccccatggtgtacttttttagaggtgggaggggaaggtaaaatcagagagaaactta
tagaaaaaaccgcatagatgcaattatcggattaccaccaaatattttctttggtacaggtattcctactattataatggtccttaaaagaattcgccctacttcagacgtgt
tgattatagatgcatctaaagggttttgagaaagttggaaagaataacaaattgagagcctgtgcattaaaaaaattgctgacactgttaagagcagagaatccattgaa
aagtattcgactcttgtttctaaggaaaccatccgagaaaatggctataaccttaatatccctcgctatgttaattccttagaacctgcagaaagttgggatattcatgcgact
atgtttggtggaatacctgtaaaggaagtagaccaactatttgagtattgggaggcttttcccgaactcaaagatgcaattttttcggaaaatttctaatgaatatttagctgtg
aaatgcgatgatattaaagcggctattacctctcatgagtcattgaaaatctataaacaggcattctcaaatgaatttggtaattttttatgaagaacttaaaaatgatttgatt
gaagaaattcttgatgtatctgctgagcatgagaaagaaaaggtaagcaaggatattttttataagaatagaaaatgtaaaacttgctgacaagtataaagcgtaccagat
actttcggataattgggatgtgatttcaacagatttggaaatgattcagtcagaaggttttgaggttatcaatcaagtggatcctaacatgattttaaagaagaaagaagct
aacgatgatgaggttccagaggtacaagatgggtggaagggtcatatactgccttttttgatttggttcagagagagattcttactgaagatttagaagaacttcaggcaata
gaaaaaagattaactgaaatcacttctttgtatggtgaaattattgattcgcttgatgaagaagaaagagaaagcagtgtgttgaatgaagctaacgatgcttttgtagcaa
aagaagttaagagttttgttgcagaagccctcagcgatgtggaaaatgatgaaattaaagcattaagaggatatctaagcctttcaaagaaaaaagaaaagctagattat
gtaaatataatgtgatatagtttcgtggaatttaatggaacaaggttctgatggagcatataagaaaggttctgttattagtagaataagcgaattgcaaaggatgtatgaat
tcccgaaagattcctttgaacagaaagtgatgaccgtattatctcttatggaagaagaaagccaggctaaaaaagatctaaaacagaaatcggaagccctccatattaag
accaaagaaaccattgaaaatctggatgaagacgaatctttgcgtttgttagaattaaaatggataaagccattagtagattccctttttgctattccagatgaaatcatcgg
agagctgattaacaaagtaattcatctacacgataaatattgcactacattttccgatattgaacatgatatcgaaaacacaagtgcgaaattatcaaatatgattgataag
cttgttggcagtgtggcagatattgagggattagaagaattgaagaagatttttggggggtatagtaaaaataagagttaccttaaatggtaactctttattttttttaatattgttt
catagtatttcttttgtcgaccgatgcccttgagagccttcaacccagtcagctccttccggtgggcgcggggcatgactatcgtcgccgcacttatgactgtcttctttatcatg
caactcgtaggacaggtgccggcagcgctctgggtcattttcggcgaggaccgctttcgctggagcgcgacgatgatcggcctgtcgcttgccgtattcggaatcttgcacg
ccctcgctcaagccttcgtcactggtcccgccaccaaacgtttcggcgagaagcaggccattatcgccggcatggcggccgacgcgctgggctacgtcttgctggcgttcgc
gacgcgaggctggatggccttccccattatgattcttctcgcttccggcggcatcgggatgcccgcgttgcaggccatgctgtccaggcaggtagatgacgaccatcaggga
cagctagttctagagtcggtgaacgctctcctgagtaggacaaatccgccggggagcggatttgaacgttgcgaagcaacgcccggagggtggcgggcaggacgcccgc
cataaactgccaggcatcaaattaagcagaaggccatcctgacggatggccttttttgcgtttctacaaactcttttgtttatttttctaaatacattcaaatatgtatccgctca
tgagacaataaccctgataaatgcttcaataatattgaaaaaggaagagtatgagtattcaacatttccgtgtcgcccttattcccttttttgccgcattttgccttcctgttttt
gctcacccagaaacgctggtgaaagtaaaagatgctgaagatcagttgggtgcacgagtgggttacatcgaactggatctcaacagcggtaagatccttgagagttttcgc
cccgaagaacgttttccaatgatgagcacttttaaagttctgctatgtggcgcggtattatcccgtgttgacgccgggcaagagcaactcggtcgccgcatacactattctca
gaatgacttggttgagtactcaccagtcacagaaaagcatcttacggatggcatgacagtaagagaattatgcagtgctgccataaccatgagtgataacactgcggcca
acttacttctgcaacgatcggaggaccgaaggagctaaccgcttttttgcacaacatgggggatcatgtaactcgccttgatcgttgggaaccggagctgaatgaagcca
taccaaacgacgagcgtgacaccacgatgcctgtagcaatggcaacaacgttgcgcaaactattaactggcgaactacttactctagcttcccggcaacaattaatagact
ggatggaggcggataaagttgcaggaccacttctgcgctcggcccttccggctggctggtttattgctgataaatctggagccggtgagcgtgggtctcgcggtatcattgc
agcactggggccagatggtaagccctcccgtatcgtagttatctacacgacggggagtcaggcaactatggatgaacgaaatagacagatcgctgagataggtgcctcac
tgattaagcattggtaactgtcagaccaagtttactcatatatactttagattgatttaaaaagttggcccagggcttcccggtatcaacagggacaccaggatttatttattc
tgcgaagtgatcttccgtcacaggtatttattcggcgcaaagtgcgtcgggtgatgctgccaacttactgatttagtgtatgatggtgtttttgaggtgctccagtggcttctgt
ttctatcagctgtccctcctgttcagctactgacggggtggtgcgtaacggcaaaagcaccgccggacatcagcgctagcggagtgtatactggcttactatgttggcactg
atgagggtgtcagtgaagtgcttcatgtggcaggagaaaaaaggctgcaccggtgcgtcagcagaatatgtgatacaggatatattccgcttcctcgctcactgactcgct
acgctcggtcgttcgactgcggcgagcggaaatggcttacgaacggggcggagatttcctggaagatgccaggaagatacttaacagggaagtgagagggccgcggca
aagccgttttccataggctccgcccccctgacaagcatcacgaaatctgacgctcaaatcagtggtggcgaaacccgacaggactataaagataccaggcgtttccccct
ggcggctccctcgtgcgctctcctgttcctgcctttcggtttaccggtg

COMPOSITIONS AND METHODS FOR CLOSTRIDIAL TRANSFORMATION

CROSS-REFERENCE TO RELATED APPLICATIONS

This application is a U.S. National Phase patent application, filed under 35 U.S.C. § 371, of International Application No. PCT/US2014/043424, filed on Jun. 20, 2014, which claims priority to U.S. Provisional Patent Application No. 61/838,224, filed Jun. 21, 2013; the contents of which are incorporated herein by reference in their entirety.

INCORPORATION BY REFERENCE

The content of the following submission on ASCII text file is incorporated herein by reference in its entirety: a computer readable form (CRF) of the Sequence Listing (file name: 48768-545N01USSEQLIST.txt, date recorded: Dec. 17, 2015, size: 128,217 bytes).

FIELD OF THE INVENTION

The invention provides compositions and methods for the genetic engineering of clostridial bacteria to produce and/or to improve efficiency of production of industrial bioproducts.

BACKGROUND OF THE INVENTION

Bacterial restriction-modification (R-M) systems are diverse in specificity and strategy, but their general function is to protect bacteria from foreign DNA, such as DNA from bacteriophages. R-M systems can consist of a DNA methyltransferase and a restriction endonuclease. DNA methyltransferases catalyze the transfer of a methyl group from the donor S-adenosyl-L-methionine (also known as "SAM" or "AdoMet") onto adenine or cytosine residues within particular DNA sequences of the host bacterium, which are called recognition sequences. There are three major classes of DNA methyltransferases, classified according to the nature of the product they produce. The first class consists of amino-methyltransferases which catalyze the methylation of the exocyclic amino group of adenine to form the product N6-methyladenine. The second class consists of amino-methyltransferases that catalyze the formation of the exocyclic amino group of cytosine to form the product N4-methylcytosine, while the third class consists of methyltransferases that methylate the cyclic carbon-5 atom of cytosine to form 5-methylcytosine. These methylated bases serve important functions in bacterial R-M systems, as they protect the host chromosome against the otherwise deleterious action of the partner restriction enzyme, which cleaves unmethylated recognition sequence DNA but ignores fully methylated DNA. Thus, it is the combined action of the DNA methyltransferase and its cognate restriction endonuclease that protects the host bacterium from any unmodified foreign DNA. While R-M systems perform an important protective function, they also inhibit the transfer of plasmids between bacterial species and even between strains of the same species of bacteria, as multiple R-M systems within a single bacterial strain can all participate in the restriction barrier. Thus, R-M systems act as a barrier for the genetic manipulation of many bacteria, including the biotechnologically important genus *Clostridium*.

The genus *Clostridium* consists of a large number of species with a wide range of biochemical and physiological traits. See Cato et al., 1986, *Genus Clostridium*, pp. 1141-1200, in P. H. Sneath et al. (eds.), *Bergey's Manual of Systematic Bacteriology*, Vol. 2, Williams and Wilkins, Baltimore, Md. There are four criteria that need to be met for an isolate to be assigned to the genus *Clostridium*: (1) the ability to form endospores, (2) anaerobic energy metabolism, (3) the inability for dissimilatory sulfate reduction, and (4) possession of a Gram positive cell wall. See Andresson et al., 1989, *Introduction to the physiology and biochemistry of the genus Clostridium*, pp. 27-62, in Minton and Clarke (eds.), *Clostridia*, Plenum Press, New York. Acetogenic bacteria of the genus *Clostridium* use synthesis gas (syngas) as a source of carbon and reducing power for growth under anaerobic conditions. Syngas is composed of a mixture of $H_2$, CO and $CO_2$, which is produced by gasification of any organic material, from municipal waste to agricultural by-products. The use of syngas as a feedstock for the biological production of commodity enzymes and chemicals is attractive due to its low cost and the breadth and flexibility of sources from which it is derived. However, the acetogens within the genus *Clostridium* are relatively uncharacterized, and the ability to genetically manipulate these organisms, particularly through the introduction of heterologous nucleic acids that are stable and not cleaved by clostridial restriction endonucleases, is largely undeveloped. The ability to transform clostridial bacteria is a necessary and fundamental first step for their effective use in the production of industrial bio-products (e.g, isoprene, butadiene and ethanol).

Efforts to overcome R-M systems in *Clostridium* have typically involved the in vivo methylation of heterologous DNA prior to its transformation to protect it from degradation by restriction endonucleases in the host cells; for example, methylation can be performed in vivo by transforming shuttle plasmids into a strain (e.g., *E. coli*) expressing one or more heterologous methyltransferases (e.g., a methyltransferase from *Bacillus subtilis* phage Φ3T). After the methylated DNA is isolated, it may be transformed into host anaerobic cells (e.g, *Clostridium aceticum* cells) via electroporation, protoplast transformation, conjugal transformation, gene gun, or other method known in the art.

Other methods of overcoming clostridial R-M systems involve the methylation of heterologous DNA in vitro using one or more purified methyltransferase enzymes available for purchase from commercial vendors (e.g., New England BioLabs), or involve the creation and use of clostridial host cells deficient in at least one restriction endonuclease gene in their restriction-modification system. See, e.g., Dong et al., PLoS ONE 2010 5(2):e9038. In Dong et al. (2010), a putative type II restriction endonuclease (Cac824I), identified from the publicly-available genome of *Clostridium acetobutylicum* ATCC 824, was disrupted using the ClosTron group II intron insertion-based gene knockout system. The ClosTron system, similar to most group II intron approaches, uses an element derived from the broad host range LI.LtrB intron of *Lactococcus lactis*. See, e.g., Kuehne et al., 2011, ClosTron-mediated engineering of *Clostridium. Methods in Molecular Biology*, Vol. 765:389-407. The resulting cells deficient in Cac824I could be transformed with unmethylated DNA (e.g., unmethylated plasmid DNA) via electroporation.

However, these processes for overcoming the restriction-modification systems in clostridial bacteria depend upon the identification of the specific methyltransferases and restriction endonucleases present in the clostridial bacteria of interest. For example, in order to transform a clostridial bacterial species with a plasmid of interest, treating the desired plasmid in vivo or in vitro with a heterologous methyltransferase (e.g., with *Bacillus subtilis* phage Φ3T methyltransferase) will only protect the plasmid from cleavage if the restriction endonuclease inside the host cell has the same DNA recognition sequence as the heterologous methyltransferase. To improve the effectiveness of such an approach, multiple heterologous methyltransferases, each with different DNA recognition sequences, may be used; however, this increases the time and cost of each attempted transformation. If the methyltransferases used do not recognize the same sequence as the restriction endonuclease present inside the clostridial cell of interest, the heterologous DNA will not be protected from cleavage.

Accordingly, there remains a need to identify and circumvent restriction-modification systems in clostridial bacteria to facilitate their use in the production of industrial bioproducts including, but not limited to, isoprene, butadiene, and ethanol.

Throughout the specification, various publications (including sequences), patents, and patent applications are disclosed. All of these are hereby incorporated by reference in their entirety for all purposes.

BRIEF SUMMARY OF THE INVENTION

The invention provides, inter alia, elucidation of a specific restriction-modification system in clostridial bacteria (e.g., *Clostridium aceticum*) that cleaves at CCWGG site (W can be A or T) and methyltransferases that can be used to protect against cleavage, as further described herein. The knowledge about this restriction-modification system allows for engineering of Clostridial bacteria that enables the biological production of various industrial products (e.g., bioproducts).

Accordingly, in one aspect, the invention provides for isolated polynucleotides having at least 90% sequence identity to SEQ ID NO: 1, wherein the polynucleotides encode for a polypeptide with methyltransferase activity. In any of the embodiments described herein, the polynucleotide is SEQ ID NO: 2. In any of the embodiments described herein, the encoded polypeptide methylates a polynucleotide at a sequence comprising CCWGG. In any of the embodiments described herein, the sequence comprising CCWGG is selected from the group consisting of CCAGG (SEQ ID NO: 9) and/or CCTGG (SEQ ID NO: 10). In any of the embodiments described herein, the encoded polypeptide methylates a polynucleotide at SEQ ID NO: 9 and/or SEQ ID NO: 10.

In another aspect, the invention provides for plasmids comprising one or more isolated polynucleotides having at least 90% sequence identity to SEQ ID NO: 1, operably linked to one or more control sequences such that the encoded polypeptide is capable of being expressed in an expression host. In any of the embodiments described herein, the expression host is *E. coli*. In any of the embodiments described herein, the plasmid further comprises SEQ ID NO: 14. In any of the embodiments described herein, the plasmid is transformed into an *E. coli* S17-1 cell.

In another aspect, the invention provides for recombinant host cells comprising isolated polynucleotides having at least 90% sequence identity to SEQ ID NO: 1, wherein the polynucleotides encode for a polypeptide with methyltransferase activity.

In another aspect, the invention provides for recombinant host cells comprising plasmids comprising one or more isolated polynucleotides having at least 90% sequence identity to SEQ ID NO: 1, operably linked to one or more control sequences such that the encoded polypeptide is capable of being expressed in an expression host.

In another aspect, the invention provides for isolated polypeptides comprising an amino acid sequence having at least 90% sequence identity to SEQ ID NO: 3, wherein said polypeptide is capable of methylating a polynucleotide at a sequence comprising CCWGG. In any of the embodiments described herein, the polypeptide is capable of methylating a polynucleotide at a sequence comprising SEQ ID NO: 9 and/or SEQ ID NO: 10. In any of the embodiments described herein, the polypeptide is capable of methylating a polynucleotide at SEQ ID NO: 9 and/or SEQ ID NO: 10.

In another aspect, the invention provides for isolated polypeptides comprising an amino acid sequence having at least 90% sequence identity to SEQ ID NO: 3, wherein said polypeptide is capable of methylating a polynucleotide at a sequence comprising CCWGG. In any of the embodiments described herein, the polypeptide is capable of methylating a polynucleotide at a sequence comprising SEQ ID NO: 9 and/or SEQ ID NO: 10. In any of the embodiments described herein, the polypeptide is capable of methylating a polynucleotide at SEQ ID NO: 9 and/or SEQ ID NO: 10. In any of the embodiments described herein, the polypeptide is SEQ ID NO: 3.

In another aspect, the invention provides for isolated polypeptides produced by polynucleotides having at least 90% sequence identity to SEQ ID NO: 1, wherein the polypeptide has methyltransferase activity.

In another aspect, the invention provides for methods of producing a DNA methyltransferase, comprising: (a) cultivating a recombinant host cell comprising isolated polynucleotides having at least 90% sequence identity to SEQ ID NO: 1, wherein the polynucleotides encode for a polypeptide with methyltransferase activity, wherein the host cell is cultivated under suitable conditions for production of the encoded DNA methyltransferase, and (b) recovering the DNA methyltransferase.

In another aspect, the invention provides for methods of producing a recombinant *Clostridium* bacterial transformant, comprising: introducing a polynucleotide encoding for a DNA methyltransferase into a *Escherichia* bacterial host cell, (a) culturing the *Escherichia* bacterial host cell under conditions suitable for expression of the DNA methyltransferase, (b) transferring the methylated polynucleotide from the *Escherichia* bacterial host cell to a *Clostridium* bacterial host cell, wherein the bacteria transformed using this method are selected from the group consisting of *Clostridium aceticum, Clostridium ljungdahlii, Clostridium acetobutylicum*, and *Clostridium autoethanogenum*.

In another aspect, the invention provides for isolated polynucleotides having at least 90% sequence identity to SEQ ID NO: 4, wherein the polynucleotide encodes a polypeptide with endonuclease activity. In any of the embodiments described herein, the encoded polypeptide is capable of cleaving a polynucleotide at a sequence comprising CCWGG. In any of the embodiments described herein, the encoded polypeptide is capable of cleaving a polynucleotide at a sequence comprising SEQ ID NO: 9 and/or SEQ ID NO: 10. In any of the embodiments described herein, the encoded polypeptide is capable of cleaving a polynucleotide at SEQ ID NO: 9 and/or SEQ ID NO: 10. In any of the embodiments described herein, the polynucleotide is SEQ ID NO: 4.

In another aspect, the invention provides for plasmids comprising isolated polynucleotides having at least 90% sequence identity to SEQ ID NO: 4, wherein the polynucleotide encodes a polypeptide with endonuclease activity, and wherein the plasmid is operably linked to one or more control sequences such that the encoded polypeptide is capable of being expressed in an expression host. In any of the embodiments described herein, the encoded polypeptide is capable of being expressed in an *E. coli* expression host.

In another aspect, the invention provides for recombinant host cells comprising isolated polynucleotides having at least 90% sequence identity to SEQ ID NO: 4, wherein the polynucleotide encodes a polypeptide with endonuclease activity.

In another aspect, the invention provides for recombinant host cells comprising plasmids comprising isolated polynucleotides having at least 90% sequence identity to SEQ ID NO: 4, wherein the polynucleotide encodes a polypeptide with endonuclease activity, and wherein the plasmid is operably linked to one or more control sequences such that the encoded polypeptide is capable of being expressed in an expression host.

In another aspect, the invention provides for a method of reducing endonuclease cleavage of a heterologous nucleic acid in a *Clostridium* host cell, the method comprising methylating a sequence comprising CCWGG. In any of the embodiments described herein, the method comprises methylating a sequence comprising SEQ ID NO: 9 and/or SEQ ID NO: 10 in the heterologous nucleic acid. In any of the embodiments described herein, the method comprises methylating SEQ ID NO: 9 and/or SEQ ID NO: 10. In any of the embodiments described herein, the endonuclease has at least 90% sequence identity to SEQ ID NO: 5. In any of the embodiments described herein, the endonuclease is SEQ ID NO: 5. In any of the embodiments described herein, the methyltransferase is SEQ ID NO: 3.

In another aspect, the invention provides for a shuttle plasmid comprising pDW280 (SEQ ID NO: 15).

In another aspect, the invention provides for a shuttle plasmid comprising pMCS537 (SEQ ID NO: 16).

In another aspect, the invention provides for a shuttle plasmid comprising pMCS200 (SEQ ID NO: 17).

In another aspect, the invention provides for a shuttle plasmid comprising pMCS201 (SEQ ID NO: 18).

In another aspect, the invention provides for a shuttle plasmid comprising pMCS444 (SEQ ID NO: 19).

In another aspect, the invention provides for a shuttle plasmid comprising pMCS445 (SEQ ID NO: 20).

In another aspect, the invention provides for a shuttle plasmid comprising pMCS94 (SEQ ID NO: 22).

In another aspect, the invention provides for a plasmid comprising pMCS466 (SEQ ID NO: 23).

In another aspect, the invention provides for methods for the delivery one or more nucleic acid(s) of interest into a *Clostridium* bacterial cell, the methods comprising the steps of:
  co-transforming an *E. coli* cell with:
    a plasmid comprising a polynucleotide encoding a polypeptide with methyltransferase activity, and
    at least one shuttle plasmid selected from the group of pDW280, pMCS537, pMCS200, pMCS201, pMCS444 or pMCS445, wherein the shuttle plasmid further comprises the one or more nucleic acid(s) of interest;
  culturing the *E. coli* cell of step (a) with a *Clostridium* bacterial cell under conditions which permit conjugative transfer of (a)(1) and (a)(2), thereby delivering one or more nucleic acid(s) into a *Clostridium* bacterial cell.

In any embodiment described herein, the *Clostridium* bacterial cell is selected from the group consisting of: *Clostridium aceticum*, *Clostridium ljungdahlii*, *Clostridium acetobutylicum*, and *Clostridium autoethanogenum*. In any embodiment described herein, the *E. coli* cell is of the 517-1 strain.

In another aspect, the invention provides for recombinant *Clostridium* bacterial cells comprising:
  a) a plasmid comprising pDW268 (SEQ ID NO: 14), and
  b) at least one shuttle plasmid selected from the group of pDW280 (SEQ ID NO: 15), pMCS537 (SEQ ID NO: 16), pMCS200 (SEQ ID NO: 17), pMCS201 (SEQ ID NO: 18), pMCS444 (SEQ ID NO: 19) or pMC4245 (SEQ ID NO: 20), wherein the shuttle plasmid further comprises one or more nucleic acid(s) of interest.

In another aspect, the invention provides for recombinant *Clostridium* bacterial cells produced by: (a) co-transforming an *E. coli* cell with: (1) a plasmid comprising a polynucleotide encoding a polypeptide with methyltransferase activity, and (2) at least one shuttle plasmid selected from the group of pDW280, pMCS537, pMCS200, pMCS201, pMCS444 or pMCS445, wherein the shuttle plasmid further comprises the one or more nucleic acid(s) of interest; (b) culturing the *E. coli* cell of step (a) with a *Clostridium* bacterial cell under conditions which permit conjugative transfer of (a)(1) and (a)(2), thereby delivering one or more nucleic acid(s) into a *Clostridium* bacterial cell.

In another aspect, the invention provides for *Clostridium* expression systems for the expression of one or more nucleic acid(s) of interest, the system comprising:
  a) a plasmid comprising pDW268 (SEQ ID NO: 14),
  b) a shuttle plasmid selected from the group of pDW280 (SEQ ID NO: 15), pMCS537 (SEQ ID NO: 16), pMCS200 (SEQ ID NO: 17), pMCS201 (SEQ ID NO: 18), pMCS444 (SEQ ID NO: 19) or pMC4245 (SEQ ID NO: 20), wherein the shuttle plasmid further comprises one or more nucleic acid(s) of interest for expression,
  c) an *Escherichia* bacterial cell capable of interacting with a *Clostridium* bacterial cell to allow the transfer of (a) and (b); and
  d) a *Clostridium* bacterial cell capable of interacting with an *Escherichia* bacterial cell such that the one or more nucleic acid(s) is expressed in the *Clostridium* bacterial cell.

In any embodiment described herein, the *Clostridium* bacterial cell is selected from the group consisting of *Clostridium aceticum*, *Clostridium ljungdahlii*, *Clostridium acetobutylicum*, and *Clostridium autoethanogenum*. In any embodiment described herein, the *Clostridium* bacterial cell is *Clostridium aceticum*.

BRIEF DESCRIPTION OF THE DRAWINGS

FIG. 1 shows the codon-optimized DNA sequence (1422 bp) of a *Clostridium* aceticum DNA methyltransferase (M.CacI), as optimized for expression in *E. coli* (SEQ ID NO: 1).

FIG. 2 shows the wild-type DNA sequence (1425 bp) for a *Clostridium aceticum* methyltransferase (M.CacI, RYBO02455) (SEQ ID NO. 2).

FIG. 3 shows the deduced amino acid sequence (474 aa) for a *Clostridium aceticum* DNA methyltransferase (M.CacI) (SEQ ID NO. 3).

FIG. 4A shows the wild-type DNA sequence (714 bp) of a restriction endonuclease from *Clostridium aceticum* strain ATCC35044 (CacI, RYBO02454) (SEQ ID NO. 4). FIG. 4C also shows CacI (circled arrow) was mis-annotated as a glycosyl hydrolase by the Genbank database.

FIG. 5 shows the deduced amino acid sequence (237 aa) for the *Clostridium* aceticum restriction endonuclease CacI (SEQ ID NO. 5).

FIG. 7A-B show the pCA1 DNA sequence (5720 bp) (SEQ ID NO. 6).

FIG. 9 shows the pMCS203 DNA sequence (3729 bp) (SEQ ID NO. 7).

FIG. 11 shows the pMCS244 DNA sequence (3270 bp) (SEQ ID NO. 8).

FIG. 15 shows the DNA sequence (3270 bp) for pDW265 (SEQ ID NO. 11).

FIG. 20A-C show the DNA sequence (8285 bp) for pDW263 (SEQ ID NO. 12).

FIG. 22A-C show the DNA sequence (8285) for pDW264 (SEQ ID NO. 13).

FIG. 24A-C show the DNA sequence (6758 bp) for pDW268 (SEQ ID NO. 14).

FIG. 28A-C show the DNA sequence (8398 bp) for pDW280 (SEQ ID NO. 15).

FIG. 31A-B show the DNA sequence for pMCS537 (SEQ ID NO. 16).

FIG. 33A-B show the DNA sequence (5254 bp) for pMCS200 (SEQ ID NO. 17).

FIG. 35A-B show the DNA sequence (4476 bp) for pMCS201 (SEQ ID NO. 18).

FIG. 50 shows the DNA sequence (5367 bp) for pMCS444.
FIG. 52 shows the DNA sequence (4589 bp) for pMCS445.
FIG. 54 shows the DNA sequence for pMCljs (7571 bp).
FIG. 56 shows the DNA sequence for pMCS94 (5056 bp).
FIG. 58 shows the DNA sequence for pMCS466 (6334 bp).

DETAILED DESCRIPTION OF THE INVENTION

Figure 4B:
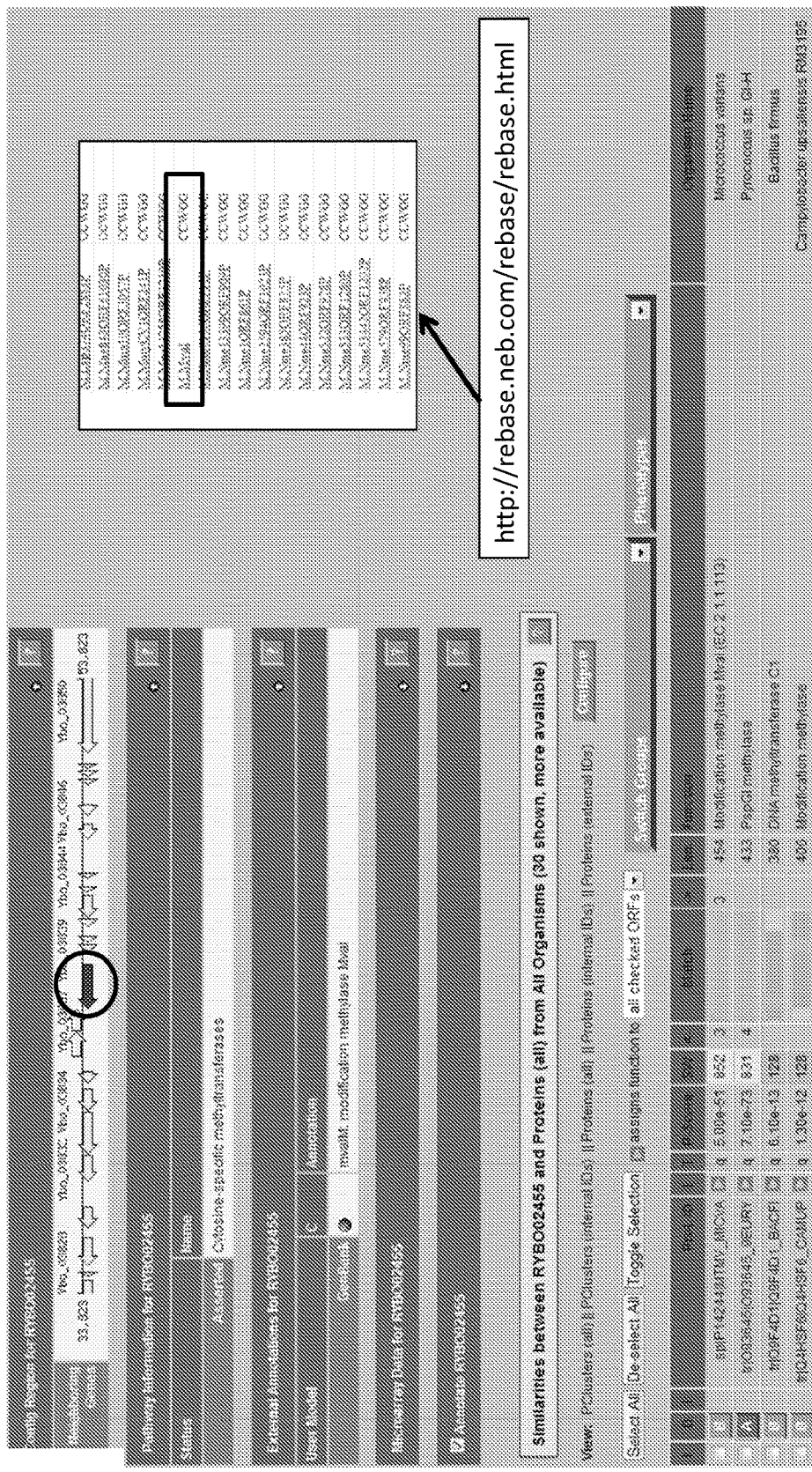
FIG. 4B and FIG. 4C show the genomic location and annotations of M.CacI (FIG. 4B, RYBO02455—SEQ ID NO. 2) and CacI (FIG. 4C, RYBO02454; SEQ ID NO. 4), respectively, in *Clostridium aceticum* strain ATCC35044. M.CacI and CacI are located adjacent to each other, but on opposite strands of the *C. aceticum* chromosome (FIG. 4B-C).
Figure 4C:
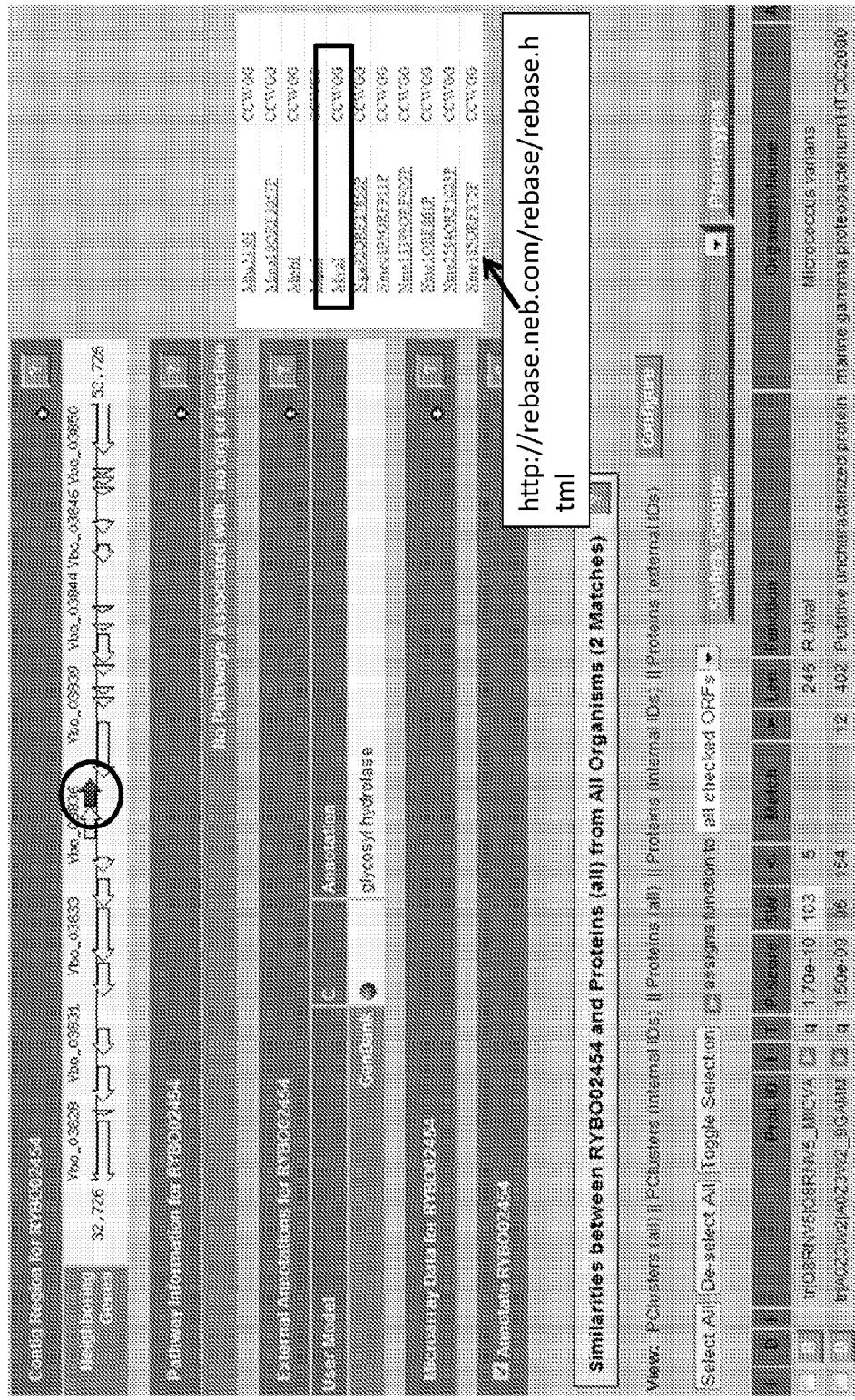

The invention provides, inter alia, elucidation of a specific restriction-modification system in clostridial bacteria (e.g., *Clostridium aceticum*) that cleaves at CCWGG site (W can be A or T) and methyltransferases that can be used to protect against cleavage, as further described herein. The knowledge about this restriction-modification system allows for engineering of Clostridial bacteria that enables the biological production of various industrial products (e.g., bioproducts).

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as *Handbook on Clostridia* (P. Durre, ed., 2004), *Biotechnology: A Textbook of Industrial Microbiology* (Brock, Sinauer Associates, Inc., Second Edition, 1989), *Molecular Cloning: A Laboratory Manual* (Sambrook et al., 1989, $2^{nd}$ ed.); *Oligonucleotide Synthesis* (M. J. Gait, ed., 1984); *Methods in Enzymology* (Academic Press, Inc.); *Current Protocols in Molecular Biology* (F. M. Ausubel et al., eds., 1987, and periodic updates); *PCR: The*

*Polymerase Chain Reaction* (Mullis et al., eds., 1994), *Dictionary of Microbiology and Molecular Biology* (Singleton et al., 2nd ed., J. Wiley and Sons, New York, N.Y., 1994); and *Advanced Organic Chemistry Reactions, Mechanisms and Structure* (March, 4th ed., John Wiley and Sons, New York, N.Y., 1992), which provide one skilled in the art with a general guide to many of the terms and methods used in the present disclosure.

Unless defined otherwise, technical and scientific terms used herein have the same meaning as commonly understood by one of ordinary skill in the art to which this invention belongs.

Definitions

"Isoprene" refers to 2-methyl-1,3-butadiene (CAS#78-79-5). It can refer to the direct and final volatile C5 hydrocarbon product from the elimination of pyrophosphate from 3,3-dimethylallyl pyrophosphate (DMAPP). It may not involve the linking or polymerization of one or more isopentenyl diphosphate (IPP) molecules to one or more DMAPP molecules. Isoprene is not limited by the method of its manufacture.

"Industrial bio-products" can include, but are not limited to, isoprene, isoprenoids, isoprenoid precursors, butadiene and ethanol. Industrial products can also include, but are not limited to, bio-products derived directly or indirectly from 2-keto acids, malonyl-CoA, and acetoacetyl-CoA. Industrial bio-products can also include, but are not limited to, monoterpenes, diterpenes, triterpenes, tetraterpenes, sequiterpene, polyterpene, abietadiene, amorphadiene, carene, α-farnesene, β-farnesene, farnesol, geraniol, geranylgeraniol, linalool, limonene, myrcene, nerolidol, ocimene, patchoulol, β-pinene, sabinene, γ-terpinene, terpindene, valencene. Industrial bio-products can further include, but are not limited to, non-fermentative alcohols (e.g., 1-propanol, 1-butanol, isobutanol, 2-methyl-1-butanol, 3-methyl-1-butanol, 3-methyl-1-pentanol, 4-methyl-1-pentanol and 1-hexanol), fatty acid-derived hydrocarbons (fatty alcohols, fatty esters, olefins, and alkanes), and fermentative alcohols (e.g., butanol).

A "nucleic acid" or "polynucleotide" refers to two or more deoxyribonucleotides and/or ribonucleotides in either single or double-stranded form.

A "nucleic acid of interest" refers to a polynucleotide encoding a polypeptide that is a part of the synthetic pathway for any industrial product.

An "endogenous nucleic acid" is a nucleic acid whose nucleic acid sequence is naturally found in the host cell. In some aspects, an endogenous nucleic acid is identical to a wild-type nucleic acid that is found in the host cell in nature. In some aspects, one or more copies of endogenous nucleic acids are introduced into a host cell.

A "heterologous nucleic acid" can be a nucleic acid whose nucleic acid sequence is from another species than the host cell or another strain of the same species of the host cell. In some aspects, the sequence is not identical to that of another nucleic acid naturally found in the same host cell. In some aspects, a heterologous nucleic acid is not identical to a wild-type nucleic acid that is found in the same host cell in nature. In various embodiments of the invention, a heterologous nucleic acid encodes for one or more industrial bio-products.

"Polypeptides" includes polypeptides, proteins, peptides, fragments of polypeptides, fusion polypeptides and variants.

An "endogenous polypeptide" is a polypeptide whose amino acid sequence is naturally found in the host cell. In some aspects, an endogenous polypeptide is identical to a wild-type polypeptide that is found in the host cell in nature.

A "heterologous polypeptide" is a polypeptide encoded by a heterologous nucleic acid. In some aspects, the sequence is not identical to that of another polypeptide encoded by a nucleic acid naturally found in the same host cell.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

Identification of a Clostridial Restriction-Modification System

The inventors have discovered a specific restriction-modification (R-M) system in clostridial bacteria. In one aspect, the R-M system is in *Clostridium aceticum* that recognizes the sequence CCWGG where W can be A or T. Prior to this discovery, this R-M system was as a major barrier to the introduction of heterologous nucleic acids into clostridial bacteria (e.g., *Clostridium aceticum*). The heterologous nucleic acids can encode for the production of desired industrial products in the clostridial bacteria. However, some of the challenges of trying to biologically produce industrial products in clostridial bacteria were that the heterologous nucleic acids were digested by endogenous endonucleases in the clostridial bacterial cell or were otherwise adversely affected in way that the desired industrial bio-product could not be produced. The invention provides for the identification of the restriction site for an endonuclease, endonucleases that can bind to the restriction site, and methyltransferases that can protect against undesired cleavage of nucleic acids of interest. It is to be understood that compositions and/or systems, methods of making and using these aspects and/or embodiments are encompassed within the scope of the invention.

Compositions and Methods of Use

As a result of this discovery, the inventors have created (and herein describe) polynucleotides, polypeptides, plasmids, vectors, expression systems, host cells, etc. based on the components of this clostridial restriction-methylation system, as well as methods of making and using these components to facilitate the genetic manipulation of clostridial bacteria (e.g., *Clostridium aceticum, Clostridium acetobutylicum, Clostridium ljungdahlii*, and *Clostridium autoethanogenum*) to produce industrial bio-products such as (but not limited to) isoprene, butadiene, and ethanol.

Restriction Endonucleases

The invention provides for compositions of specific restriction endonucleases that act in clostridial cells to cleave nucleic acids and methods of identifying them and using them. Several exemplary restriction endonucleases are described herein and also in the Examples section (e.g. CacI restriction endonuclease). These restriction endonucleases recognize CCWGG sequences (where W can be A or T). In one embodiment of the present invention, the disclosed polynucleotide and amino acid sequence of the CacI restriction endonuclease can be used to identify other related restriction endonucleases with homology to CacI that have the same functionality. In another embodiment of the invention, the nucleic acid sequence or amino acid sequence of CacI may be used to design a nucleic acid probe to identify and clone DNA encoding polypeptides having restriction endonuclease activity from strains of different genera or species according to methods well known in the art.

These identified homologs can then be inactivated to facilitate introduction of one or more polynucleotides of interest into the host cell. As used herein, "homology" refers to sequence similarity or identity, with identity being preferred. This homology is determined using standard techniques known in the art (See e.g., Smith and Waterman, Adv Appl Math, 2:482, 1981; Needleman and Wunsch, J Mol Biol, 48:443, 1970; Pearson and Lipman, Proc Natl Acad Sci USA, 85:2444, 1988; programs such as GAP, BESTFIT, FASTA, and TFASTA in the Wisconsin Genetics Software Package, Genetics Computer Group, Madison, Wis.; and Devereux et al., Nucl Acid Res, 12:387-395, 1984).

The inactivation of restriction endonucleases may be accomplished through methods well known in the art, such as insertions, disruptions, replacements, or deletions of all or a segment of the restriction endonuclease gene(s) present in the cell (e.g., by gene disruption techniques to eliminate or reduce expression of the gene, such as the group II intron insertion-based ClosTron method). See, e.g., Dong et al., PLoS ONE 2010 5(2):e9038. In Dong et al. (2010), a putative type II restriction endonuclease (Cac824I), identified from the publicly-available genome of *Clostridium acetobutylicum* ATCC 824, was disrupted using the ClosTron group II intron insertion-based gene knockout system. The resulting cells deficient in Cac824I could be transformed with unmethylated DNA (e.g., unmethylated plasmid DNA) via electroporation. The ClosTron system, similar to most group II intron approaches, uses an element derived from the broad host range LI.LtrB intron of *Lactococcus lactis*. See, e.g., Kuehne et al., 2011, ClosTron-mediated engineering of *Clostridium. Methods in Molecular Biology*, Vol. 765:389-407.

A similar gene disruption approach can be used to inactivate the CacI gene in other bacteria in the genus *Clostridium*, thus facilitating the circumvention of their restriction-modification system(s). Using methods well known in the art, (e.g., sequence alignment programs such as BLAST or CLUSTAL W) homologs to CacI in other clostridial bacteria can be found and inactivated using the ClosTron or similar gene targeting system. The portion of the gene inactivated may be, for example, the coding region or a regulatory element required for expression of the coding region. An example of such a regulatory sequence may be a promoter sequence or functional part thereof, for example, a part that is sufficient for affecting expression of the nucleotide sequence. Other control sequences for possible modification include, but are not limited to, a leader sequence, propeptide sequence, signal sequence, transcription terminator, and transcriptional activator.

Inactivation of a restriction endonuclease may also be accomplished by random or specific mutagenesis using chemical mutagenesis (see, e.g., Hopwood, The Isolation of Mutants, *Methods of Microbiology* (J. R. Norris and D. W. Ribbons, eds., pp. 363-433, Academic Press, New York, 1970) and transposition (e.g., Youngman et al., 1983, PNAS 80: 2305-2309). Modification of the restriction endonuclease gene may be performed by subjecting the parent cell to mutagenesis and screening for mutant cells in which expression of the restriction endonuclease has been reduced or eliminated. The mutagenesis, which may be specific or random, may be performed by, for example, use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

In another aspect, the clostridial endonuclease can be used as a target for binding molecules, such as antibodies. Antibodies to a clostridial endonuclease can be useful as a research tool (e.g., detection of presence of endonuclease in clostridial lysates), laboratory tool, or medicinal tool.

Modification of CacI Recognition Sites

CacI recognition sites can be modified such that they are no longer recognized by endonucleases in clostridial cells. These CacI recognition sites can be in nucleic acids of interest, for example, heterologous nucleic acids that encode for various industrial bio-products. In some embodiments of the present invention, the introduction of a polynucleotide of interest into a *Clostridium* cell can be accomplished by modifying the polynucleotide of interest to mutate or delete any identified CacI-specific DNA recognition sites (e.g., by mutating any CCWGG CacI DNA recognition sequences), so the introduced polynucleotide is not degraded by the restriction endonuclease of the bacterial host cell. In other embodiments of the present invention, the polynucleotide of interest is modified to mutate or delete one or more CCWGG CacI DNA recognition sequences. In other embodiments of the present invention, the polynucleotide of interest is modified to mutate or delete one or more CCAGG (SEQ ID NO: 9) sites. In other embodiments of the present invention, the polynucleotide of interest is mutated to delete one or more CCTGG (SEQ ID NO: 10) sites.

The presence of any CacI sites on a polynucleotide of interest (e.g., a shuttle plasmid for use between *E. coli* and one or more *Clostridium* species that contains genes from the DXP pathway for isoprene synthesis) can be determined using sequencing methods known in the art or disclosed herein. The modification of the polynucleotide of interest can be accomplished by mutagenesis using methods well known in the art, including, but not limited to, site-directed mutagenesis or PCR generated mutagenesis. See, e.g., Shimada, 1996, *Methods in Molecular Biology*, Vol. 57: 157-165, which is hereby incorporated herein its entirety, particularly as it pertains to site-directed mutagenesis.

The modified polynucleotide may contain an insertion, substitution, or deletion of one or more nucleotides present in the DNA recognition sequence CCWGG. In some embodiments, the modified polynucleotide of interest may contain an insertion, substitution, or deletion of one or more nucleotides present in the DNA recognition sequence CCAGG (SEQ ID NO: 9). In some embodiments, the modified polynucleotide of interest may contain an insertion, substitution, or deletion of one or more nucleotides present in the DNA recognition sequence CCTGG (SEQ ID NO: 10). In some embodiments, the modified polynucleotide of interest may contain an insertion, substitution, or deletion of one or more nucleotides present in the DNA recognition sequence CCAGG (SEQ ID NO: 9) and may contain an insertion, substitution, or deletion of one or more nucleotides present in the DNA recognition sequence CCTGG (SEQ ID NO: 10), for example, as in the CacI-resistant plasmid pDW265 disclosed in Example 6 of the instant application. Furthermore, mutagenesis may be performed using any combination of mutagenizing methods.

Methyltransferases

The invention also provides for compositions of specific methyltransferases that act in clostridial cells to protect nucleic acids from being cleaved by endonucleases as well as methods of identifying them and using them. In one embodiment of the invention, the nucleic acid sequence or amino acid sequence of M.CacI may be used to design a nucleic acid probe to identify and clone DNA encoding polypeptides having methyltransferase activity from strains of different genera or species according to methods well known in the art.

Methyltransferases of the invention can be obtained from various clostridial species, for example, *C. aceticum* and *C. ljungdhalii*. In particular, such probes can be used for hybridization with the genomic DNA of the genus or species of interest, followed by standard Southern blotting procedures, in order to identify and isolate the corresponding gene therein. Such probes can be considerably shorter than the entire sequences, but should be at least 14, preferably at least 25, more preferably at least 35, and most preferably at least 70 nucleotides in length. Both DNA and RNA probes can be used, and the probes can be labeled for detecting the corresponding gene (for example, with 32P, 3H, 35S, biotin or avidin). Such probes are encompassed by the present invention.

Methylation can be used in various ways, for example, in vitro methylation or in vivo methylation.

In Vitro Methylation

The circumvention of a clostridial restriction-modification system can be accomplished using in vitro methylation of one or more polynucleotides of interest followed by their introduction into a clostridial host cell.

A polynucleotide of interest is first analyzed to confirm the presence of one or more CacI restriction endonuclease DNA recognition sequences, CCWGG. In some embodiments, the polynucleotide of interest comprises one or more CCAGG (SEQ ID NO. 9) DNA recognition sequences. In some embodiments, the polynucleotide comprises one or more CCTGG (SEQ ID NO: 10) DNA recognition sequences. In some embodiments, the polynucleotide of interest comprises one or more CCAGG (SEQ ID NO: 9) and CCTGG (SEQ ID NO: 10) DNA recognition sequences.

Non-limiting examples of sequence analysis methods include Maxam-Gilbert sequencing, Sanger sequencing, capillary array DNA sequencing, thermal cycle sequencing (Sears et al., Biotechniques, 13:626-633 (1992)), solid-phase sequencing (Zimmerman et al., *Methods in Molecular Cell Biology*, 3:39-42 (1992)), sequencing with mass spectrometry such as matrix-assisted laser desorption/ionization time-of-flight mass spectrometry (MALDI-TOF/MS; Fu et al., *Nature Biotechnology*, 16:381-384 (1998)), and sequencing by hybridization. Chee et al., *Science*, 274:610-614 (1996); Drmanac et al., *Science*, 260:1649-1652 (1993); Drmanac et al., *Nature Biotechnology*, 16:54-58 (1998).

Once the presence of one or more of the CacI DNA recognition sequences has been confirmed in a polynucleotide of interest, a methyltransferase is used to methylate the CCWGG sequence (W=T or A) in vitro. This can be accomplished, for example, by transforming the coding sequence of a methyltransferase (e.g., a methyltransferase with at least 90% sequence identity to SEQ ID NO: 2) that recognizes the DNA recognition sequence CCWGG (W=T or A) into a vector capable of expression in a recombinant host cell (e.g., an arabinose-inducible pBAD33 vector capable of expression *E. coli*). This vector comprising a polynucleotide encoding a methyltransferase that specifically recognizes CCWGG (W=T or A) can be transformed into a recombinant host cell (e.g., an *E. coli* cell) and cultivated under suitable conditions (e.g., as described in Example 4 of the instant application) for the production of the encoded DNA methyltransferase. The DNA methyltransferase produced can then be recovered and purified using well-known methods in the art such as chromatography (e.g., ion exchange, affinity, hydrophobic, chromatofocusing, and size exclusion), electrophoretic procedures (e.g., preparative isoelectric focusing), and differential solubility (e.g., ammonium sulfate precipitation). See, e.g., *Protein Purification*, J. C. Janson and Lars Ryden, (eds), VCH Publishers, New York, N.Y. 1989; and Lodish et al. (eds.), 2000. Purifying, Detecting, and Characterizing Proteins, in *Molecular Biology of the Cell*, 4$^{th}$ edition, hereby incorporated in their entirety, particularly as they pertain to protein purification. The purified methyltransferase can then be used to methylate the polynucleotide of interest in vitro using S-adenosyl-L-methionine and DNA methylation protocols that are well-known in the art, thus resulting in the formation of S-adenosyl-L-homocysteine and methylated polynucleotide. Methylation of the polynucleotide of interest can be confirmed using radioactive labeling with [$^3$H]S-adenosyl-methionine and mapping and sequencing of individual methylation sites (e.g., Bitinaite et al., 1992, *Nucleic Acids Research*, Vol. 20: 4981-4985), as well as assays based on Sanger sequencing (e.g., Bart et al., 2005, *Nucleic Acids Research*, Vol. 33: e124) or single-molecule, real-time (SMRT) DNA sequencing (e.g., Clark et al., 2012, *Nucleic Acids Research*, Vol. 40, No. 4, e29). All of the references cited herein are hereby incorporated in their entirety, particularly as they pertain to methylation assays and mapping of methylation sites.

In some embodiments of the present invention, a polynucleotide encoding a methyltransferase with at least 90% sequence identity to SEQ ID NO: 1 that specifically recognizes CCWGG (W=T or A) DNA recognition sites can be used. In other embodiments, a polynucleotide encoding a methyltransferase with at least 90% sequence identity to SEQ ID NO: 2 that specifically recognizes CCWGG (W=T or A) DNA recognition sites can be used. In other embodiments, a polynucleotide encoding a methyltransferase with at least 90% sequence identity to SEQ ID NO: 1 or SEQ ID NO: 2 can be obtained through chemical synthesis methods (e.g., DNA2.0) or created using standard molecular biology techniques.

In some embodiments of the present invention, an isolated polynucleotide having at least about any of 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100% nucleic acid sequence identity to SEQ ID NO. 1 can be used, wherein the polynucleotide encodes for a polypeptide with methyltransferase activity that specifically recognizes CCWGG (W=T or A). In other embodiments of the present invention, an isolated polynucleotide having at least about any of 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100% nucleic acid sequence identity to SEQ ID NO. 2 can be used, wherein the polynucleotide encodes for a polypeptide with methyltransferase activity that specifically recognizes CCWGG (W=T or A).

In some embodiments, the present invention relates to an isolated polypeptide comprising an amino acid sequence having at least 90% sequence identity to SEQ ID NO. 3, wherein said polypeptide is capable of methylating a polynucleotide at SEQ ID NO. 9 and/or SEQ ID NO. 10. In other embodiments, the present invention relates to an isolated polypeptide having at least about any of 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100% amino acid sequence identity to SEQ ID NO. 3, wherein said polypeptide is capable of methylating a polynucleotide at SEQ ID NO. 9 and/or SEQ ID NO. 10. In still other embodiments, the isolated polypeptide having methyltransferase activity that is capable of methylating a polynucleotide at a sequence comprising CCWGG is SEQ ID NO. 3.

Once one or more polynucleotides of interest have been methylated, these polynucleotides of interest may be introduced into clostridial host cells using transformation methods such as electroporation, conjugation, protoplast transformation, gene gun, or other transformation method known in the art or discussed in any of the examples of the instant application. See e.g., Davis et al., "Gene cloning in Clostridia" (P. Durre, P., ed. 2005) *Handbook on Clostridia*); *Current Protocols in Molecular Biology* (F. M. Ausubel et al. (eds) Chapter 9, 1987); Sambrook et al., *Molecular Cloning: A Laboratory Manual*, $2^{nd}$ ed., Cold Spring Harbor, 1989; Campbell et al., *Current Genetics*, Vol. 16: 53-56, 1989.

In Vivo Methylation (Shuttle Vectors)

In some embodiments of the present invention, the circumvention of a clostridial restriction-modification system can be accomplished using in vivo methylation and shuttle vectors capable of propagating in two or more different host species. In addition to containing any polynucleotides of interest (e.g., polynucleotides encoding isoprene synthase enzyme and/or any components of the DXP pathway), the shuttle vectors can contain a polynucleotide encoding a methyltransferase that specifically recognizes CCWGG (W=T or A). Alternatively, the methyltransferase that specifically recognizes CCWGG can be provided in a separate plasmid (e.g., as described in Examples 7-10).

Exemplary shuttle vectors are able to replicate in *E. coli* and in an obligate anaerobe, such as *Clostridium aceticum*. See, e.g., Heap et al., 2009, *Journal of Microbiological Methods*, Vol. 78: 79-85, hereby incorporated by reference in its entirety, particularly with respect to the creation and components of shuttle vectors for use between *E. coli* and clostridial bacterial species.

Methods used to ligate a construct (e.g. DNA construct) comprising a polynucleotide of interest (e.g., a methyltransferase or endonuclease nucleic acid), a promoter, a terminator, and other sequences and to insert them into a suitable vector, are well known in the art. For example, restriction enzymes can be used to genetically manipulate methyltransferase or endonuclease nucleic acid such that they can be put into one or more vector(s). Then, the compatible ends of the cleaved methyltransferase or endonuclease nucleic acid and the cleaved vector can be ligated. Linking is generally accomplished by ligation at convenient restriction sites. If such sites do not exist, the synthetic oligonucleotide linkers are used in accordance with conventional practice. See Sambrook et al., (1989), *Molecular Cloning: A Laboratory Manual* ($2^{nd}$ ed., Cold Spring Harbor), hereby incorporated by reference in its entirety, particularly with respect to the isolation of DNA, the construction of vectors, and the use of oligonucleotide linkers. Additionally, vectors can be constructed using known recombination techniques (e.g., Invitrogen Life Technologies, Gateway Technology), or they can be purchased from commercial suppliers of chemically synthesized polynucleotides (e.g., DNA2.0). The shuttle plasmids of the claimed invention may be created using any combination of methods well known in the art, including those described in any of the examples of the instant application.

For example, to successfully transform *C. aceticum* with heterologous DNA, shuttle vectors for propagation in *E. coli* can be built as described in Example 7 of the instant application. Briefly, the construction of a series of modular shuttle vectors between *E. coli* and various clostridial bacterial species (known as "the pMTL80000 series") is described in Heap et al., 2009 *Journal of Microbiological Methods*, Vol. 78: 79-85. These pMTL80000 vectors carry one of four Gram positive replicons, a p15A or ColE1 origin of replication in *E. coli*, a multiple cloning site with flanking transcriptional terminators, and an antibiotic resistant marker selected from the group of, catP, ermB, aad9 or tetA. Some of the vectors also carry a *C. sporogenes* ferredoxin promoter (Pfdx) and ribosome binding site (RBS) or a *C. acetobutylicum* thiolase promoter and RBS for gene expression.

To create the shuttle vector pDW280, the plasmid backbone of pMCS203 (also known as plasmid pMTL85151) was amplified by PCR (PfuUltra II, Agilent Technologies) using the primer pairs indicated in Table 4 (e.g., GA CA1_1 203 For and GA CA1_1 203 Rev). The plasmid map and DNA sequence for pMCS203 are provided in FIG. 8 and FIG. 9A-B, respectively. The pCA1 plasmid was amplified using the indicated primer pairs (e.g., GA CA1_1 Plasmid For and GA CA1_1 Plasmid Rev, as listed in Table 4). The plasmid map and DNA sequence for pCA1 are provided in FIG. 6 and FIG. 7A-B, respectively. PCR products of the appropriate molecular weight by gel electrophoresis were purified (Qiagen) and combined using the GeneArt Seamless Cloning kit (Life Technologies). These PCR products were then transformed into chemically competent *E. coli* TOP10 cells (Life Technologies) according to the manufacturer's recommended protocol. Cells were recovered and plated on selective medium, and transformants resistant to chloramphenicol were selected for further analysis. Several individual colonies were grown overnight in selective LB medium, and the next day plasmids were purified (Qiagen) and molecular weights were compared to that of the parental pCA1 plasmid by gel electrophoresis. This resulted in plasmid pDW264.

As indicated in the pDW264 plasmid map shown in FIG. 20, the pDW264 shuttle vector contains the native *Clostridium aceticum* pCA1 plasmid and DNA cassettes that allow for replication in *E. coli*, conjugal transfer, and resistance to the antibiotic chloramphenicol. The DNA sequence for pDW264 is shown in FIG. 22A-C. Next, pDW264 was cut with FseI and PmeI restriction enzymes (New England Biolabs), following the manufacturer's recommended protocol, to remove the chloramphenicol resistance cassette. This vectors was then ligated (T4 ligase, NEB) to an erythromycin resistance cassette which had been isolated from the template pDW265 by restriction digest with FseI, PmeI, and AscI, and transformed into Top10 chemically competent *E. coli* cells (Life Technologies), using standard molecular biology techniques. The resulting conjugative shuttle plasmid, pDW280, contained the entire *Clostridium aceticum* pCA1 native sequence, an origin of transfer, an origin of replication in *E. coli*, and the erythromycin resistance cassette. The plasmid map and sequence for pDW280 are provided in FIG. 27 and FIG. 28A-C, respectively.

The resulting shuttle vector may be introduced into a host cell comprising a methyltransferase that specifically recognizes the CCWGG DNA recognition sequence (e.g., an *E. coli* S17-1 host cell expressing M.CacI methyltransferase from a pDW268 plasmid) for the purpose of methylating the shuttle vector. In some embodiments, the shuttle vector can be methylated at a sequence comprising CCWGG. In some embodiments, the shuttle vector can be methylated at a sequence comprising CCAGG (SEQ ID NO: 9). In some embodiments, the shuttle vector can be methylated at a sequence comprising CCTGG (SEQ ID NO: 10). In some embodiments, the shuttle vector can be methylated at CCWGG. In some embodiments, the shuttle vector can be methylated at the DNA recognition sequence CCAGG (SEQ ID NO: 9) and/or at the DNA recognition sequence CCTGG (SEQ ID NO: 10).

The methylated shuttle vector can then be isolated and introduced into a *Clostridium* bacterial host cell for expression of the polynucleotide of interest. Introduction of the methylated DNA into the *Clostridium* bacterial host cell can be accomplished by the methods described in any of the examples of the instant application (e with the total length preferably being limited by the ease of preparation and use in the intended recombinant DNA protocol.

Polynucleotides and fusions thereof may be prepared, manipulated and/or expressed using any of a variety of well-established techniques known and available in the art. For example, polynucleotide sequences which encode polypeptides of the invention, or fusion proteins or functional equivalents thereof, may be used in recombinant DNA molecules to direct expression of a selected enzyme in appropriate host cells. Due to the inherent degeneracy of the genetic code, other DNA sequences that encode substantially the same or a functionally equivalent amino acid sequence may be produced and these sequences may be used to clone and express a given polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell. In particular, a heterologous polypeptide is not identical to a wild-type polypeptide that is found in the same host cell in nature.

In order to express a desired polypeptide, a nucleotide sequence encoding the polypeptide, or a functional equivalent, may be inserted into appropriate expression vector, i.e., a vector that contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. Polypeptides include enzymatic polypeptides, or "enzymes," which typically catalyze (i.e., increase the rate of) various chemical reactions, (e.g., DNA methyltransferases or restriction endonucleases).

"Sequence identity," as used herein, refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected.

Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc., 1994-1998, Chapter 15.

Additionally, standard sequence alignment and/or structure prediction programs can be used to identify additional methyltransferase or endonuclease polypeptides and nucleic acids based on the similarity of their primary and/or predicted polypeptide secondary structure with that of known methyltransferase or endonuclease polypeptides and nucleic acids. Standard databases such as the SwissProt-Trembl database (world-wide web at "expasy.org", Swiss Institute of Bioinformatics Swiss-Prot group CMU-1 rue Michel Servet CH-1211 Geneva 4, Switzerland) can also be used to identify methyltransferase or endonuclease polypeptides and nucleic acids. The secondary and/or tertiary structure of a methyltransferase or endonuclease polypeptide can be predicted using the default settings of standard structure prediction programs, such as PredictProtein. Alternatively, the actual secondary and/or tertiary structure of a methyltransferase or endonuclease polypeptide can be determined using standard methods.

Exemplary Methods for Isolating Nucleic Acids

Nucleic acids encoding methyltransferases or restriction endonucleases can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, polynucleotides encoding methyltransferases or endonucleases that specifically recognize CCWGG (W=T or A) can be chemically synthesized using standard methods (e.g., DNA2.0).

Exemplary Vectors, Promoters and Other Elements

Vectors

Any of the methyltransferase or endonuclease nucleic acids described herein (alone or in any combination) can be included in one or more vectors. Accordingly, the invention also features vectors with one or more nucleic acids encoding any of the methyltransferase or endonuclease polypeptides that are described herein. As used herein, a "vector" means a construct that is capable of delivering, and desirably expressing, one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation, such as an arabinose-inducible promoter. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., erythromycin, chloramphenicol, thiamphenicol, kanamycin, ampicillin, carbenicillin, gentamicin, hygromycin, streptomycin, phleomycin, bleomycin, or neomycin) and/or nucleic acids that confer a metabolic advantage, such as a nutritional advantage on the host cell. Suitable vectors are those which are compatible with the host cell employed. Suitable vectors can be derived, for example, from a bacterium, a virus (such as bacteriophage T7 or an M-13 derived phage), a cosmid, a yeast, or a plant. Protocols for obtaining and using such vectors are known to those in the art (see, for example, Sambrook et al., *Molecular Cloning: A Laboratory Manual*, $2^{nd}$ ed., Cold Spring Harbor, 1989, which is hereby incorporated by reference in its entirety, particularly with respect to the use of vectors).

Promoters

Suitable promoters are used to express any of the heterologous nucleic acids described herein. Suitable promoters may be used to drive production of methyltransferase or endonuclease polypeptides, or to reduce degradation of methyltransferase or endonuclease polypeptides in host cells.

Suitable promoters may be used to optimize the expression of methyltransferase or endonuclease polypeptides in a host cell. Any of the nucleic acids described herein (e.g., a nucleic acid encoding methyltransferase or endonuclease polypeptides) may be operably linked to a promoter. Any of the promoters described herein may be used, such as the native *Clostridium aceticum* promoter contained in the plasmid pCA1 (SEQ ID NO. 6).

High expression levels in certain clostridial cells may cause degradation of engineered polypeptide(s) including methyltransferases or endonucleases. To improve methyltransferase or endonuclease production, an inducible expression system that allows both the timing and magnitude of expression of engineered polypeptide(s) to be controlled may be used. The tighter control may facilitate the expression of engineered polypeptide(s) at a concentration and period during the growth of the cells that is toxic to the cells, and results in the production of higher amounts of the desired polypeptide.

A promoter used in any of the cells described herein may be an inducible promoter. An arabinose-inducible expression system may be used; for example, the $P_{BAD}$ arabinose-inducible system as described in Guzman et al., "Tight Regulation, Modulation, and High-Level Expression by Vectors Containing the Arabinose PBAD Promoter." *Journal of Bacteriology*, Vol. 177, No. 14: 4121-4130 (July 1995), which is hereby incorporated by reference in its entirety, particularly with respect to its disclosure of pBAD vectors that use the arabinose-inducible $P_{BAD}$ promoter. Alternatively, a gluconate-inducible expression system may be used, for example, a gluconate-inducible expression system endogenous to *C. ljungdahlii*. ORFs clju19880 and clju30510 are predicted to code for transcription factors that repress the expression of genes involved in gluconate import and metabolism. In the presence of gluconate, gluconate binds to and represses these transcription factors, thus allowing expression of genes involved in gluconate import and metabolism. ORF clju11610 has been annotated as "gluconokinase" in the *C. ljungdahlii* genome. In *Corynebacterium glutamicum*, the gluconate kinase (alternate name for gluconokinase) promoter exhibits the strongest increase in expression in response to gluconate induction (Frunzke et al. 2008, Mol Microbiol., 67(2):305-22). Thus, in some aspects, the promoter can be a gluconate-inducible promoter. In some aspects, the promoter may be from *C. acetobutylicum*, *C. ljungdahlii*, *C. autoethanogenum*, or *C. aceticum*. In some aspects, the promoter can be the promoter present in clju19880 ORF, clju 11610 ORF, or clju30510 ORF in an anaerobic cell (e.g., *C. ljungdahlii*). In some aspects, the promoter can be a native *C. aceticum* promoter, such as is found in the pCA1 plasmid (SEQ ID NO. 6). In some aspects, the promoter is a promoter present in pCA1. In some aspects, the promoter is an arabinose inducible promoter. In some aspects, the promoter is a gluconate-inducible promoter such as the gluconate kinase promoter. The promoter may also be a promoter that is induced when the cells are cultured in the presence of synthesis gas, carbohydrates (e.g., fructose or glucose), or any combinations thereof.

A promoter used in any of the cells described herein may be a constitutive promoter. Constitutive promoters do not require induction by artificial means (such as IPTG for the induction of the lac operon) and hence can result in considerable cost reduction for large scale fermentations. Constitutive promoters that function in anaerobes (e.g., *C. acetobutylicum, C. aceticum* and *C. ljungdahlii*) may be used. Promoters that have low expression may be desirable in certain embodiments. The ptb (phosphotransbutyrylase) promoter of *C. acetobutylicum* is strongly active during the exponential growth phase of *C. acetobutylicum* cultures. Promoters that may be used in the present invention may have less activity than the ptb (phosphotransbutyrylase) promoter. The spoIIE (Stage II sporulation protein E) promoter, also from *C. acetobutylicum*, has been shown to be transiently active in mid-stationary phase. The spoIIE (Stage II sporulation protein E) promoter may be used in the present invention. Thus, in some aspects, the promoter is spoIIE promoter (e.g., *Clostridium acetobutylicum* spoIIE promoter). In some aspects, the promoter has a strength that is at a level lower than ptb (e.g, the promoter has a reduced ability of driving expression compared to ptb such as *Clostridium acetobutylicum* ptb). In some aspects, the promoter has a strength that is at a level similar to spoIIE (e.g., the promoter has a similar ability of driving expression compared to spoIIE). In some aspects, the promoter is active post-exponential growth phase. In some aspects, the promoter is active during linear growth phase. In some aspects, the promoter is active in stationary phase. In some aspects, the promoter used in any of the cells described herein is only active in the presence of syngas. In some aspects, the promoter expresses the methyltransferase or endonuclease at a low level. In some aspects, the promoter expresses the methyltransferase or endonuclease at a level such that the methyltransferase or endonuclease does not get cleaved by a protease or a lower percentage of the methyltransferase or endonuclease gets cleaved by a protease. In some aspects, the promoter derives low level expression.

Any one of the promoters characterized or used in the Examples of the present disclosure may be used.

Promoters are well known in the art, and any promoter that functions in the host cell can be used for expression of a methyltransferase or endonuclease nucleic acid in the host cell. Initiation control regions or promoters, which are useful to drive expression of polypeptides in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, lac, trp, T7, tac, and trc, (useful for expression in *E. coli*).

Plasmids

In various embodiments, a methyltransferase or endonuclease nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the methyltransferase or endonuclease nucleic acid is operably linked to a $P_{BAD}$ promoter. In some embodiments, the methyltransferase or endonuclease nucleic acid operably linked to a $P_{BAD}$ promoter is contained in a medium or high copy plasmid. In some embodiments, the methyltransferase or endonuclease nucleic acid is operably linked to a native *Clostridium aceticum* promoter, such as is contained in the pCA1 plasmid. In some embodiments, the methyltransferase or endonuclease nucleic acid operably linked to a promoter is contained in a medium or high copy plasmid.

In some embodiments, the vector is a replicating plasmid that does not integrate into a chromosome in the cells. In some embodiments, part or all of the vector integrates into a chromosome in the cells. Additional examples of suitable expression and/or integration vectors are provided in Sambrook et al., *Molecular Cloning: A Laboratory Manual,* $2^{nd}$ ed., Cold Spring Harbor, 1989, and *Current Protocols in Molecular Biology* (F. M. Ausubel et al. (eds) 1987, Supplement 30, section 7.7.18) which are both hereby incorporated by reference in their entirety, particularly with respect to vectors. Particularly useful vectors include pFB6, pBR322, PUC18, pUC100, and pENTR/D.

Other Elements

Other molecular biology elements may also be used, such as termination sequence, origins of replication, and the like.

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. Optionally, a termination site may be included. For effective expression of the polypeptides, DNA encoding the polypeptide are linked operably through initiation codons to selected expression control regions such that expression results in the formation of the appropriate messenger RNA.

A methyltransferase or endonuclease nucleic acid can be incorporated into a vector, such as an expression vector, using standard techniques (Sambrook et al., *Molecular Cloning: A Laboratory Manual*, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as a methyltransferase or endonuclease nucleic acid), a promoter, a terminator, and other sequences and to insert them into a suitable vector are well known in the art. For example, restriction enzymes can be used to cleave the methyltransferase or endonuclease nucleic acid and the vector. Then, the compatible ends of the cleaved methyltransferase or endonuclease nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., *Molecular Cloning: A Laboratory Manual,* $2^{nd}$ ed., Cold Spring Harbor, 1989, and Bennett and Lasure, *More Gene Manipulations in Fungi*, Academic Press, San Diego, pp. 70-76, 1991, which are both hereby incorporated by reference in their entirety, particularly with respect to oligonucleotide linkers). Additionally, vectors can be constructed using known recombination techniques (e.g., Invitrogen Life Technologies, Gateway Technology).

Different types of origins of replication can be used. One, two or more origins of replication can be used. The origins of replication can be from different organisms and/or gram positive or gram negative organisms. Exemplary uses of origins of replication to practice the invention are further described in the Examples.

Clostridial Transformation Methods

Currently, methods of clostridial transformation include but are not limited to: (i) electroporation, whereby cells are exposed to high intensity electrical fields which cause the cell membrane to become transiently porus, thus allowing the entry of DNA into the cell; (ii) conjugal transfer (or conjugation) of plasmid DNA from a donor organism such as *E. coli*, whereby DNA is transferred from the donor cell to a recipient cell through cell-to-cell contact; (iii) protoplast transformation, whereby the clostridial cell wall is stripped away enzymatically or chemically to form protoplasts that incorporate plasmids into their cytoplasm when they are incubated with DNA; and/or (iv) Gene Gun (biolistic particle delivery system), whereby a small heavy metal particle is coated with plasmid DNA and subsequently propelled at high speed toward the bacterial cell. These and other transformation techniques are described in the art, see e.g., Davis et al., "Gene cloning in Clostridia" (P. Durre, P., ed. 2005) *Handbook on Clostridia*); *Current Protocols in Molecular Biology* (F. M. Ausubel et al. (eds) Chapter 9, 1987); Sambrook et al., *Molecular Cloning: A Laboratory Manual*, 2$^{nd}$ ed., Cold Spring Harbor, 1989; Campbell et al., *Current Genetics*, Vol. 16: 53-56, 1989.

Primers, oligonucleotides and polynucleotides employed in the present invention can be generated using standard techniques known in the art.

Clostridial Expression Systems

The invention provides for *Clostridium* expression systems for the production of one or more industrial bio-products (e.g., isoprene, butadiene, or ethanol). The expression system can include any combination of elements required for the production of one or more industrial bio-product. In some embodiments, the system can include one or more of: (a) a methyltransferase (e.g., a plasmid comprising pDW268 or pMCS466), (b) a shuttle plasmid (e.g., pDW280, pMCS537, pMCS200, pMCS201, pMCS444, or PMCS445), (c) an *E. coli* bacterial cell capable of interacting with a *Clostridium* bacterial cell to allow the transfer of (a) and (b); and (d) a *Clostridium* bacterial cell capable of interacting with an *Escherichia* bacterial cell such that the one or more nucleic acid(s) is expressed in the *Clostridium* bacterial cell. In some embodiments, the *E. coli* bacteria cell capable of interacting with a *Clostridium* bacterial cell is an *E. coli* S17-1 cell. In some embodiments, the *Clostridium* bacterial cell capable of interacting with an *Escherichia* bacterial cell is selected from the group of *Clostridium aceticum, Clostridium ljungdahlii, Clostridium autoethanogenum*, or *Clostridium acetobutylicum*. In some embodiments, the system provides for the expression of one or more nucleic acids of interest (e.g., nucleic acids encoding isoprene synthase or enzymes involved in the production of ethanol from acetyl-CoA).

Host Cells for Production of Industrial Bio-Products

Various types of clostridial bacterial cells can be used as host cells to produce industrial bio-products. Exemplary host cells include, but are not limited to, species of the genus *Clostridium* such as *Clostridium aceticum, Clostridium ljungdahlii, Clostridium acetobutylicum, Clostridium autoenthanogenum*. Exemplary host cells also include, but are not limited to species of the genus *Clostridium* such as *Clostridium carboxydivorans, Clostridium difficile, Clostridium botulinum, Clostridium tetani, Clostridium perfringens, Clostridium thermoaceticum* (also known as *Moorella thermoacetica*), *Clostridium aminobutyricum, Clostridium beijerinckii, Clostridium beijerinckii* NCIMB 8052, *Clostridium beijerinckii* NRRL B593, *Clostridium kluyveri, Clostridium kluyveri* DSM 555. *Clostridium novyi* NT, *Clostridium propionicum*, and *Clostridium saccharoperbutylacetonicum*.

Growth and/or Production Parameters

The clostridrial cells and compositions thereof, can be engineered to produce industrial bio-product in a fermentation system. In one embodiment the system is substantially free of oxygen. In some embodiments, the fermentation system contains a carbohydrate as the energy and/or carbon source. In some embodiments, the fermentation system contains carbohydrate and hydrogen as an energy and/or carbon source.

The compositions and methods of the invention utilize substantially oxygen-free conditions. In one aspect, substantially oxygen-free conditions are conditions under which anaerobic organisms can grow and/or produce the desired products. The conditions can refer to the fermentation system (e.g., bioreactor) in addition to the culture medium. In other aspects, substantially oxygen-free conditions refers to fermentation system wherein there is less than about any of 5, 4, 3, 2, 1, 0.5, 0.2, or 0.1% by weight of oxygen. In some aspects, the fermentation system comprises less than about 0.01% by weight of oxygen. In some aspects, the fermentation system comprises less than about 0.001% by weight of oxygen.

In some aspects, the fermentation system comprises less than about 100 ppm of oxygen. In some aspects, fermentation system comprises less than about 90, 80, 70, 60, 50, 40, 30, 20, 10, 5, 2, or 1 ppm of oxygen. In some aspects, the amount of oxygen in the fermentation system is at a level low enough that an obligate anaerobe is able to reproduce and/or produce isoprene. In some aspects, the amount of oxygen in the fermentation system is at a level low enough that a facultative anaerobe favors anaerobic fermentation over aerobic respiration.

In some aspects, steps are taken to remove oxygen from the culture medium. Oxygen can be removed by adding a catalyst and optionally adding hydrogen to the culture medium. In some aspects, the catalyst is copper.

Feedstock

Various types of feedstock can be used for the recombinant clostridial cells described herein. The feedstock can be a carbon source or syngas. Information about exemplary feedstock is provided below.

Carbon Source

Any carbon source can be used to cultivate the host cells. The term "carbon source" refers to one or more carbon-containing compounds capable of being metabolized by recombinant clostridial cells described herein. For example, the cell medium used to cultivate the recombinant clostridial cells described herein may include any carbon source suitable for maintaining the viability or growing the cells.

In some embodiments, the carbon source is a carbohydrate (such as monosaccharide, disaccharide, oligosaccharide, or polysaccharids), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the cells are cultured under limited glucose conditions. By "limited glucose conditions" is meant that the amount of glucose that is added is less than or about 105% (such as about 100%) of the amount of glucose that is consumed by the cells. In particular embodiments, the amount of glucose that is added to the culture medium is approximately the same as the amount of glucose that is consumed by the cells during a specific period of time. In some embodiments, the rate of cell growth is controlled by limiting the amount of added glucose such that the cells grow at the rate that can be supported by the amount of glucose in the cell medium. In some embodiments, glucose does not accumulate during the time the cells are cultured. In various embodiments, the cells are cultured under limited glucose conditions for greater than or about 1, 2, 3, 5, 10, 15, 20, 25, 30, 35, 40, 50, 60, or 70 hours. In various embodiments, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions may allow more favorable regulation of the cells.

In some embodiments, the cells are cultured in the presence of an excess of glucose. In particular embodiments, the amount of glucose that is added is greater than about 105% (such as about or greater than 110, 120, 150, 175, 200, 250, 300, 400, or 500%) or more of the amount of glucose that is consumed by the cells during a specific period of time. In some embodiments, glucose accumulates during the time the cells are cultured. Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.,* 53(2) 541-543, 1989, which is hereby incorporated by reference in its entirety, particularly with respect to carbon sources) and in bacteria (Hunter et. al., *Biochemistry,* 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

Syngas

Syngas can be used as a source of energy and/or carbon for any of the recombinant clostridial cells described herein. Syngas can include CO and $H_2$. In some aspects, the syngas comprises CO, $CO_2$, and $H_2$. In some aspects, the syngas further comprises $H_2O$ and/or $N_2$. For example, the syngas may comprise CO, $H_2$, and $H_2O$ (e.g., CO, $H_2$, $H_2O$ and $N_2$). The syngas may comprise CO, $H_2$, and $N_2$. The syngas may comprise CO, $CO_2$, $H_2$, and $H_2O$ (e.g., CO, $CO_2$, $H_2$, $H_2O$ and $N_2$). The syngas may comprise CO, $CO_2$, $H_2$, and $N_2$. The CO and/or $CO_2$ in the synthesis gas may be used as carbon source for cells.

In some aspects, the molar ratio of hydrogen to carbon monoxide in the syngas is about any of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, or 10.0. In some aspects, the syngas comprises about any of 10, 20, 30, 40, 50, 60, 70, 80, or 90% by volume carbon monoxide. In some aspects, the syngas comprises about any of 10, 20, 30, 40, 50, 60, 70, 80, or 90% by volume hydrogen. In some aspects, the syngas comprises about any of 10, 20, 30, 40, 50, 60, 70, 80, or 90% by volume carbon dioxide. In some aspects, the syngas comprises about any of 10, 20, 30, 40, 50, 60, 70, 80, or 90% by volume water. In some aspects, the syngas comprises about any of 10, 20, 30, 40, 50, 60, 70, 80, or 90% by volume nitrogen.

The synthesis gas of the present invention may be derived from natural or synthetic sources. In some aspects, the syngas is derived from biomass (e.g., wood, switch grass, agriculture waste, municipal waste) or carbohydrates (e.g., sugars). In other aspects, the syngas is derived from coal, petroleum, kerogen, tar sands, oil shale, natural gas, or a mixture thereof. In other aspects, the syngas is derived from rubber, such as from rubber tires. In some aspects, the syngas is derived from a mixture (e.g., blend) of biomass and coal. In some aspects, the mixture has about or at least about any of 1%, 2%, 5%, 10%, 15%, 20%, 25%, 30%, 35%, 40%, 45%, 50%, 55%, 60%, 65%, 70%, 75%, 80%, 90%, 95%, or 99% biomass. In some aspects, the mixture has about or at least about any of 1%, 2%, 5%, 10%, 15%, 20%, 25%, 30%, 35%, 40%, 45%, 50%, 55%, 60%, 65%, 70%, 75%, 80%, 90%, 95%, or 99% coal. In some aspects, the ratio of biomass to coal in the mixture is about any of 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5.

Syngas can be derived from a feedstock by a variety of processes, including methane reforming, coal liquefaction, co-firing, fermentative reactions, enzymatic reactions, and biomass gasification. Biomass gasification is accomplished by subjecting biomass to partial oxidation in a reactor at temperatures above about 700° C. in the presence of less than a stoichiometric amount of oxygen. The oxygen is introduced into the bioreactor in the form of air, pure oxygen, or steam. Gasification can occur in three main steps: 1) initial heating to dry out any moisture embedded in the biomass; 2) pyrolysis, in which the biomass is heated to 300-500° C. in the absence of oxidizing agents to yield gas, tars, oils and solid char residue; and 3) gasification of solid char, tars and gas to yield the primary components of syngas. Co-firing is accomplished by gasification of a coal/biomass mixture. The composition of the syngas, such as the identity and molar ratios of the components of the syngas, can vary depending on the feedstock from which it is derived and the method by which the feedstock is converted to syngas.

Synthesis gas can contain impurities, the nature and amount of which vary according to both the feedstock and the process used in production. Fermentations may be tolerant to some impurities, but there remains the need to remove from the syngas materials such as tars and particulates that might foul the fermentor and associated equipment. It is also advisable to remove compounds that might contaminate the isoprene product such as volatile organic compounds, acid gases, methane, benzene, toluene, ethylbenzene, xylenes, $H_2S$, COS, $CS_2$, HCl, $O_3$, organosulfur compounds, ammonia, nitrogen oxides, nitrogen-containing organic compounds, and heavy metal vapors. Removal of impurities from syngas can be achieved by one of several means, including gas scrubbing, treatment with solid-phase adsorbents, and purification using gas-permeable membranes.

Examples of other fermentation systems and culture conditions which can be used are described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/078457, and WO2010/148256, which are hereby incorporated in their entirety, particularly with respect to fermentation systems and culture conditions for clostridial bacteria.

In some aspects, the culture medium is prepared using anoxic techniques. In some aspects, the culture medium comprises one or more of $NH_4Cl$, NaCl, KCl, $KH_2PO_4$, $MgSO_4 \cdot 7H_2O$, $CaCl_2 \cdot 2H_2O$, $NaHCO_3$, yeast extract, cysteine hydrochloride, $Na_2S \cdot 9H_2O$, trace metals, and vitamins. In some aspects, the culture medium contains, per liter, about 1.0 g $NH_4Cl$, about 0.8 g NaCl, about 0.1 g KCl, about 0.1 g $KH_2PO_4$, about 0.2 g $MgSO_4 \cdot 7H_2O$, about 0.02 g $CaCl_2 \cdot 2H_2O$, about 1.0 g $NaHCO_3$, about 1.0 g yeast extract, about 0.2 g cysteine hydrochloride, about 0.2 g $Na_2S \cdot 9H_2O$, about 10 mL trace metal solution, and about 10 mL vitamin solution. In some aspects, the culture condition comprises mevalonate.

The growth conditions, carbon sources, energy sources, and culture media may be according to any of the growth conditions, carbon sources, energy sources, and culture media described in the Examples of the present disclosure.

Clostridial Expression Systems

The invention provides for *Clostridium* expression systems for the production of one or more industrial bio-products (e.g., isoprene, butadiene, or ethanol). In some embodiments, the system can include one or more of: (a) a methyltransferase (e.g., a plasmid comprising pDW268 or pMCS466), (b) a shuttle plasmid (e.g., pDW280, pMCS537, pMCS200, pMCS201, pMCS444, or PMCS445), (c) an *E. coli* bacterial cell capable of interacting with a *Clostridium* bacterial cell to allow the transfer of (a) and (b); and (d) a *Clostridium* bacterial cell capable of interacting with an *Escherichia* bacterial cell such that the one or more nucleic acid(s) is expressed in the *Clostridium* bacterial cell. In some embodiments, the *E. coli* bacteria cell capable of interacting with a *Clostridium* bacterial cell is an *E. coli* S17-1 cell. In some embodiments, the *Clostridium* bacterial cell capable of interacting with an *Escherichia* bacterial cell is selected from the group of *Clostridium aceticum, Clostridium ljungdahlii, Clostridium autoethanogenum,* or *Clostridium acetobutylicum*. In some embodiments, the system provides for the expression of one or more nucleic acids of interest (e.g., nucleic acids encoding isoprene synthase or enzymes involved in the production of ethanol from acetyl-CoA). As described herein, the clostridial restriction-modification system can be used to engineer clostridial cells so that the restriction-modification system can be bypassed. This engineering allows for using the clostridial cells to produce various industrial bio-products, including but not limited to, isoprene, butadiene, ethanol, propanediol (e.g., 1,2-propanediol, 1,3-propanediol), hydrogen, acetate, microbial fuels, non-fermentative alcohols, fatty alcohols, fatty acid esters, isoprenoid alcohols, alkenes, alkanes, terpenoids, isoprenoids, carotenoids or other C5, C10, C15, C20, C25, C30, C35, or C40 product. The production of these industrial bio-products is described in further detail below and herein.

Methods of Using Engineered Clostridial Bacteria for Production of Industrial Bio-Products As described herein, the clostridial restriction-modification system can be used to engineer clostridial cells so that the restriction-modification system can be bypassed. This engineering allows for using the clostridial cells to produce various industrial bio-products, including but not limited to, isoprene, butadiene, ethanol, propanediol (e.g., 1,2-propanediol, 1,3-propanediol), hydrogen, acetate, microbial fuels, non-fermentative alcohols, fatty alcohols, fatty acid esters, isoprenoid alcohols, alkenes, alkanes, terpenoids, isoprenoids, carotenoids or other C5, C10, C15, C20, C25, C30, C35, or C40 product. The production of these industrial bio-products is described in further detail below and herein.

Isoprene Production

In some embodiments, the compositions and methods disclosed herein can be used to transform clostridial bacteria that contain one or more pathways for the production of isoprene (e.g., clostridial bacteria that contain the pathways illustrated in FIG. 41 to FIG. 45) with one or more heterologous polynucleotides encoding one or more isoprene pathway enzymes expressed in a sufficient amount to produce isoprene.

Exemplary Isoprene Synthase Polypeptides and Nucleic Acids

In some embodiments, the compositions and methods disclosed herein can be used to transform clostridial bacteria with polynucleotides encoding an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo (e.g., as described in Example 1 of U.S. Pat. No. 420,360 B2, which is incorporated herein in its entirety, particularly with respect to methods for assessing isoprene synthase activity). Isoprene synthase polypeptide activity in cell extracts can be measured, for example, as described in Silver et al., *J. Biol. Chem.* 270:13010-13016, 1995 and references therein, which are each hereby incorporated by reference in their entireties, particularly with respect to assays for isoprene synthase polypeptide activity.

In some embodiments, the isoprene synthase polypeptide or nucleic acid is from the family Fabaceae, such as the Faboideae subfamily. In some embodiments, the isoprene synthase polypeptide or nucleic acid is a naturally-occurring polypeptide or nucleic acid from *Pueraria montana* (kudzu) (Sharkey et al., *Plant Physiology* 137: 700-712, 2005), *Pueraria lobata*, poplar (such as *Populus alba×tremula* CAC35696) Miller et al., Planta 213: 483-487, 2001) aspen (such as *Populus tremuloides*) Silver et al, JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY1 82241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is not a naturally-occurring polypeptide or nucleic acid from poplar (such as *Populus alba×tremula* CAC35696).

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

Exemplary DXS Polypeptides and Nucleic Acids

In some embodiments, the compositions and methods disclosed herein can be used to transform clostridial bacteria with polynucleotides encoding 1-deoxy-D-xylulose-5-phosphate synthase (DXS) polypeptides. DSX polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo (see, e.g., U.S. Pat. No. 8,420,360 B2, which is hereby incorporated herein in its entirety, particularly with respect to methods of assessing DXS polypeptide activity). Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

In some embodiments, the compositions and methods disclosed herein can be used to transform clostridial bacteria with polynucleotides encoding isopentenyl diphosphate isomerase polypeptides (isopentenyl-diphosphate delta-isomerase or IDI). IDI catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods can be used to determine whether a polypeptide has IDI polypeptide activity by measuring the ability of the polypeptide to interconvert IPP and DMAPP in vitro, in a cell extract, or in vivo (see, e.g., U.S. Pat. No. 8,420,360 B2, which is hereby incorporated by reference in its entirety, particularly with respect to assays for IDI activity). Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

In some embodiments, the compositions and methods disclosed herein can be used to transform clostridial bacteria with polynucleotides encoding MVA pathway polypeptides. MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo. [0213]3-hydroxy-3-methylglutaryl-CoA synthase (HMG-CoA synthase or HMGS) polypeptides convert acetoacetyl-CoA into S-hydroxy-S-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptides phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonte decarboxylase (MVD or DPMDC) polypeptides convert mevalonate-5-diphosphate into isopentenyl diphosphate polypeptides (IPP). Standard methods (such as those described) can be used to determine whether a polypeptide has MVD polypeptide activity by measuring the ability of the polypeptide to convert mevalonate-5-diphosphate into IPP in vitro, in a cell extract, or in vivo.

In some embodiments, the compositions and methods described herein can be used to transform clostridial bacteria that have been engineered to produce isoprene from syngas and/or from carbohydrates or mixtures thereof.

Method of Using Engineered Clostridial Cells for Butadiene Production

Figure 46:
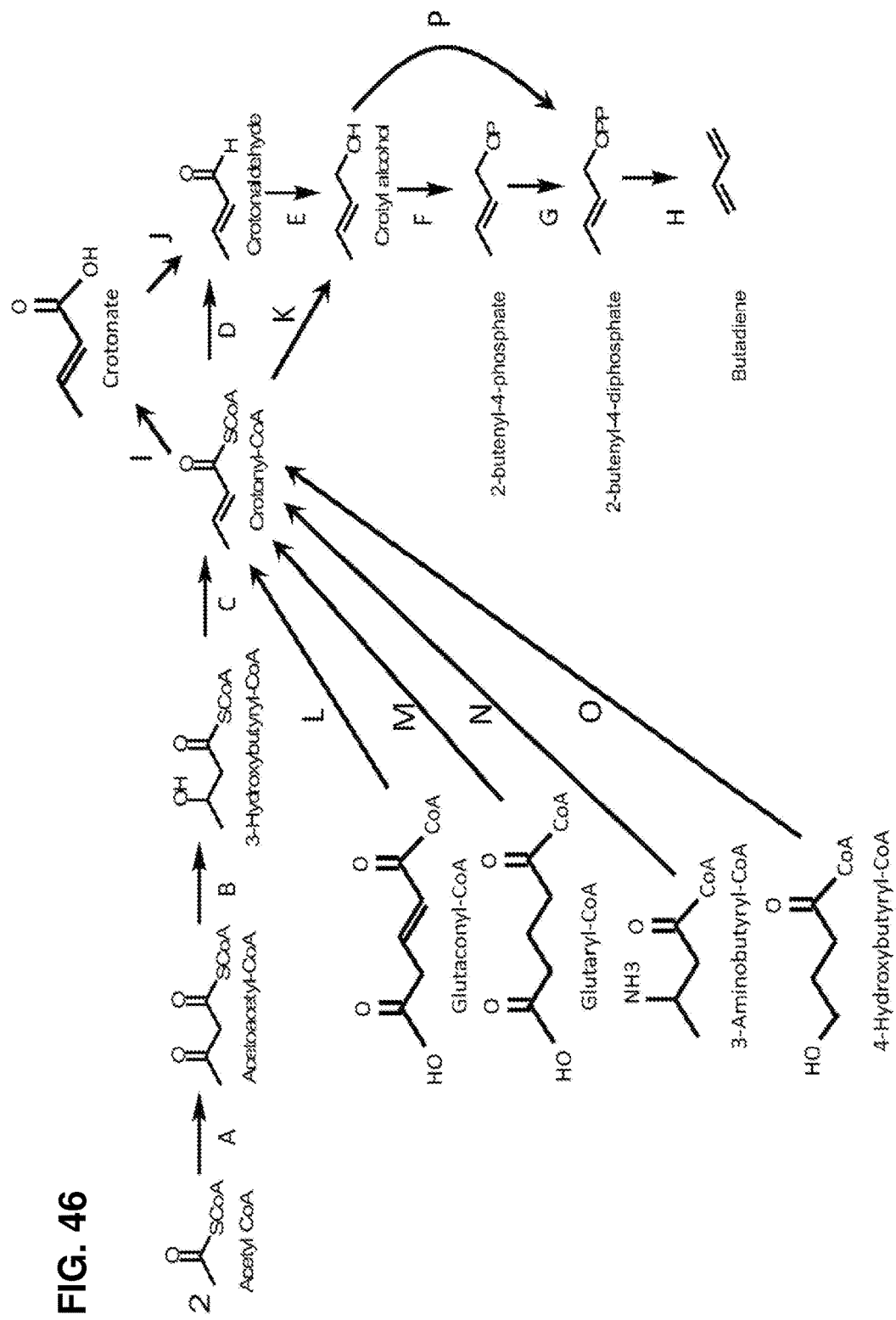
FIG. 46 shows exemplary pathways for production of butadiene from acetyl-CoA, glutaconyl-CoA, glutaryl-CoA, 3-aminobutyryl-CoA or 4-hydroxybutyryl-CoA via crotyl alcohol. Enzymes for transformation of the identified substrates to products include: A. acetyl-CoA:acetyl-CoA acyltransferase, B. acetoacetyl-CoA reductase, C. 3-hydroxybutyryl-CoA dehydratase, D. crotonyl-CoA reductase (aldehyde forming), E. crotonaldehyde reductase (alcohol forming), F. crotyl alcohol kinase, G. 2-butenyl-4-phosphate kinase, H. butadiene synthase, I. crotonyl-CoA hydrolase, synthetase, transferase, J. crotonate reductase, K. crotonyl-CoA reductase (alcohol forming), L. glutaconyl-CoA decarboxylase, M. glutaryl-CoA dehydrogenase, N. 3-aminobutyryl-CoA deaminase, O. 4-hydroxybutyryl-CoA dehydratase, P. crotyl alcohol diphosphokinase.
Figure 47:
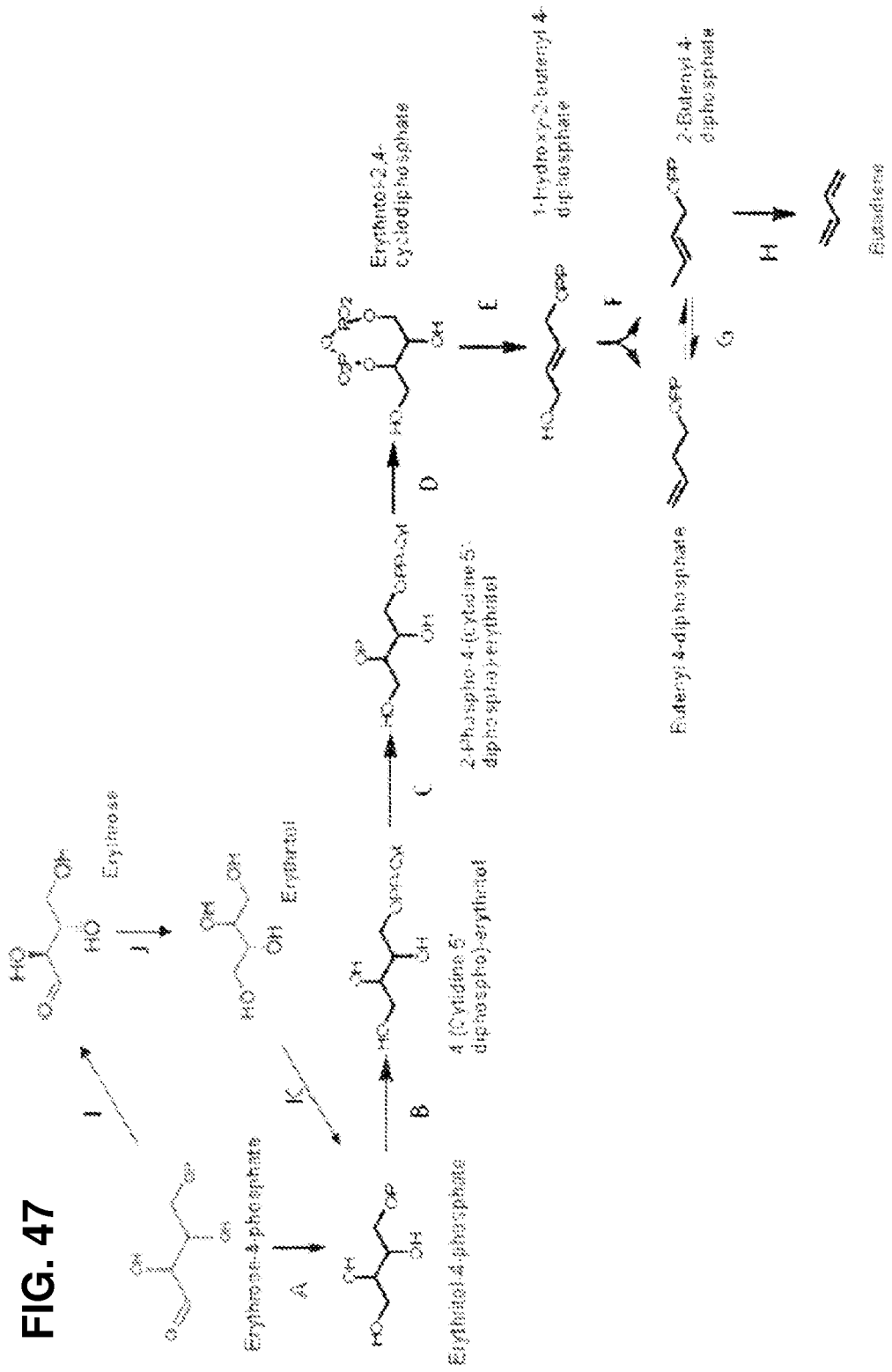
FIG. 47 shows exemplary pathways for production of butadiene from erythrose-4-phosphate. Enzymes for transformation of the identified substrates to products include: A. Erythrose-4-phosphate reductase, B. Erythritol-4-phospate cytidylyltransferase, C. 4-(cytidine 5'-diphospho)-erythritol kinase, D. Erythritol 2,4-cyclodiphosphate synthase, E. 1-Hydroxy-2-butenyl 4-diphosphate synthase, F. 1-Hydroxy-2-butenyl 4-diphosphate reductase, G. Butenyl 4-diphosphate isomerase, H. Butadiene synthase I. Erythrose-4-phosphate kinase, J. Erythrose reductase, K. Erythritol kinase.
Figure 48:
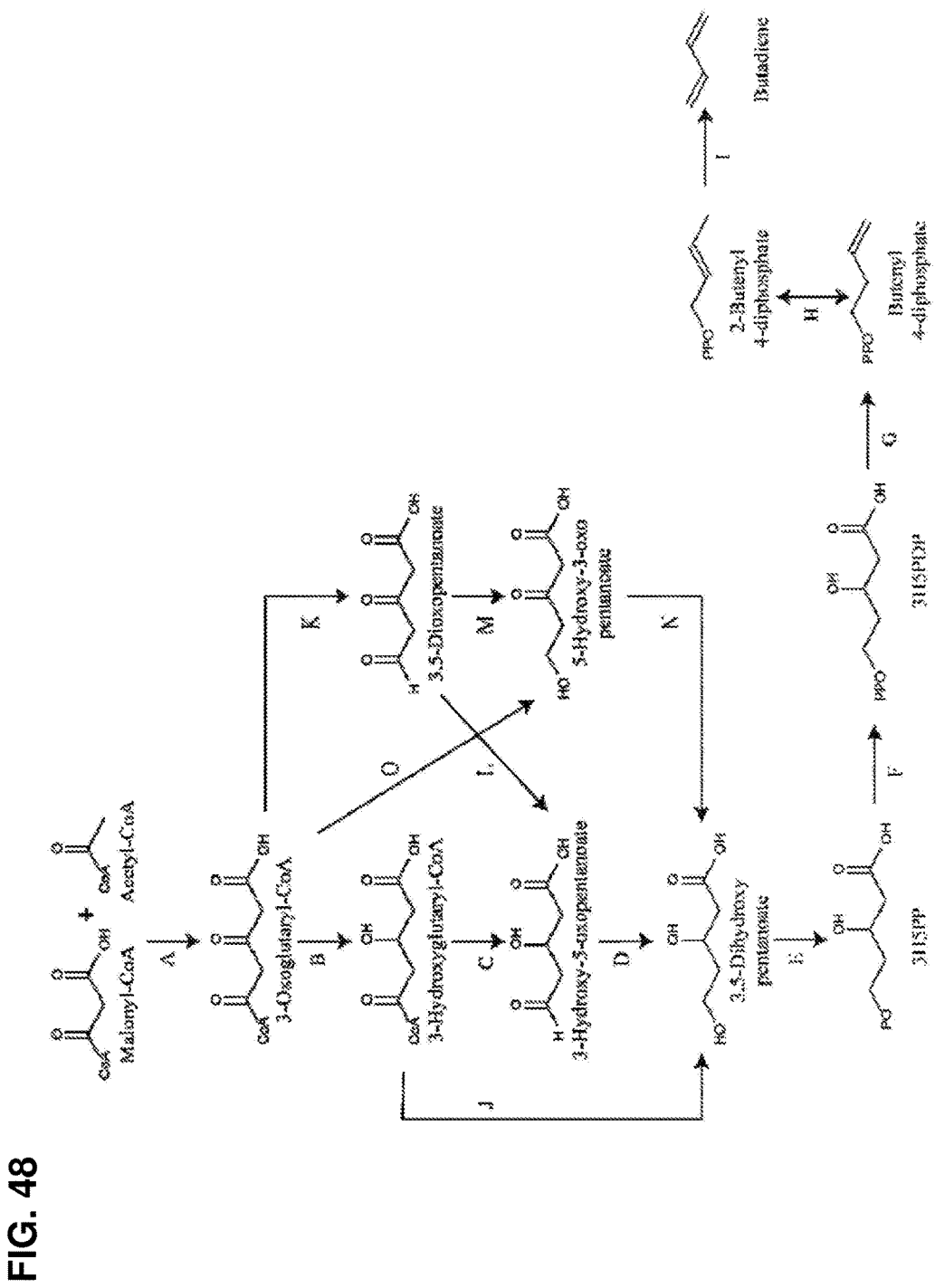
FIG. 48 shows an exemplary pathway for production of butadiene from malonyl-CoA plus acetyl-CoA. Enzymes for transformation of the identified substrates to products include: A. malonyl-CoA:acetyl-CoA acyltransferase, B. 3-oxoglutaryl-CoA reductase (ketone-reducing), C. 3-hydroxyglutaryl-CoA reductase (aldehyde forming), D. 3-hydroxy-5-oxopentanoate reductase, E. 3,5-dihydroxypentanoate kinase, F. 3H5PP kinase, G. 3H5PDP decarboxylase, H. butenyl 4-diphosphate isomerase, I. butadiene synthase, J. 3-hydroxyglutaryl-CoA reductase (alcohol forming), K. 3-oxoglutaryl-CoA reductase (aldehyde forming), L. 3, 5-dioxopentanoate reductase (ketone reducing), M. 3,5-dioxopentanoate reductase (aldehyde reducing), N. 5-hydroxy-3-oxopentanoate reductase, O. 3-oxo-glutaryl-CoA reductase (CoA reducing and alcohol forming). Compound abbreviations include: 3H5PP=3-Hydroxy-5-phosphonatooxypentanoate and 3H5PDP=3-Hydroxy-5-[hydroxy(phosphonooxy)phosphoryl]oxy pentanoate.

In some embodiments, the compositions and methods disclosed herein can be used to transform clostridial bacteria that contain one or more pathways for the production of butadiene (shown in FIG. 46 to FIG. 48) with one or more heterologous polynucleotides encoding one or more butadiene pathway enzymes expressed in a sufficient amount to produce butadiene. The butadiene pathway includes an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase, a butadiene synthase, a crotonyl-CoA hydrolase, synthetase, or transferase, a crotonate reductase, a crotonyl-CoA reductase (alcohol forming), a glutaconyl-CoA decarboxylase, a glutaryl-CoA dehydrogenase, an 3-aminobutyryl-CoA deaminase, a 4-hydroxybutyryl-CoA dehydratase or a crotyl alcohol diphosphokinase. The production of butadiene from bacteria is described in WO 2011/140171 A2, hereby incorporated by reference in its entirety, particularly with respect to the pathways for production of butadiene from acetyl-CoA (FIG. 46), from erythrose-4-phosphate (FIG. 47), and from malonyl-CoA plus acetyl-CoA (FIG. 48).

Method of Using Engineered Clostridial Cells for Ethanol Production

Several bacteria in the genus *Clostridium* are known to produce ethanol through the acetyl-CoA pathway, which can utilize both carbon monoxide and hydrogen as carbon sources and as energy sources. The production of ethanol from clostridial bacteria is described in Kopke et al., 2011, Fermentative production of ethanol from carbon monoxide, *Current Opinion in Biotechnology*, Vol. 22:320-323, and in Wilkins et al., 2011, Microbial production of ethanol from carbon monoxide, *Current Opinion in Biotechnology*, Vol. 22:326-330, both of which are hereby incorporated in their entirety, particularly with respect to their discussion of the pathway for the production of ethanol from acetyl-CoA in clostridial bacteria.

In some embodiments, the compositions and methods disclosed herein can be used to transform clostridial bacteria that contain the ethanol pathway (including, but not limited to *Clostridium aceticum*, *Clostridium ljungdahli*, *Clostridium acetobutylicum*, or *Clostridium autoethanogenum*) with one or more heterologous polynucleotides encoding one or more ethanol pathway enzymes expressed in sufficient amount to produce ethanol. In clostridial bacteria, the pathway for production of ethanol from acetyl-CoA includes the aldehyde dehydrogenase enzyme and the alcohol dehydrogenase enzyme (see, e.g., FIG. 41).

Method of Using Engineered Clostridial Cells for Production of Other Industrial Bio-Products In some aspects of the invention, any of the methods described herein may be used to produce products other than isoprene, butadiene, and ethanol. Such products may be excreted, secreted, or intracellular products. Any one of the methods described herein may be used to produce isoprene and/or one or more of the other products. The products described herein may be, for example, propanediol (e.g., 1,2-propanediol, 1,3-propanediol), hydrogen, acetate, or microbial fuels. Exemplary microbial fuels are fermentative alcohols (e.g., ethanol or butanol), non-fermentative alcohols (e.g., isobutanol, methyl butanol, 1-propanol, 1-butanol, methyl pentanol, or 1-hexanol), fatty alcohols, fatty acid esters, isoprenoid alcohols, alkenes, and alkanes. The products described herein may also be a terpenoid, isoprenoid (e.g., farnesene), or carotenoid or other C5, C10, C15, C20, C25, C30, C35, or C40 product.

In some aspects, the terpenoids are selected from the group consisting of hemiterpenoids, monoterpenoids, sesquiterpenoids, diterpenoids, sesterterpenoids, triterpenoids, tetraterpenoids, and higher polyterpenoids. In some aspects, the hemiterpenoid is prenol, isoprenol, or isovaleric acid. In some aspects, the monoterpenoid is geranyl pyrophosphate, eucalyptol, limonene, or pinene. In some aspects, the sesquiterpenoid is farnesyl pyrophosphate, artemisinin, or bisabolol. In some aspects, the diterpenoid is geranylgeranyl pyrophosphate, retinol, retinal, phytol, taxol, forskolin, or aphidicolin. In some aspects, the triterpenoid is squalene or lanosterol. In some aspects, the tetraterpenoid is lycopene or carotene. In some aspects, the carotenoids are selected from the group consisting of xanthophylls and carotenes. In some aspects, the xanthophyll is lutein or zeaxanthin. In some aspects, the carotene is α-carotene, β-carotene, γ-carotene, β-cryptoxanthin or lycopene.

The products described herein may be derived from Acetyl-CoA produced via syngas fermentation or via fermentation of other carbon sources such as fructose. In some aspects, the cell is grown under conditions suitable for the production of the product(s) other than isoprene.

The products described herein may be naturally produced by the cell. In some aspects, the cells naturally produce one or more products including excreted, secreted, or intracellular products. In some aspects, the cells naturally produce ethanol, propanediol, hydrogen, or acetate. In some aspects, production of a naturally occurring product is increased relative to wild-type cells. Any method known in the art to increase production of a metabolic cellular product may be used to increase the production of a naturally occurring product. In some aspects, the nucleic acid encoding all or a part of the pathway for production of a product described herein is operably linked to a promoter such as a strong promoter. In some aspects, the nucleic acid encoding all or a part of the pathway for production of a product described herein is operably linked to a constitutive promoter. In some aspects, the cell is engineered to comprise additional copies of an endogenous nucleic acid encoding a polypeptide for the production of a product described herein. In some aspects, the product described herein is not naturally produced by the cell. In some aspects, the cell comprises one or more heterologous nucleic acids encoding one or more polypeptides for the production of a product described herein.

Under normal growth conditions, acetogens produce acetate and ethanol. Acetate is produced in a 2-step reaction in which acetyl-CoA is firstly converted to acetyl-phosphate by phosphotransacetylase (pta), then acetyl-phosphate is dephosphorylated by acetate kinase (ack) to form acetate. Ethanol is formed by a two-step process in which acetyl-CoA is converted to acetaldehyde and then to ethanol by the multifunctional enzyme alcohol dehydropgenase (adhE). The production of acetate and ethanol may not be desirable in isoprene-producing cells, as it fluxes carbon away from isoprene and ultimately results in decreased yield of isoprene. Thus, some or all of the genes coding for phosphotransacetylase (pta), acetate kinase (ack), and alcohol dehydrogenase (adhE) may be disrupted or the expressions thereof are reduced in anaerobic cells for the purpose of redirecting carbon flux away from acetate and/or ethanol and increasing the production of isoprene.

In some aspects, the cells are deficient in at least one polypeptide involved in production of acetate, ethanol, succinate, and/or glycerol. In some aspects, one or more pathways for production of a metabolite other than isoprene (e.g., lactate, acetate, ethanol (or other alcohol(s)), succinate, or glycerol) are blocked, for example, the production of a metabolite other than isoprene may be reduced by at least about any of 10%, 20%, 30%, 40%, 50%, 60%, 70%, 80%, 90%, or 95%. In some aspects, one or more of the pathways for production of lactate, acetate, ethanol, succinate, or glycerol is blocked, for example, the production for lactate, acetate, ethanol, succinate, and/or glycerol is reduced by at least about any of 10%, 20%, 30%, 40%, 50%, 60%, 70%, 80%, 90%, or 95%. In some aspects, the cells are deficient in at least one polypeptide in pathways(s) of producing acetate, ethanol, succinate, and/or glycerol. Polypeptides in pathways(s) of producing acetate, ethanol, succinate, and/or glycerol may have reduced activities or the expressions thereof are reduced. Nucleic acids encoding polypeptides in pathways(s) of producing acetate, ethanol, succinate, and/or glycerol may be disrupted. The polypeptides involved in various pathways (e.g., pathways for producing ethanol and/or acetate) are known to one skilled in the art, including, for example, those described in Misoph et al. 1996, *Journal of Bacteriology*, 178(11):3140-45, the contents of which are expressly incorporated by reference in its entirety with respect to the polypeptides involved in pathways of producing succinate, acetate, lactate, and/or ethanol.

In some aspects, the cells are deficient in pta. In some aspects, the cells are deficient in ack. In some aspects, the cells are deficient in adhE. In some aspects, the cells are deficient in pta, ack, and/or adhE. In some aspects, the expressions of phosphotransacetylase, acetate kinase, and/or alcohol dehydrogenase are reduced. In some aspects, the activities of phosphotransacetylase, acetate kinase, and/or alcohol dehydrogenase are reduced. In some aspects, the cells are deficient in polypeptide(s) having similar activities as phosphotransacetylase, acetate kinase, and/or alcohol dehydrogenase. The expression of pta, ack, adhE, and/or polypeptide(s) having similar activities as phosphotransacetylase, acetate kinase, and/or alcohol dehydrogenase may be reduced by any of the methods known to one skilled in the art, for example, the expression may be reduced by antisense RNA(s) (e.g., antisense RNA driven by any of the promoters described herein such as any of the inducible promoters). In some aspects, the antisense RNA(s) are operably linked to a suitable promoter such as any of the promoters described herein including inducible promoters.

In some aspects, isoprene and product(s) other than isoprene are both recovered from the gas phase. In some aspects, isoprene is recovered from the gas phase (e.g. from the fermentation of gas), and the other product(s) are recovered from the liquid phase (e.g. from the cell broth).

Bioreactors

A variety of different types of reactors can be used for production of isoprene or other industrial bio-products. In some embodiments, a carbohydrate is used as energy and/or carbon source. In some embodiments, a carbohydrate and hydrogen are used as energy and/or carbon source. In some embodiments, synthesis gas is used as energy and/or carbon source. There are a large number of different types of fermentation processes that are used commercially. Bioreactors for use in the present invention should be amenable to anaerobic conditions. The bioreactor can be designed to optimize the retention time of the cells, the residence time of liquid, and the sparging rate of syngas.

In various aspects, the cells are grown using any known mode of fermentation, such as batch, fed-batch, continuous, or continuous with recycle processes. In some aspects, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some aspects, cells in log phase are responsible for the bulk of the isoprene production. In some aspects, cells in stationary phase produce isoprene.

In some aspects, a variation on the standard batch system is used, such as the Fed-Batch system. Fed-Batch fermentation processes comprise a typical batch system with the exception that the carbon source (e.g. syngas, glucose, fructose) is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., syngas, glucose, fructose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: A Textbook of Industrial Microbiology, Second Edition (1989) Sinauer Associates, Inc.

In some aspects, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: A Textbook of Industrial Microbiology, Second Edition (1989) Sinauer Associates, Inc., which is hereby incorporated by reference in its entirety, particularly with respect to cell culture and fermentation conditions.

A variation of the continuous fermentation method is the continuous with recycle method. This system is similar to the continuous bioreactor, with the difference being that cells removed with the liquid content are returned to the bioreactor by means of a cellmass separation device. Crossfiltration units, centrifuges, settling tanks, wood chips, hydrogels, and/or hollow fibers are used for cellmass separation or retention. This process is typically used to increase the productivity of the continuous bioreactor system, and may be particularly useful for anaerobes, which may grow more slowly and in lower concentrations than aerobes.

In one aspect, a membrane bioreactor can be used for the growth and/or fermentation of the anaerobic cells described herein, in particular, if the cells are expected to grow slowly. A membrane filter, such as a crossflow filter or a tangential flow filter, can be operated jointly with a liquid fermentation bioreactor that produces isoprene gas. Such a membrane bioreactor can enhance fermentative production of isoprene gas by combining fermentation with recycling of select broth components that would otherwise be discarded. The MBR filters fermentation broth and returns the non-permeating component (filter "retentate") to the reactor, effectively increasing reactor concentration of cells, cell debris, and other broth solids, while maintaining specific productivity of the cells. This substantially improves titer, total production, and volumetric productivity of isoprene, leading to lower capital and operating costs.

The liquid filtrate (or permeate) is not returned to the reactor and thus provides a beneficial reduction in reactor volume, similar to collecting a broth draw-off. However, unlike a broth draw-off, the collected permeate is a clarified liquid that can be easily sterilized by filtration after storage in an ordinary vessel. Thus, the permeate can be readily reused as a nutrient and/or water recycle source. A permeate, which contains soluble spent medium, may be added to the same or another fermentation to enhance isoprene production.

Recovery Methods

Any of the methods described herein further include recovering the industrial bio-product (e.g., isoprene, butandiene, ethanol, etc.). For example, the isoprene produced using the compositions and methods of the invention can be recovered using standard techniques, such as gas stripping, membrane enhanced separation, fractionation, adsorption/desorption, evaporation, thermal or vacuum desorption of isoprene from a solid phase, or extraction of isoprene immobilized or absorbed to a solid phase with a solvent (see, for example, U.S. Pat. Nos. 4,703,007 and 4,570,029). In one aspect, the isoprene is recovered by absorption stripping (see, e.g., International Patent Application No. PCT/US2010/060552 (WO 2011/075534)). In particular aspects, extractive distillation with an alcohol (such as ethanol, methanol, propanol, or a combination thereof) is used to recover the isoprene. In some aspects, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some aspects, membrane enrichment of a dilute isoprene vapor stream above the dew point of the vapor resulting in the condensation of liquid isoprene. In some aspects, the isoprene is compressed and condensed.

The recovery of isoprene may involve one step or multiple steps. In some aspects, the removal of isoprene vapor from the fermentation off-gas and the conversion of isoprene to a liquid phase are performed simultaneously. For example, isoprene can be directly condensed from the off-gas stream to form a liquid. In some aspects, the removal of isoprene vapor from the fermentation off-gas and the conversion of isoprene to a liquid phase are performed sequentially. For example, isoprene may be adsorbed to a solid phase and then extracted from the solid phase with a solvent.

In some aspects, any of the methods described herein further include a step of recovering the compounds produced. In some aspects, any of the methods described herein further include a step of recovering the isoprene. In some aspects, the isoprene is recovered by absorption stripping (See, e.g., U.S. Publ. No. 2011/0178261).

Isoprene compositions recovered from fermentations in anaerobic organisms may contain impurities. The identities and levels of impurities in an isoprene composition can be analyzed by standard methods, such as GC/MS, GC/FID, and $^1$H NMR. An impurity can be of microbial origin, or it can be a contaminant in the synthesis gas feed or other fermentation raw materials.

In some aspects, the isoprene composition recovered from fermentation in an anaerobic organism comprises one or more of the following impurities: hydrogen sulfide, carbonyl sulfide, carbon disulfide, ethanol, acetone, methanol, acetaldehyde, methacrolein, methyl vinyl ketone, 2-methyl-2-vinyloxirane, cis- and trans-3-methyl-1,3-pentadiene, a C5 prenyl alcohol (such as 3-methyl-3-buten-1-ol or 3-methyl-2-buten-1-ol), 2-heptanone, 6-methyl-5-hepten-2-one, 2,4,5-trimethylpyridine, 2,3,5-trimethylpyrazine, citronellal, methanethiol, ethanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, (E,E)-3,7,11-trimethyl-1,3,6,10-dodecatetraene and (E)-7,11-dimethyl-3-methylene-1,6,10-dodecatriene, 3-hexen-1-ol, 3-hexen-1-yl acetate, limonene, geraniol (trans-3,7-dimethyl-2,6-octadien-1-ol), citronellol (3,7-dimethyl-6-octen-1-ol), (E)-3-methyl-1,3-pentadiene, (Z)-3-methyl-1,3-pentadiene, thiol(s), mono and disulfide(s), or gas(es) such as $CS_2$ and COS. The isoprene composition recovered from syngas fermentation in an anaerobic organism may comprise one or more of the components described in Rimbault A et al. 1986, J of Chromatography, 375:11-25, the contents of which are expressly incorporated herein by reference in its entirety with respect to various components in gases of *Clostridium* cultures.

In some aspects, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some aspects, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some aspects, the isoprene is at least about 20%, by weight, free from other components that are present when the isoprene is produced. In various aspects, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some aspects, at least a portion of the gas phase remaining after one or more recovery steps for the removal of isoprene is recycled by introducing the gas phase into a cell culture system (such as a fermentor) for the production of isoprene.

In some embodiments, recovery of industrial enzymes can use any method known to one of skill in the art and/or any of the exemplary protocols that are disclosed in U.S. Appl. Pub. Nos. 2009/0311764, 2009/0275080, 2009/0252828, 2009/0226569, 2007/0259397 and U.S. Pat. Nos. 7,629,451; 7,604,974; 7,541,026; and 7,527,959 and for neutraceuticals (see, e.g., U.S. Pat. No. 7,622,290), and for antimicrobials (see, e.g., U.S. Appl Pub. No. 2009/0275103).

The following examples have been provided for illustrative purposes only and are not intended to limit the invention.

EXAMPLES

Example 1: Methods and Materials

The bacterial strains used in the Examples described herein are listed in Table 1 below.

TABLE 1

| Bacterial strains | | |
|---|---|---|
| Strain | Description | Reference/Source |
| *Escherichia coli* | | |
| TOP10 | mcrA, ΔmcrBC, recA1, StrR | Life Technologies, Carlsbad CA |
| XL1-Blue | Δ(mcrA)183 Δ(mcrCB-hsdSMR-mrr)171 endA1 supE44 thi-1 recA1 gyrA96 relA1 lac (F'proAB lacI$^q$ ZΔM15 Tn10 (tetR)) | Stratagene, La Jolla CA |
| S17-1 | Tp$^R$, Sm$^R$, recA$^-$, thi, pro, hsdR–, hsdM+ | American Type Culture Collection, strain 47055 |
| Anaerobes | ATCC accession number | |
| *Clostridium acetobutylicum* | ATCC 824 | American Type Culture Collection |
| *Clostridium ljungdahlii* | ATCC 55383 | American Type Culture Collection |
| *Clostridium aceticum* | ATCC 35044 | American Type Culture Collection |
| *Clostridium autoethanogenum* | DSM 10061 | American Type Culture Collection |

All plasmids were constructed in *E. coli* TOP10 cells and are listed in Table 2.

TABLE 2

Figure 10A:
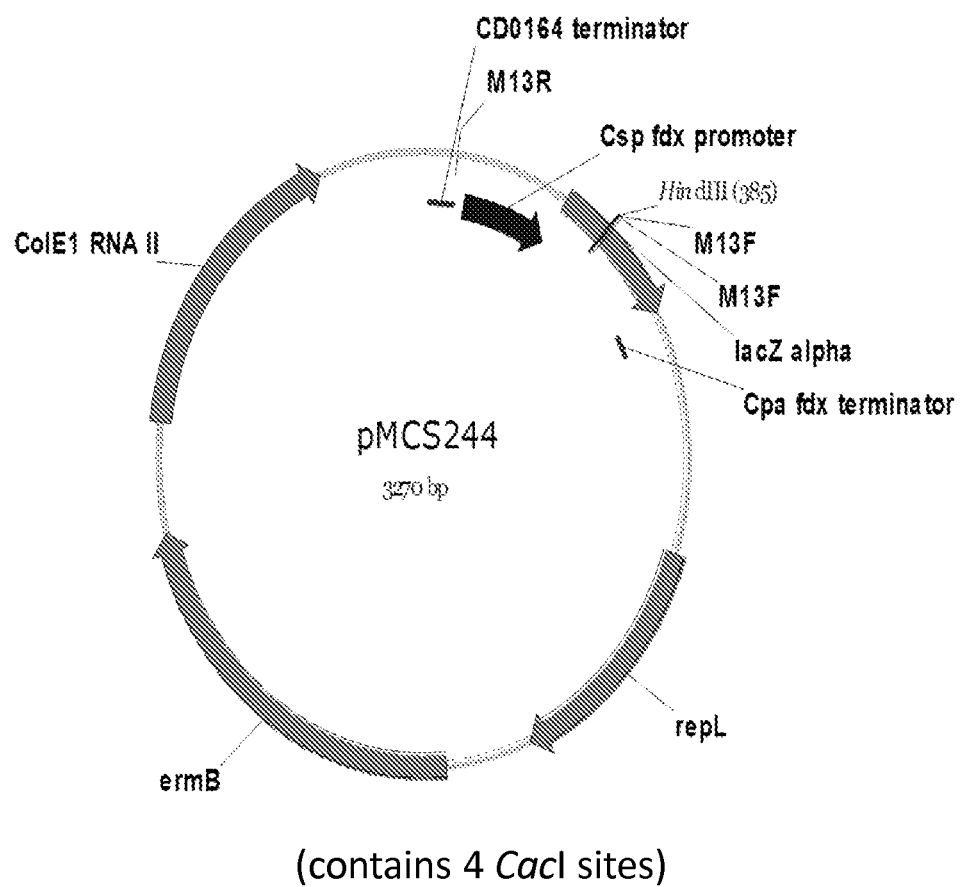
FIG. 10A shows the plasmid map for pMCS244.
Figure 10B:
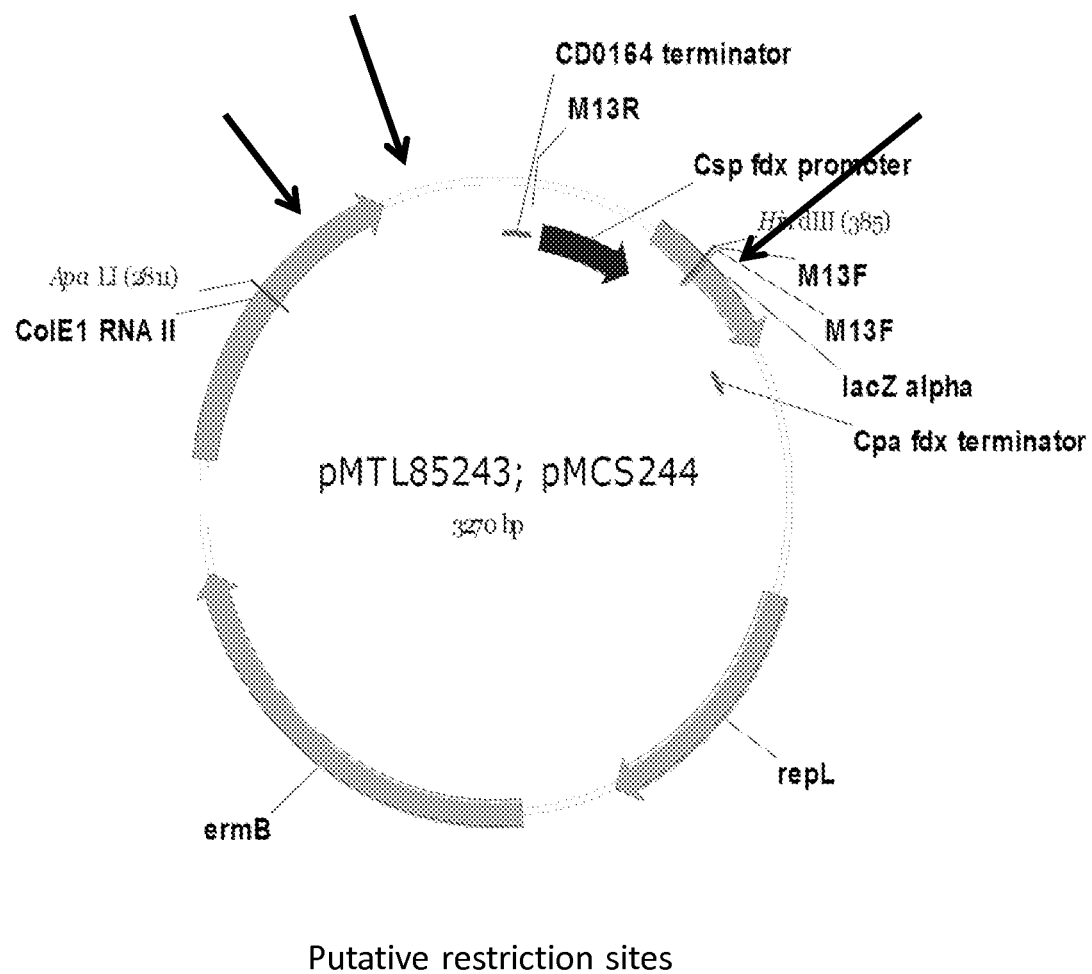
FIG. 10B shows the plasmid map of pMCS244 with arrows indicating the approximate locations of its four CacI restriction sites (marked with bold arrows). Two CacI sites in the ColE1 RNA 11 region of the plasmid are located close together, and are represented by only one arrow.
Figure 14:
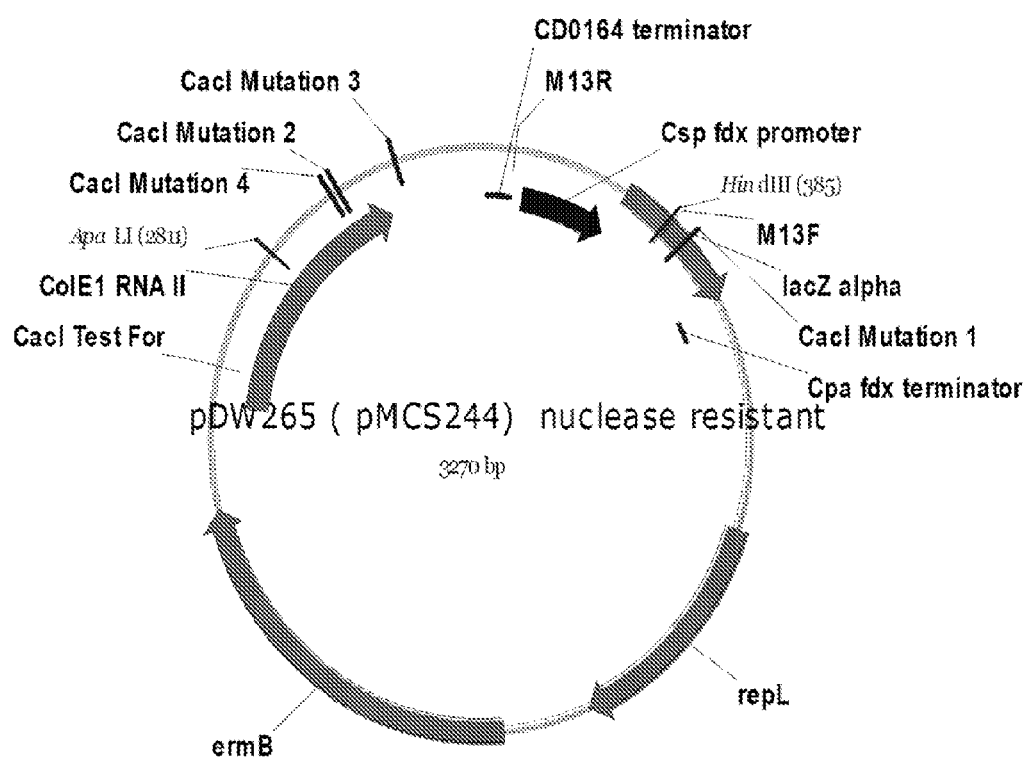
FIG. 14 shows the plasmid map for pDW265, with the locations of the four mutated CacI DNA recognition sites indicated therein.

| Plasmids | | |
|---|---|---|
| Plasmid Identifier | Features | Described In |
| pMCS244 | ermB, ColE1 RNA II, lacZ alpha, repL (has 4 naturally occurring CCWGG sites) | FIG. 10A-B and FIG. 11 |
| pDW265 | ermB, ColE1 RNA II, lacZ alpha, repL (all 4 naturally occurring CCWGG sites mutated) | FIG. 14 and FIG. 15 |

TABLE 2-continued

Plasmids

Figure 6:
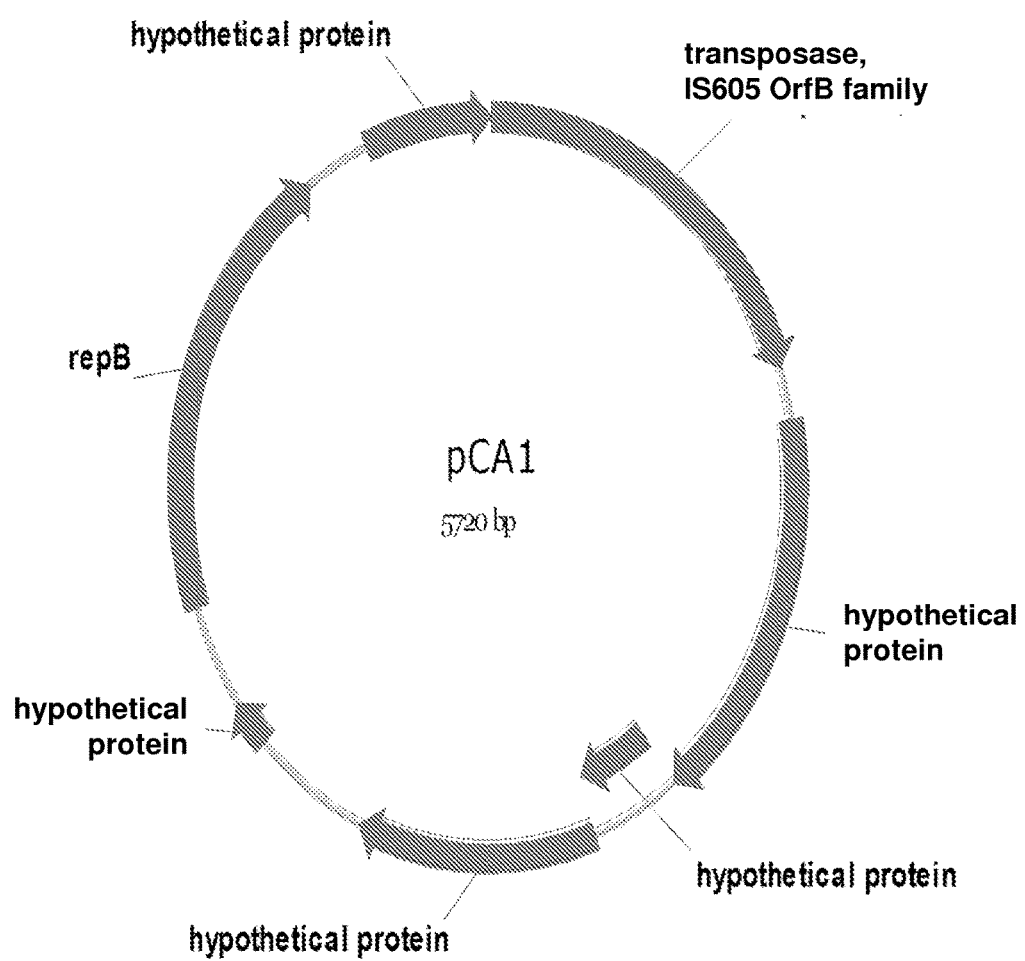
FIG. 6 shows the plasmid map for pCA1.
Figure 8:
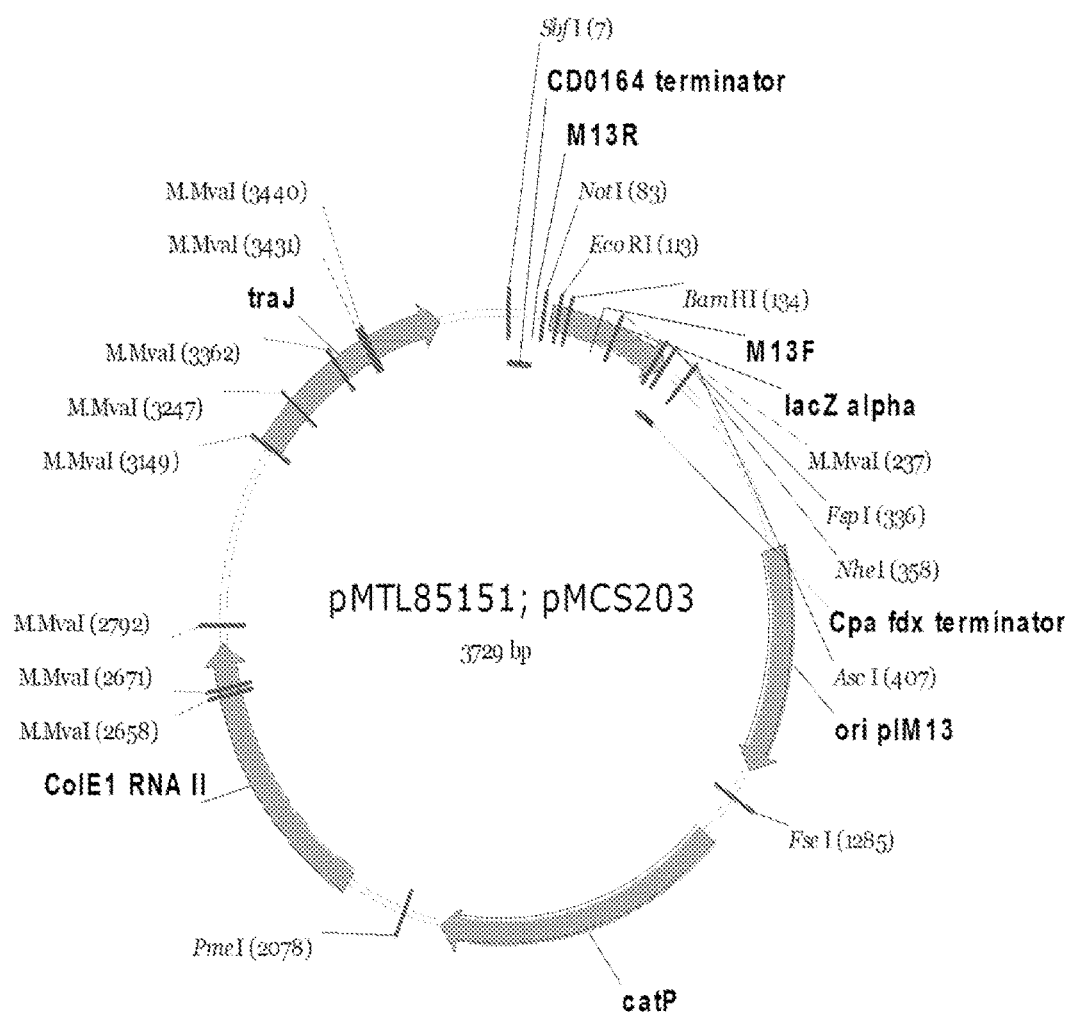
FIG. 8 shows the plasmid map for pMCS203.
Figure 30:
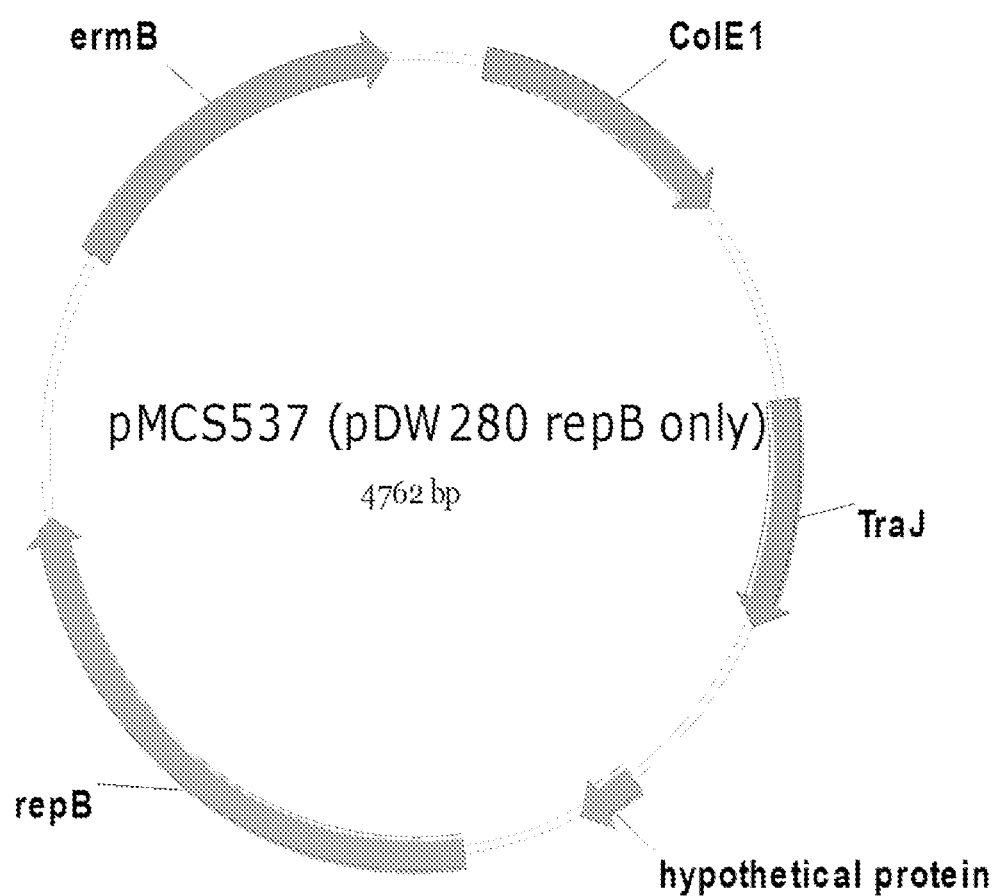
FIG. 30 shows a plasmid map for pMCS537.
Figure 32:
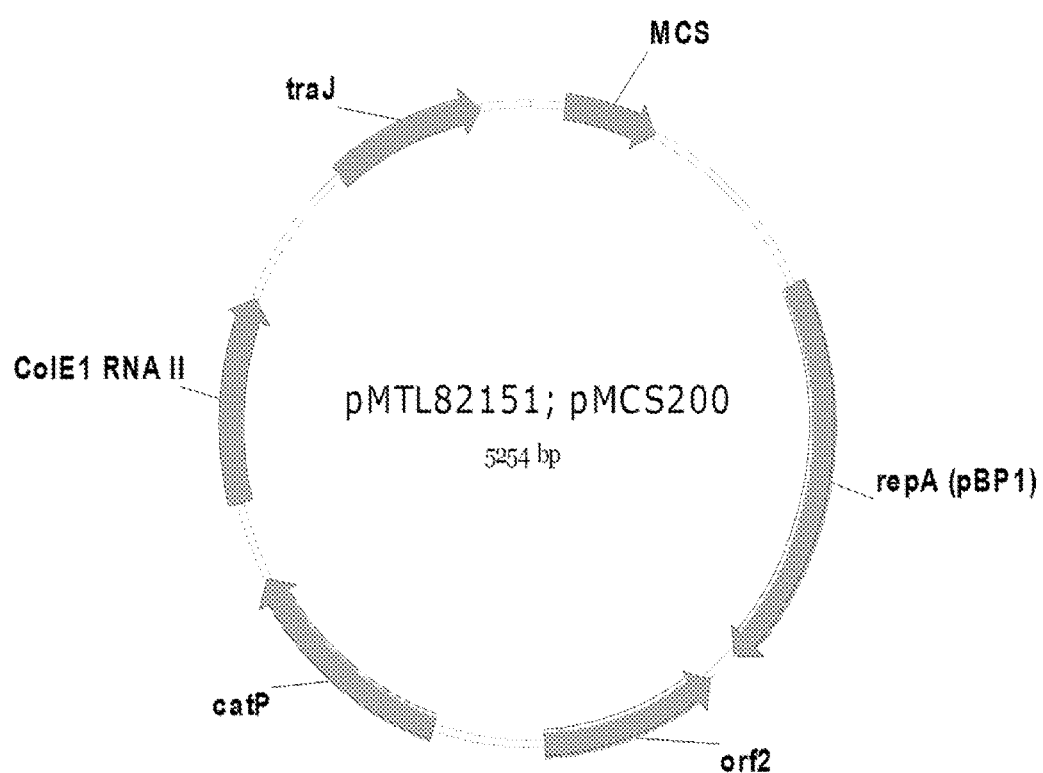
FIG. 32 shows the plasmid map for pMCS200, also referred to as pMTL82151.
Figure 34:
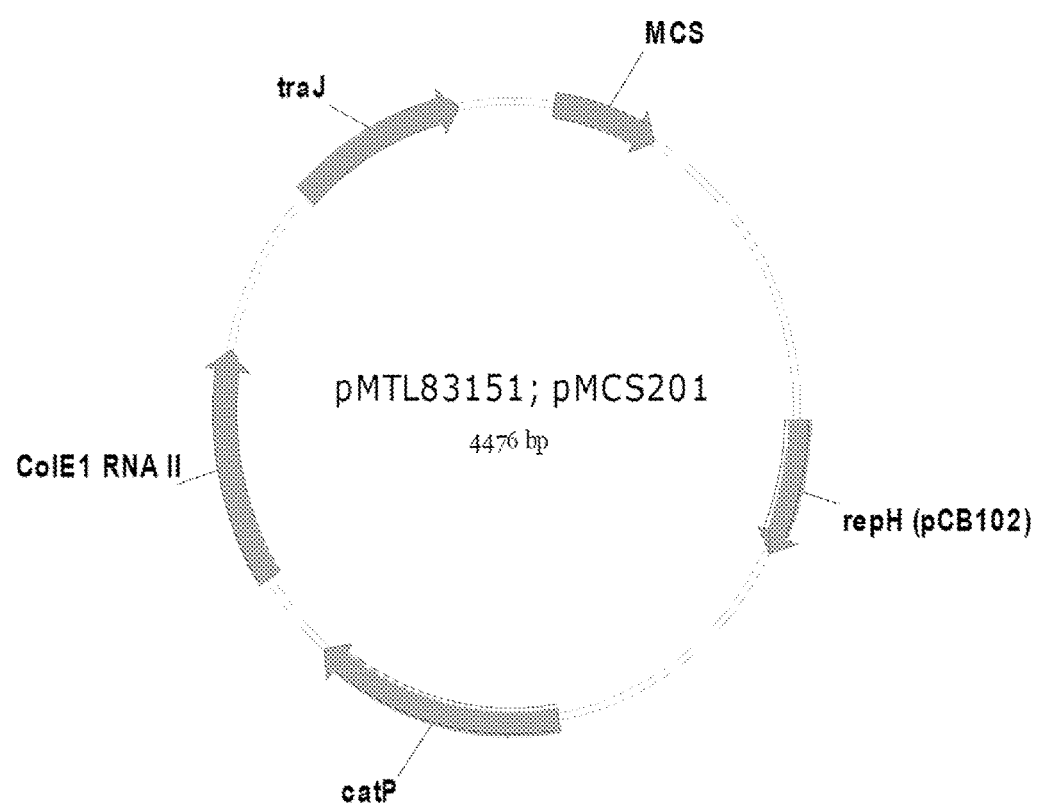
FIG. 34 shows the plasmid map for pMCS201, also referred to as pMTL83151.
Figure 49:
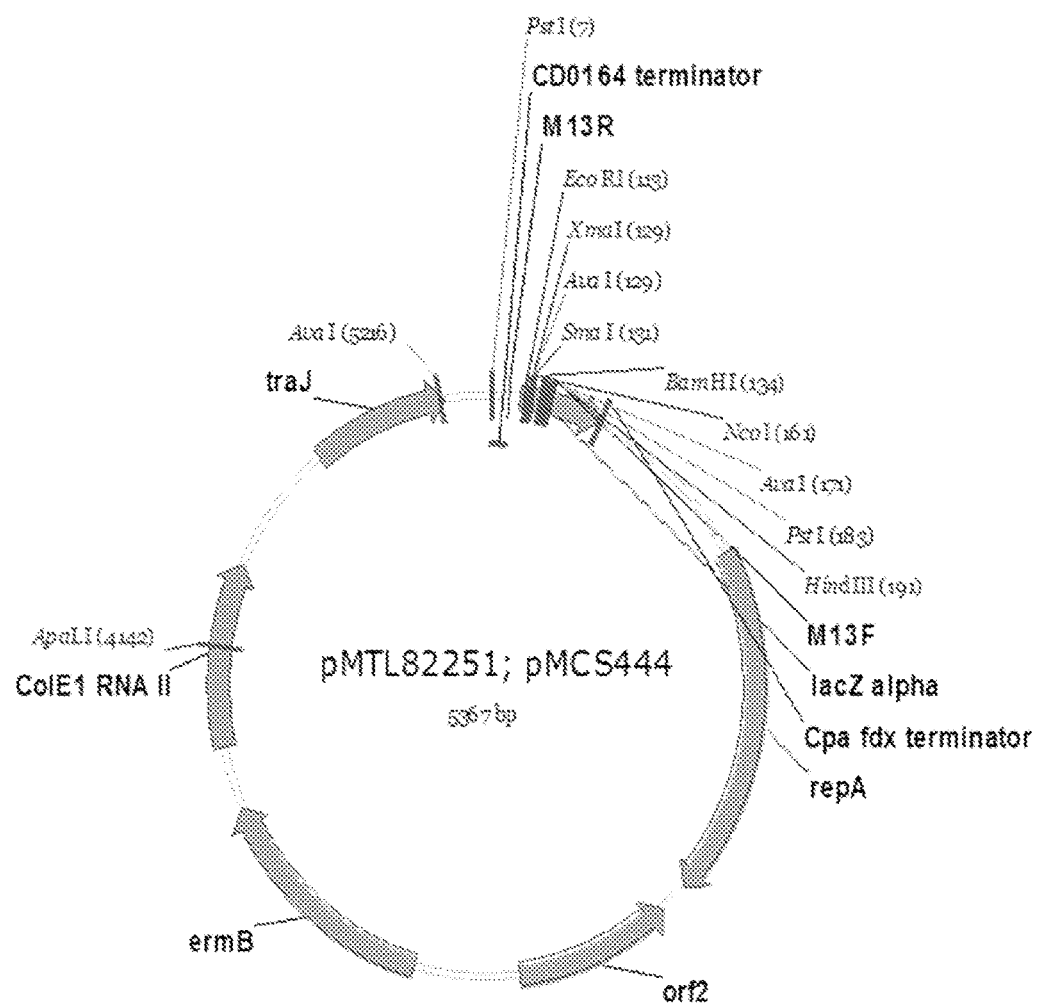
FIG. 49 shows the plasmid map for plasmid pMCS444.
Figure 51:
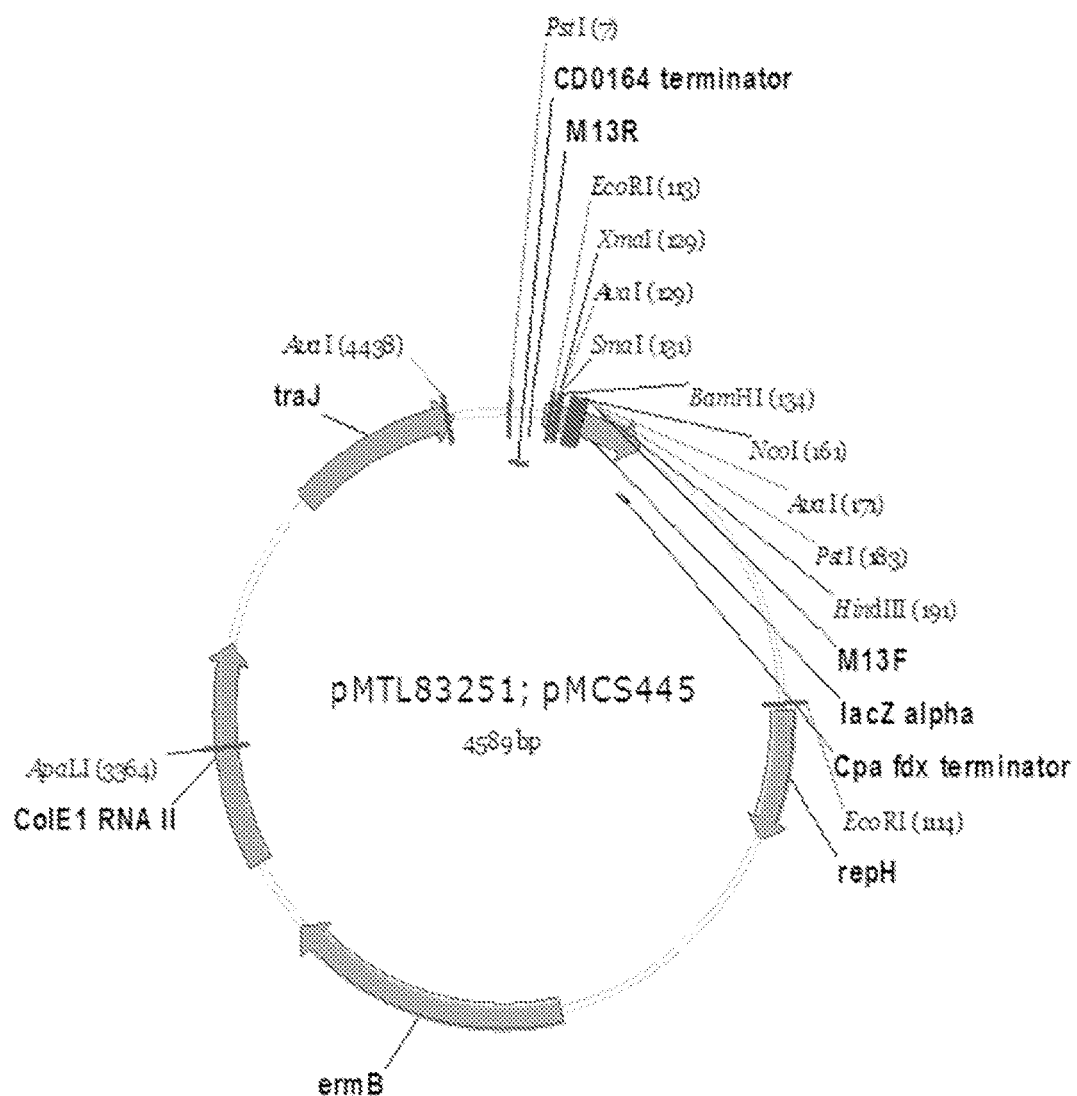
FIG. 51 shows the plasmid map for plasmid pMCS445.
Figure 53:
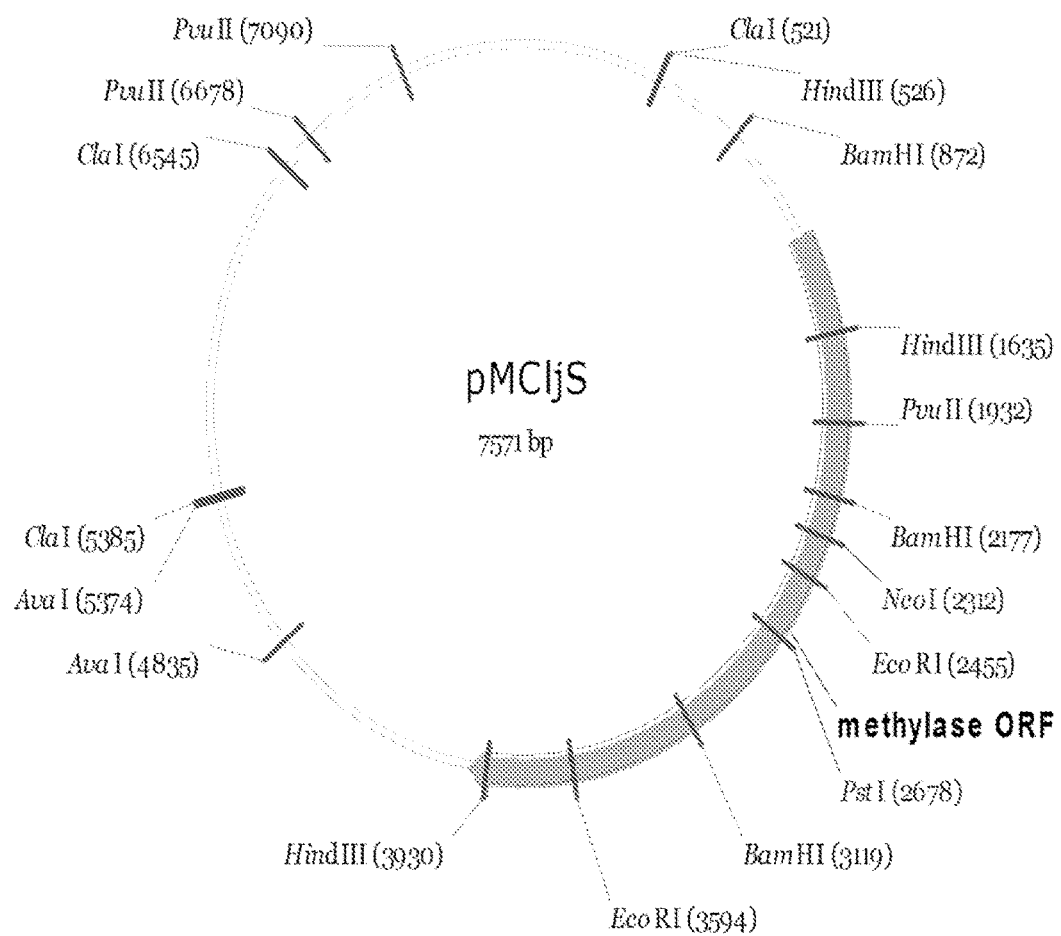
FIG. 53 shows the plasmid map for plasmid PMCljs.
Figure 55:
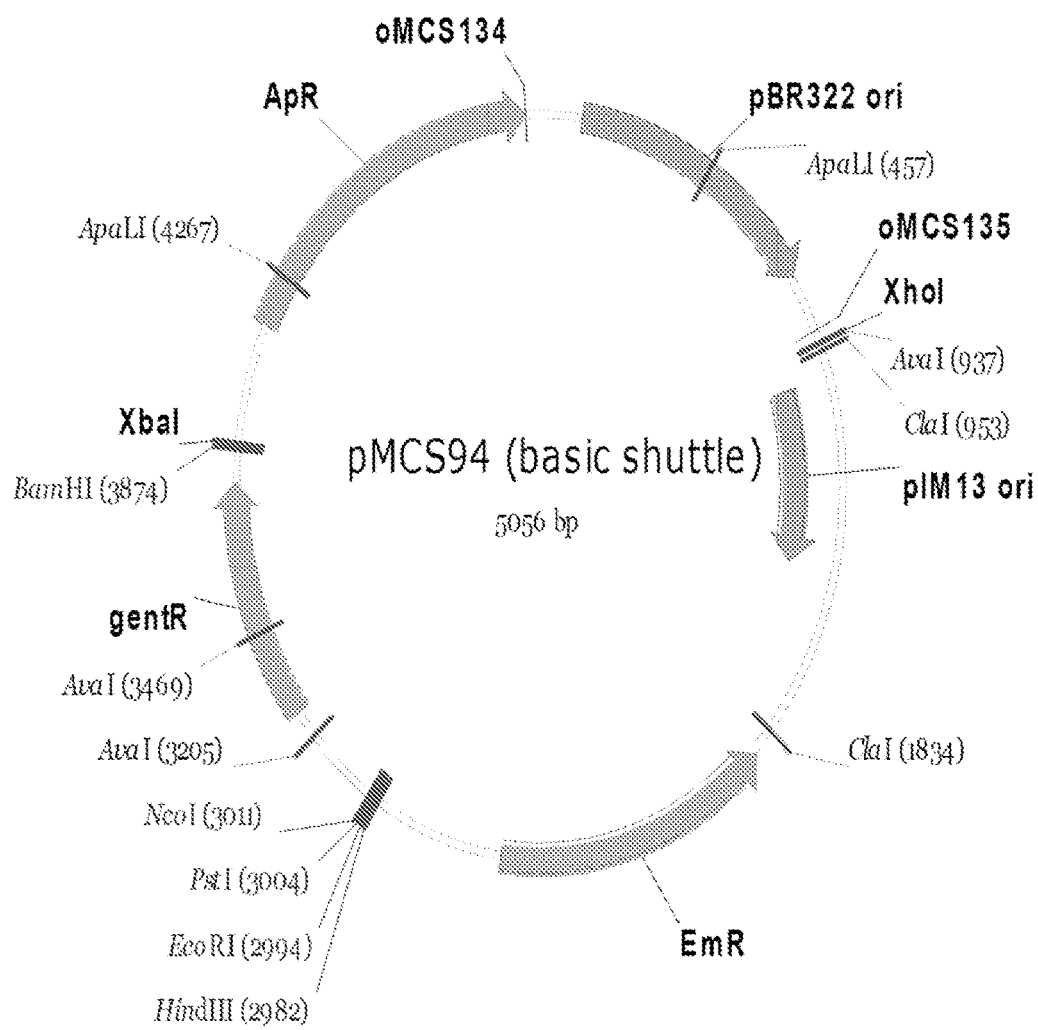
FIG. 55 shows the plasmid map for pMCS94.
Figure 57:
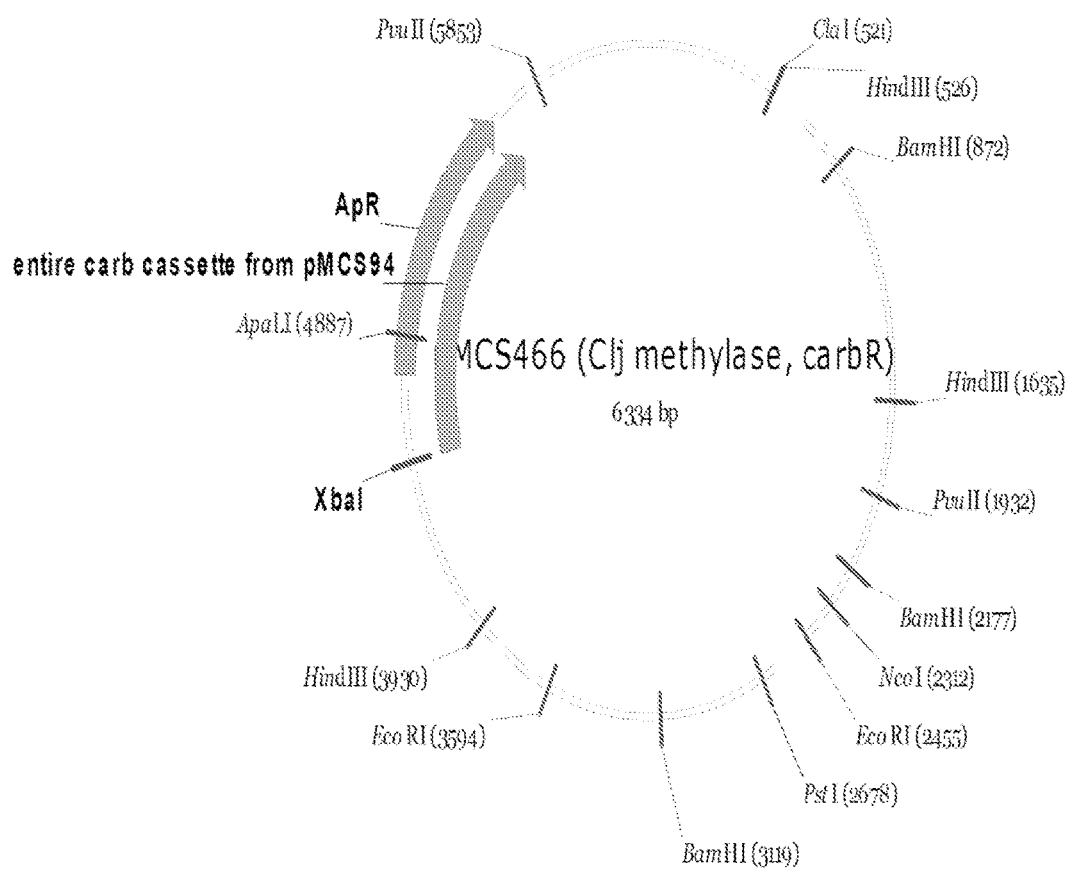
FIG. 57 shows the plasmid map for pMCS466.

| Plasmid Identifier | Features | Described In |
|---|---|---|
| pDW268 | $P_{BAD}$ promoter, RBS from pBAD, RYBO02455 methyltransferase, rrnB terminator, araC | FIG. 23 and FIG. 24A-C |
| pBAD33 | $P_{BAD}$ promoter, 5s and rrnB $T_1T_2$ terminators, truncated bla, $Cm^R$, pACYC184 ori, araC | Guzman et al., 1995, *Journal of Bacteriology*, Vol. 177, No. 14: 4121-4130. |
| pCA1 | repB, IS605 OrfB family transposase, | FIG. 6 and FIG. 7A-B |
| pMCS203 | ori pIM13, catP, TraJ, lacZ alpha,, ColE1 RNA II | FIG. 8 and FIG. 9 |
| pDW263 | repB chloramphenicol resistance marker, ColE1 RNA II, TraJ, IS605 OrfB family transposase, | FIG. 19 and FIG. 20A-C |
| pDW264 | repB, chloramphenicol resistance marker, ColE1 RNA II, TraJ, IS605 OrfB family transposase | FIG. 21 and FIG. 22A-C |
| pDW280 | repB, ermB, ColE1 RNA II, TraJ, IS605 OrfB family transposase | FIG. 23 and FIG. 24A-C |
| pMCS537 | repB, ermB, ColE1 RNA II, TraJ | FIG. 30 and FIG. 31A-B |
| pMCS444 | repA, ermB, ColE1 RNA II, TraJ | FIG. 49 and FIG. 50 |
| pMCS445 | repH, ermB, ColE1 RNA II, TraJ | FIG. 51 and FIG. 52 |
| pMCS200 | repA, ermB, ColE1 RNA II, TraJ | FIG. 32 and FIG. 33A-B |
| pMCS201 | repH, ermB, ColE1 RNA II, TraJ | FIG. 34 and FIG. 35A-B |
| pMCljs | *Clostridium ljungdahlii* methyltransferase ORF | FIG. 53 and FIG. 54 |
| pMCS94 | pIM13 ori, pB322 ori, EmR, gentR, ApR, | FIG. 55 and FIG. 56 |
| pMCS466 | ApR, Carb Cassette from pMCS94, *Clostridium ljungdahlii* methyltransferase ORF | FIG. 57 and FIG. 58 |

Example 2: Identification of Endonuclease in *Clostridium*

To identify an active restriction endonuclease in *Clostridium aceticum*, overnight cultures of wild type bacteria grown in AcM liquid medium (Table 3) were harvested by centrifugation and resuspended in a solution containing lysozyme, penicillin G and 0.6 M sucrose to induce protoplast formation. After several hours, the suspended protoplasts were subjected to hypotonic lysis by centrifugation and resuspension in buffer containing 100 mM Tris pH 7.4, 50 mM NaCl, and 1 mM PMSF. The lysed cells were removed by centrifugation, and the supernatant was used in all subsequent experiments to examine and identify endonuclease activity. All techniques and methods used followed standard microbiology and molecular biology practices.

TABLE 3

AcM Recipe

| Component | Amount in 1 L AcM |
|---|---|
| $NH_4Cl$ | 10 ml |
| $KH_2PO_4$ | 3.3 ml |
| $K_2HPO_4$ | 4.5 ml |
| $MgSO_4 \cdot 7H_2O$ | 1 ml |
| Cysteine HCl | 10 ml |
| Wolfe's mineral solution | 20 ml |
| Wolfe's vitamin solution | 20 ml |
| Resazurin (0.1% solution) | 1 ml |
| $NaHCO_3$ | 10 g |
| Yeast Extract | 2 g |
| pH | 7.4 |
| $H_2O$ | To 1 L |

Figure 12A:
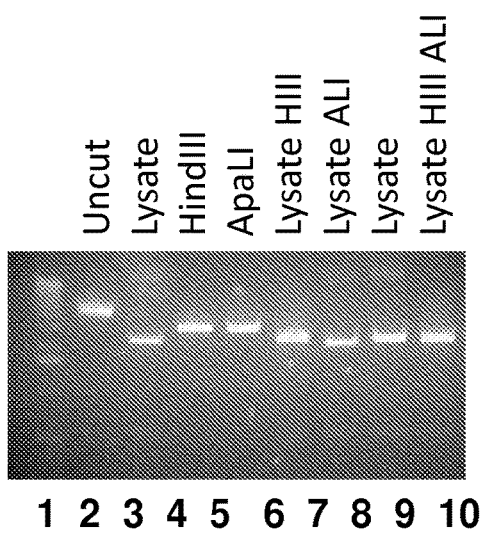
FIG. 12A shows the results of a restriction endonuclease assay using 500 ng of pMCS244 treated with 1 µL *Clostridium aceticum* lysate, 1 µL of the HindIII restriction endonuclease, 1 µL of the ApaLI restriction endonuclease, or the indicated combinations thereof. From left to right, Lane 1: Roche DNA Molecular Weight Marker X, Lane 2: uncut pMCS244, Lane 3: pMCS244 and *Clostridium aceticum* lysate, Lane 4: pMCS244 and HindIII, Lane 5: pMCS244 and ApaLI, Lane 6: pMCS244 with *Clostridium aceticum* lysate and HindIII, Lane 7: pMCS244 with *Clostridium aceticum* lysate and ApaLI, Lane 8: pMCS244 with *Clostridium aceticum* lysate, Lane 9: pMCS44 with *Clostridium aceticum* lysate, HindIII, and ApaLI combined.
Figure 12B:
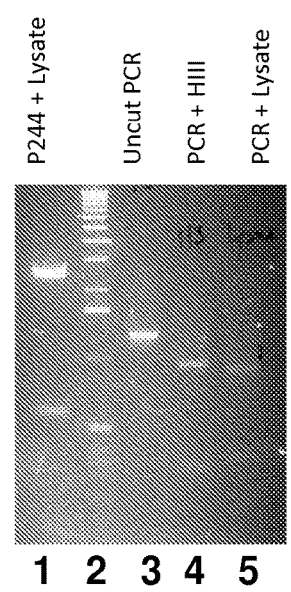
FIG. 12B shows the results of a precision mapping assay. Lane 1: 500 ng of pMCS244 and 1 µL of *Clostridium aceticum* lysate, Lane 2: Roche DNA Molecular Weight Marker X, Lane 3: 100 ng of linear PCR product generated from pMCS244 using primers M13R and oMCS25: Lane 4: 100 ng of linear PCR product generated from pMCS244 using primers M13R and oMCS25 and 1 uL of HindIII, Lane 5: 100 ng of linear PCR product generated from pMCS244 using primers M13R and oMCS25 and 1 µL of *Clostridium aceticum* lysate.
Figure 13:
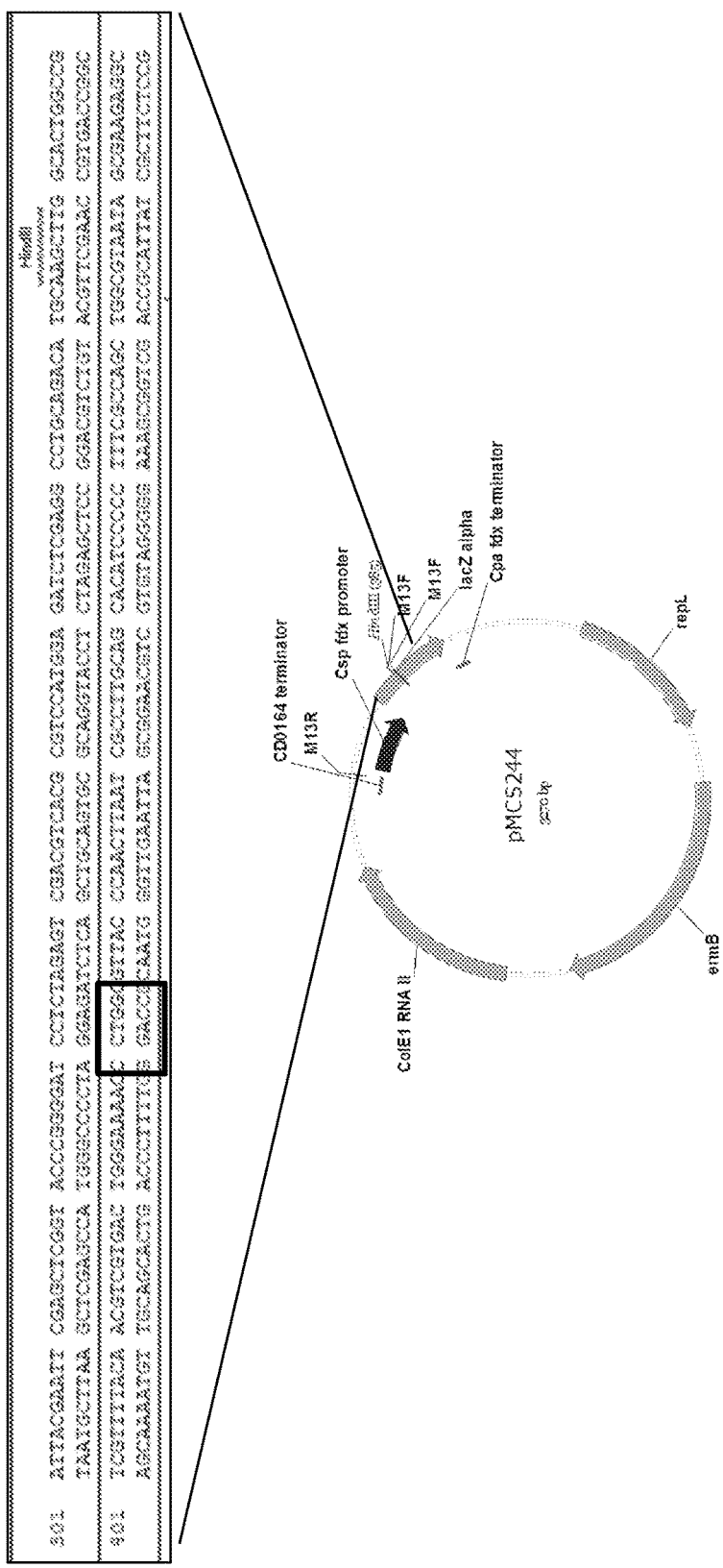
FIG. 13 shows the CCWGG (W=T or A) Type II restriction endonuclease recognition sequence that is proximal to the HindIII cleavage site in a linear PCR product generated from pMCS244 using primers M13R and oMCS25. Both CCAGG (SEQ ID NO. 9) and CCTGG (SEQ ID NO. 10) are recognized by CacI and M.CacI.

Example 3: Identification of the DNA Recognition Sequence for the Restriction Endonuclease Plasmid pMCS244, an $erm^R$ vector used for transforming *E. coli* to confer resistance to erythromycin, was incubated with 1 µl of the *C. aceticum* lysate in NEB Buffer 2 at a final volume of 20 µl for 30 minutes at 30° C., and the restriction digest pattern was observed via gel electrophoresis (E-gel, Life Technologies). A discrete restriction pattern was observed (FIG. 12A), and the unidentified *Clostridium aceticum* endonuclease was called "CacI," in accordance with conventional nomenclature for restriction enzymes. CacI cleavage sites were also mapped relative to the cleavage sites of the HindIII and ApaLI restriction enzymes in pMCS244 (FIG. 12A, lanes 4 and 5, respectively). HindIII and ApaLI are commercially available restriction endonucleases with well-established DNA recognition sequences of AAGCTT and GTGCAC, respectively. The restriction map was further refined by generating a linear PCR product, using primers M13R and oMCS25 (Table 4), subjecting it to digest by the *C. aceticum* lysate, and determining the proximity of any cleavage sites relative to HindIII. FIG. 12B shows the restriction digest patterns of the PCR product. Using this sequence information, the recognition sequence CCWGG (W=T or A) was identified as the recognition site of the CacI enzyme that is present in the *C. aceticum* lysate. The CCTGG sequence (SEQ ID NO: 10) that is proximal to the HindIII recognition sequence of AAGCTT is shown in FIG. 13.

Thus, this example illustrates the identification of the DNA recognition sequence, CCWGG (W=T or A), for the restriction endonuclease, CacI, present in *C. aceticum* lysate.

TABLE 4

| Primer names and sequences | |
|---|---|
| CacI M1 For | gaaaaccctgacgttacccaactta |
| CacI M1 Rev | tgggtaacgtcagggttttccca |
| CacI M2 For | gaaacgcctgntatctttatagtcct |
| CacI M2 Rev | acaggactataaagatancaggcgt |
| CacI M3 For | acggttcctgacctttgctggcct |
| CacI M3 Rev | ggccagcaaaggtcaggaaccgta |
| CacI M2 Rev 2 | ataaagatancaggcgtttcccctn gaagctccctcgtgcgct |
| CacI M2 Rev 3 | ataaagatancaggcgtttcccnnng gaagctccctcgtgcgct |
| CacI M2 Rev 4 | ataaagataacaggcgtttccccta gaagctccctcgtgcgct |
| CacI M2 Rev 5 | ataaagataacaggcgtttcccnntg gaagctccctcgtgcgctctcctgt |
| CacI M2 For 2 | gaaacgcctgttatctttatagtcct |
| M13R | caggaaacagctatgacc |
| oMCS25 | ctcattagtagttcagggtttaaca |
| Bad33 2455 frag 1 forward | tacccggggaggaataataaatggccgt actccgcaatattgat |
| Bad33 2455 frag 2 reverse | ttattattcctccccgggtaccgagctc gaattcgcta |
| Bad33 2455 frag 2 forward | caaagatcgttgaggctgttttggcgga tgagagaagat |
| Bad33 2455 frag 1 reverse | aacagcctcaacgatctttgcgcagcac gacgatgtgctcgttcgt |
| O105 | agggacagctagttctagagtcggtaa cgctctcc |
| O106 | ccaacttttttaaatcaatctaaagtata tatgagtaaacttggtctgac |
| O107 | gatttaaaaagttggcccagggcttccc gg |
| O108 | gaactagctgtccctgatggtcgtcatc tac |
| oMCS158 | cagcacttaacattaaccatataatcac gaac |
| oMCS159 | cagctatagcagctactctttggtatta ttatcaaaatg |
| oMCS418 | ggtagaccctaattatcgtgaacgc |
| oMCS419 | tgattattattatgaaccgattgtaaat gattttttag |
| oMCS420 | ttggatgagaagatacttaaagatgtaa ggg |
| oMCS421 | ttcagagtatattttcttaaatacgta aatattttttc |
| oMCS422 | atgaacaaaatataaaatattctcaaa actttttaac |
| oMCS423 | ttatttcctcccgttaaataatagataa ctatta |
| oMCS426 | ctataaatattagcgttggacttttttc ttcccttttaaatc |
| oMCS427 | tccaacgctaatatttatagtatcagtt ttaaactgaaactgcaac |
| GA CA1_1 Plasmid For | ccgcggccgccattatagcataaagagg gct |
| GA CA1_1 Plasmid Rev | agattgacctttattattcagagtatat ttttct |
| GA CA1_1 203 For | tgaataataaaggtcaatctatgaaatg cga |
| GA CA1_1 203 Rev | tgctataatggcggccgcggtcatagct gtt |
| GA CA1_2 Plasmid For | ccgcggccgccagctatagcagctactc tt |
| GA CA1_2 Plasmid Rev | agattgacctcagcacttaacattaacc at |
| GA CA1_2 203 For | ttaagtgctgaggtcaatctatgaaatg cga |
| GA CA1_2 203 Rev | gctatagctggcggccgcggtcatagct gtt |

Figure 25:
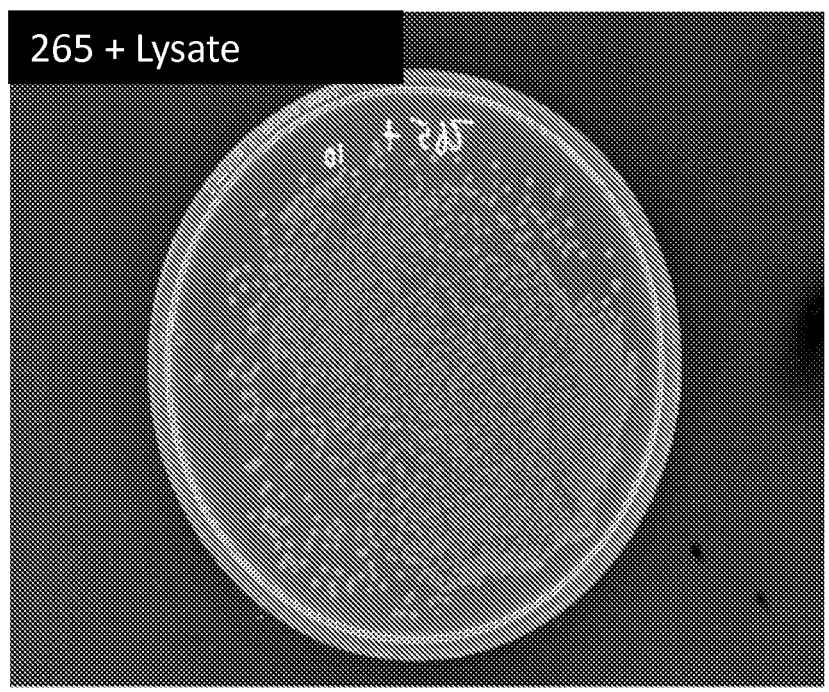
FIG. 25 shows the results when plasmid pDW265 is incubated with *Clostridium aceticum* lysate and transformed into *E. coli*.
Figure 26:
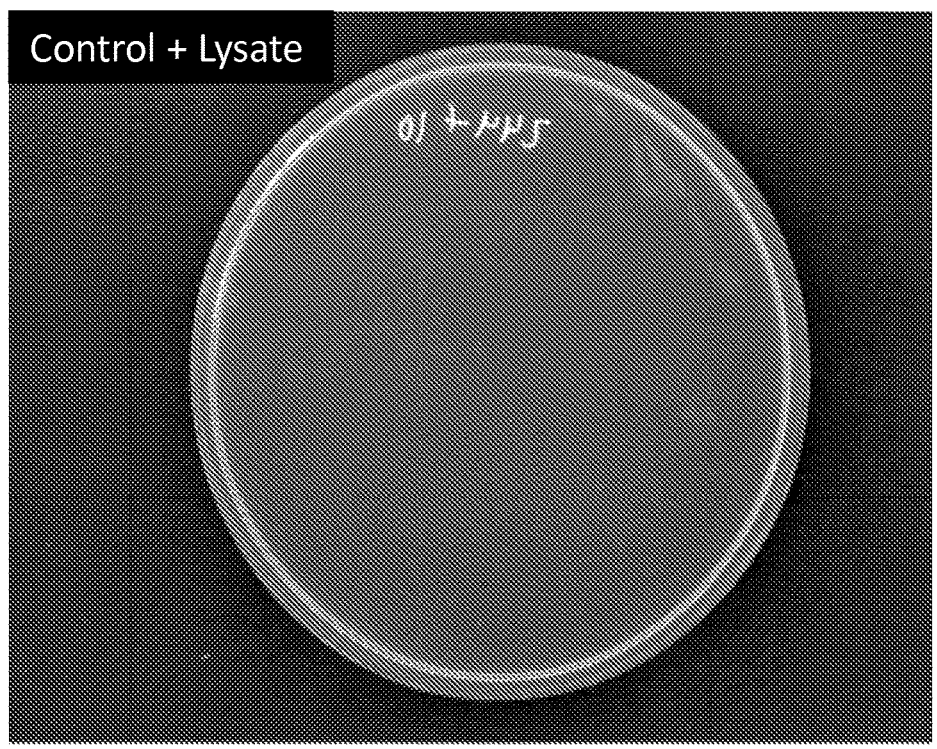
FIG. 26 shows the results when unmethylated pMCS244 is incubated with *Clostridium aceticum* lysate and transformed into *E. coli*.
Figure 27:
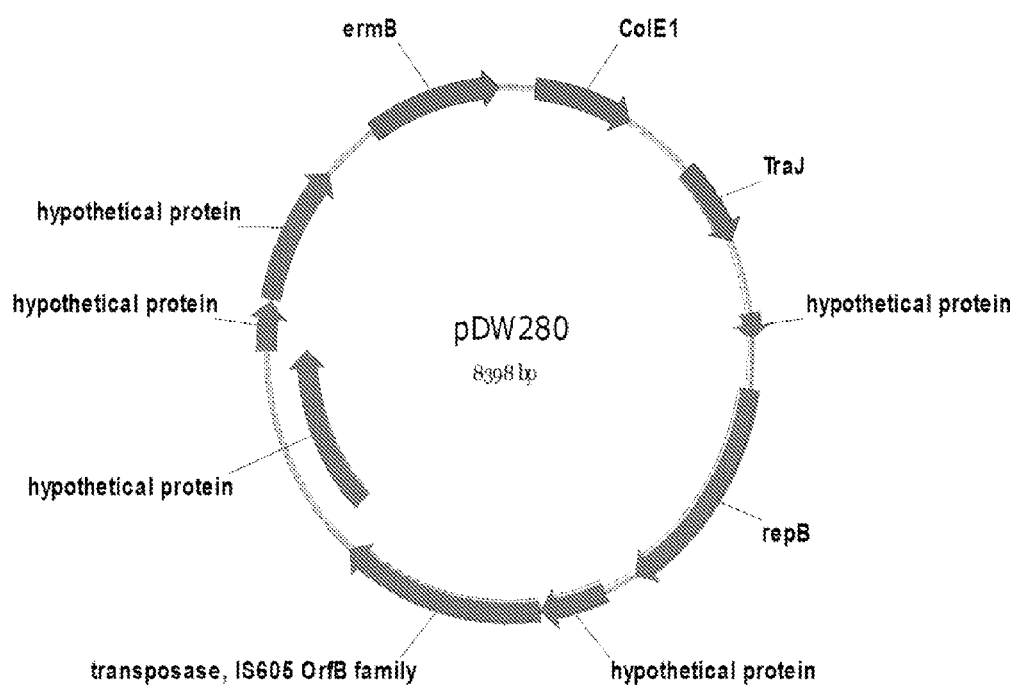
FIG. 27 shows a plasmid map for pDW280.

Example 4: Identification of the *Clostridium aceticum* Methyltransferase (M.CacI, RYBO02455) and Characterization of its Activity The *Clostridium aceticum* open reading frame RYBO02455 (SEQ ID NO: 2) encodes an enzyme with homology to M.MvaI, a methyltransferase from *Micrococcus varians* that transfers a methyl group onto the 4-amino moiety of the second cytosine residue of the recognition sequence CCWGG (W=T or A) (Butkus et al., 1985, *Nucl. Acids Res.*, Vol. 13, No. 16: 5727-5746). To determine if the protein product of RYBO02455 methylates CCWGG, and thus protects this recognition sequence from being cleaved by the CacI activity in the *C. aceticum* lysate, the coding sequence of RYBO02455 was codon optimized by the company DNA2.0 for expression in *E. coli* and cloned by GeneArt seamless cloning (Life Technologies) into the pBAD33 arabinose-inducible vector to create the pDW268 plasmid. The primers used are provided in Table 4, and the plasmid map for pDW268, as well as its DNA sequence, are shown in FIG. 23 and FIG. 24A-C(SEQ ID NO. 14), respectively.

pDW268 was then cotransformed with pMCS244 into *E. coli* Top10 chemically competent cells (Life Technologies). Cells were grown overnight in LB with appropriate antibiotics, back-diluted the next day into fresh medium in a 1:1 ratio, and induced with arabinose (120 µl of a 15% w/v solution into 5 ml of LB) for 3 hours. Plasmids were then purified (Qiagen) and subjected to cleavage by the *C. aceticum* lysate. FIG. 25 shows that DNA methylated by RYBO02455 was resistant to cleavage by CacI, because pMCS244 could be retransformed into *E. coli* after incubation in *C. aceticum* lysate. Conversely, FIG. 26 shows it was not possible to transform *E. coli* cells with unmethylated pMCS244 after incubation in *C. aceticum* lysate, due to complete digestion by the endonuclease activity of CacI. The enzyme encoded by RYBO02455 was named "M.CacI,"

Example 5: Identification of the Open Reading Frame (ORF) Encoding the CacI Restriction Endonuclease RYBO02454 is an ORF that is directly adjacent to, and transcribed in the opposite direction of, RYBO02455 (M.CacI). RYBO02454 encodes an enzyme with low sequence identity to M.MvaI, a restriction endonuclease from *Micrococcus varians* that cleaves CCWGG. Because of its proximity to M.CacI, its homology to an enzyme known to cleave the CCWGG recognition sequence, and the tendency of restriction/methylation enzyme pairs to be colocalized in bacterial genomes, RYBO02454 was considered a candidate to encode CacI, a restriction enzyme in the *C. aceticum* lysate.

Example 6: Creation of a CacI-Resistant Plasmid, pDW265

To determine if CacI, which targets CCWGG, was the predominant restriction endonuclease activity in the *C. aceticum* lysate, the plasmid pDW265, in which all 4 identified CCWGG recognition sites were mutated, was assembled using both the GeneArt seamless cloning kit (Life Technologies) and QuikChange PCR mutagenesis (Stratagene) according to the manufacturer's recommended protocols (see Table 4 for primers). The plasmid map for pDW265 is provided in FIG. 14, and the DNA sequence for pDW265 is provided in FIG. 15A (SEQ ID NO. 11).

Figure 16:
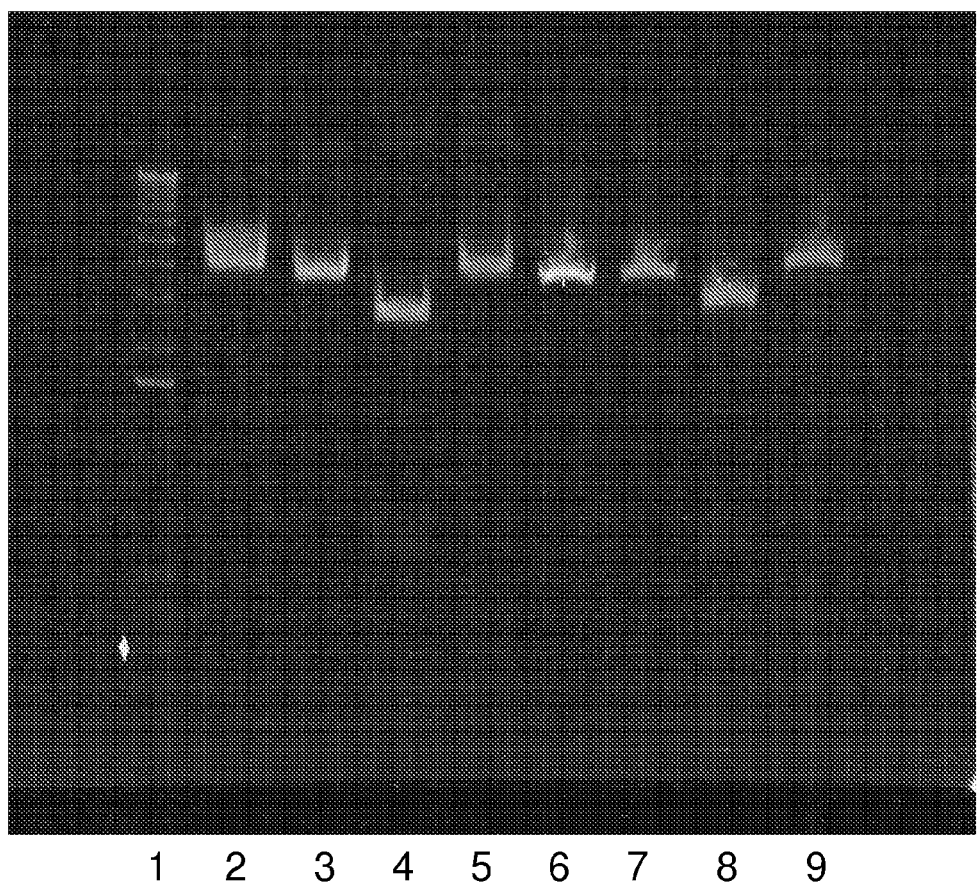
FIG. 16 shows the results of a restriction endonuclease assay using 500 ng of control plasmid pMCS244 or 500 ng of the pDW265 plasmid (which has all four CacI DNA recognition sites mutated) treated with 1 µL *Clostridium aceticum* lysate, 1 µL of HindIII, or both. Lane 1: Roche DNA Molecular Weight Ladder X, Lane 2: control plasmid pMCS244; Lane 3: untreated pDW265 plasmid; Lane 4: pMCS244 control treated with *C. aceticum* lysate; Lane 5: pDW265 plasmid treated with *C. aceticum* lysate; Lane 6: pMCS244 treated with HindIII; Lane 7: pDW265 treated with HindIII; Lane 8: pMCS244 plasmid treated with both *C. aceticum* lysate and HindIII; Lane 9: pDW265 with both *C. aceticum* lysate and HindIII.

FIG. 16 shows the results of a restriction endonuclease assay using a control plasmid, pMCS244, or the pDW265 plasmid (which had all four CCWGG CacI DNA recognition sites mutated) treated with *Clostridium aceticum* lysate, the HindIII restriction endonuclease, or both. Lane 1: Roche DNA Molecular Weight Ladder X; Lane 2: control plasmid pMCS244; Lane 3: untreated pDW265 plasmid; Lane 4: pMCS244 control treated with *C. aceticum* lysate; Lane 5: pDW265 plasmid treated with *C. aceticum* lysate; Lane 6: pMCS244 treated with HindIII; Lane 7: pDW265 treated with HindIII; Lane 8: pMCS244 plasmid treated with both *C. aceticum* lysate and HindIII; Lane 9: pDW265 with both *C. aceticum* lysate and HindIII.

Figure 17A:
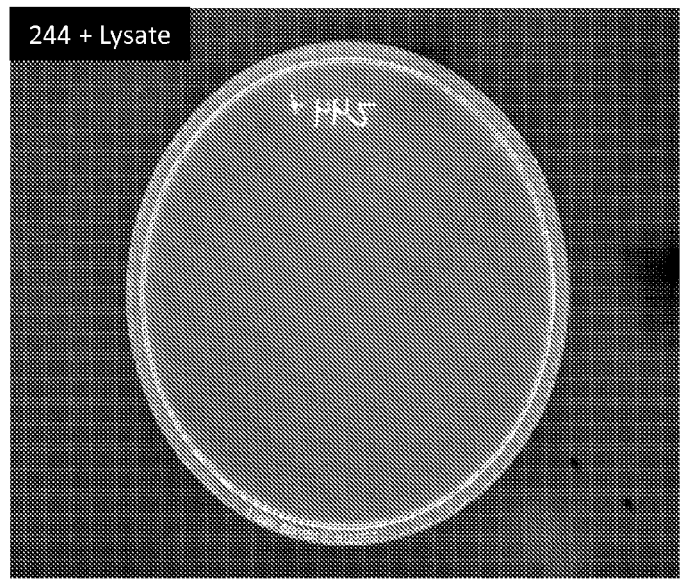
FIG. 17A shows the results when pMCS244, which contains 4 CacI recognition sequence sites, is incubated with *Clostridium aceticum* lysate and then transformed into *E. coli*.
Figure 17B:
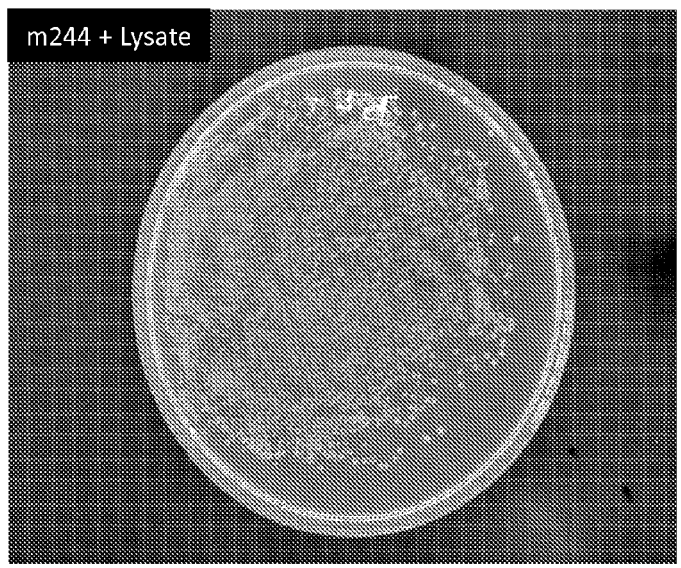
FIG. 17B shows the results when pDW265, which is identical to pMCS244 except that all four CacI sites have been mutated, is incubated with *Clostridium aceticum* lysate and then transformed into *E. coli*.

Lanes 5, 7, and 9 of FIG. 16 show that pDW265 resists cleavage when incubated with *Clostridium aceticum* lysate (Lane 5), when incubated with HindIII (Lane 7), or when incubated with both (Lane 9). Conversely, FIG. 16 also shows that the plasmid pMCS244, which is identical to pDW265 except that it still contains all 4 identified CCWGG recognition sites, does not resist cleavage when incubated with *Clostridium aceticum* lysate (compare untreated pMCS244 in Lane 2 with *C. aceticum*-treated pMCS244 in lane 4), HindIII (Lane 6), or both (Lane 8).

pDW265 and pMCS244 were then incubated with the *C. aceticum* lysate as described above and transformed into Top10 chemically competent *E. coli* cells (Life Technologies) according to the manufacturer's recommended protocol. The following day, the presence of erythromycin-resistant colonies transformed with pDW265 (FIG. 17), and the complete absence of resistant colonies transformed with pMCS244 (FIG. 18), confirmed that pDW265 was protected from cleavage by the *C. aceticum* lysate containing CacI, which specifically recognizes CCWGG.

Example 7: Creation of a Conjugative *E. coli-C. aceticum* Shuttle Plasmid, pDW280

To successfully transform *C. aceticum* with heterologous DNA, shuttle vectors for propagation in *E. coli* were first built. The construction of a series of modular shuttle vectors between *E. coli* and various clostridial bacterial species (known as "the pMTL80000 series") is described in Heap et al., 2009 (*Journal of Microbiological Methods*, Vol. 78: 79-85). These pMTL80000 vectors carry one of four Gram positive replicons, a p15A or ColE1 origin of replication in *E. coli*, a multiple cloning site with flanking transcriptional terminators, and an antibiotic resistant marker, catP, ermB, aad9 or tetA. Some of the vectors also carry a *C. sporogenes* ferredoxin promoter (Pfdx) and ribosome binding site (RBS) or a *C. acetobutylicum* thiolase promoter and RBS for gene expression.

To create the shuttle vector pDW280, the plasmid backbone of pMCS203 (pMTL85151) was amplified by PCR (PfuUltra II, Agilent Technologies) using the primer pairs indicated in Table 4 (e.g., GA CA1_1 203 For and GA CA1_1 203 Rev). The plasmid map and DNA sequence for pMCS203 are provided in FIG. 8 and FIG. 9A-B, respectively. The pCA1 plasmid was amplified using the indicated primer pairs (e.g., GA CA1_1 Plasmid For and GA CA1_1 Plasmid Rev, as listed in Table 4). The plasmid map and DNA sequence for pCA1 are provided in FIG. 6 and FIG. 7A-B, respectively. PCR products of the appropriate molecular weight by gel electrophoresis were purified (Qiagen) and combined using the GeneArt Seamless Cloning kit (Life Technologies). These PCR products were then transformed into chemically competent *E. coli* TOP10 cells (Life Technologies) according to the manufacturer's recommended protocol. Cells were recovered and plated on selective medium, and transformants resistant to chloramphenicol were selected for further analysis. Several individual colonies were grown overnight in selective LB medium, and the next day plasmids were purified (Qiagen) and molecular weights were compared to that of the parental pCA1 plasmid by gel electrophoresis. This resulted in plasmid pDW264. As indicated in the pDW264 plasmid map shown in FIG. 20, the pDW264 shuttle vector contains the native *Clostridium aceticum* pCA1 plasmid and DNA cassettes that allow for replication in *E. coli*, conjugal transfer, and resistance to the antibiotic chloramphenicol. The DNA sequence for pDW264 is shown in FIG. 22A-C.

Next, pDW264 was cut with FseI and PmeI restriction enzymes (New England Biolabs), following the manufacturer's recommended protocol, to remove the chloramphenicol resistance cassette. These vectors were then ligated (T4 ligase, NEB) to an erythromycin resistance cassette which had been isolated from the template pDW265 by restriction digest with FseI, PmeI, and AscI, and transformed into Top10 chemically competent *E. coli* cells (Life Technologies), using standard molecular biology techniques. The resulting conjugative shuttle plasmid, pDW280, contained the entire *Clostridium aceticum* pCA1 native sequence, an origin of transfer, an origin of replication in *E. coli*, and the erythromycin resistance cassette. The plasmid map and sequence for pDW280 are provided in FIG. 27 and FIG. 28A-C, respectively.

Example 8: Creation of Conjugative *E. coli-C. aceticum* Shuttle Plasmids pMCS537, pMCS244, and pMCS245

The conjugative shuttle plasmid pDW280 (shown in its unmodified form in FIG. 27) was modified by the removal of its four hypothetical proteins as well as by the removal of the transposase open reading frame downstream of repB to create the smaller conjugative E. coli-C. aceticum shuttle plasmid pMCS537. Briefly, plasmid pDW280 was amplified by PCR using primers oMCS426 and oMCS427 (Table 4) and then purified and subjected to self-ligation using the Invitrogen GeneArt Seamless Cloning Kit.

pMCS444 and pMCS445 were created by replacing the catP cassette with the emR cassette on plasmids pMCS200 and pMCS201. This was done using digestion-ligation methods described for the modular plasmid collection (clostron.com) or as indicated in Heap et al., 2009. The plasmid map for pMCS444 is shown in FIG. 49, and its DNA sequence is provided in FIG. 50, while the plasmid map for pMCS445 is shown in FIG. 51, and its DNA sequence is provided in FIG. 52.

Example 9: Creation of Conjugative E. coli-C. ljungdahlii Shuttle Plasmids pMCS200 and pMCS201

To successfully transform C. ljungdahlii with heterologous DNA, shuttle vectors for propagation in E. coli were first built. The construction of a series of modular shuttle vectors between E. coli and various clostridial bacterial species (known as "the pMTL80000 series") is described in Heap et al., 2009 (Journal of Microbiological Methods, Vol. 78: 79-85). These pMTL80000 vectors carry one of four Gram positive replicons, a p15A or ColE1 origin of replication in E. coli, a multiple cloning site with flanking transcriptional terminators, and an antibiotic resistant marker, catP, ermB, aad9 or tetA, Some of the vectors also carry a C. sporogenes ferredoxin promoter (IPfdx) and ribosome binding site (RBS) or a C. acetobutylicum thiolase promoter and RBS for gene expression.

The vector pMTL82151, renamed pMCS200 carries the pCB102 Gram positive origin of replication, the catP chloramphenicol resistance marker, and the ColE1 E. coli origin of replication. The plasmid map for pMCS201/pMTL83151 is provided in FIG. 32 and the DNA sequence is provided in FIG. 33A-B, and SEQ ID NO: 17.

The vector pMTL83151, renamed pMCS201 carries the pCB102 Gram positive origin of replication, the catP chloramphenicol resistance marker, and the ColE1 E. coli origin of replication. The plasmid map for pMCS201/pMTL83151 is provided in FIG. 34, and the DNA sequence is provided in FIG. 35A-B and SEQ ID NO:18.

Example 10: Clostridium aceticum Transformation by Conjugal Transfer (pDW268 with pDW280 or with pMCS537)

Conjugal transfer involves the transfer of DNA from one bacterial cell to another through direct cell-to-cell contact. The mobilizing donor strain used in the Examples of the instant application is the E. coli S17-1 strain, which contains a derivative of the RP4 plasmid integrated into its chromosomal DNA and is devoid of the E. coli K12-specific DNA restriction enzyme, thus allowing for efficient uptake of foreign cloned DNA (McFarlane et al., 1987, Journal of Microbiological Methods, Vol. 6: 301-305). The oriT site of RP4 is the origin of conjugative transfer, corresponding to the site at which the DNA duplex is nicked in preparation for transfer of a single strand from donor to recipient (William et al., 1990, Journal of General Microbiology, Vol. 136: 819-826; Burkhardt et al., 1979, Journal of General Microbiology, Vol. 114:341-348). The E. coli S17-1 strain also contains an insertion of the T7n transposon, which results in the trimethoprim and low level streptomycin resistance of this strain.

Figure 29:
FIG. 29 shows multiply passaged *Clostridium aceticum* bacteria growing on AcM media with 10 ug/ml nalidixic acid and 20 ug/ml erythromycin after successful conjugation with *E. coli* S17-1 cells harboring pDW268 and pDW280 plasmids.

To generate an E. coli S17-1 strain capable of both methylation in and conjugation from E. coli into C. aceticum, E. coli S17-1 cells were cotransformed (using standard techniques) with pDW268, a plasmid encoding arabinose-inducible M.CacI, and either pDW280 or plasmid pMCS537. Briefly, S17-1 strains with both the pDW268 methylation plasmid and either the pDW280 or the pMCS537 shuttle plasmid were grown overnight in liquid LB medium containing the appropriate antibiotics, and diluted the next day into fresh medium. During mid-exponential phase, at an OD600 of approximately 0.6, 5 ml of cells were harvested by centrifugation, washed three times in liquid LB medium without antibiotics, and resuspended in 250 µl of LB with 12 µl of a 15% arabinose solution prior to conjugation. Concurrently, a culture of C. aceticum in liquid AcM medium was harvested by centrifugation and resuspended in 100 µl of liquid AcM. The E. coli cells were then brought into the anaerobic chamber, and cell suspensions (100 µl of each) were mixed and plated together on an AcM solid medium plate. The next day, cells were scraped from the surface of the conjugation plate, and plated onto fresh AcM plates containing nalidixic acid (10 µg/ml) and erythromycin (5 µg/ml) to select for positive transformants. Colonies resistant to erythromycin and nalidixic acid were passaged successively to verify transformation. FIG. 29 shows multiply passaged C. aceticum cells growing on plates with erythromycin and nalidixic acid.

Figure 18:
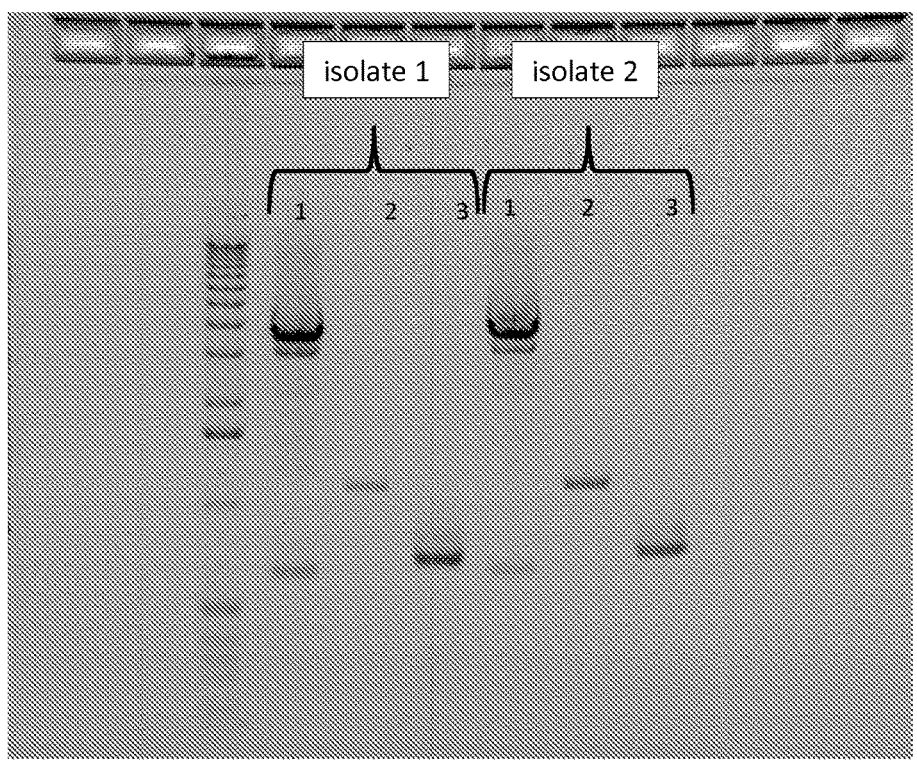
FIG. 18 shows PCR products amplified from plasmids isolated from a conjugally transformed *Clostridium aceticum* strain, using primers oMCS418 through oMCS423 (Table 4), that confirm the presence of the entire heterologous sequence (on pDW280), the *Clostridium aceticum* origin of replication, and the erythromycin resistance cassette, respectively.
Figure 19:
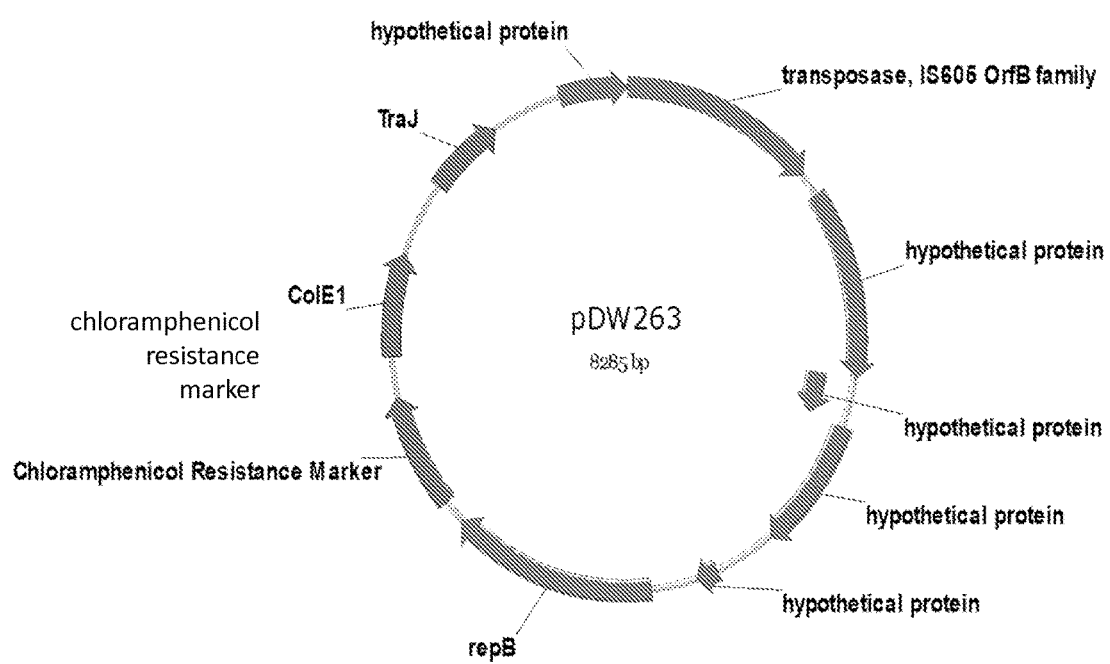
FIG. 19 shows the plasmid map for pDW263.
Figure 21:
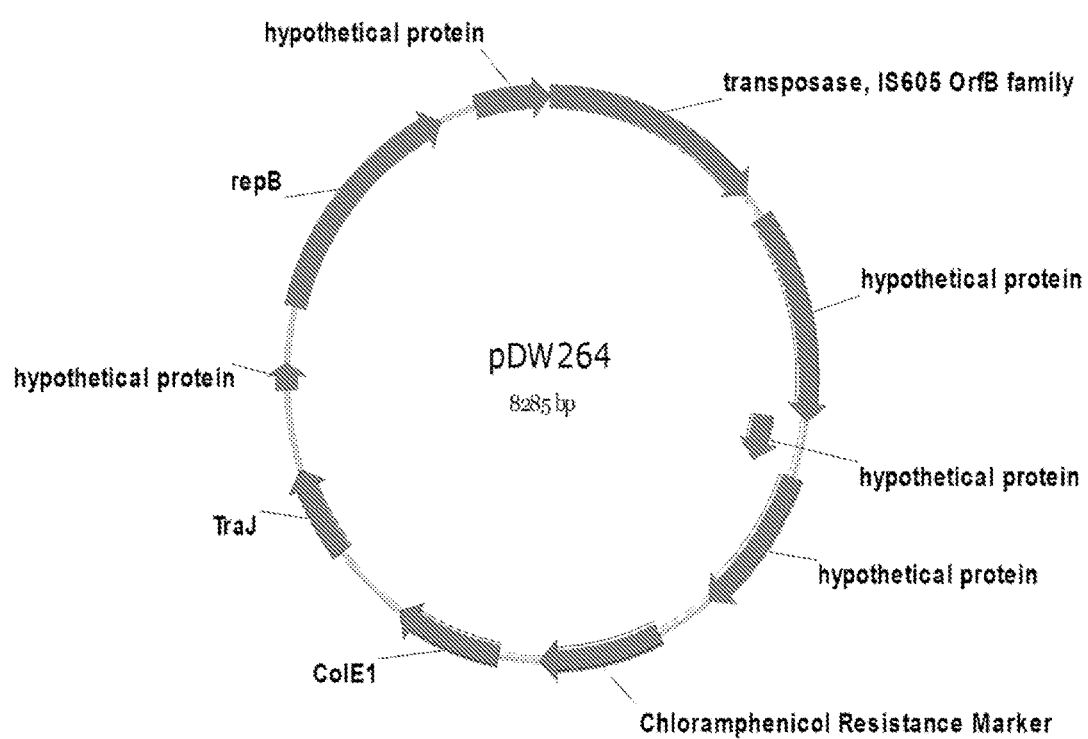
FIG. 21 shows the plasmid map for pDW264.
Figure 23:
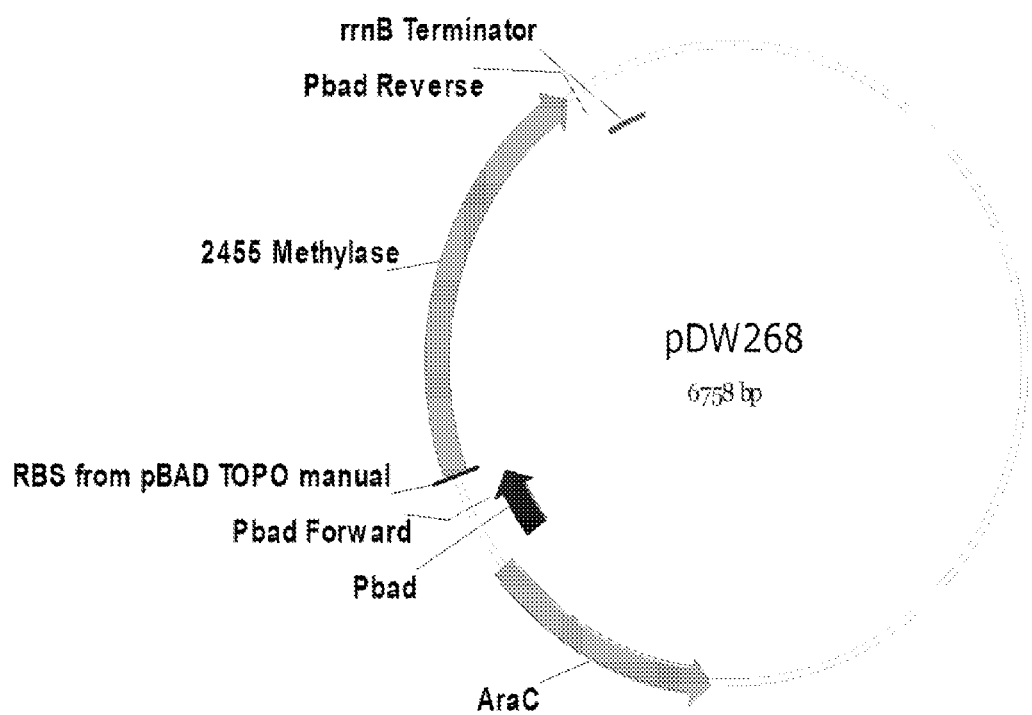
FIG. 23 shows the plasmid map for pDW268.

Transformed C. aceticum strains were further validated by streaking onto LB and testing for aerobic growth (C. aceticum will not grow aerobically), plasmid purification (Qiagen) from the transformed C. aceticum strain, retransformation into E. coli Top10 chemically competent cells, plasmid purification from the retransformed E. coli, and confirmation by complete sequencing (Quintara BioSciences). For further confirmation, PCR products amplified from pDW280 plasmids isolated from a transformed C. aceticum strain, using primers oMCS418 through oMCS423 (listed in Table 4), confirmed the presence of the entire heterologous sequence, the C. aceticum origin of replication, and the erythromycin resistance cassette, respectively (FIG. 18).

Example 11: Clostridium aceticum Transformation by Conjugal Transfer (pDW268 with pMCS444 or with pMCS445)

To generate an E. coli S17-1 strain capable of both methylation in and conjugation from E. coli into C. aceticum, E. coli S17-1 cells were co-transformed (using standard techniques) with pDW268, a plasmid encoding arabinose-inducible M.CacI, and either pMCS444 or plasmid pMCS445. S17-1 strains with both the pDW268 methylation plasmid and either the pMCS444 or the pMCS445 shuttle plasmid were grown overnight in liquid LB medium containing the appropriate antibiotics, and diluted the next day into fresh medium. During mid-exponential phase, at an OD600 of approximately 0.6, 5 ml of cells were harvested by centrifugation, washed three times in liquid LB medium without antibiotics, and resuspended in 250 µl of LB with 12 µl of a 15% arabinose solution prior to conjugation. Concurrently, a culture of C. aceticum in liquid AcM medium was harvested by centrifugation and resuspended in 100 µl of liquid AcM. The E. coli cells were then brought into the anaerobic chamber, and cell suspensions (100 µl of each) were mixed and plated together on an AcM solid medium plate. The next day, cells were scraped from the surface of the conjugation plate, and plated onto fresh AcM plates containing nalidixic acid (10 µg/ml) and erythromycin (5 µg/ml) to select for positive transformants. Colonies resistant to erythromycin and nalidixic acid were passaged successively to verify transformation.

Transformed *C. aceticum* strains were further validated by streaking onto LB and testing for aerobic growth (*C. aceticum* will not grow aerobically), plasmid purification (Qiagen) from the transformed *C. aceticum* strain, retransformation into *E. coli* Top10 chemically competent cells, plasmid purification from the retransformed *E. coli*, and confirmation by complete sequencing (Quintara BioSciences).

Together, Examples 10 and 11 demonstrate the successful transformation of *Clostridium aceticum* with four plasmids (pDW280, pMCS537, pMCS444 and pMCS445) having a total of three distinct replication origins into *Clostridium aceticum*.

Example 12: Comparison of Transformation Methods for *Clostridium aceticum*

Protoplasts of *Clostridium aceticum* were generated and recovered according to the method of Allock et al., 1982, "*Clostridium acetobutylicum* protoplast formation and regeneration," *Applied Environmental Microbiology*, Vol. 43, No. 3: 719-721.

As indicated in Table 5, Applicants tested multiple methods for transforming *Clostridium aceticum*, including: (1) electroporation of protoplasts (according to the method described in Romero et al. for the transformation of protoplasts of *Bacillus subtilis*; (2) Polyethylene-glycol (PEG)-mediated transformation, according to the method described in Chang and Cohen for the transformation of protoplasts of *Bacillus subtilis*; (3) liposome-mediated transformation (using DOTAP), according to the method of Metcalf et al. for the transformation of *Methanosarcina acetivorans*; and (4) the conjugal transfer of plasmids pDW268 and either pDW280 or pMCS537 as described in Example 9 of the instant application.

successful transformation of *Clostridium aceticum*. No successful transformants of *Clostridium aceticum* could be obtained using protoplast electroporation, PEG-mediated protoplast transformation, or liposome-mediated transformation. Additionally, no successful transformants of *Clostridium aceticum* could be obtained using vegetative cell electroporation.

Examples 9 and 10 demonstrate the successful transformation of four plasmids (pDW280, pMCS537, pMCS444, and pMCS445) into *Clostridium aceticum*, three of which harbor distinct replication origins (pDW280 and pMCS537 have the repB replication origin, while pMCS444 has a repA replication origin and pMCS445 has a repH replication origin).

Example 13: *Clostridium ljungdahlii* Transformation by Conjugal Transfer (pMCS466 with pMCS200 or with pMCS201)

To generate an *E. coli* S17-1 strain capable of both methylation in and conjugation from *E. coli* into *C. ljungdahlii*, *E. coli* S17-1 cells were cotransformed (using standard techniques) with pMCS466 and either pMCS200 or plasmid pMCS201. The plasmid pMCS466 encodes the *C. ljungdahlii* methyltransferase that protects DNA from degradation by the endogenous *C. ljungdahlii* restriction-modification system. To create plasmid pMCS466, plasmid a pMCljS was amplified by PCR with primers o107 and o108 (Table 4). The carbenicillin resistance cassette was amplified from plasmid pMCS94 with primers o105 and o106 (Table 4). The two PCR products were annealed using the Seamless Cloning methods (invitrogen) to create plasmid pMCS466, a derivative of plasmid pMCljS where the resistance marker has been changed from spectinomycin to carbenicillin.

S17-1 strains with both the pMCS466 methylation plasmid and either the pMCS200 or the pMCS201 shuttle plasmid were grown overnight in liquid LB medium containing the appropriate antibiotics, and diluted the next day into fresh medium. During mid-exponential phase, at an $OD_{600}$ of approximately 0.6, 5 ml of cells were harvested by

TABLE 5

Results of attempts to transform *Clostridum aceticum* using various methods

| Transformation Method | Result of Test | Method Adapted From |
|---|---|---|
| Protoplast electroporation | Cell lysis | Romer et al., 2006. "Transformation of undomesticated strains of *Bacillus subtilis* by protoplast electroporation." *Journal of Microbiological Methods*, Vol. 66: 556-559. |
| Protoplasts + PEG | False positives | Chang and Cohen, 1979. "High frequency transformation of *Bacillus subtilis* protoplasts by plasmid DNA." *Molecular Genes and Genetics*, Vol. 168(1): 111-115. |
| Protoplasts + DOTAP | False positives | Metcalf et al., 1997. "A genetic system for Archaea of the genus *Methanosarcina*: liposome-mediated transformation and construction of shuttle vectors." *Proceedings of the National Academy of Sciences*, Vol. 94: 2626-2631. |
| Conjugation from *E. coli* Using pDW268 and (pDW280 or pMCS537) | True positive | Instant application. |

Only conjugation from *E. coli* harboring the arabinose-inducible plasmid pDW268 and the conjugative shuttle plasmid pDW280 (or the smaller conjugative shuttle plasmid pMCS537 or pMCS444), as described by Applicants in Examples 9 and 10 of the instant application, resulted in the centrifugation, washed three times in liquid LB medium without antibiotics, and resuspended in 250 µl of LB with 12 µl of a 15% arabinose solution prior to conjugation. Concurrently, a culture of *C. ljundahlii* in liquid MES-F medium was harvested by centrifugation and resuspended in 100 µl of liquid MES-F. The *E. coli* cells were then brought into the anaerobic chamber, and cell suspensions (100 µl of each) were mixed and plated together on solid MES-F medium plate. The next day, cells were scraped from the surface of the conjugation plate, and plated onto fresh MES-F plates containing nalidixic acid (10 µg/ml) and the appropriate antibiotic to select for positive transformants. Colonies resistant to antibiotic and nalidixic acid were passaged successively to verify transformation.

Transformed *C. ljungdahlii* strains were further validated by plasmid purification (Qiagen) from the transformed *C. ljungdahlii* strain, retransformation into *E. coli* Top10 chemically competent cells, plasmid purification from the retransformed *E. coli*, and confirmation by gel electrophoresis.

This Example demonstrates the successful transformation of *Clostridium ljungdahlii* with two plasmids harboring distinct replication origins: (1) pMCS200, with a repA replication origin (also called pBP1), and (2) pMCS201, with a repH replication origin (also called pCB102).

Figure 36A:
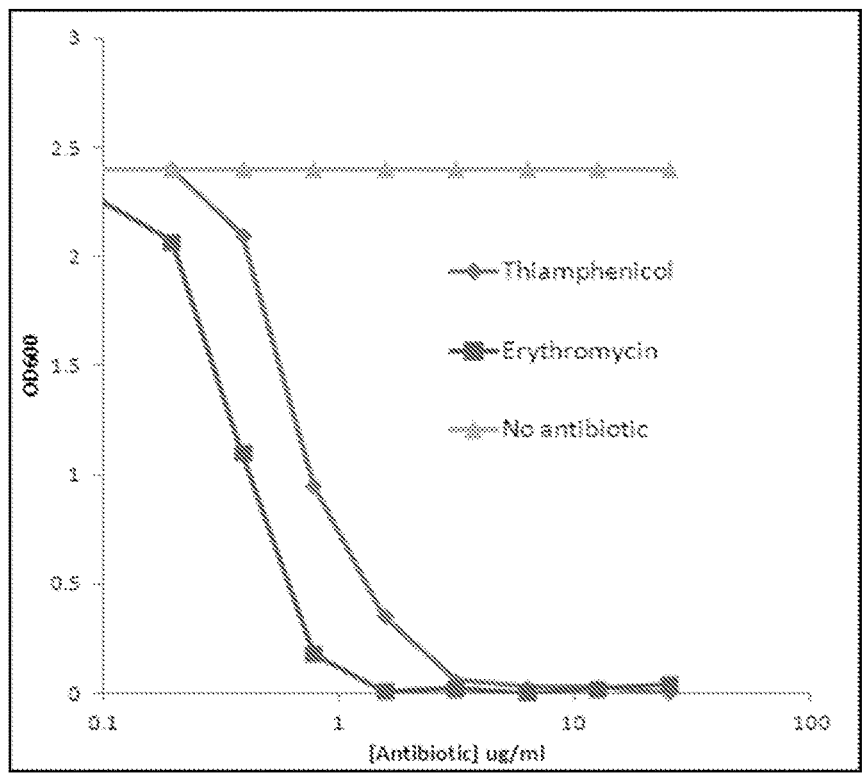
FIG. 36A-B show the results of assays to determine the minimum inhibitory concentration of antibiotics thiamphenicol (Thi) and erythromycin (Em) for *Clostridium aceticum* grown in liquid culture (FIG. 36A) or for *Clostridium aceticum* grown on plates of *Clostridium aceticum* growth media (AcM media) (FIG. 36B).
Figure 38A:
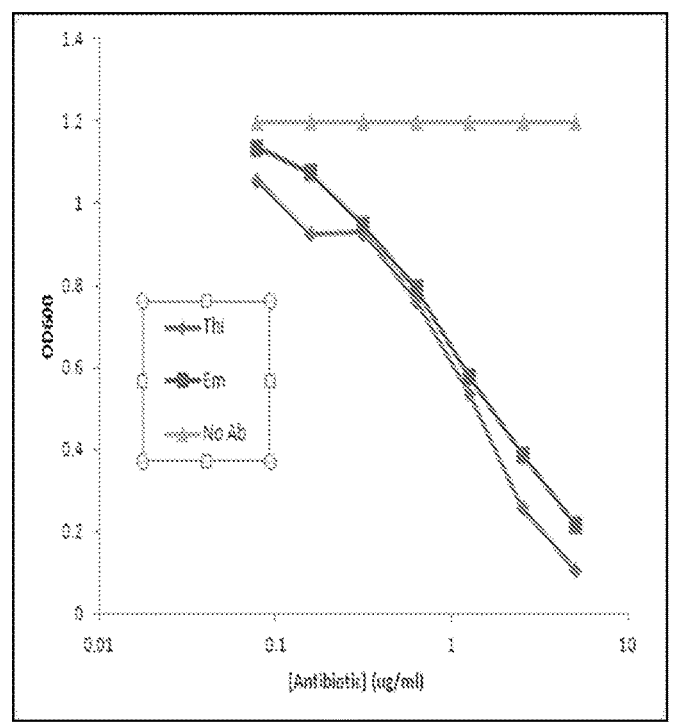
FIG. 38A-B shows the results for assays to determine the minimum inhibitory concentration of antibiotics thiamphenicol (Thi) and erythromycin (Em) for *Clostridium ljungdahlii* gown in liquid culture (FIG. 38A) or for *Clostridium ljungdahlii* gown on plates (FIG. 38B).

Example 14: Determining Minimum Inhibitory Antibiotic Concentrations (MIC) for Clostridial Bacteria The minimum inhibitory concentration (MIC) is the lowest concentration of antibiotic determined to have an inhibitory effect on the growth of an organism. The minimum inhibitory concentrations of thiamphenicol and erythromycin for *Clostridium aceticum* (in liquid AcM media) and *Clostridium ljungdahlii* in liquid MES-F or MES-X media (Table 6) were determined empirically by serially diluting the media specific to each strain spiked with antibiotic. The starting concentration was 30 ug/ml. A 1:20 volume inoculum of an overnight culture of *Clostridium aceticum* was added to each serial dilution and allowed to grow overnight. The $OD_{600}$ of each sample was measured and the MIC determined to be the lowest concentration of antibiotic at which no overnight growth had been observed. The results for *Clostridium aceticum* are shown in FIG. 36A. The results for *Clostridium ljungdahlii* are shown in FIG. 38A.

Figure 36B:
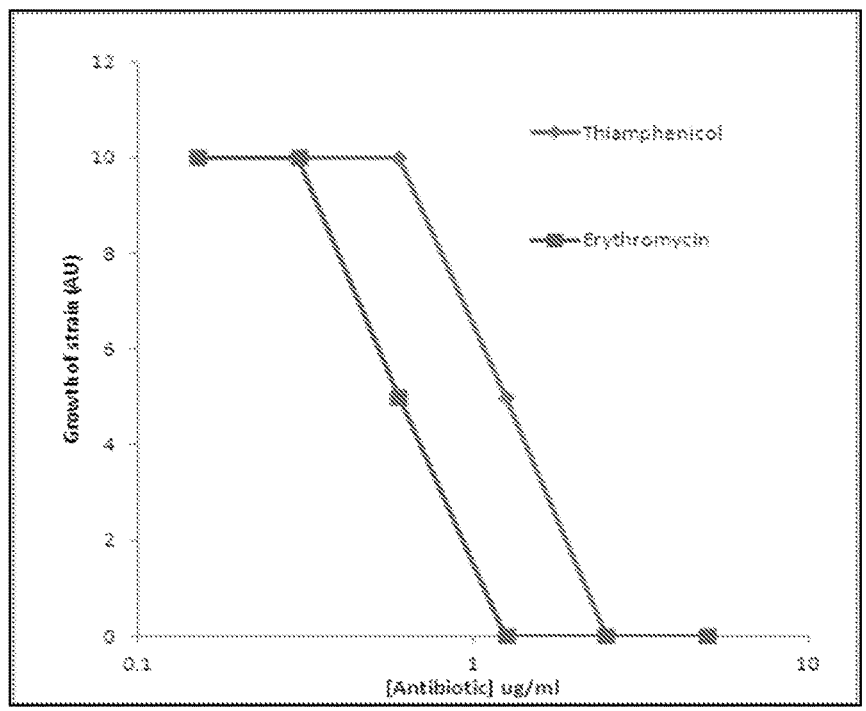
Figure 37:
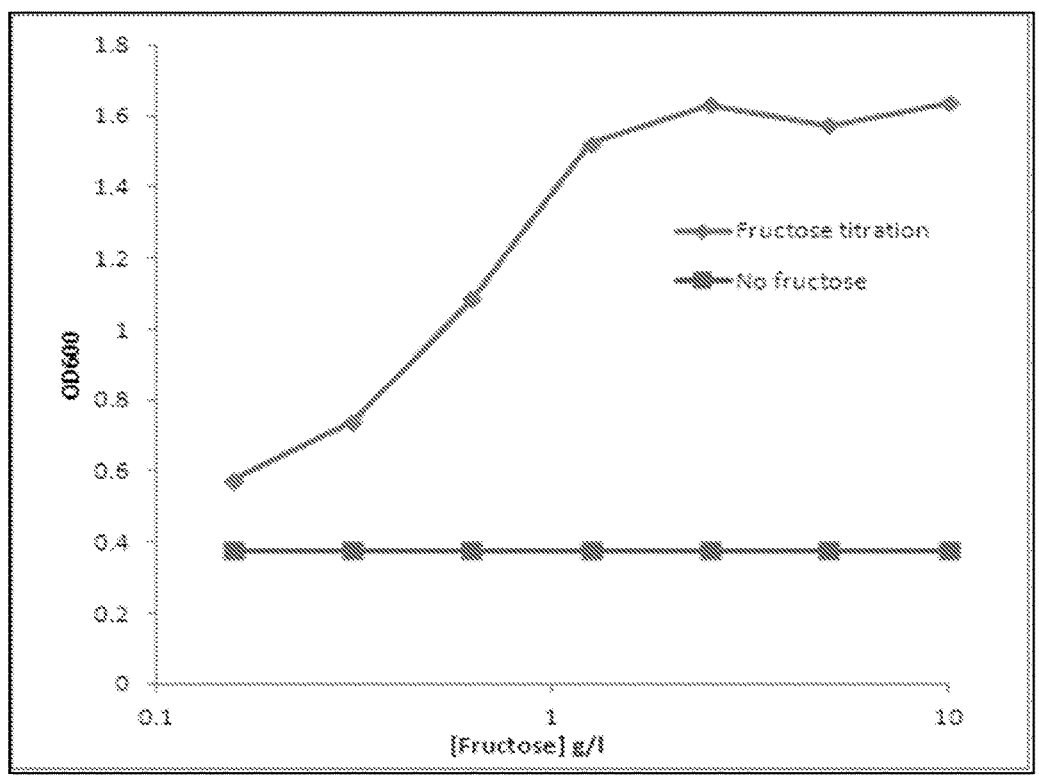
FIG. 37 shows the results of fructose titration for *Clostridium aceticum*, demonstrating 10 g/l of fructose was not limiting, and that fructose only becomes limiting at concentrations less than ~1.5 g/l.
Figure 38B:
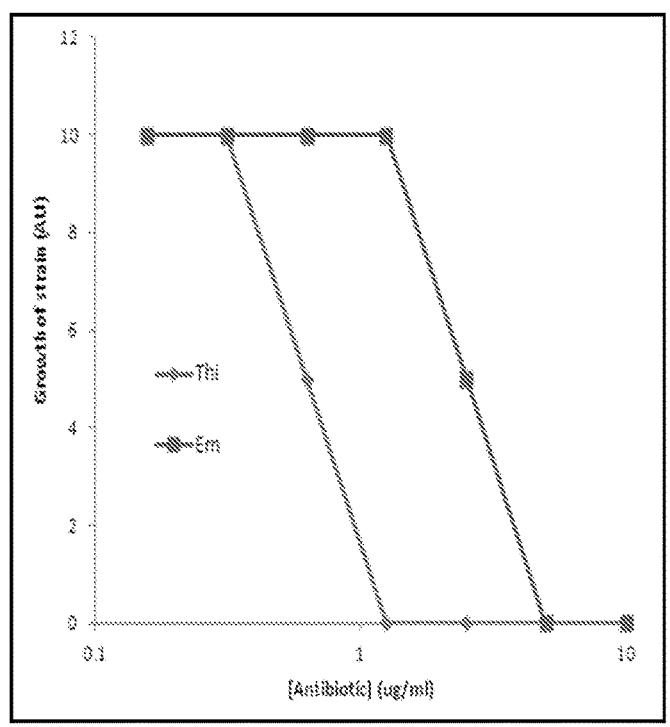
Figure 39:
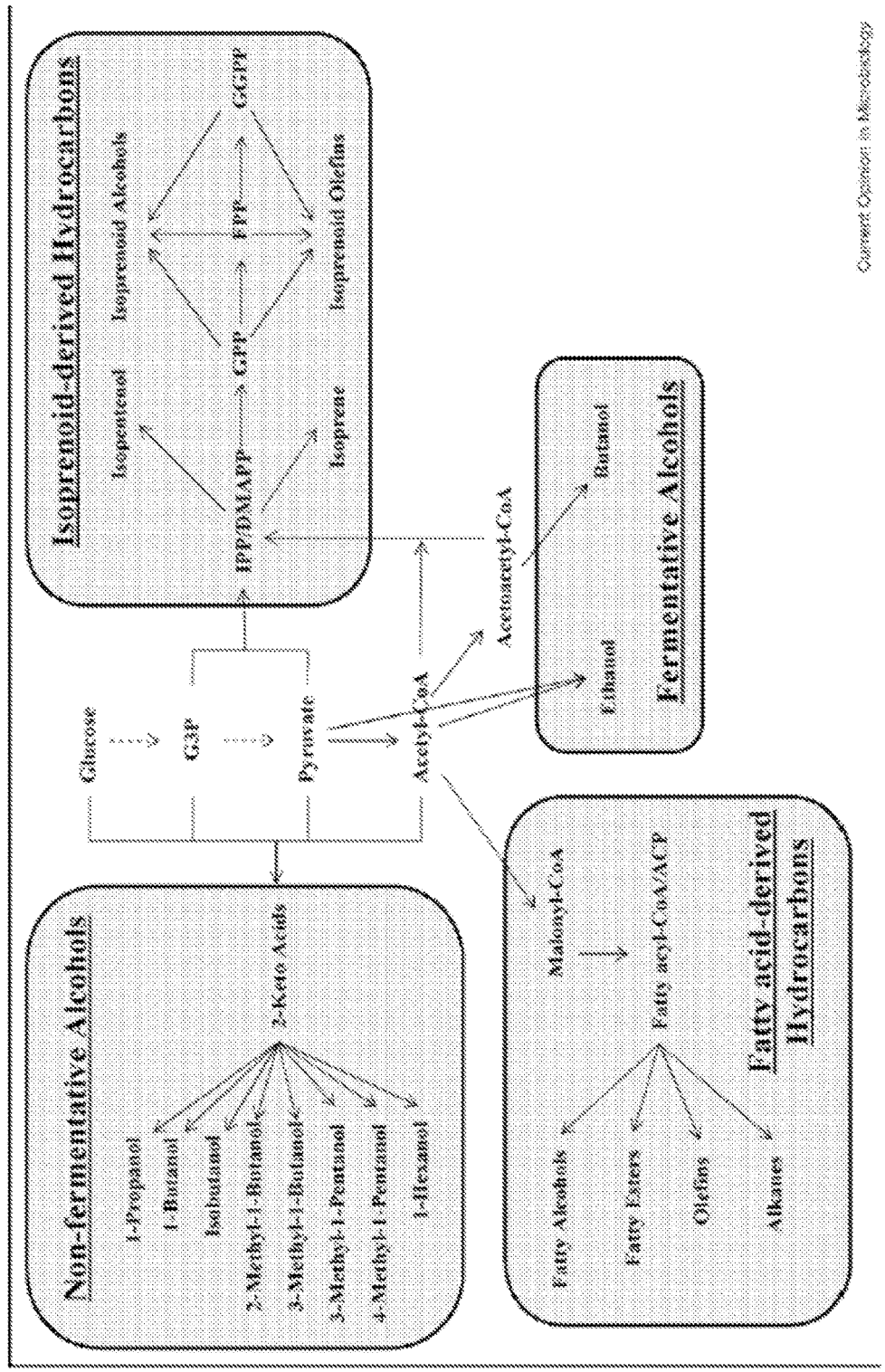
FIG. 39 shows the microbial fuels that can be produced from syngas via cellular pathways.
Figure 40:
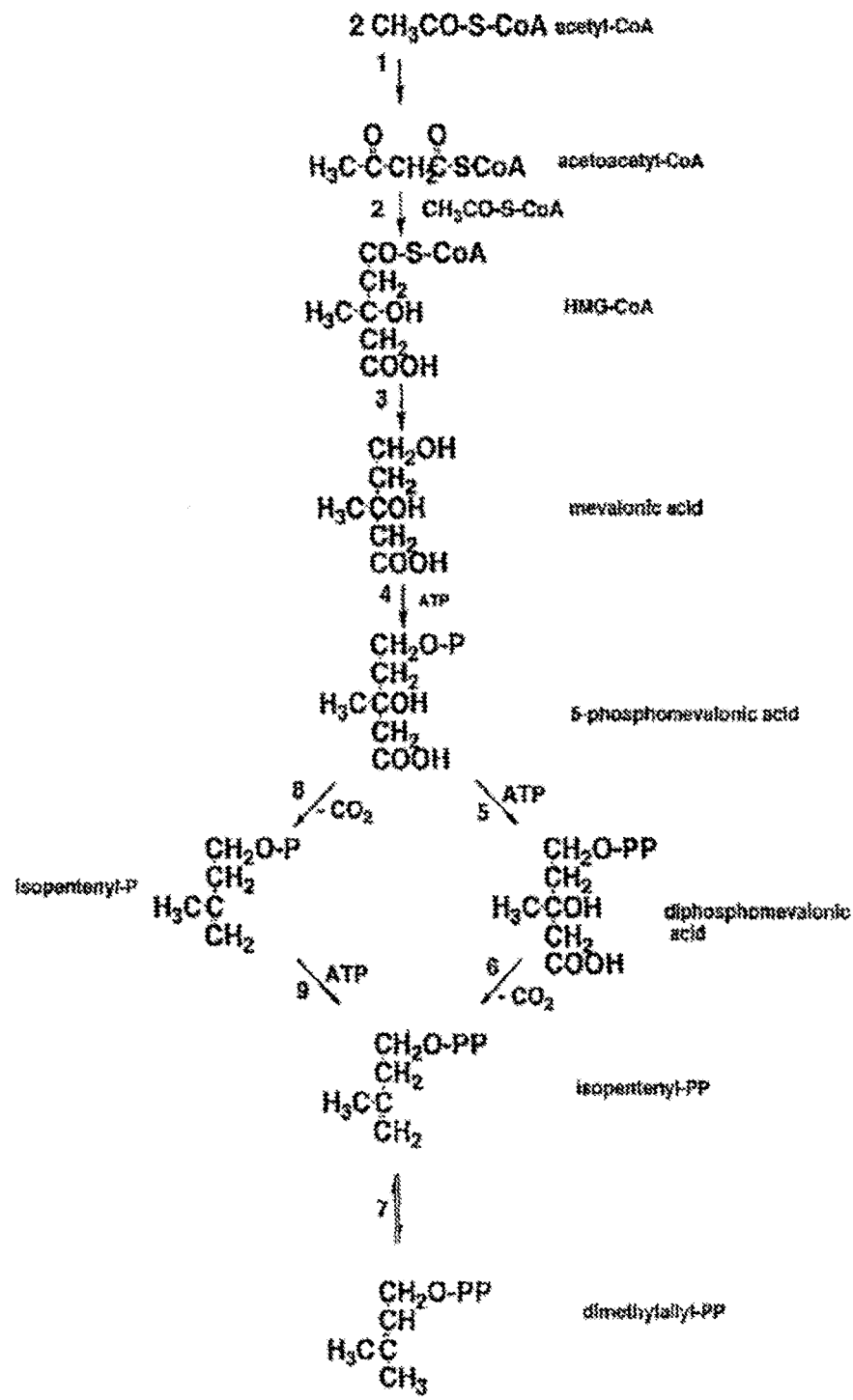
FIG. 40 shows the classical and modified MVA pathways. 1, acetyl-CoA acetyltransferase (AACT); 2, HMG-CoA synthase (HMGS); 3, HMG-CoA reductase (HMGR); 4, mevalonate kinase (MVK); 5, phosphomevalonate kinase (PMK); 6, diphosphomevalonate decarboxylase (MVD or DPMDC); 7, isopentenyl diphosphate isomerase (IDI); 8, phosphomevalonate decarboxylase (PMDC); 9, isopentenyl phosphate kinase (IPK). The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology Reviews*, 71:97-120, 2007, which is incorporated by reference in its entirety, particularly with respect to nucleic acids and polypeptides of the modified MVA pathway. The modified MVA pathway is present, for example, in some archaeal organisms, such as *Methanosarcina mazei*.
Figure 41:
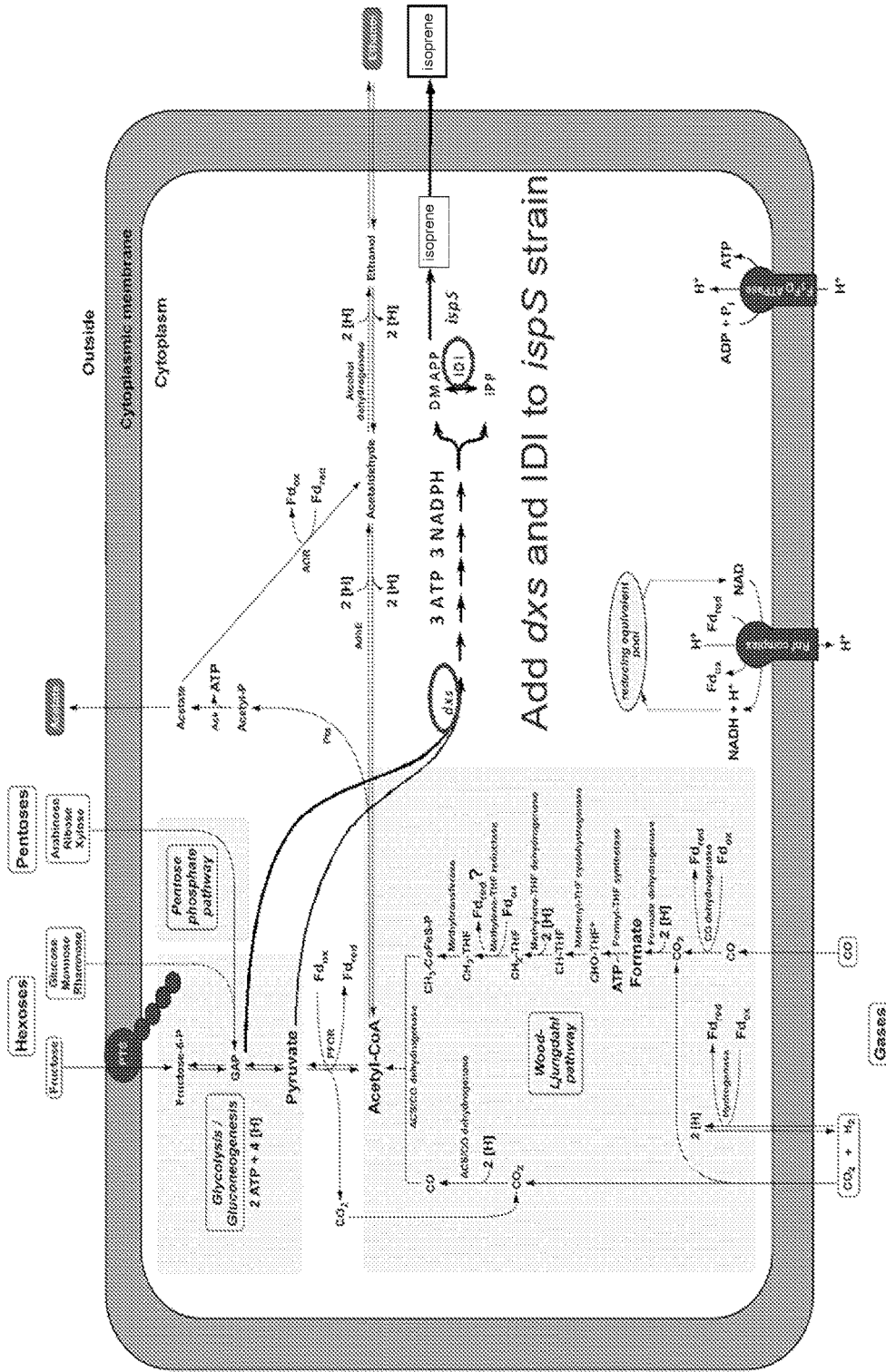
FIG. 41 shows a schematic representation of an obligate anaerobe expressing (a) a heterologous IspS polypeptide, (b) a heterologous DXS polypeptide, and (c) a heterologous IDI polypeptide to increase DXP pathway flux and isoprene production.
Figure 42:
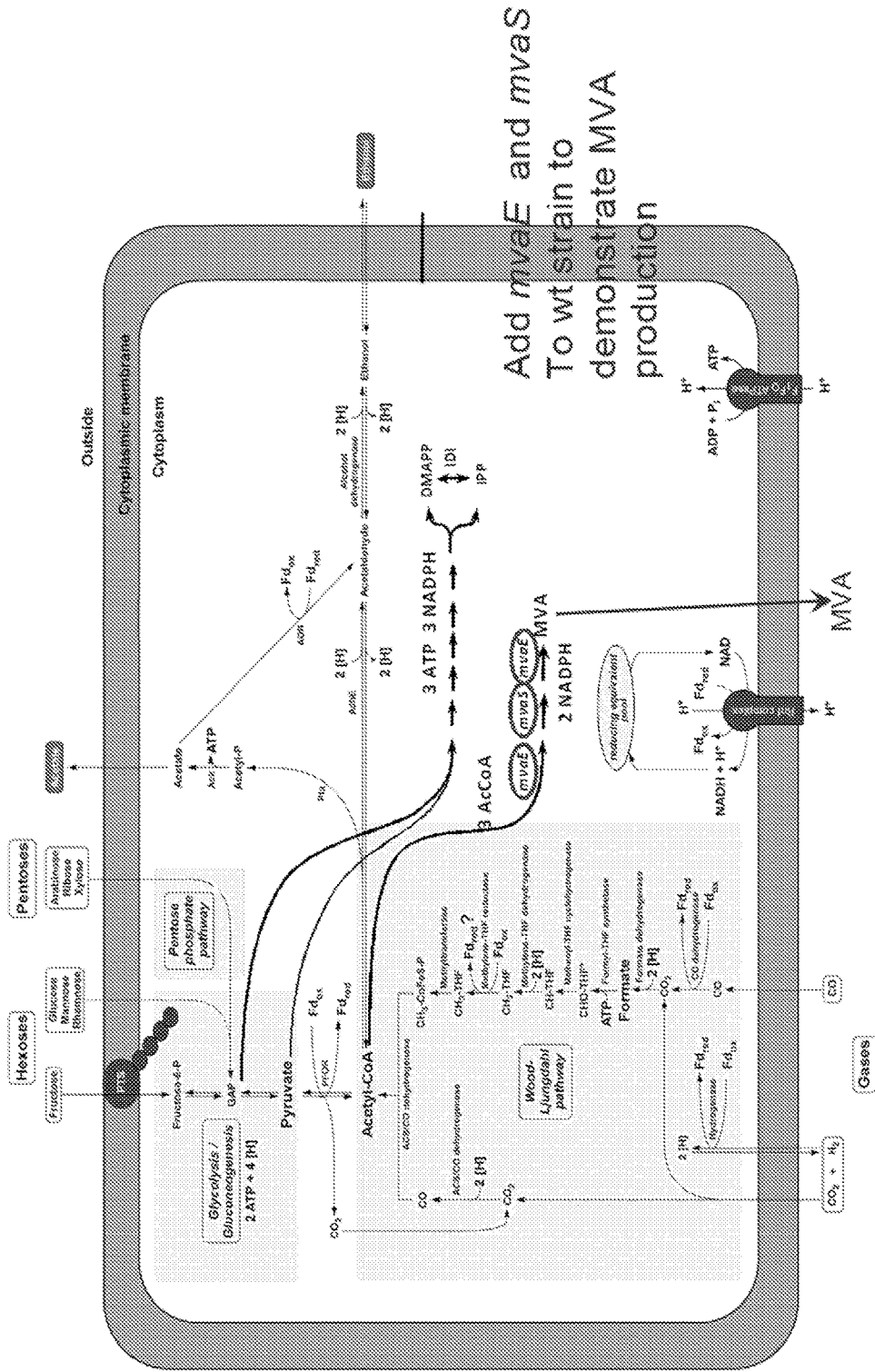
FIG. 42 shows a schematic representation of an obligate anaerobe engineered with mvaE and mvaS to express the upper MVA pathway.
Figure 43:
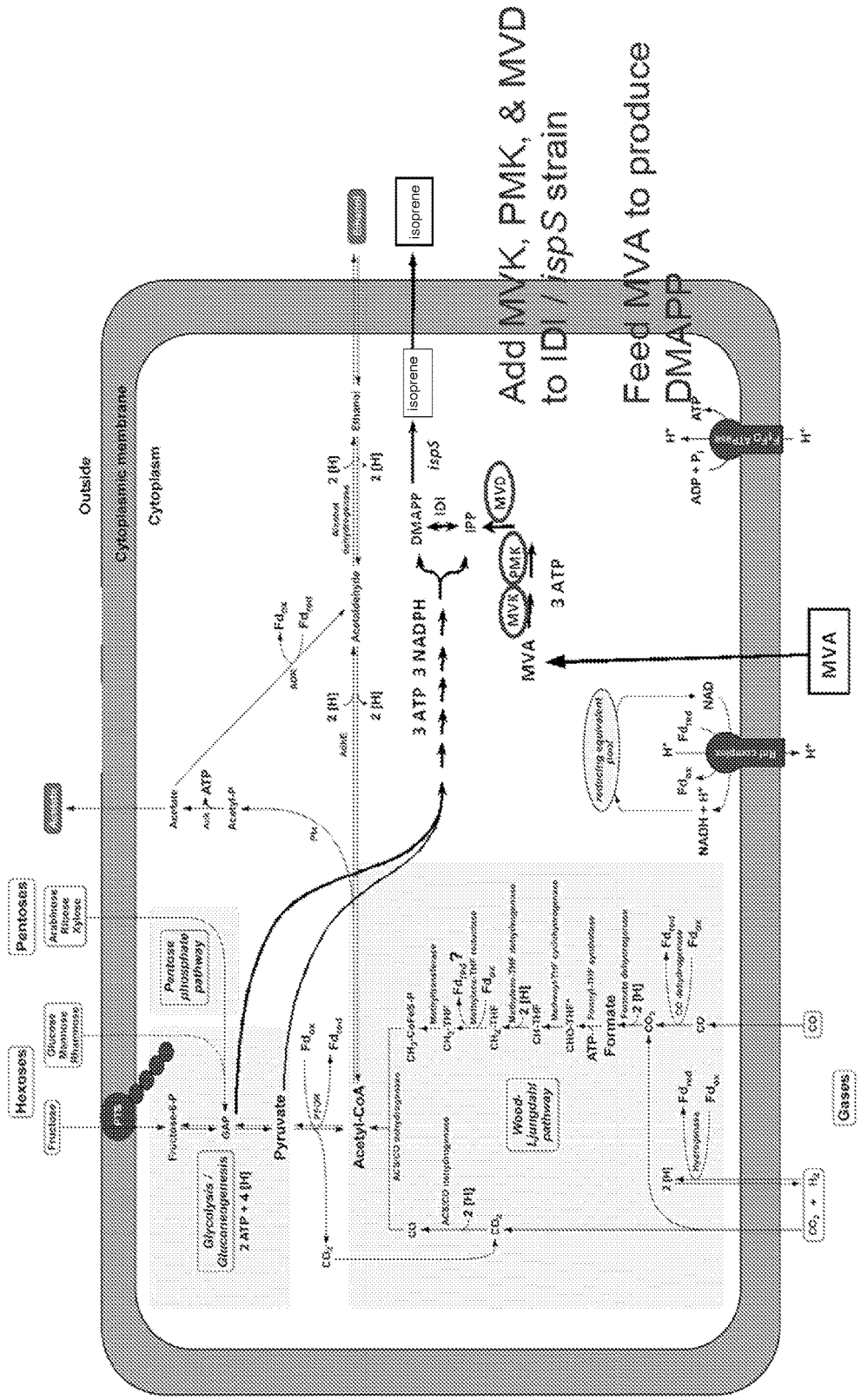
FIG. 43 shows a schematic representation of expressing the lower MVA pathway in an obligate anaerobe including expressing (a) a heterologous MVK polypeptide, (b) a heterologous PMK polypeptide, and (c) a heterologous MVD polypeptide in the cells expressing heterologous IDI polypeptide and heterologous IspS polypeptide for the purpose of increasing isoprene production.
Figure 44:
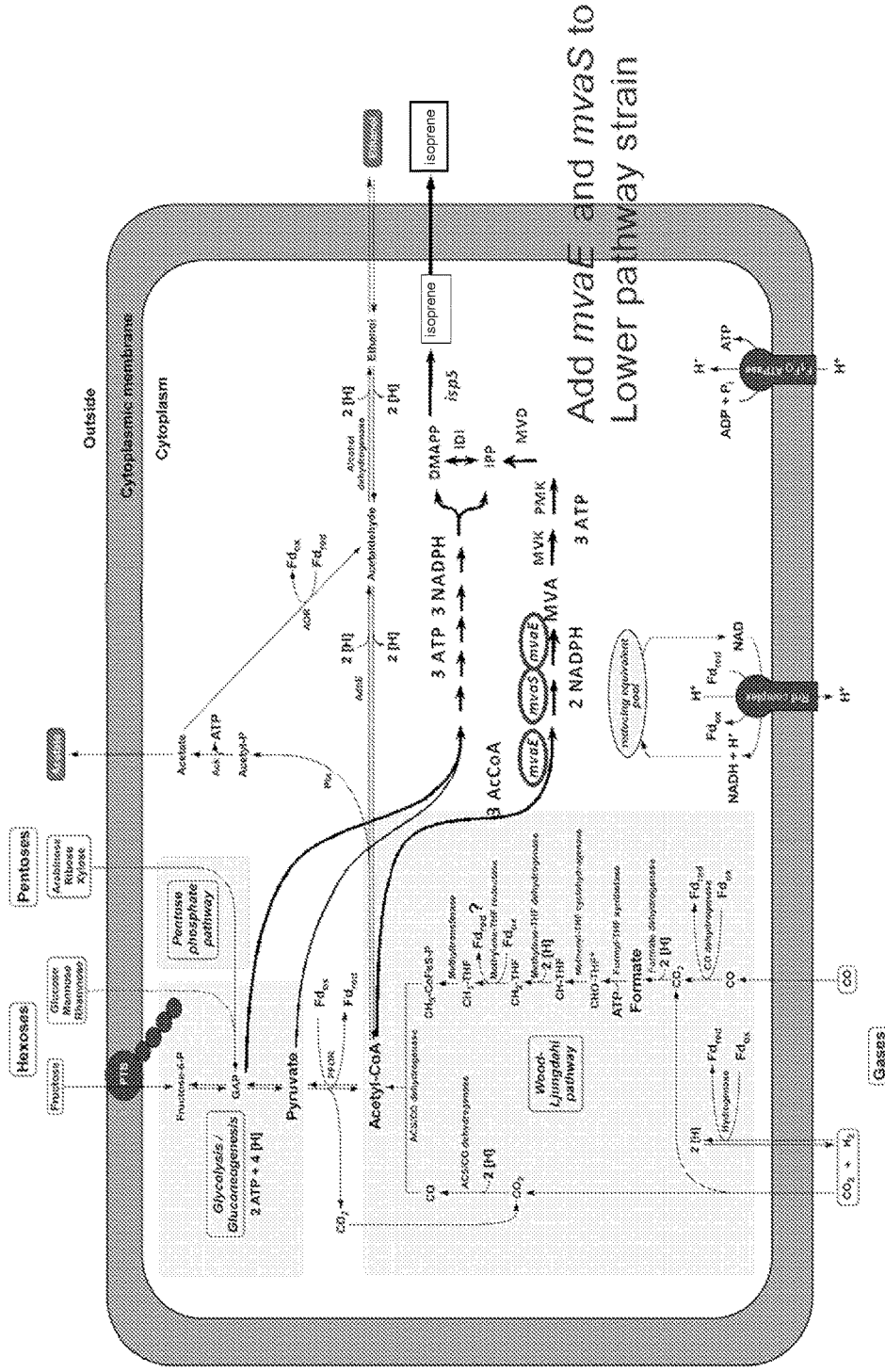
FIG. 44 shows a schematic representation of expressing the entire MVA pathway in an obligate anaerobe by introducing mvaE and mvaS in the cells expressing (a) a heterologous MVK polypeptide, (b) a heterologous PMK polypeptide, (c) a heterologous MVD polypeptide, (d) a heterologous IDI polypeptide, and (e) a heterologous IspS polypeptide for the purpose of increasing isoprene production.
Figure 45:
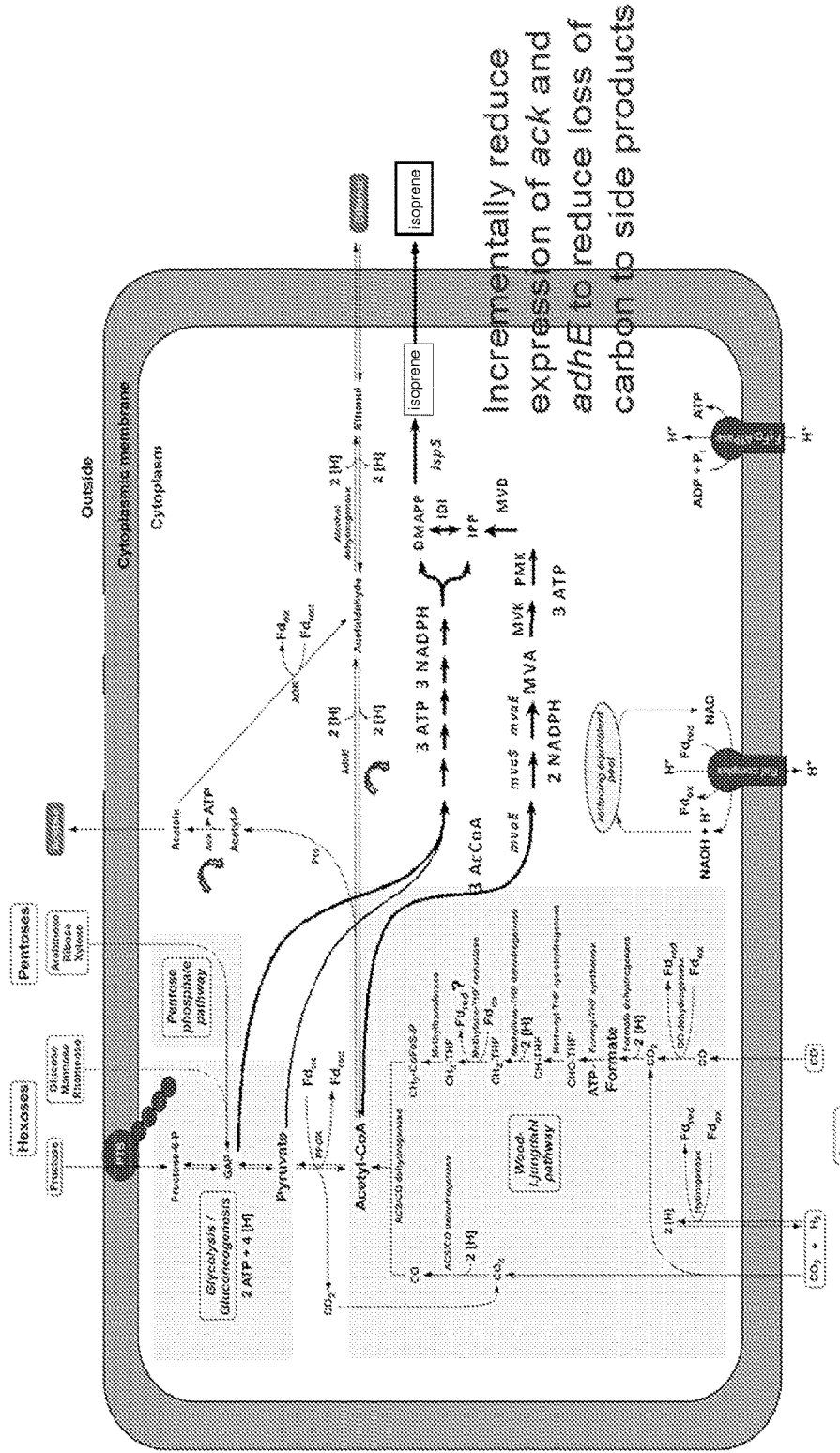
FIG. 45 shows a schematic representation of redirecting carbon flux away from acetate by reducing expression of ack and adhE to reduce loss of carbon to side products. The arrows next to Ack or AdhE used in the production of acetate and ethanol, respectively, indicate a reduction of activity or enzyme expression for pathways leading to fermentation products such as acetate, ethanol, or any other alcohol, or carbon containing end product. The purpose is to maximize carbon channeling to isoprene via genetic manipulation.

To determine the MIC of either thiamphenicol or erythromycin in agar-solidified plates, serial dilutions of antibiotic were made into molten agar-media from a starting concentration of 30 ug/ml. The media was poured into petri dishes and allowed to solidify, then transferred into the anaerobic chamber and allowed to equilibrate for 48 hours. A 10 ul sample of an overnight culture was spread on each agar plate and allowed to grow for 48 hours. The MIC was the lowest concentration of antibiotic at which no growth was observed. The results for *Clostridium aceticum* (grown on AcM media) are shown in FIG. 36B and the results for *Clostridium ljungdahlii* grown on MES-F media (described in Tables 6 and 7) are shown in FIG. 38B.

TABLE 6

MES-Fructose (MES-F) or MES-Xylose (MES-X) Recipe

| Media Component | f. wt | stock g/L | stock molarity (M) | vol. stock/liter | 1x MES F final (mM) |
|---|---|---|---|---|---|
| $NH_4Cl$ | 53.4 g | 100 | 1.87 | 10 ml | 18.7 |
| $KH_2PO_4$ | 136.09 | 100 | 0.73 | 2 ml | 1.46 |
| $MgSO_4·7H_2O$ | 246.47 | 100 | 0.406 | 2 ml | 0.811 |
| KCl | 74.55 | 100 | 1.34 | 1 ml | 1.34 |
| $CaCl_2·2H_2O$ | 147.01 | 20 | 0.136 | 1 ml | 0.136 |

TABLE 6-continued

MES-Fructose (MES-F) or MES-Xylose (MES-X) Recipe

| Media Component | f. wt | stock g/L | stock molarity (M) | vol. stock/liter | 1x MES F final (mM) |
|---|---|---|---|---|---|
| Sodium Acetate | 136.08 | 166 | 1.22 | 2.5 ml | 3.05 |
| Cysteine HCl | 175.6 | 879 mg | | | 5.01 |
| Wolfe's vitamin solution | | | | 10 ml | |
| *Ljungdahlii* trace metals mix | | | | 10 ml | |
| Resazurin | 229.19 | 1 | 0.00436 | 1 ml | 4.36 |
| Yeast Extract | | | | 2 g | |
| MES | 195.2 | 20 | | 20 g | 102.45 |
| Fructose* | 180.16 | 10 | | 10 g | 55.5 |

*To create MES-X media, substitute 10 grams of xylose for the 10 grams of fructose.

TABLE 7

*Ljungdahlii* trace metals mix for use in MES-F recipe

| Component | Amount |
|---|---|
| Nitrilotriacetic acid | 2.0 g |
| $MnSO_4·H_2O$ | 1.0 g |
| $Fe(SO_4)_2(NH_4)_2·6H_2O$ | 0.8 g |
| $CoCl_2·6H_2O$ | 0.2 g |
| $ZnSO_4·7H_2O$ | 0.2 mg |
| $CuCl_2·2H_2O$ | 20.0 mg |
| $NiCl_2·6H_2O$ | 20.0 mg |
| $Na_2MoO_4·2H_2O$ | 20.0 mg |
| $Na_2SeO_4$ | 20.0 mg |
| $Na_2WO_4$ | 20.0 mg |
| Distilled water | Bring up to 1.0 L |

Example 15: Conjugal Transfer of ispS-Containing Shuttle Plasmid pMCS537-IspS into *C. aceticum*

A pMCS537 shuttle vector is modified to include a truncated, codon-optimized copy of the ispS (isoprene synthase) gene from *Poplus alba* to create the shuttle plasmid pMCS537-IspS, and transformed into *Clostridium aceticum* by conjugative transfer.

The *E. coli* conjugal transfer strain S17-1 is cotransformed with pDW268, a plasmid encoding arabinose-inducible M.CacI, and the pMCS537-IspS plasmid, to generate an *E. coli* S17-1 strain capable of both methylation in and conjugation from *E. coli* into *C. aceticum*.

S17-1 strains with both the pDW268 methylation plasmid and the pMCS537-IspS shuttle plasmid are grown overnight in liquid LB medium containing the appropriate antibiotics, and diluted the next day into fresh medium. During mid-exponential phase, at an OD600 of approximately 0.6, are harvested by centrifugation, washed three times in liquid LB medium without antibiotics, and resuspended in 250 µl of LB with 12 µl of a 15% arabinose solution prior to conjugation. Concurrently, a culture of *C. aceticum* in liquid AcM medium is harvested by centrifugation and resuspended in 100 µl of liquid AcM. The *E. coli* cells are then brought into an anaerobic chamber, and cell suspensions (100 µl of each) are mixed and plated together on an AcM solid medium plate. The next day, cells are scraped from the surface of the conjugation plate, and plated onto fresh plates containing nalidixic acid (10 µg/ml) and the appropriate antibiotic to select for positive transformants. Colonies resistant to the appropriate antibiotic and nalidixic acid are passaged successively to verify transformation. Transformed *C. aceticum* strains are further validated by streaking onto LB and testing for aerobic growth (*C. aceticum* will not grow aerobically), plasmid purification (Qiagen) from the transformed *C. aceticum* strain, retransformation into *E. coli* Top10 chemically competent cells, plasmid purification from the retransformed *E. coli*, and confirmation by complete sequencing (Quintara BioSciences). For further confirmation, PCR products are amplified from plasmids isolated from a transformed *C. aceticum* strain to confirm the presence of the entire heterologous sequence, the *C. aceticum* origin of replication, the ispS gene from *Poplus alba*, and the erythromycin resistance cassette, respectively.

Example 16: Production of Isoprene by *Clostridium aceticum* Transformed with pMCS537-IspS and Grown on Fructose

*Clostridium aceticum* harboring shuttle plasmid pMCS537-IspS is grown for isoprene production in DSZM medium 135 supplemented with fructose. After growth the headspace is sampled by solid phase microextraction (SPME) and software known in the art is used to extract for m/z 67 ion that is characteristic of isoprene. An authenticated isoprene standard is used to confirm the spectrum and retention time, and a peak at the expected isoprene elution time (demonstrated by the isoprene standard) would demonstrate that the transformed *C. aceticum* produces detectable levels of isoprene when grown on fructose.

Example 17: *Clostridium ljungdahlii* transformation by conjugal transfer (pDW268 with pMCS200-A1)

To improve upon the ethanol production levels of wild-type *Clostridium ljungdahlii*, the pMCS200 shuttle vector is modified (e.g., using any of the techniques disclosed herein) to include heterologous aldehyde dehydrogenase and alcohol dehydrogenase genes, thus creating the shuttle vector pMCS200-A1. The heterologous genes are from another clostridial organism, or from any organism known to possess these two genes. To generate an *E. coli* S17-1 strain capable of both methylation in and conjugation from *E. coli* into *C. ljungdahlii*, *E. coli* S17-1 cells are cotransformed with pDW268, a plasmid encoding arabinose-inducible M.CacI, and pMCS200-A1. Briefly, S17-1 strains with both the pDW268 methylation plasmid and the pMCS200-A1 shuttle plasmid are grown overnight in liquid LB medium containing the appropriate antibiotics, and diluted the next day into fresh medium. During mid-exponential phase, cells are harvested by centrifugation, washed three times in liquid LB medium without antibiotics, and resuspended in 250 µl of LB with 12 µl of a 15% arabinose solution prior to conjugation. Concurrently, a culture of *C. ljundahlii* in liquid MES-F medium (Tables 6 and 7) is harvested by centrifugation and resuspended in 100 µl of liquid MES-F. The *E. coli* cells are brought into the anaerobic chamber, and cell suspensions mixed and plated together on solid MES-F medium plate. The next day, cells are scraped from the surface of the conjugation plate, and plated onto fresh MES-F plates containing nalidixic acid (10 µg/ml) and the appropriate antibiotic to select for positive transformants. Colonies resistant to the appropriate antibiotic and nalidixic acid are passaged successively to verify transformation.

Transformed *C. ljungdahlii* strains are further validated by plasmid purification (Qiagen) from the transformed *C. ljungdahlii* strain, retransformation into *E. coli* Top10 chemically competent cells, plasmid purification from the retransformed *E. coli*, and subsequent gel electrophoresis.

Example 18: Production of Ethanol by *Clostridium ljungdahlii* Transformed with pMCS200-A1 and Grown on Fructose

*Clostridium ljungdahlii* harboring shuttle plasmid pMCS200-A1 is grown for ethanol production in MES-F media (Tables 6 and 7). After growth, a sample is analyzed by solid phase microextraction (SPME) and software known in the art is used to extract for the m/z ion characteristic of ethanol. An authenticated ethanol standard is used to confirm the spectrum and retention time, and a peak at the expected ethanol elution time (demonstrated by the standard) demonstrates that the transformed *C. ljungdahlii* produces detectable levels of ethanol when grown on fructose. It is expected that *Clostridium aceticum* transformed with pMCS200-A1 and grown on fructose will produce more ethanol than wild-type *Clostridium aceticum* which has not been transformed with pMCS200-A1.

The invention claimed is:

1. A method of producing a recombinant *Clostridium* bacterial transformant, comprising:
   a) introducing a polynucleotide encoding for a DNA methyltransferase into a *Escherichia* bacterial host cell, wherein the polynucleotide encoding for a DNA methyltransferase has at least 90% sequence identity to SEQ ID NO: 1,
   b) culturing the *Escherichia* bacterial host cell under conditions suitable for expression of the DNA methyltransferase, wherein the encoded DNA methyltransferase methylates a polynucleotide,
   c) transferring the methylated polynucleotide from the *Escherichia* bacterial host cell to a *Clostridium* bacterial host cell, wherein the bacteria transformed using this method are selected from the group consisting of *Clostridium aceticum*, *Clostridium ljungdahlii*, *Clostridium acetobutylicum*, and *Clostridium autoethanogenum*.

2. The method of claim 1, wherein the polynucleotide encoding for a DNA methyltransferase is SEQ ID NO: 2.

3. The method of claim 1, wherein the encoded DNA methyltransferase methylates a polynucleotide at a sequence comprising CCWGG.

4. The method of claim 3, wherein the sequence comprising CCWGG is selected from the group consisting of CCAGG (SEQ ID NO: 9) and CCTGG (SEQ ID NO: 10).

* * * * *

SEQUENCE LISTING

```
<160> NUMBER OF SEQ ID NOS: 62

<210> SEQ ID NO 1
<211> LENGTH: 1422
<212> TYPE: DNA
<213> ORGANISM: Clostridium aceticum

<400> SEQUENCE: 1
atggccgtac tccgcaatat tgatgagcaa ctgaccgagg aatttaagaa actgccgatc      60
gactattggg actttgaggg tgaggacacg aaagaactga cgcacggcct gcacaactat     120
ccggcggtga tggtttatcc gatctaccgt aacattatcg acatcgtgaa gcgtcacggt     180
gaggtcgaaa cctttctgga cccgtttatg ggtagcggta cgggcctggt ggaaggcaag     240
ctggcgggtt tcaacaaagt gtacggtacg gatctgaatc ctctggcagt gctgctgagc     300
aaggttaaga ccaccgtctt gaaagaggat agcgtggata ttcaggacaa gctgctgcgc     360
gagaatattg agcaggcgtt cgtgtccagc aaacagctgc tggataacat tgacaattac     420
attgcggaga agggcctgga cgtcagcgcc aaagacggct ggggctctga tgcgcatgtc     480
```

| | |
|---|---|
| attttgcgcg agtatctgga tacctacaac agcggtctga aaatcccaga ctttaagaat | 540 |
| atgggttatt ggttcaaacc gcgcgttatt ctggagctgc aactgattaa ggatatcatt | 600 |
| ctgcagatcg agaatgagga cttccgtaac ttctttctgg tctgcttctc tgaaactgcc | 660 |
| cgctacgtga gcaacacccg taatggtgag ttcaagctgt tccgtatcaa gaaagaaaaa | 720 |
| gtggcagatt tcaatccgga cgttaagatc gagttttaca atatctggat cgtaacatc | 780 |
| gaaaagatta agactttga caaacgttgt aacaacgatt gcgaagttag cgttgctttt | 840 |
| gaagataccc gcattctgga ctcggttccg gacaatagca tcgatctgat gattaccagc | 900 |
| ccaccgtacg gcgatagcaa aactacggtg gcgtacggtc aatttagccg tccgtctttg | 960 |
| tggtggttgg atctggaatt gatggacatc gaagagctga atcaagttga caacaatctg | 1020 |
| ctgggtggta agaaggtgga caaagacttc gagtgtgaac tgagctcccg taccttggag | 1080 |
| aaggcgatta agaaatcaa agaaaaggac ctggaccgcg cacgtgacgt ttatagcttc | 1140 |
| tacgaggatt tggataaggc tatggagtcc attacgaaaa agatgcgtca taacagctac | 1200 |
| cagttctggg ttgtcggtaa ccgtaccgtt aaagaagtca aactgctgac caacgaaatc | 1260 |
| attagcgaac tgggcgagaa atatggtttg gttgaggttt acgatatccc gcgtaacatc | 1320 |
| ccgaataagg tcatgccgag ccgtaattcc ccgaccaatg aaaccggcaa gacggtcagc | 1380 |
| accatgacga acgagcacat cgtcgtgctg cgcaaagatc gt | 1422 |

<210> SEQ ID NO 2
<211> LENGTH: 1425
<212> TYPE: DNA
<213> ORGANISM: Clostridium aceticum

<400> SEQUENCE: 2

| | |
|---|---|
| atggctgtat tgagaaatat tgatgaacaa ttaacagaag aattcaaaaa actaccaata | 60 |
| gattattggg attttgaagg tgaagataca aaagaattaa cgcatggact tcacaattac | 120 |
| cctgctgtta tggtatatcc tatatataga aatataatag atattgtcaa aaggcatggt | 180 |
| gaggtagaaa cttttttaga tcctttcatg ggttctggta caggacttgt agagggaaaa | 240 |
| ttggcaggct ttaataaagt ttatgggaca gatttaaacc cttagcggt cttattaagt | 300 |
| aaggttaaaa caactgtatt aaaagaagat tctgtagata ttcaagataa attacttaga | 360 |
| gagaatattg aacaagcatt tgttagcagc aaacaattac ttgataatat tgataattac | 420 |
| attgcagaaa aaggtttaga tgtatctgct aaagatggat ggggttcaga tgcacatgtt | 480 |
| attctgagag aatacttaga tacatataac tcaggtttaa aaattccaga cttcaaaaat | 540 |
| atgggtact ggtttaaacc acgtgtgata ttagagcttc aacttattaa ggatataata | 600 |
| ctacaaatag aaaacgaaga ttttagaaat ttcttcttag tatgttttag tgaaactgca | 660 |
| agatatgtta gtaatacaag aaatggtgag tttaaactat ttagaattaa aaaggaaaaa | 720 |
| gtagcagatt tcaatcctga tgttaaaatc gagttctata agtatttaga tagaaacatc | 780 |
| gaaaaaataa aagactttga taaagatgt aataacgact gcgaagttag tgttgcattt | 840 |
| gaggatacta ggatttttaga tagtgtacct gacaatagca tagatttaat gataactagt | 900 |
| ccaccatatg gtgattctaa aactactgta gcatatggac agttcagtag accctcttta | 960 |
| tggtggttag atctagagct tatggacata gaagaattaa atcaagtaga taacaaccta | 1020 |
| ctaggcggta agaagttga caaggatttt gaatgtgaat tatcaagtag aactttagaa | 1080 |
| aaagcaataa aagagattaa ggaaaaagac cttgatagag caagagatgt ttatagtttc | 1140 |
| tatgaggact tagataaagc aatggaatca ataactaaga aaatgagaca taatagttat | 1200 |

-continued

```
caattctggg ttgttgggaa cagaacagta aaagaagtta agctattaac taatgaaatt      1260
atttcagaat taggtgaaaa gtacggttta gtggaagtat atgatatacc tagaaatata      1320
ccaaataaag ttatgccaag caggaattca ccaactaatg aaacaggaaa aactgtaagt      1380
acaatgacaa atgaacatat agtagtatta agaaaagata gggaa                     1425
```

```
<210> SEQ ID NO 3
<211> LENGTH: 474
<212> TYPE: PRT
<213> ORGANISM: Clostridium aceticum

<400> SEQUENCE: 3
```

Met Ala Val Leu Arg Asn Ile Asp Glu Gln Leu Thr Glu Glu Phe Lys
1               5                   10                  15

Lys Leu Pro Ile Asp Tyr Trp Asp Phe Glu Gly Glu Asp Thr Lys Glu
            20                  25                  30

Leu Thr His Gly Leu His Asn Tyr Pro Ala Val Met Val Tyr Pro Ile
        35                  40                  45

Tyr Arg Asn Ile Ile Asp Ile Val Lys Arg His Gly Glu Val Glu Thr
    50                  55                  60

Phe Leu Asp Pro Phe Met Gly Ser Gly Thr Gly Leu Val Glu Gly Lys
65                  70                  75                  80

Leu Ala Gly Phe Asn Lys Val Tyr Gly Thr Asp Leu Asn Pro Leu Ala
                85                  90                  95

Val Leu Leu Ser Lys Val Lys Thr Thr Val Leu Lys Glu Asp Ser Val
            100                 105                 110

Asp Ile Gln Asp Lys Leu Leu Arg Glu Asn Ile Glu Gln Ala Phe Val
        115                 120                 125

Ser Ser Lys Gln Leu Leu Asp Asn Ile Asp Asn Tyr Ile Ala Glu Lys
    130                 135                 140

Gly Leu Asp Val Ser Ala Lys Asp Gly Trp Gly Ser Asp Ala His Val
145                 150                 155                 160

Ile Leu Arg Glu Tyr Leu Asp Thr Tyr Asn Ser Gly Leu Lys Ile Pro
                165                 170                 175

Asp Phe Lys Asn Met Gly Tyr Trp Phe Lys Pro Arg Val Ile Leu Glu
            180                 185                 190

Leu Gln Leu Ile Lys Asp Ile Ile Leu Gln Ile Glu Asn Glu Asp Phe
        195                 200                 205

Arg Asn Phe Phe Leu Val Cys Phe Ser Glu Thr Ala Arg Tyr Val Ser
    210                 215                 220

Asn Thr Arg Asn Gly Glu Phe Lys Leu Phe Arg Ile Lys Lys Glu Lys
225                 230                 235                 240

Val Ala Asp Phe Asn Pro Asp Val Lys Ile Glu Phe Tyr Lys Tyr Leu
                245                 250                 255

Asp Arg Asn Ile Glu Lys Ile Lys Asp Phe Asp Lys Arg Cys Asn Asn
            260                 265                 270

Asp Cys Glu Val Ser Val Ala Phe Glu Asp Thr Arg Ile Leu Asp Ser
        275                 280                 285

Val Pro Asp Asn Ser Ile Asp Leu Met Ile Thr Ser Pro Pro Tyr Gly
    290                 295                 300

Asp Ser Lys Thr Thr Val Ala Tyr Gly Gln Phe Ser Arg Pro Ser Leu
305                 310                 315                 320

Trp Trp Leu Asp Leu Glu Leu Met Asp Ile Glu Glu Leu Asn Gln Val
                325                 330                 335

Asp Asn Asn Leu Leu Gly Gly Lys Lys Val Asp Lys Asp Phe Glu Cys
            340                 345                 350

Glu Leu Ser Ser Arg Thr Leu Glu Lys Ala Ile Lys Glu Ile Lys Glu
        355                 360                 365

Lys Asp Leu Asp Arg Ala Arg Asp Val Tyr Ser Phe Tyr Glu Asp Leu
370                 375                 380

Asp Lys Ala Met Glu Ser Ile Thr Lys Met Arg His Asn Ser Tyr
385                 390                 395                 400

Gln Phe Trp Val Val Gly Asn Arg Thr Val Lys Glu Val Lys Leu Leu
                405                 410                 415

Thr Asn Glu Ile Ile Ser Glu Leu Gly Glu Lys Tyr Gly Leu Val Glu
            420                 425                 430

Val Tyr Asp Ile Pro Arg Asn Ile Pro Asn Lys Val Met Pro Ser Arg
        435                 440                 445

Asn Ser Pro Thr Asn Glu Thr Gly Lys Thr Val Ser Thr Met Thr Asn
    450                 455                 460

Glu His Ile Val Val Leu Arg Lys Asp Arg
465                 470

<210> SEQ ID NO 4
<211> LENGTH: 714
<212> TYPE: DNA
<213> ORGANISM: Clostridium aceticum

<400> SEQUENCE: 4
atgtataccc tagagagatt aaaaattagg ttaagagaaa taaatcaaat gggatatgtt      60
agaactcaca ggagtggtcc tactggaata ggtaaaactc ttgaagattt attaggaatt     120
gcagagaata tattgctgg agcagatctt gaccatcttg gcgagttaaa atcatgtaga     180
aacgggcaaa ttagcatggt tacattgttt acaaaaagtc ctagccctcc acgagtaaac     240
actgcacttc tagaatccta tggctatgtt gaccctacaa gaggcggacg aaaaatactt     300
cacacaactt taaatggtgt taactacaat actgtaaacg gaaccccta tggattcaaa     360 gtcgaagtta gaggaagtag gttatattta ctttctaatt tccctacgca agttaatgct     420
tattgggaaa gagaagattt acgttatgct tttgaaagta aacttccacg tctaatattt     480
gttaaagcaa attcacgagg tgctggaaga atgaagaat ttcattttgt agaagcctat     540
catcttgaag ctttagtttt tgaacaattt gaagatttac tagaacaagg aattataaaa     600
atcgacattc gtataggaca atatccagat ggacgaaccc atgaccatgg tacagctttt     660
agaattatga atgacagaat agatgactta tttgaaaata aaataagatt atta           714

<210> SEQ ID NO 5
<211> LENGTH: 237
<212> TYPE: PRT
<213> ORGANISM: Clostridium aceticum

<400> SEQUENCE: 5

Met Tyr Thr Leu Glu Arg Leu Lys Ile Arg Leu Arg Glu Ile Asn Gln
1               5                   10                  15

Met Gly Tyr Val Arg Thr His Arg Ser Gly Pro Thr Gly Ile Gly Lys
            20                  25                  30

Thr Leu Glu Asp Leu Leu Gly Ile Ala Glu Asn Asn Ile Ala Gly Ala
        35                  40                  45

Asp Leu Asp His Leu Gly Glu Leu Lys Ser Cys Arg Asn Gly Gln Ile
    50                  55                  60

Ser Met Val Thr Leu Phe Thr Lys Ser Pro Ser Pro Arg Val Asn
65                  70                  75                  80

Thr Ala Leu Leu Glu Ser Tyr Gly Tyr Val Asp Pro Thr Arg Gly Gly
                85                  90                  95

Arg Lys Ile Leu His Thr Thr Leu Asn Gly Val Asn Tyr Asn Thr Val
            100                 105                 110

Asn Gly Thr Pro Tyr Gly Phe Lys Val Glu Val Arg Gly Ser Arg Leu
        115                 120                 125

Tyr Leu Leu Ser Asn Phe Pro Thr Gln Val Asn Ala Tyr Trp Glu Arg
    130                 135                 140

Glu Asp Leu Arg Tyr Ala Phe Glu Ser Lys Leu Pro Arg Leu Ile Phe
145                 150                 155                 160

Val Lys Ala Asn Ser Arg Gly Ala Gly Arg Asn Glu Glu Phe His Phe
                165                 170                 175

Val Glu Ala Tyr His Leu Glu Gly Phe Ser Phe Glu Gln Phe Glu Asp
            180                 185                 190

Leu Leu Glu Gln Gly Ile Ile Lys Ile Asp Ile Arg Ile Gly Gln Tyr
        195                 200                 205

Pro Asp Gly Arg Thr His Asp His Gly Thr Ala Phe Arg Ile Met Asn
    210                 215                 220

Asp Arg Ile Asp Asp Leu Phe Glu Asn Lys Ile Arg Leu
225                 230                 235

<210> SEQ ID NO 6
<211> LENGTH: 5720
<212> TYPE: DNA
<213> ORGANISM: Artificial Sequence
<220> FEATURE:
<223> OTHER INFORMATION: Synthetic Construct

<400> SEQUENCE: 6
ttgaagaaca aaaacaagg gggtgaaaca atgcagataa cagtaaaatt taatattatt      60
ttgacaaaag aacaagtaca actaatagaa tctatatcaa agaatatat ccatactgtt    120 aatagccttg tttcatctac gctccaatca gaagaaagag taaagctatc atctaaagat    180 gttttttgcaa atatgccaag tgcagtgaaa atcaatcta ttagagatgc aaaagtatc     240 tgtactaagt acaagaaagc tatcaaggct aattccaaac tgcctactga taaacaaaaa    300
gtaatcaatg tagctaccct taaaaaacct gtctgtatat ggaataatca aaattattca    360
cttaaagacg gtattcttag ttttcccgtt attatagatg ggaaatcgca gcgtattcaa    420
actagaacta tcatgacaga ctatcagcta aaacaactag aaggtcattt gggagcattg    480
cgtataacta agaaaagcaa taatatatc gctcaaataa gtgttgaaaa agtatctcat    540
atagttaaag gtgatgttgt aatgggtgtt gacttaggcc taaaagttcc tgctgtagct    600
gtaaccgatt caggaaaaac gttttttttt ggaaacggta ggcaaaataa atacgtcaaa    660
cgtaaatata aagcgaaacg taaaaaactt ggaaaagcca agaagcttaa agtcattaaa    720
aagcttgatg ataaagaaca acgttggatg acagaccaag accacaaagt aagtagagaa    780
ataattaatt ttgcagtaaa taataatgtt tctgatattc ggcttgaaaa attaacgaat    840
atcagaaaca cggcaagaac aagccgtaaa aacgaaaaaa atctacatac atggtcattc    900
tatcgtctag ctcaattcat agagtataag gcactattga aggggataaa ggttgaatat    960
gttgatccta atacacttc tcaaatatgc cctgaatgta agaaactaaa taagcaaga    1020 gatagaaaat ataaatgctc ctgtggtttt aaaacacata gggatagagt aggtgctata   1080

```
aatataatta atgcacctgt agtagatggt aaaagtctac tagcctaggg tactatatgt    1140
actgctctag gaggggtaat ggcatacoct aagcttgagg tcatactccg atagcagaaa    1200
tgtacttcgg tttaatcact caagaatccc actgctttag ctgtgggagt gtcaaatgaa    1260
gcatgatggt catttatctg taactagtga aggaagattg tattatgctg gtagtcaaaa    1320
aattagtttt aatagtggta tacctttaaa tacaggagat ggagttgttg tttggaatga    1380
aattcaagat ttaatttcaa cttctgatgt ttattccgat gttactttaa cggatgaaat    1440
tgcaaattca aattatccaa atataaattt gaatatgat ggaaaagaac cgattagcaa      1500 tccgtttttgg gattatgaaa acttacatac aggtactaga agtattgata taggtgcaaa    1560
tccagattta tcagctctag tagggaaaac atatgaagat gttattagtg aaaatccaag    1620
tcaacaaaat cctatggtgc ctccgatacc atttcctgat tcatggtttg gcaaatggaa    1680
agatatagtt aacgatagtg gaacatggca aggggaaggc atagatggaa gtactggaac    1740
tgcaatagat agtcctccat tagatattcc tggaacgtgg caaggcaaat ggtcttggac    1800
agcagacggt caattagttt tcgatggttc tttttcaggt tctgacggaa caacatggca    1860
aggaacatat acgcatacag gaataggtgt tcagaatcct gtactaaatc caccactaac    1920
cccggattta acaggaataa caggttggtt atcatctata agttcatggt taactagttt    1980
gtttgcgttt ccaactgatt ttagtttgaa tttagacccg ttgaaaaatc tacctatagc    2040
aacaaaattt cctttctgtt tgccatttga tttaaaaaat agcattgaat cattgcaatc    2100
tcctgtcgtt gtcccagttt ttacgactac ttggaattta ccctttatc aaggagatat      2160 agagattaat ttagcagcta tggaacgatt tgcacaaata acacgttggg gaacgttaat    2220
tgtatttaat cttggtttaa tacttgttac aaggaaggtg ttatcatgat atggcaagca    2280
ctagcatctt ttattaatct acttattaaa gcattaggaa cggttttagg ggcaattatc    2340
ggattattac cttcaagtcc ttttcaaact atttcaaatt cagcagtaac agaatattta    2400
ggcatgttga attggtttat atccgtagat gccatgataa ctatattaac ttactggact    2460
actgcaatta aagttacta tgtaatatca actgcgatga gatggggaaa acaattgaa      2520 taggggata atatgataag tttttatagt ggtactccag gaagtggaaa aagtcttaat     2580
atagctagat acatatggat taaagttcga catgctaaac aaaatataat acttgttaat    2640
atgacagtta atagagagta tcttattaca tcaaaactga agcaacttgt taataaaatt    2700
agattgaaat taaaacttaa acctattaat actaagttaa aagactatgg caaaatctat    2760
tctataagac tcgatcagct gaacacaaaa tttctagaag attatgctat gaaatttcac    2820
atggtgggca ttgaaggaca atcaaaaata ataatagatg aggcacaact gatttggtcc    2880
ccaacggtga tgaaaaataa aaagcaggta gaccctaatt atcgtgaacg ctggatagag    2940
tttatgacac tccatagaca cttaggtttt gacatgataa ttataagtca atttgatagg    3000
ttgatagatg cacaaatacg ttgtctattt gaatacaatc atattcatcg aaagtcaat    3060 aacttttgta taggttattg gctaaaccta ttcaaaataa aagtatttgc agaagtgcaa    3120
tattggtatg gagttagagc aaggattgga gttaatttct tcgctattac tccatggact    3180
tcaaaacact ataggaaaat ttataacgca cataaaaggt tctcagattt aaagggaaag    3240
aaaaaagtag cgtagcgttg gactttttttc ttcccttaa atcaagaaat ataatgttcg      3300
taaaaaaatg aatcctgatg tcatggatca cgtggcagca gtcaatatttt agatctaaaa    3360 attgaataat atccaaacaa ataggaggtg tgtaaaataa atgttcgtga ttatatggtt    3420
```

```
aatgttaagt gctgcagcta tagcagctac tctttggtat tattatcaaa atgcttaata    3480
aaatagattt acaaaagtgt ctatacatga tagtatatat ttaatgatat ataggggggt    3540
gtatagattg tttacaagga aaccagaaac taaaaataag tctttagttc ttagaatgac    3600
agaaacgcaa aagaagatac ttgagattat ggctaatgag agaggtttat cacaatcaga    3660
attaattatg atattattgg agaatgaatt caagaagcct gtattagaaa taaagcagca    3720
agattaaact tgccgccttg gatagcggag caacggtttt atccaagcgg taaacaatat    3780
tctaaacagc ggtgtttaaa attatcaact agaagtgtat taatggctgc ggaaagaaat    3840
attaaaccag tactatcaca attcgcacct taaaagtaag ttttttaatg tttaattttg    3900
gcacggaact tgctctttct tgatatatta caaacaagtc ggctaaaatt gaaattttaa    3960
cgttatcctg aaaggggggc aaaatttgga tgagaagata cttaaagatg taagggtttc    4020
taaaaatcat ttacaatcgg ttcataataa taatcagtat aataagttga ttgtaggtta    4080
ttacaatcaa tacatagaag attctagacc tgtaaagaag aaaaagacta ttttggatta    4140
tactagattt acttatgaag attattttgt tgaaaaatta gaacataaaa gagataagtt    4200
agctaattgt aataagaaat gggaagttga agtttatgaa aaacttaaag taaaagatta    4260
tgtgtctact ttattatgta atgataagtt ttgtagtaat tgtaagaaag taaagcaagc    4320
ttcaaggatg gcgaaaaata tgcctttgct tgaacagtat aaagataaat tatatcaaat    4380
ggttttaact acaccaaata ttgtagatca tacaggggaa gaattgaaaa aagagattaa    4440
aaagcaattt aaagcattaa cttatttaac agaatattta aaaggtaaaa aacaagtaaa    4500
gggtttagat tttgatattg gatacttagg tgcaataagg tcgttggagg taacttatag    4560
cggtgactat tatcatccgc atttgcattt gatattagta ttggataatc aaaatgaatt    4620
tataacagat aaaaaaaata taaataacta ttcttatgat tattataaaa aaagaccaac    4680
tagattattt tcagattttg aaatattgtt acagaaatct tggtatcttt tatataatgg    4740
ggaaagattg actaaggaaa atatagataa actggaaaaa ggttatagtt gcatgatgga    4800
taaggcaaaa gaagatgatt ttttagaagt ttttaaatac atggtgaaga atgatccggc    4860
agaggagaat gtaaaaggta gtaacaaaat gacttataaa aattttagag tattagaata    4920
tgcattgcat agtataagac agatacaagg ttatggagtt ttttataata ttaaagatat    4980
attaatggct gaagaagtaa atgaaatgta tgaatggata agagagtatt taatcaaaaa    5040
tgaaggagaa gctcctgcat atcgtgttga aagatacag aagcttctag atgatactga    5100
gtatactctt atatcaagga aaaaaatatt tacgtattta agaaaaatat actctgaata    5160
ataacattat agcataaaga gggcttaatt gctctctttt ttaatttctt ttaaagcttc    5220
atttgggtgt atgtttaata gattacagta aattcgcctg aaagcccacg gtttcaatcg    5280
tgggatgaaa ggcgtttctt ttaatcttct tgttgcagtt tcagtttaaa actgatacta    5340
taaatatatg ggacaagatt atagaagaac acaaacaaca gtatctttaa taaactatca    5400
ttttgttttc tgtccaaggt acagacgtaa agttctagtt ggagaagttg aaataaaatt    5460
taaacagctt ctcaatgaga tttgtaaaga cattgaaata gaaattttgg caatagaatg    5520
tgataaagac cactgccatc tttttgtcaa tgcacttcct catttaagtc cagcagacat    5580
aatggcaaaa gtgaaaggag tgacttctcg attattaagg caggaattta acatctgcg    5640 acatttgcca gtctttggaa caagaagcta ttttgtatct accgcaggaa atgtatcaag    5700
tgaaactata aaacgatatg                                                5720
```

<210> SEQ ID NO 7
<211> LENGTH: 3729
<212> TYPE: DNA
<213> ORGANISM: Artificial Sequence
<220> FEATURE:
<223> OTHER INFORMATION: Synthetic Construct

<400> SEQUENCE: 7

| | | | | | |
|---|---|---|---|---|---|
| cctgcaggat | aaaaaaattg | tagataaatt | ttataaaata | gttttatcta | caattttttt | 60 |
| atcaggaaac | agctatgacc | gcggccgctg | tatccatatg | accatgatta | cgaattcgag | 120 |
| ctcggtaccc | ggggatcctc | tagagtcgac | gtcacgcgtc | catggagatc | tcgaggcctg | 180 |
| cagacatgca | agcttggcac | tggccgtcgt | tttacaacgt | cgtgactggg | aaaaccctgg | 240 |
| cgttacccaa | cttaatcgcc | ttgcagcaca | tccccctttc | gccagctggc | gtaatagcga | 300 |
| agaggcccgc | accgatcgcc | cttcccaaca | gttgcgcagc | ctgaatggcg | aatggcgcta | 360 |
| gcataaaaat | aagaagcctg | catttgcagg | cttcttattt | ttatggcgcg | ccgcattcac | 420 |
| ttcttttcta | tataaatatg | agcgaagcga | taagcgtcg | gaaaagcagc | aaaaagtttc | 480 |
| cttttgctg | ttggagcatg | ggggttcagg | gggtgcagta | tctgacgtca | atgccgagcg | 540 |
| aaagcgagcc | gaagggtagc | atttacgtta | gataacccc | tgatatgctc | cgacgcttta | 600 |
| tatagaaaag | aagattcaac | taggtaaaat | cttaatatag | gttgagatga | taaggtttat | 660 |
| aaggaatttg | tttgttctaa | ttttcactc | attttgttct | aatttctttt | aacaaatgtt | 720 |
| ctttttttt | tagaacagtt | atgatatagt | tagaatagtt | taaaataagg | agtgagaaaa | 780 |
| agatgaaaga | aagatatgga | acagtctata | aaggctctca | gaggctcata | gacgaagaaa | 840 |
| gtggagaagt | catagaggta | gacaagttat | accgtaaaca | aacgtctggt | aacttcgtaa | 900 |
| aggcatatat | agtgcaatta | ataagtatgt | tagatatgat | tggcggaaaa | aaacttaaaa | 960 |
| tcgttaacta | tatcctagat | aatgtccact | taagtaacaa | tacaatgata | gctacaacaa | 1020 |
| gagaaatagc | aaaagctaca | ggaacaagtc | tacaaacagt | aataacaaca | cttaaaatct | 1080 |
| tagaagaagg | aaatattata | aaaagaaaaa | ctggagtatt | aatgttaaac | cctgaactac | 1140 |
| taatgagagg | cgacgaccaa | aaacaaaaat | acctcttact | cgaatttggg | aactttgagc | 1200 |
| aagaggcaaa | tgaaatagat | tgacctccca | ataacaccac | gtagttattg | ggaggtcaat | 1260 |
| ctatgaaatg | cgattaaggg | ccggccagtg | ggcaagttga | aaaattcaca | aaaatgtggt | 1320 |
| ataatatctt | tgttcattag | agcgataaac | ttgaatttga | gagggaactt | agatggtatt | 1380 |
| tgaaaaaatt | gataaaaata | gttggaacag | aaaagagtat | tttgaccact | actttgcaag | 1440 |
| tgtaccttgt | acctacagca | tgaccgttaa | agtggatatc | acacaaataa | aggaaaaggg | 1500 |
| aatgaaacta | tatcctgcaa | tgctttatta | tattgcaatg | attgtaaacc | gccattcaga | 1560 |
| gtttaggacg | gcaatcaatc | aagatggtga | attgggggata | tatgatgaga | tgataccaag | 1620 |
| ctatacaata | tttcacaatg | atactgaaac | attttccagc | ctttggactg | agtgtaagtc | 1680 |
| tgactttaaa | tcattttag | cagattatga | aagtgatacg | caacggtatg | aaacaatca | 1740 |
| tagaatggaa | ggaaagccaa | atgctccgga | aaacattttt | aatgtatcta | tgataccgtg | 1800 |
| gtcaaccttc | gatggcttta | atctgaattt | gcagaaagga | tatgattatt | tgattcctat | 1860 |
| ttttactatg | gggaaatatt | ataaagaaga | taacaaaatt | atacttcctt | tggcaattca | 1920 |
| agttcatcac | gcagtatgtg | acggatttca | catttgccgt | tttgtaaacg | aattgcagga | 1980 |
| attgataaat | agttaacttc | aggtttgtct | gtaactaaaa | acaagtattt | aagcaaaaac | 2040 |
| atcgtagaaa | tacggtgttt | tttgttaccc | taagtttaaa | ctccttttg | ataatctcat | 2100 |

| | |
|---|---|
| gaccaaaatc ccttaacgtg agttttcgtt ccactgagcg tcagaccccg tagaaaagat | 2160 |
| caaaggatct tcttgagatc ctttttttct gcgcgtaatc tgctgcttgc aaacaaaaaa | 2220 |
| accaccgcta ccagcggtgg tttgtttgcc ggatcaagag ctaccaactc ttttttccgaa | 2280 |
| ggtaactggc ttcagcagag cgcagatacc aaatactgtt cttctagtgt agccgtagtt | 2340 |
| aggccaccac ttcaagaact ctgtagcacc gcctacatac ctcgctctgc taatcctgtt | 2400 |
| accagtggct gctgccagtg gcgataagtc gtgtcttacc gggttggact caagacgata | 2460 |
| gttaccggat aaggcgcagc ggtcgggctg aacggggggt tcgtgcacac agcccagctt | 2520 |
| ggagcgaacg acctacaccg aactgagata cctacagcgt gagctatgag aaagcgccac | 2580 |
| gcttcccgaa gggagaaagg cggacaggta tccggtaagc ggcagggtcg aacaggaga | 2640 |
| gcgcacgagg gagcttccag ggggaaacgc ctggtatctt tatagtcctg tcgggtttcg | 2700 |
| ccacctctga cttgagcgtc gatttttgtg atgctcgtca ggggggcgga gcctatggaa | 2760 |
| aaacgccagc aacgcggcct ttttacggtt cctggccttt tgctggcctt ttgctcacat | 2820 |
| gttctttcct gcgttatccc ctgattctgt ggataaccgt attaccgcct ttgagtgagc | 2880 |
| tgataccgct cgccgcagcc gaacgaccga gcgcagcgag tcagtgagcg aggaagcgga | 2940 |
| agagcgccca atacgcaggg ccccctgctt cggggtcatt atagcgattt tttcggtata | 3000 |
| tccatccttt ttcgcacgat atacaggatt ttgccaaagg gttcgtgtag actttccttg | 3060 |
| gtgtatccaa cggcgtcagc cgggcaggat aggtgaagta ggcccacccg cgagcgggtg | 3120 |
| ttccttcttc actgtccctt attcgcacct ggcggtgctc aacgggaatc ctgctctgcg | 3180 |
| aggctggccg gctaccgccg gcgtaacaga tgagggcaag cggatggctg atgaaaccaa | 3240 |
| gccaaccagg aagggcagcc cacctatcaa ggtgtactgc cttccagacg aacgaagagc | 3300 |
| gattgaggaa aaggcggcgg cggccggcat gagcctgtcg gcctacctgc tggccgtcgg | 3360 |
| ccagggctac aaaatcacgg gcgtcgtgga ctatgagcac gtccgcgagc tggcccgcat | 3420 |
| caatggcgac ctgggccgcc tgggcggcct gctgaaactc tggctcaccg acgacccgcg | 3480 |
| cacggcgcgg ttcggtgatg ccacgatcct cgccctgctg gcgaagatcg aagagaagca | 3540 |
| ggacgagctt ggcaaggtca tgatgggcgt ggtccgcccg agggcagagc catgactttt | 3600 |
| ttagccgcta aaacggccgg ggggtgcgcg tgattgccaa gcacgtcccc atgcgctcca | 3660 |
| tcaagaagag cgacttcgcg gagctggtga agtacatcac cgacgagcaa ggcaagaccg | 3720 |
| atcgggccc | 3729 |

<210> SEQ ID NO 8
<211> LENGTH: 3270
<212> TYPE: DNA
<213> ORGANISM: Artificial Sequence
<220> FEATURE:
<223> OTHER INFORMATION: Synthetic Construct

<400> SEQUENCE: 8

| | |
|---|---|
| cctgcaggat aaaaaaattg tagataaatt ttataaaata gttttatcta caattttttt | 60 |
| atcaggaaac agctatgacc gcggccgcgt gtagtagcct gtgaaataag taaggaaaaa | 120 |
| aaagaagtaa gtgttatata tgatgattat tttgtagatg tagataggat aatagaatcc | 180 |
| atagaaaata taggttatac agttatataa aaattacttt aaaaattaat aaaaacatgg | 240 |
| taaaatataa atcgtataaa gttgtgtaat ttttaaggag gtgtgttaca tatgaccatg | 300 |
| attacgaatt cgagctcggt acccggggat cctctagagt cgacgtcacg cgtccatgga | 360 |
| gatctcgagg cctgcagaca tgcaagcttg gcactggccg tcgttttaca acgtcgtgac | 420 |

```
tgggaaaacc ctggcgttac ccaacttaat cgccttgcag cacatccccc tttcgccagc      480
tggcgtaata gcgaagaggc ccgcaccgat cgcccttccc aacagttgcg cagcctgaat      540
ggcgaatggc gctagcataa aaataagaag cctgcatttg caggcttctt atttttatgg      600
cgcgccgcat tcacttcttt tctatataaa tatgagcgaa gcgaataagc gtcggaaaag      660
cagcaaaaag tttccttttt gctgttggag catgggggtt caggggtgc agtatctgac       720 gtcaatgccg agcgaaagcg agccgaaggg tagcatttac gttagataac ccctgatat      780 gctccgacgc tttatataga aagaagatt caactaggta aaatcttaat ataggttgag      840
atgataaggt ttataaggaa tttgtttgtt ctaattttc actcattttg ttctaatttc      900
ttttaacaaa tgttcttttt tttttagaac agttatgata tagttagaat agtttaaaat     960
aaggagtgag aaaagatga aagaaagata tggaacagtc tataaaggct ctcagaggct    1020
catagacgaa gaaagtggag aagtcataga ggtagacaag ttataccgta aacaaacgtc    1080
tggtaacttc gtaaaggcat atatagtgca attaataagt atgttagata tgattggcgg    1140
aaaaaaactt aaaatcgtta actatatcct agataatgtc cacttaagta acaatacaat    1200
gatagctaca acaagagaaa tagcaaaagc tacaggaaca agtctacaaa cagtaataac    1260
aacacttaaa atcttagaag aaggaaatat tataaaaaga aaaactggag tattaatgtt    1320
aaaccctgaa ctactaatga gaggcgacga ccaaaaacaa aaatacctct tactcgaatt    1380
tgggaacttt gagcaagagg caaatgaaat agattgacct cccaataaca ccacgtagtt    1440
attgggaggt caatctatga aatgcgatta agggccggcc gaagcaaact taagagtgtg    1500
ttgatagtgc agtatcttaa aattttgtat aataggaatt gaagttaaat tagatgctaa    1560
aaatttgtaa ttaagaagga gtgattacat gaacaaaaat ataaatatt ctcaaaactt     1620 tttaacgagt gaaaaagtac tcaaccaaat aataaaacaa ttgaatttaa aagaaaccga    1680
taccgtttac gaaattggaa caggtaaagg gcatttaacg acgaaactgg ctaaaataag    1740
taaacaggta acgtctattg aattagacag tcatctattc aacttatcgt cagaaaaatt    1800
aaaactgaat actcgtgtca ctttaattca ccaagatatt ctacagtttc aattccctaa    1860
caaacagagg tataaaattg ttgggagtat tccttaccat ttaagcacac aaattattaa    1920
aaaagtggtt tttgaaagcc atgcgtctga catctatctg attgttgaag aaggattcta    1980
caagcgtacc ttggatattc accgaacact agggttgctc ttgcacactc aagtctcgat    2040
tcagcaattg cttaagctgc cagcggaatg cttttcatcct aaaccaaaag taaacagtgt    2100
cttaataaaa cttacccgcc ataccacaga tgttccagat aaatattgga agctatatac    2160
gtactttgtt tcaaaatggg tcaatcgaga atatcgtcaa ctgtttacta aaaatcagtt    2220
tcatcaagca atgaaacacg ccaaagtaaa caatttaagt accgttactt atgagcaagt    2280
attgtctatt tttaatagtt atctattatt taacgggagg aataattct atgagtcgct     2340 tttgtaaatt tggaaagtta cacgttacta aaggaatgt gtttaaactc cttttttgata    2400 atctcatgac caaaatccct taacgtgagt tttcgttcca ctgagcgtca gaccccgtag    2460
aaaagatcaa aggatcttct tgagatcctt ttttttctgcg cgtaatctgc tgcttgcaaa    2520
caaaaaaacc accgctacca gcggtggttt gtttgccgga tcaagagcta ccaactcttt    2580
ttccgaaggt aactggcttc agcagagcgc agataccaaa tactgttctt ctagtgtagc    2640
cgtagttagg ccaccacttc aagaactctg tagcaccgcc tacatacctc gctctgctaa    2700
tcctgttacc agtggctgct gccagtggcg ataagtcgtg tcttaccggg ttggactcaa    2760
```

| | |
|---|---|
| gacgatagtt accggataag gcgcagcggt cgggctgaac ggggggttcg tgcacacagc | 2820 |
| ccagcttgga gcgaacgacc tacaccgaac tgagatacct acagcgtgag ctatgagaaa | 2880 |
| gcgccacgct tcccgaaggg agaaaggcgg acaggtatcc ggtaagcggc agggtcggaa | 2940 |
| caggagagcg cacagggag cttccagggg gaaacgcctg gtatctttat agtcctgtcg | 3000 |
| ggtttcgcca cctctgactt gagcgtcgat ttttgtgatg ctcgtcaggg gggcggagcc | 3060 |
| tatggaaaaa cgccagcaac gcggccttt tacggttcct ggccttttgc tggccttttg | 3120 |
| ctcacatgtt ctttcctgcg ttatccctg attctgtgga taaccgtatt accgcctttg | 3180 |
| agtgagctga taccgctcgc cgcagccgaa cgaccgagcg cagcgagtca gtgagcgagg | 3240 |
| aagcggaaga gcgcccaata cgcagggccc | 3270 |

<210> SEQ ID NO 9
<211> LENGTH: 5
<212> TYPE: DNA
<213> ORGANISM: Artificial Sequence
<220> FEATURE:
<223> OTHER INFORMATION: Synthetic Construct

<400> SEQUENCE: 9

| | |
|---|---|
| ccagg | 5 |

<210> SEQ ID NO 10
<211> LENGTH: 5
<212> TYPE: DNA
<213> ORGANISM: Artificial Sequence
<220> FEATURE:
<223> OTHER INFORMATION: Synthetic Construct

<400> SEQUENCE: 10

| | |
|---|---|
| cctgg | 5 |

<210> SEQ ID NO 11
<211> LENGTH: 3270
<212> TYPE: DNA
<213> ORGANISM: Artificial Sequence
<220> FEATURE:
<223> OTHER INFORMATION: Synthetic Construct

<400> SEQUENCE: 11

| | |
|---|---|
| cctgcaggat aaaaaattg tagataaatt ttataaaata gttttatcta caattttttt | 60 |
| atcaggaaac agctatgacc gcggccgcgt gtagtagcct gtgaaataag taaggaaaaa | 120 |
| aaagaagtaa gtgttatata tgatgattat tttgtagatg tagataggat aatagaatcc | 180 |
| atagaaaata taggttatac agttatataa aaattacttt aaaaattaat aaaaacatgg | 240 |
| taaaatataa atcgtataaa gttgtgtaat ttttaaggag gtgtgttaca tatgaccatg | 300 |
| attacgaatt cgagctcggt acccggggat cctctagagt cgacgtcacg cgtccatgga | 360 |
| gatctcgagg cctgcagaca tgcaagcttg gcactggccg tcgttttaca acgtcgtgac | 420 |
| tgggaaaacc ctgacgttac ccaacttaat cgccttgcag cacatccccc tttcgccagc | 480 |
| tggcgtaata gcgaagaggc ccgcaccgat cgcccttccc aacagttgcg cagcctgaat | 540 |
| ggcgaatggc gctagcataa aaataagaag cctgcatttg caggcttctt attttttatgg | 600 |
| cgcgccgcat tcacttcttt tctatataaa tatgagcgaa gcgaataagc gtcggaaaag | 660 |
| cagcaaaaag tttccttttt gctgttggag catgggggtt caggggggtgc agtatctgac | 720 |
| gtcaatgccg agcgaaagcg agccgaaggg tagcatttac gttagataac cccctgatat | 780 |
| gctccgacgc tttatataga aaagaagatt caactaggta aatcttaat ataggttgag | 840 |

```
atgataaggt ttataaggaa tttgtttgtt ctaattttc actcattttg ttctaatttc      900
ttttaacaaa tgttctttt tttttagaac agttatgata tagttagaat agtttaaaat      960
aaggagtgag aaaagatga aagaaagata tggaacagtc tataaaggct ctcagaggct     1020
catagacgaa gaaagtggag aagtcataga ggtagacaag ttataccgta aacaaacgtc     1080
tggtaacttc gtaaaggcat atatagtgca attataagt atgttagata tgattggcgg     1140
aaaaaaactt aaaatcgtta actatatcct agataatgtc cacttaagta acaatacaat     1200
gatagctaca acaagagaaa tagcaaaagc tacaggaaca agtctacaaa cagtaataac     1260
aacacttaaa atcttagaag aaggaaatat tataaaaaga aaaactggag tattaatgtt     1320
aaaccctgaa ctactaatga gaggcgacga ccaaaaacaa aaatacctct tactcgaatt     1380
tgggaacttt gagcaagagg caaatgaaat agattgacct cccaataaca ccacgtagtt     1440
attgggaggt caatctatga aatgcgatta agggccggcc gaagcaaact taagagtgtg     1500
ttgatagtgc agtatcttaa aattttgtat aataggaatt gaagttaaat tagatgctaa     1560
aaatttgtaa ttaagaagga gtgattacat gaacaaaaat ataaaatatt ctcaaaactt     1620
tttaacgagt gaaaaagtac tcaaccaaat aataaaacaa ttgaatttaa agaaaccga     1680
taccgtttac gaaattggaa caggtaaagg gcatttaacg acgaaactgg ctaaaataag     1740
taaacaggta acgtctattg aattagacag tcatctattc aacttatcgt cagaaaaatt     1800
aaaactgaat actcgtgtca ctttaattca ccaagatatt ctacagtttc aattccctaa     1860
caaacagagg tataaaattg ttgggagtat tccttaccat ttaagcacac aaattattaa     1920
aaaagtggtt tttgaaagcc atgcgtctga catctatctg attgttgaag aaggattcta     1980
caagcgtacc ttggatattc accgaacact agggttgctc ttgcacactc aagtctcgat     2040
tcagcaattg cttaagctgc cagcggaatg ctttcatcct aaaccaaaag taaacagtgt     2100
cttaataaaa cttaccccgcc ataccacaga tgttccagat aaatattgga agctatatac     2160
gtactttgtt tcaaaatggg tcaatcgaga atatcgtcaa ctgtttacta aaaatcagtt     2220
tcatcaagca atgaaaacacg ccaaagtaaa caatttaagt accgttactt atgagcaagt     2280
attgtctatt tttaatagtt atctattatt taacgggagg aaataattct atgagtcgct     2340
tttgtaaatt tggaaagtta cacgttacta aagggaatgt gtttaaactc cttttttgata     2400
atctcatgac caaaatccct taacgtgagt tttcgttcca ctgagcgtca gaccccgtag     2460
aaaagatcaa aggatcttct tgagatcctt ttttttctgcg cgtaatctgc tgcttgcaaa     2520
caaaaaaacc accgctacca gcggtggttt gtttgccgga tcaagagcta ccaactcttt     2580
ttccgaaggt aactggcttc agcagagcgc agataccaaa tactgttctt ctagtgtagc     2640
cgtagttagg ccaccacttc aagaactctg tagcaccgcc tacatacctc gctctgctaa     2700
tcctgttacc agtggctgct gccagtggcg ataagtcgtg tcttaccggg ttggactcaa     2760
gacgatagtt accggataag gcgcagcggt cgggctgaac ggggggttcg tgcacacagc     2820
ccagcttgga gcgaacgacc tacaccgaac tgagatacct acagcgtgag ctatgagaaa     2880
gcgccacgct tcccgaaggg agaaaggcgg acaggtatcc ggtaagcggc agggtcggaa     2940
caggagagcg cacgagggag cttctagggg gaaacgcctg atatctttat agtcctgtcg     3000
ggtttcgcca cctctgactt gagcgtcgat ttttgtgatg ctcgtcaggg gggcggagcc     3060
tatgaaaaa cgccagcaac gcggcctttt tacggttcct gacctttgc tggccttttg     3120
ctcacatgtt ctttcctgcg ttatccctg attctgtgga taaccgtatt accgcctttg     3180
```
agtgagctga taccgctcgc cgcagccgaa cgaccgagcg cagcgagtca gtgagcgagg    3240
aagcggaaga gcgcccaata cgcagggccc                                    3270

<210> SEQ ID NO 12
<211> LENGTH: 8285
<212> TYPE: DNA
<213> ORGANISM: Artificial Sequence
<220> FEATURE:
<223> OTHER INFORMATION: Synthetic Construct

<400> SEQUENCE: 12
ttgaagaaca aaaacaagg gggtgaaaca atgcagataa cagtaaaatt taatattatt      60
ttgacaaaag aacaagtaca actaatagaa tctatatcaa agaatatat ccatactgtt    120 aatagccttg tttcatctac gctccaatca gaagaaagag taaagctatc atctaaagat    180 gttttttgcaa atatgccaag tgcagtgaaa atcaatctta ttagagatgc caaaagtatc    240
tgtactaagt acaagaaagc tatcaaggct aattccaaac tgcctactga taaacaaaaa    300
gtaatcaatg tagctaccct taaaaaacct gtctgtatat ggaataatca aaattattca    360
cttaaagacg gtattcttag ttttcccgtt attatagatg ggaaatcgca gcgtattcaa    420
actagaacta tcatgacaga ctatcagcta aaacaactag aaggtcattt gggagcattg    480
cgtataacta agaaaagcaa taaatatatc gctcaaataa gtgttgaaaa agtatctcat    540
atagttaaag gtgatgttgt aatgggtgtt gacttaggcc taaaagttcc tgctgtagct    600
gtaaccgatt caggaaaaac gttttttttt ggaaacggta ggcaaaataa atacgtcaaa    660
cgtaaatata aagcgaaacg taaaaaactt ggaaaagcca agaagcttaa agtcattaaa    720
aagcttgatg ataaagaaca acgttggatg acagaccaag accacaaagt aagtagagaa    780
ataattaatt ttgcagtaaa taataatgtt tctgatattc ggcttgaaaa attaacgaat    840
atcagaaaca cggcaagaac aagccgtaaa aacgaaaaaa atctacatac atggtcattc    900
tatcgtctag ctcaattcat agagtataag gcactattga aggggataaa ggttgaatat    960
gttgatccta atacacttc tcaaatatgc cctgaatgta agaaactaaa taaagcaaga   1020
gatagaaaat ataaatgctc ctgtggtttt aaaaacacata gggatagagt aggtgctata   1080
aatataatta atgcacctgt agtagatggt aaaagtctac tagcctaggg tactatatgt   1140
actgctctag gaggggtaat ggcatacct aagcttgagg tcatactccg atagcagaaa   1200
tgtacttcgg tttaatcact caagaatccc actgctttag ctgtgggagt gtcaaatgaa   1260
gcatgatggc catttatctg taactagtga aggaagattg tattatgctg gtagtcaaaa   1320
aattagtttt aatagtggta tactttaaa tacaggagat ggagttgttg tttggaatga   1380
aattcaagat ttaatttcaa cttctgatgt ttattccgat gttacttaaa cggatgaaat   1440
tgcaaattca aattatccaa atataaattt tgaatatgat ggaaaagaac cgattagcaa   1500
tccgtttggg gattatgaaa acttacatac aggtactaga agtattgata taggtgcaaa   1560
tccagattta tcagctctag tagggaaaac atatgaagat gttattagtg aaaatccaag   1620
tcaacaaaat cctatggtgc ctccgatacc atttcctgat tcatggtttg gcaaatggaa   1680
agatatagtt aacgatagtg gaacatggca agggaaaggc atagatggaa gtactggaac   1740
tgcaatagat agtcctccat tagatattcc tggaacgtgg caaggcaaat ggtcttggac   1800
agcagacggt caattagttt tcgatggttc ttttttcaggt tctgacggaa caacatggca   1860
aggaacatat acgcatacag gaataggtgt tcagaatcct gtactaaatc cacccactaac   1920 cccggattta acaggaataa caggttggtt atcatctata agttcatggt taactagttt   1980

```
gtttgcgttt ccaactgatt ttagtttgaa tttagacccg ttgaaaaatc tacctatagc    2040
aacaaaattt cctttctgtt tgccatttga tttaaaaaat agcattgaat cattgcaatc    2100
tcctgtcgtt gtcccagttt ttacgactac ttggaattta ccctttatc aaggagatat    2160 agagattaat ttagcagcta tggaacgatt tgcacaaata acacgttggg gaacgttaat    2220
tgtatttaat cttggtttaa tacttgttac aaggaaggtg ttatcatgat atggcaagca    2280
ctagcatctt ttattaatct acttattaaa gcattaggaa cggttttagg ggcaattatc    2340
ggattattac cttcaagtcc ttttcaaact atttcaaatt cagcagtaac agaatattta    2400
ggcatgttga attggtttat atccgtagat gccatgataa ctatattaac ttactggact    2460
actgcaatta taagttacta tgtaatatca actgcgatga gatggggaaa aacaattgaa    2520 taggggata atatgataag ttttatagt ggtactccag gaagtggaaa aagtcttaat    2580
atagctagat acatatggat taaagttcga catgctaaac aaaatataat acttgttaat    2640
atgacagtta atagagagta tcttattaca tcaaaactga agcaacttgt taataaaatt    2700
agattgaaat taaaacttaa acctattaat actaagttaa aagactatgg caaaatctat    2760
tctataagac tcgatcagct gaacacaaaa tttctagaag attatgctat gaaatttcac    2820
atggtgggca ttgaaggaca atcaaaaata ataatagatg aggcacaact gatttggtcc    2880
ccaacggtga tgaaaaataa aaagcaggta gaccctaatt atcgtgaacg ctggatagag    2940
tttatgacac tccatagaca cttaggtttt gacatgataa ttataagtca atttgatagg    3000
ttgatagatg cacaaatacg ttgtctattt gaatacaatc atattcatcg gaaagtcaat    3060
aacttttgta taggttattg gctaaaccta ttcaaaataa aagtatttgc agaagtgcaa    3120
tattggtatg gagttagagc aaggattgga gttaatttct tcgctattac tccatggact    3180
tcaaaacact ataggaaaat ttataacgca cataaaaggt tctcagattt aaagggaaag    3240 aaaaagtag cgtagcgttg gacttttttc ttcccttaaa atcaagaaat ataatgttcg    3300
taaaaaaatg aatcctgatg tcatggatca cgtggcagca gtcaatattt agatctaaaa    3360
attgaataat atccaaacaa ataggagtg tgtaaaataa atgttcgtga ttatatggtt    3420
aatgttaagt gctgcagcta tagcagctac tctttggtat tattatcaaa atgcttaata    3480
aaatagattt acaaaagtgt ctatacatga tagtatatat ttaatgatat ataggggggt    3540
gtatagattg tttacaagga aaccagaaac taaaaataag tctttagttc ttagaatgac    3600
agaaacgcaa aagaagatac ttgagattat ggctaatgag agaggtttat cacaatcaga    3660
attaattatg atattattgg agaatgaatt caagaagcct gtattagaaa taagcagca    3720 agattaaact tgccgccttg gatagcggag caacggtttt atccaagcgg taaacaatat    3780
tctaaacagc ggtgtttaaa attatcaact agaagtgtat taatggctgc ggaaagaaat    3840
attaaaccag tactatcaca attcgcacct taaaagtaag gtttttaatg tttaattttg    3900
gcacggaact tgctctttct tgatatatta caaacaagtc ggctaaaatt gaaattttaa    3960
cgttatcctg aaaggggggc aaaatttgga tgagaagata cttaaagatg taagggtttc    4020
taaaaatcat ttcaatcgg ttcataataa taatcagtat aataagttga ttgtaggtta    4080
ttacaatcaa tacatagaag attctagacc tgtaagaag aaaaagacta ttttggatta    4140
tactagattt acttatgaag attattttgt tgaaaaatta gaacataaaa gagataagtt    4200
agctaattgt aataagaaat gggaagttga agtttatgaa aaacttaaag taaaagatta    4260
tgtgtctact ttattatgta atgataagtt ttgtagtaat tgtaagaaag taaagcaagc    4320
```

```
ttcaaggatg gcgaaaaata tgcctttgct tgaacagtat aaagataaat tatatcaaat    4380
ggttttaact acaccaaata ttgtagatca tacaggggaa gaattgaaaa aagagattaa    4440
aaagcaattt aaagcattaa cttatttaac agaatattta aaaggtaaaa aacaagtaaa    4500
gggtttagat tttgatattg gatacttagg tgcaataagg tcgttggagg taacttatag    4560
cggtgactat tatcatccgc atttgcattt gatattagta ttggataatc aaaatgaatt    4620
tataacagat aaaaaaaata taaataacta ttcttatgat tattataaaa aaagaccaac    4680
tagattattt tcagattttg aaatattgtt acagaaatct tggtatcttt tatataatgg    4740
ggaaagattg actaaggaaa atatagataa actggaaaaa ggttatagtt gcatgatgga    4800
taaggcaaaa gaagatgatt ttttagaagt ttttaaatac atggtgaaga atgatccggc    4860
agaggagaat gtaaaggta gtaacaaaat gacttataaa aattttagag tattagaata    4920
tgcattgcat agtataagac agatacaagg ttatggagtt ttttataata ttaaagatat    4980
attaatggct gaagaagtaa atgaaatgta tgaatggata agagagtatt taatcaaaaa    5040
tgaaggagaa gctcctgcat atcgtgttga gaagatacag aagcttctag atgatactga    5100
gtatactctt atatcaagga aaaaaatatt tacgtattta agaaaaatat actctgaata    5160
ataaggtca atctatgaaa tgcgattaag ggccggccag tgggcaagtt gaaaaattca    5220
caaaaatgtg gtataatatc tttgttcatt agagcgataa acttgaattt gagagggaac    5280
ttagatggta tttgaaaaaa ttgataaaaa tagttggaac agaaaagagt attttgacca    5340
ctactttgca agtgtaccttt gtacctacag catgaccgtt aaagtggata tcacacaaat    5400
aaaggaaaag ggaatgaaac tatatcctgc aatgctttat tatattgcaa tgattgtaaa    5460
ccgccattca gagtttagga cggcaatcaa tcaagatggt gaattgggga tatatgatga    5520
gatgatacca agctatacaa tatttcacaa tgatactgaa acatttttcca gcctttggac    5580
tgagtgtaag tctgacttta aatcattttt agcagattat gaaagtgata cgcaacggta    5640
tggaaacaat catagaatgg aaggaaagcc aaatgctccg gaaaacattt ttaatgtatc    5700
tatgataccg tggtcaacct tcgatggctt taatctgaat ttgcagaaag gatatgatta    5760
tttgattcct atttttacta tggggaaata ttataaagaa gataacaaaa ttatacttcc    5820
tttggcaatt caagttcatc acgcagtatg tgacggattt cacatttgcc gttttgtaaa    5880
cgaattgcag gaattgataa atagttaact tcaggtttgt ctgtaactaa aaacaagtat    5940
ttaagcaaaa acatcgtaga aatacggtgt tttttgttac cctaagttta aactccttt    6000
tgataatctc atgaccaaaa tcccttaacg tgagttttcg ttccactgag cgtcagaccc    6060
cgtagaaaag atcaaaggat cttcttgaga tcctttttt ctgcgcgtaa tctgctgctt    6120
gcaaacaaaa aaaccaccgc taccagcggt ggtttgtttg ccggatcaag agctaccaac    6180
tcttttttccg aaggtaactg gcttcagcag agcgcagata ccaaatactg ttcttctagt    6240
gtagccgtag ttaggccacc acttcaagaa ctctgtagca ccgcctacat acctcgctct    6300
gctaatcctg ttaccagtgg ctgctgccag tggcgataag tcgtgtctta ccgggttgga    6360
ctcaagacga tagttaccgg ataaggcgca gcggtcgggc tgaacggggg gttcgtgcac    6420
acagcccagc ttggagcgaa cgacctacac cgaactgaga tacctacagc gtgagctatg    6480
agaaagcgcc acgcttcccg aagggagaaa ggcggacagg tatccggtaa gcggcagggt    6540
cggaacagga gagcgcacga gggagcttcc agggggaaac gcctggtatc tttatagtcc    6600
tgtcgggttt cgccacctct gacttgagcg tcgatttttg tgatgctcgt caggggggcg    6660
gagcctatgg aaaaacgcca gcaacgcggc cttttacgg ttcctggcct tttgctggcc    6720
```

```
ttttgctcac atgttctttc ctgcgttatc ccctgattct gtggataacc gtattaccgc    6780
ctttgagtga gctgataccg ctcgccgcag ccgaacgacc gagcgcagcg agtcagtgag    6840
cgaggaagcg gaagagcgcc caatacgcag ggccccctgc ttcggggtca ttatagcgat    6900
tttttcggta tatccatcct ttttcgcacg atatacagga ttttgccaaa gggttcgtgt    6960
agactttcct tggtgtatcc aacggcgtca gccgggcagg ataggtgaag taggcccacc    7020
cgcgagcggg tgttccttct tcactgtccc ttattcgcac ctggcggtgc tcaacgggaa    7080
tcctgctctg cgaggctggc cggctaccgc cggcgtaaca gatgagggca agcggatggc    7140
tgatgaaacc aagccaacca ggaagggcag cccacctatc aaggtgtact gccttccaga    7200
cgaacgaaga gcgattgagg aaaaggcggc ggcggccggc atgagcctgt cggcctacct    7260
gctggccgtc ggccagggct acaaaatcac gggcgtcgtg gactatgagc acgtccgcga    7320
gctggcccgc atcaatggcg acctgggccg cctgggcggc ctgctgaaac tctggctcac    7380
cgacgacccg cgcacggcgc ggttcggtga tgccacgatc ctcgccctgc tggcgaagat    7440
cgaagagaag caggacgagc ttggcaaggt catgatgggc gtggtccgcc cgagggcaga    7500
gccatgactt ttttagccgc taaaacggcc ggggggtgcg cgtgattgcc aagcacgtcc    7560
ccatgcgctc catcaagaag agcgacttcg cggagctggt gaagtacatc accgacgagc    7620
aaggcaagac cgatcgggcc ccctgcagga taaaaaaatt gtagataaat tttataaaat    7680
agttttatct acaattttt tatcaggaaa cagctatgac cgcggccgcc attatagcat    7740
aaagagggct taattgctct cttttttaat ttcttttaaa gcttcatttg ggtgtatgtt    7800
taatagatta cagtaaattc gcctgaaagc ccacggtttc aatcgtggga tgaaaggcgt    7860
ttcttttaat cttcttgttg cagtttcagt taaaactga tactataaat atatgggaca    7920
agattataga agaacacaaa caacagtatc tttaataaac tatcattttg ttttctgtcc    7980
aaggtacaga cgtaaagttc tagttggaga agttgaaata aaatttaaac agcttctcaa    8040
tgagatttgt aaagacattg aaatagaaat tttggcaata gaatgtgata aagaccactg    8100
ccatcttttt gtcaatgcac ttcctcattt aagtccagca gacataatgg caaaagtgaa    8160
aggagtgact tctcgattat taaggcagga atttaaacat ctgcgacatt tgccaagtct    8220
ttggacaaga agctattttg tatctaccgc aggaaatgta tcaagtgaaa ctataaaacg    8280
atatg    8285
```

<210> SEQ ID NO 13
<211> LENGTH: 8285
<212> TYPE: DNA
<213> ORGANISM: Artificial Sequence
<220> FEATURE:
<223> OTHER INFORMATION: Synthetic Construct

<400> SEQUENCE: 13

```
ttgaagaaca aaaacaagg gggtgaaaca atgcagataa cagtaaaatt taatattatt      60
ttgacaaaag aacaagtaca actaatagaa tctatatcaa agaatatat ccatactgtt     120 aatagccttg tttcatctac gctccaatca gaagaaagag taaagctatc atctaaagat     180 gttttgtgcaa atatgccaag tgcagtgaaa atcaatccta ttagagatgc caaaagtatc     240
tgtactaagt acaagaaagc tatcaaggct aattccaaac tgcctactga taaacaaaaa     300
gtaatcaatg tagctaccct taaaaaacct gtctgtatat ggataatca aaattattca     360 cttaaagacg gtattcttag ttttcccgtt attatagatg ggaaatcgca gcgtattcaa     420
```

| | |
|---|---|
| actagaacta tcatgacaga ctatcagcta aaacaactag aaggtcattt gggagcattg | 480 |
| cgtataacta agaaaagcaa taaatatatc gctcaaataa gtgttgaaaa agtatctcat | 540 |
| atagttaaag gtgatgttgt aatgggtgtt gacttaggcc taaaagttcc tgctgtagct | 600 |
| gtaaccgatt caggaaaaac gttttttttt ggaaacggta ggcaaaataa atacgtcaaa | 660 |
| cgtaaatata aagcgaaacg taaaaaactt ggaaaagcca agaagcttaa agtcattaaa | 720 |
| aagcttgatg ataaagaaca acgttggatg acagaccaag accacaaagt aagtagagaa | 780 |
| ataattaatt ttgcagtaaa taataatgtt tctgatattc ggcttgaaaa attaacgaat | 840 |
| atcagaaaca cggcaagaac aagccgtaaa aacgaaaaaa atctacatac atggtcattc | 900 |
| tatcgtctag ctcaattcat agagtataag gcactattga aggggataaa ggttgaatat | 960 |
| gttgatccta aatacacttc tcaaatatgc cctgaatgta agaaactaaa taaagcaaga | 1020 |
| gatagaaaat ataaatgctc ctgtggtttt aaaacacata gggatagagt aggtgctata | 1080 |
| aatataatta atgcacctgt agtagatggt aaaagtctac tagcctaggg tactatatgt | 1140 |
| actgctctag gaggggtaat ggcatacccct aagcttgagg tcatactccg atagcagaaa | 1200 |
| tgtacttcgg tttaatcact caagaatccc actgctttag ctgtgggagt gtcaaatgaa | 1260 |
| gcatgatggt catttatctg taactagtga aggaagattg tattatgctg gtagtcaaaa | 1320 |
| aattagtttt aatagtggta tacctttaaa tacaggagat ggagttgttg tttggaatga | 1380 |
| aattcaagat ttaatttcaa cttctgatgt ttattccgat gttactttaa cggatgaaat | 1440 |
| tgcaaattca aattatccaa atataaattt tgaatatgat ggaaaagaac cgattagcaa | 1500 |
| tccgtttggg gattatgaaa acttacatac aggtactaga agtattgata taggtgcaaa | 1560 |
| tccagattta tcagctctag tagggaaaac atatgaagat gttattagtg aaaatccaag | 1620 |
| tcaacaaaat cctatggtgc ctccgatacc atttcctgat tcatggtttg gcaaatggaa | 1680 |
| agatatagtt aacgatagtg gaacatggca aggggaaggc atagatggaa gtactggaac | 1740 |
| tgcaatagat agtcctccat tagatattcc tggaacgtgg caaggcaaat ggtcttggac | 1800 |
| agcagacggt caattagttt tcgatggttc ttttttcaggt tctgacggaa caacatggca | 1860 |
| aggaacatat acgcatacag gaataggtgt tcagaatcct gtactaaatc caccactaac | 1920 |
| cccggattta acaggaataa caggttggtt atcatctata agttcatggt taactagttt | 1980 |
| gtttgcgttt ccaactgatt ttagtttgaa tttagacccg ttgaaaaatc tacctatagc | 2040 |
| aacaaaattt cctttctgtt tgccatttga tttaaaaaat agcattgaat cattgcaatc | 2100 |
| tcctgtcgtt gtcccagttt ttacgactac ttggaattta cccttttatc aaggagatat | 2160 |
| agagattaat ttagcagcta tggaacgatt tgcacaaata acacgttggg gaacgttaat | 2220 |
| tgtatttaat cttggtttaa tacttgttac aaggaaggtg ttatcatgat atggcaagca | 2280 |
| ctagcatctt ttattaatct acttattaaa gcattaggaa cggttttagg ggcaattatc | 2340 |
| ggattattac cttcaagtcc ttttcaaact atttcaaatt cagcagtaac agaatatttta | 2400 |
| ggcatgttga attggtttat atccgtagat gccatgataa ctatattaac ttactggact | 2460 |
| actgcaatta aagttactat gtaatatca actgcgatga gatggggaaa acaattgaa | 2520 |
| taggggata atatgataag ttttatagt ggtactccag gaagtggaaa aagtcttaat | 2580 |
| atagctagat acatatggat taaagttcga catgctaaac aaaatataat acttgttaat | 2640 |
| atgacagtta atagagagta tcttattaca tcaaaactga agcaacttgt taataaaatt | 2700 |
| agattgaaat taaaacttaa acctattaat actaagttaa aagactatgg caaaatctat | 2760 |
| tctataagac tcgatcagct gaacacaaaa tttctagaag attatgctat gaaatttcac | 2820 |

```
atggtgggca ttgaaggaca atcaaaaata ataatagatg aggcacaact gatttggtcc    2880
ccaacggtga tgaaaaataa aaagcaggta gaccctaatt atcgtgaacg ctggatagag    2940
tttatgacac tccatagaca cttaggtttt gacatgataa ttataagtca atttgatagg    3000
ttgatagatg cacaaatacg ttgtctattt gaatacaatc atattcatcg aaagtcaat    3060
aacttttgta taggttattg gctaaaccta ttcaaaataa aagtatttgc agaagtgcaa    3120
tattggtatg gagttagagc aaggattgga gttaatttct tcgctattac tccatggact    3180
tcaaaacact ataggaaaat ttataacgca cataaaggt tctcagattt aaagggaaag    3240
aaaaaagtag cgtagcgttg gacttttttc ttcccttaa atcaagaaat ataatgttcg    3300
taaaaaaatg aatcctgatg tcatggatca cgtggcagca gtcaatattt agatctaaaa    3360
attgaataat atccaaacaa ataggagtg tgtaaaataa atgttcgtga ttatatggtt    3420
aatgttaagt gctgaggtca atctatgaaa tgcgattaag ggccggccag tgggcaagtt    3480
gaaaaattca caaaatgtg gtataatatc tttgttcatt agagcgataa acttgaattt    3540
gagagggaac ttagatggta tttgaaaaaa ttgataaaaa tagttggaac agaaaagagt    3600
attttgacca ctactttgca agtgtaccct gtacctacag catgaccgtt aaagtggata    3660
tcacacaaat aaaggaaaag ggaatgaaac tatatcctgc aatgctttat tatattgcaa    3720
tgattgtaaa ccgccattca gagtttagga cggcaatcaa tcaagatggt gaattgggga    3780
tatatgatga gatgatacca agctatacaa tatttcacaa tgatactgaa acattttcca    3840
gcctttggac tgagtgtaag tctgacttta atcattttt agcagattat gaaagtgata    3900
cgcaacggta tggaaacaat catagaatgg aaggaaagcc aaatgctccg gaaaacattt    3960
ttaatgtatc tatgataccg tggtcaacct tcgatggctt taatctgaat ttgcagaaag    4020
gatatgatta tttgattcct atttttacta tggggaaata ttataaagaa gataacaaaa    4080
ttatacttcc tttggcaatt caagttcatc acgcagtatg tgacggattt cacatttgcc    4140
gttttgtaaa cgaattgcag gaattgataa atagttaact tcaggtttgt ctgtaactaa    4200
aaacaagtat ttaagcaaaa acatcgtaga aatacggtgt tttttgttac cctaagttta    4260
aactcctttt tgataatctc atgaccaaaa tcccttaacg tgagttttcg ttccactgag    4320
cgtcagaccc cgtagaaaag atcaaaggat cttcttgaga tcctttttt ctgcgcgtaa    4380
tctgctgctt gcaaacaaaa aaaccaccgc taccagcggt ggtttgtttg ccggatcaag    4440
agctaccaac tcttttttccg aaggtaactg gcttcagcag agcgcagata ccaaatactg    4500
ttcttctagt gtagccgtag ttaggccacc acttcaagaa ctctgtagca ccgcctacat    4560
acctcgctct gctaatcctg ttaccagtgg ctgctgccag tggcgataag tcgtgtctta    4620
ccgggttgga ctcaagacga tagttaccgg ataaggcgca gcggtcgggc tgaacggggg    4680
gttcgtgcac acagcccagc ttggagcgaa cgacctacac cgaactgaga tacctacagc    4740
gtgagctatg agaaagcgcc acgcttcccg aaggagaaa ggcggacagg tatccggtaa    4800
gcggcagggt cggaacagga gagcgcacga gggagcttcc agggggaaac gcctggtatc    4860
tttatagtcc tgtcgggttt cgccacctct gacttgagcg tcgattttg tgatgctcgt    4920
caggggggcg gagcctatgg aaaaacgcca gcaacgcggc cttttacgg ttcctggcct    4980
tttgctggcc ttttgctcac atgttctttc ctgcgttatc ccctgattct gtggataacc    5040
gtattaccgc ctttgagtga gctgataccg ctcgccgcag ccgaacgacc gagcgcagcg    5100
agtcagtgag cgaggaagcg gaagagcgcc caatacgcag ggcccctgc ttcggggtca    5160
```

```
ttatagcgat ttttcggta  tatccatcct ttttcgcacg atatacagga ttttgccaaa    5220
gggttcgtgt agactttcct tggtgtatcc aacggcgtca gccgggcagg ataggtgaag    5280
taggcccacc cgcgagcggg tgttccttct tcactgtccc ttattcgcac ctggcggtgc    5340
tcaacgggaa tcctgctctg cgaggctggc cggctaccgc cggcgtaaca gatgagggca    5400
agcggatggc tgatgaaacc aagccaacca ggaagggcag cccacctatc aaggtgtact    5460
gccttccaga cgaacgaaga gcgattgagg aaaaggcggc ggcggccggc atgagcctgt    5520
cggcctacct gctggccgtc ggccagggct acaaaatcac gggcgtcgtg gactatgagc    5580
acgtccgcga gctggcccgc atcaatggcg acctgggccg cctgggcggc ctgctgaaac    5640
tctggctcac cgacgacccg cgcacggcgc ggttcggtga tgccacgatc ctcgccctgc    5700
tggcgaagat cgaagagaag caggacgagc ttggcaaggt catgatgggc gtggtccgcc    5760
cgagggcaga gccatgactt ttttagccgc taaaacggcc gggggtgcg cgtgattgcc     5820 aagcacgtcc ccatgcgctc catcaagaag agcgacttcg cggagctggt gaagtacatc    5880
accgacgagc aaggcaagac cgatcgggcc ccctgcagga taaaaaaatt gtagataaat    5940
tttataaaat agttttatct acaattttt  tatcaggaaa cagctatgac cgcggccgcc    6000
agctatagca gctactcttt ggtattatta tcaaaatgct taataaaata gatttacaaa    6060
agtgtctata catgatagta tatatttaat gatatatagg ggggtgtata gattgtttac    6120
aaggaaacca gaaactaaaa ataagtcttt agttcttaga atgacagaaa cgcaaaagaa    6180
gatacttgag attatggcta atgagagagg tttatcacaa tcagaattaa ttatgatatt    6240 attgagagaat gaattcaaga agcctgtatt agaaataaag cagcaagatt aaacttgccg    6300
ccttggatag cggagcaacg gttttatcca agcggtaaac aatattctaa acagcggtgt    6360
ttaaaattat caactagaag tgtattaatg gctgcggaaa gaaatattaa accagtacta    6420
tcacaattcg caccttaaaa gtaaggtttt taatgtttaa ttttggcacg gaacttgctc    6480
tttcttgata tattacaaac aagtcggcta aaattgaaat tttaacgtta tcctgaaagg    6540
ggggcaaaat ttggatgaga agatacttaa agatgtaagg gtttctaaaa atcatttaca    6600
atcggttcat aataataatc agtataataa gttgattgta ggttattaca atcaatacat    6660
agaagattct agacctgtaa agaagaaaaa gactattttg gattatacta gatttactta    6720
tgaagattat tttgttgaaa aattagaaca taaaagagat aagttagcta attgtaataa    6780
gaaatgggaa gttgaagttt atgaaaaact taaagtaaaa gattatgtgt ctactttatt    6840
atgtaatgat aagttttgta gtaattgtaa gaaagtaaag caagcttcaa ggatggcgaa    6900
aaatatgcct ttgcttgaac agtataaaga taattatat caaatggttt taactacacc     6960
aaatattgta gatcatacag gggaagaatt gaaaaagag attaaaaagc aatttaaagc     7020
attaacttat ttaacagaat atttaaaagg taaaaacaa gtaaagggtt tagattttga    7080
tattggatac ttaggtgcaa taaggtcgtt ggaggtaact tatagcggtg actattatca    7140
tccgcatttg catttgatat tagtattgga taatcaaaat gaatttataa cagataaaaa    7200
aaatataaat aactattctt atgattatta taaaaaaaga ccaactagat tattttcaga    7260
ttttgaaata ttgttacaga aatcttggta tctttatat aatggggaaa gattgactaa     7320
ggaaaatata gataaactgg aaaaaggtta tagttgcatg atggataagg caaaagaaga    7380
tgatttttta gaagttttta aatacatggt gaagaatgat ccggcagagg agaatgtaaa    7440
aggtagtaac aaaatgactt ataaaaattt tagagtatta gaatatgcat tgcatagtat    7500
aagacagata caaggttatg gagttttta  taatattaaa gatatattaa tggctgaaga    7560
```

```
agtaaatgaa atgtatgaat ggataagaga gtatttaatc aaaaatgaag gagaagctcc    7620
tgcatatcgt gttgagaaga tacagaagct tctagatgat actgagtata ctcttatatc    7680
aaggaaaaaa atatttacgt atttaagaaa aatatactct gaataataac attatagcat    7740
aaagagggct taattgctct cttttttaat ttcttttaaa gcttcatttg ggtgtatgtt    7800
taatagatta cagtaaattc gcctgaaagc ccacggtttc aatcgtggga tgaaaggcgt    7860 ttctttaat cttcttgttg cagtttcagt ttaaaactga tactataaat atatgggaca    7920
agattataga agaacacaaa caacagtatc tttaataaac tatcatttg ttttctgtcc    7980 aaggtacaga cgtaaagttc tagttggaga agttgaaata aaatttaaac agcttctcaa    8040
tgagatttgt aaagacattg aaatagaaat tttggcaata gaatgtgata aagaccactg    8100
ccatcttttt gtcaatgcac ttcctcattt aagtccagca gacataatgg caaaagtgaa    8160
aggagtgact tctcgattat taaggcagga atttaaacat ctgcgacatt tgccaagtct    8220
ttggacaaga agctattttg tatctaccgc aggaaatgta tcaagtgaaa ctataaaacg    8280
atatg                                                                8285
```

<210> SEQ ID NO 14
<211> LENGTH: 6758
<212> TYPE: DNA
<213> ORGANISM: Artificial Sequence
<220> FEATURE:
<223> OTHER INFORMATION: Synthetic Construct

<400> SEQUENCE: 14

```
gcaaactatt aactggcgaa ctacttactc tagcttcccg gcaacaatta atagactgga      60
tggaggcgga taaagttgca ggaccacttc tgcgctcggc ccttccggct ggctggttta    120
ttgctgataa atctggagcc ggtgagcgtg gtctcgcgg tatcattgca gcactggggc     180
cagatggtaa gccctcccgt atcgtagtta tctacacgac ggggagtcag gcaactatgg    240
atgaacgaaa tagacagatc gctgagatag gtgcctcact gattaagcat tggtaactgt    300
cagaccaagt ttactcatat atactttaga ttgatttacg cgccctgtag cggcgcatta    360
agcgcggcgg gtgtggtggt tacgcgcagc gtgaccgcta cacttgccag cgccctagcg    420
cccgctcctt tcgctttctt cccttccttt ctcgccacgt tcgccggctt tccccgtcaa    480
gctctaaatc gggggctccc tttagggttc gatttagtg ctttacggca cctcgacccc     540
aaaaaacttg atttgggtga tggttcacgt agtgggccat cgccctgata cggtttttt     600 cgccctttga cgttggagtc cacgttcttt aatagtggac tcttgttcca aactgaaca     660 acactcaacc ctatctcggg ctattctttt gatttataag ggattttgcc gatttcggcc    720
tattggttaa aaaatgagct gatttaacaa aaatttaacg cgaattttaa caaaatatta    780
acgtttacaa tttaaaagga tctaggtgaa gatccttttt gataatctca tgaccaaaat    840
cccttaacgt gagttttcgt tccactgagc gtcagacccc gtagaaaaga tcaaaggatc    900
ttcttgagat cctttttttc tgcgcgtaat ctgctgcttg caaacaaaaa aaccaccgct    960
accagcggtg gtttgtttgc cggatcaaga gctaccaact ctttttccga aggtaactgg   1020
cttcagcaga gcgcagatac caaatactgt ccttctagtg tagccgtagt taggccacca   1080
cttcaagaac tctgtagcac cgcctacata cctcgctctg ctaatcctgt taccagtcag   1140
gcatttgaga agcacacggt cacactgctt ccggtagtca ataaaccggt aaaccagcaa   1200
tagacataag cggctattta acgaccctgc cctgaaccga cgaccgggtc gaatttgctt   1260
```

-continued

```
tcgaatttct gccattcatc cgcttattat cacttattca ggcgtagcac caggcgttta   1320
agggcaccaa taactgcctt aaaaaaatta cgccccgccc tgccactcat cgcagtactg   1380
ttgtaattca ttaagcattc tgccgacatg gaagccatca cagacggcat gatgaacctg   1440
aatcgccagc ggcatcagca ccttgtcgcc ttgcgtataa tatttgccca tggtgaaaac   1500
gggggcgaag aagttgtcca tattggccac gtttaaatca aaactggtga aactcaccca   1560
gggattggct gagacgaaaa acatattctc aataaaccct ttagggaaat aggccaggtt   1620
ttcaccgtaa cacgccacat cttgcgaata tatgtgtaga aactgccgga aatcgtcgtg   1680
gtattcactc cagagcgatg aaaacgtttc agtttgctca tggaaaacgg tgtaacaagg   1740
gtgaacacta tcccatatca ccagctcacc gtctttcatt gccatacgga attccggatg   1800
agcattcatc aggcgggcaa gaatgtgaat aaaggccgga taaaacttgt gcttattttt   1860
ctttacggtc tttaaaaagg ccgtaatatc cagctgaacg gtctggttat aggtacattg   1920
agcaactgac tgaaatgcct caaaatgttc tttacgatgc cattgggata tatcaacggt   1980
ggtatatcca gtgattttttt tctccatttt agcttcctta gctcctgaaa atctcgataa   2040
ctcaaaaaat acgcccggta gtgatcttat ttcattatgg tgaaagttgg aacctcttac   2100
gtgccgatca acgtctcatt ttcgccaaaa gttggcccag gcttccggg tatcaacagg    2160
gacaccagga tttatttatt ctgcgaagtg atcttccgtc acaggtattt attcggcgca   2220
aagtgcgtcg ggtgatgctg ccaacttact gatttagtgt atgatggtgt ttttgaggtg   2280
ctccagtggc ttctgtttct atcagctgtc cctcctgttc agctactgac ggggtggtgc   2340
gtaacggcaa aagcaccgcc ggacatcagc gctagcggag tgtatactgg cttactatgt   2400
tggcactgat gagggtgtca gtgaagtgct tcatgtggca ggagaaaaaa ggctgcaccg   2460
gtgcgtcagc agaatatgtg atacaggata tattccgctt cctcgctcac tgactcgcta   2520
cgctcggtcg ttcgactgcg gcgagcggaa atggcttacg aacggggcgg agatttcctg   2580
gaagatgcca ggaagatact aacaggaag tgagagggc cgcggcaaag ccgttttttcc     2640
ataggctccg ccccctgac aagcatcacg aaatctgacg ctcaaatcag tggtggcgaa    2700
acccgacagg actataaaga taccaggcgt ttccccctgg cggctccctc gtgcgctctc   2760
ctgttcctgc ctttcggttt accggtgtca ttccgctgtt atggccgcgt ttgtctcatt   2820
ccacgcctga cactcagttc cgggtaggca gttcgctcca agctggactg tatgcacgaa   2880
ccccccgttc agtccgaccg ctgcgcctta tccggtaact atcgtcttga gtccaacccg   2940
gaaagacatg caaaagcacc actggcagca gccactggta attgatttag gagttagt    3000
cttgaagtca tgcgccggtt aaggctaaac tgaaaggaca agttttggtg actgcgctcc   3060
tccaagccag ttacctcggt tcaaagagtt ggtagctcag agaaccttcg aaaaccgcc    3120
ctgcaaggcg ttttttcgt tttcagagca agagattacg cgcagaccaa aacgatctca    3180
agaagatcat cttattaatc agataaaata tttgctcatg agcccgaagt ggcgagcccg   3240
atcttcccca tcggtgatgt cggcgatata ggcgccagca accgcacctg tggcgccggt   3300
gatgccggcc acgatgcgtc cggcgtagag gatctgctca tgtttgacag cttatcatcg   3360
atgcataatg tgcctgtcaa atggacgaag cagggattct gcaaacccta tgctactccg   3420
tcaagccgtc aattgtctga ttcgttacca attatgacaa cttgacggct acatcattca   3480
ctttttcttc acaaccggca cggaactcgc tcgggctggc cccggtgcat tttttaaata   3540
cccgcgagaa atagagttga tcgtcaaaac caacattgcg accgacggtg gcgataggca   3600
tccgggtggt gctcaaaagc agcttcgcct ggctgatacg ttggtcctcg cgccagctta   3660
```

```
agacgctaat ccctaactgc tggcggaaaa gatgtgacag acgcgacggc gacaagcaaa    3720
catgctgtgc gacgctggcg atatcaaaat tgctgtctgc caggtgatcg ctgatgtact    3780
gacaagcctc gcgtacccga ttatccatcg gtggatggag cgactcgtta atcgcttcca    3840
tgcgccgcag taacaattgc tcaagcagat ttatcgccag cagctccgaa tagcgccctt    3900
ccccttgccc ggcgttaatg atttgcccaa acaggtcgct gaaatgcggc tggtgcgctt    3960
catccgggcg aaagaacccc gtattggcaa atattgacgg ccagttaagc cattcatgcc    4020
agtaggcgcg cggacgaaag taaacccact ggtgatacca ttcgcgagcc tccggatgac    4080
gaccgtagtg atgaatctct cctggcggga acagcaaaat atcacccggt cggcaaacaa    4140
attctcgtcc ctgatttttc accaccccct gaccgcgaat ggtgagattg agaatataac    4200
ctttcattcc cagcggtcgg tcgataaaaa aatcgagata accgttggcc tcaatcggcg    4260
ttaaacccgc caccagatgg gcattaaacg agtatcccgg cagcagggga tcattttgcg    4320
cttcagccat acttttcata ctcccgccat tcagagaaga aaccaattgt ccatattgca    4380
tcagacattg ccgtcactgc gtcttttact ggctcttctc gctaaccaaa ccggtaaccc    4440
cgcttattaa aagcattctg taacaaagcg ggaccaaagc catgacaaaa acgcgtaaca    4500
aaagtgtcta taatcacggc agaaaagtcc acattgatta tttgcacggc gtcacacttt    4560
gctatgccat agcattttta tccataagat tagcggatcc tacctgacgc ttttatcgc    4620
aactctctac tgtttctcca tacccgtttt tttgggctag cgaattcgag ctcggtaccc    4680
ggggaggaat aataaatggc cgtactccgc aatattgatg agcaactgac cgaggaattt    4740
aagaaactgc cgatcgacta ttgggacttt gagggtgagg acacgaaaga actgacgcac    4800
ggcctgcaca actatccggc ggtgatggtt tatccgatct accgtaacat tatcgacatc    4860
gtgaagcgtc acggtgaggt cgaaaccttt ctggacccgt ttatgggtag cggtacgggc    4920
ctggtggaag gcaagctggc gggtttcaac aaagtgtacg gtacggatct gaatcctctg    4980
gcagtgctgc tgagcaaggt taagaccacc gtcttgaaag aggatagcgt ggatattcag    5040
gacaagctgc tgcgcgagaa tattgagcag gcgttcgtgt ccagcaaaca gctgctggat    5100
aacattgaca attacattgc ggagaagggc ctggacgtca gcgccaaaga cggctggggc    5160
tctgatgcgc atgtcatttt gcgcgagtat ctggatacct acaacagcgg tctgaaaatc    5220
ccagacttta agaatatggg ttattggttc aaaccgcgcg ttattctgga gctgcaactg    5280
attaaggata tcattctgca gatcgagaat gaggacttcc gtaacttctt tctggtctgc    5340
ttctctgaaa ctgcccgcta cgtgagcaac acccgtaatg gtgagttcaa gctgttccgt    5400
atcaagaaag aaaaagtggc agatttcaat ccggacgtta agatcgagtt ttacaaatat    5460
ctggatcgta acatcgaaaa gattaaagac tttgacaaac gttgtaacaa cgattgcgaa    5520
gttagcgttg cttttgaaga tacccgcatt ctggactcgg ttccggacaa tagcatcgat    5580
ctgatgatta ccagcccacc gtacggcgat agcaaaacta cggtggcgta cggtcaattt    5640
agccgtccgt ctttgtggtg gttggatctg gaattgatgg acatcgaaga gctgaatcaa    5700
gttgacaaca atctgctggg tggtaagaag gtggacaaag acttcgagtg tgaactgagc    5760
tcccgtacct tggagaaggc gattaaagaa atcaaagaaa aggacctgga ccgcgcacgt    5820
gacgtttata gcttctacga ggatttggat aaggctatgg agtccattac gaaaaagatg    5880
cgtcataaca gctaccagtt ctgggttgtc ggtaaccgta ccgttaaaga agtcaaactg    5940
ctgaccaacg aaatcattag cgaactgggc gagaaatatg gtttggttga ggtttacgat    6000
```

| | |
|---|---|
| atcccgcgta acatcccgaa taaggtcatg ccgagccgta attccccgac caatgaaacc | 6060 |
| ggcaagacgg tcagcaccat gacgaacgag cacatcgtcg tgctgcgcaa agatcgttga | 6120 |
| ggctgttttg gcggatgaga gaagattttc agcctgatac agattaaatc agaacgcaga | 6180 |
| agcggtctga taaaacagaa tttgcctggc ggcagtagcg cggtggtccc acctgacccc | 6240 |
| atgccgaact cagaagtgaa acgccgtagc gccgatggta gtgtggggtc tccccatgcg | 6300 |
| agagtaggga actgccaggc atcaaataaa acgaaaggct cagtcgaaag actgggcctt | 6360 |
| tcgttttatc tgttgtttgt cggtgaacgc tctcctgagt aggacaaatc cgccgggagc | 6420 |
| ggatttgaac gttgcgaagc aacggcccgg agggtggcgg gcaggacgcc cgccataaac | 6480 |
| tgccaggcat caaattaagc agaaggccat cctgacggat ggcctttttg cgtttctaca | 6540 |
| aactcttttg tttattttc taaatacatt caaatatgta tccgctcatg agacaataac | 6600 |
| cctgataaat gcttcaataa tattgaaaaa ggaagagtat gagtattcaa catttccgtg | 6660 |
| tcgcccttat tccctttttt gcggcatttt gccttcctgt ttttgctcac ccagaaacgc | 6720 |
| tggtgaaagt aaaagatgct gaagatcagt tgggtgca | 6758 |

<210> SEQ ID NO 15
<211> LENGTH: 8398
<212> TYPE: DNA
<213> ORGANISM: Artificial Sequence
<220> FEATURE:
<223> OTHER INFORMATION: Synthetic Construct

<400> SEQUENCE: 15

| | |
|---|---|
| aaactccttt ttgataatct catgaccaaa atcccttaac gtgagttttc gttccactga | 60 |
| gcgtcagacc ccgtagaaaa gatcaaagga tcttcttgag atccttttt tctgcgcgta | 120 |
| atctgctgct tgcaaacaaa aaaaccaccg ctaccagcgg tggtttgttt gccggatcaa | 180 |
| gagctaccaa ctctttttcc gaaggtaact ggcttcagca gagcgcagat accaaatact | 240 |
| gttcttctag tgtagccgta gttaggccac cacttcaaga actctgtagc accgcctaca | 300 |
| tacctcgctc tgctaatcct gttaccagtg gctgctgcca gtggcgataa gtcgtgtctt | 360 |
| accgggttgg actcaagacg atagttaccg gataaggcgc agcggtcggg ctgaacgggg | 420 |
| ggttcgtgca cacagcccag cttggagcga acgacctaca ccgaactgag atacctacag | 480 |
| cgtgagctat gagaaagcgc cacgcttccc gaagggagaa aggcggacag gtatccggta | 540 |
| agcggcaggg tcggaacagg agagcgcacg agggagcttc caggggggaaa cgcctggtat | 600 |
| ctttatagtc ctgtcgggtt tcgccacctc tgacttgagc gtcgattttt gtgatgctcg | 660 |
| tcagggggggc ggagcctatg gaaaaacgcc agcaacgcgg ccttttttacg gttcctggcc | 720 |
| ttttgctggc cttttgctca catgttcttt cctgcgttat cccctgattc tgtggataac | 780 |
| cgtattaccg cctttgagtg agctgatacc gctcgccgca gccgaacgac cgagcgcagc | 840 |
| gagtcagtga gcgaggaagc ggaagagcgc ccaatacgca gggccccctg cttcggggtc | 900 |
| attatagcga ttttttttcggt atatccatcc ttttttcgcac gatatacagg attttgccaa | 960 |
| agggttcgtg tagactttcc ttggtgtatc caacggcgtc agccgggcag gataggtgaa | 1020 |
| gtaggcccac ccgcgagcgg gtgttccttc ttcactgtcc cttattcgca cctggcggtg | 1080 |
| ctcaacggga atcctgctct gcgaggctgg ccggctaccg ccggcgtaac agatgagggc | 1140 |
| aagcggatgg ctgatgaaac caagccaacc aggaagggca gcccacctat caaggtgtac | 1200 |
| tgccttccag acgaacgaag agcgattgag gaaaaggcgg cggcggccgg catgagcctg | 1260 |
| tcggcctacc tgctggccgt cggccagggc tacaaaatca cgggcgtcgt ggactatgag | 1320 |

```
cacgtccgcg agctggcccg catcaatggc gacctgggcc gcctgggcgg cctgctgaaa    1380
ctctggctca ccgacgaccc gcgcacggcg cggttcggtg atgccacgat cctcgccctg    1440
ctggcgaaga tcgaagagaa gcaggacgag cttggcaagg tcatgatggg cgtggtccgc    1500
ccgagggcag agccatgact tttttagccg ctaaaacggc cggggggtgc gcgtgattgc    1560
caagcacgtc cccatgcgct ccatcaagaa gagcgacttc gcggagctgg tgaagtacat    1620
caccgacgag caaggcaaga ccgatcgggc cccctgcagg ataaaaaaat tgtagataaa    1680
ttttataaaa tagttttatc tacaattttt ttatcaggaa acagctatga ccgcggccgc    1740
cagctatagc agctactctt tggtattatt atcaaaatgc ttaataaaat agatttacaa    1800
aagtgtctat acatgatagt atatatttaa tgatatatag gggggtgtat agattgttta    1860
caaggaaacc agaaactaaa aataagtctt tagttcttag aatgacagaa acgcaaaaga    1920
agatacttga gattatggct aatgagagag gtttatcaca atcagaatta attatgatat    1980
tattggagaa tgaattcaag aagcctgtat tagaaataaa gcagcaagat taaacttgcc    2040
gccttggata gcggagcaac ggttttatcc aagcggtaaa caatattcta acagcggtg    2100 tttaaaatta tcaactagaa gtgtattaat ggctgcggaa agaaatatta aaccagtact    2160
atcacaattc gcaccttaaa agtaaggttt ttaatgttta attttggcac ggaacttgct    2220
ctttcttgat atattacaaa caagtcggct aaaattgaaa ttttaacgtt atcctgaaag    2280
gggggcaaaa tttggatgag aagatactta agatgtaagg gtttctaaa aatcatttac    2340 aatcggttca taataataat cagtataata agttgattgt aggttattac aatcaataca    2400
tagaagattc tagacctgta aagaagaaaa agactatttt ggattatact agatttactt    2460
atgaagatta ttttgttgaa aaattagaac ataaaagaga taagttagct aattgtaata    2520
agaaatggga agttgaagtt tatgaaaaac ttaaagtaaa agattatgtg tctactttat    2580
tatgtaatga taagttttgt agtaattgta agaaagtaaa gcaagcttca aggatggcga    2640
aaaatatgcc tttgcttgaa cagtataaag ataaattata tcaaatggtt ttaactacac    2700
caaatattgt agatcataca ggggaagaat tgaaaaaaga gattaaaaag caatttaaag    2760
cattaactta tttaacagaa tatttaaaag gtaaaaaaca agtaaagggt ttagattttg    2820
atattggata cttaggtgca ataaggtcgt tggaggtaac ttatagcggt gactattatc    2880
atccgcattt gcatttgata ttagtattgg ataatcaaaa tgaatttata acagataaaa    2940
aaaatataaa taactattct tatgattatt ataaaaaaag accaactaga ttattttcag    3000
attttgaaat attgttacag aaatcttggt atcttttata taatggggaa agattgacta    3060
aggaaaatat agataaactg gaaaaaggtt atagttgcat gatggataag gcaaaagaag    3120
atgatttttt agaagttttt aaatacatgg tgaagaatga tccggcagag gagaatgtaa    3180
aaggtagtaa caaaatgact tataaaaatt ttagagtatt agaatatgca ttgcatagta    3240
taagacagat acaaggttat ggagtttttt ataatattaa agatatatta atggctgaag    3300
aagtaaatga aatgtatgaa tggataagag agtatttaat caaaaatgaa ggagaagctc    3360
ctgcatatcg tgttgagaag atacagaagc ttctagatga tactgagtat actcttatat    3420
caaggaaaaa aatatttacg tatttaagaa aaatatactc tgaataataa cattatagca    3480
taaagagggc ttaattgctc tctttttaa tttcttttaa agcttcattt gggtgtatgt    3540
ttaatagatt acagtaaatt cgcctgaaag cccacggttt caatcgtggg atgaaaggcg    3600
tttcttttaa tcttcttgtt gcagtttcag tttaaaactg atactataaa tatatgggac    3660
```

```
aagattatag aagaacacaa acaacagtat ctttaataaa ctatcatttt gttttctgtc    3720
caaggtacag acgtaaagtt ctagttggag aagttgaaat aaaatttaaa cagcttctca    3780
atgagatttg taaagacatt gaaatagaaa ttttggcaat agaatgtgat aaagaccact    3840
gccatctttt tgtcaatgca cttcctcatt taagtccagc agacataatg gcaaaagtga    3900
aaggagtgac ttctcgatta ttaaggcagg aatttaaaca tctgcgacat tgccaagtc     3960 tttggacaag aagctatttt gtatctaccg caggaaatgt atcaagtgaa actataaaac    4020
gatatgttga agaacaaaaa acaaggggt gaaacaatgc agataacagt aaaatttaat     4080
attattttga caaagaaaca agtacaacta atagaatcta tatcaaaaga atatatccat    4140
actgttaata gccttgtttc atctacgctc caatcagaag aaagagtaaa gctatcatct    4200
aaagatgttt ttgcaaatat gccaagtgca gtgaaaaatc aatctattag agatgccaaa    4260
agtatctgta ctaagtacaa gaaagctatc aaggctaatt ccaaactgcc tactgataaa    4320
caaaaagtaa tcaatgtagc tacccttaaa aaacctgtct gtatatggaa taatcaaaat    4380
tattcactta aagacggtat tcttagtttt cccgttatta tagatgggaa atcgcagcgt    4440
attcaaacta gaactatcat gacagactat cagctaaaac aactagaagg tcatttggga    4500
gcattgcgta taactaagaa aagcaataaa tatatcgctc aaataagtgt tgaaaaagta    4560
tctcatatag ttaaaggtga tgttgtaatg ggtgttgact taggcctaaa agttcctgct    4620
gtagctgtaa ccgattcagg aaaaacgttt ttttttggaa acggtaggca aaataaatac    4680
gtcaaacgta aatataaagc gaaacgtaaa aaacttggaa aagccaagaa gcttaaagtc    4740
attaaaaagc ttgatgataa agaacaacgt tggatgacag accaagacca caagtaagt     4800 agagaaataa ttaattttgc agtaaataat aatgtttctg atattcggct tgaaaaatta    4860
acgaatatca gaaacacggc aagaacaagc cgtaaaaacg aaaaaaatct acatacatgg    4920
tcattctatc gtctagctca attcatagag tataaggcac tattgaaggg gataaaggtt    4980
gaatatgttg atcctaaata cacttctcaa atatgccctg aatgtaagaa actaaataaa    5040
gcaagagata gaaaatataa atgctcctgt ggttttaaaa cacataggga tagagtaggt    5100
gctataaata taattaatgc acctgtagta gatggtaaaa gtctactagc ctagggtact    5160
atatgtactg ctctaggagg ggtaatggca taccctaagc ttgaggtcat actccgatag    5220
cagaaatgta cttcggttta atcactcaag aatcccactg ctttagctgt gggagtgtca    5280
aatgaagcat gatggtcatt tatctgtaac tagtgaagga agattgtatt atgctggtag    5340
tcaaaaaatt agttttaata gtggtatacc tttaaataca ggagatggag ttgttgtttg    5400
gaatgaaatt caagatttaa tttcaacttc tgatgtttat tccgatgtta ctttaacgga    5460
tgaaattgca aattcaaatt atccaaatat aaattttgaa tatgatggaa agaaccgat     5520 tagcaatccg ttttgggatt atgaaaactt acatacaggt actagaagta ttgatatagg    5580
tgcaaatcca gatttatcag ctctagtagg gaaaacatat gaagatgtta ttagtgaaaa    5640
tccaagtcaa caaaatccta tggtgcctcc gataccattt cctgattcat ggtttggcaa    5700
atggaaagat atagttaacg atagtggaac atggcaaggg aaggcatag atggaagtac     5760 tggaactgca atagatagtc ctccattaga tattcctgga acgtggcaag gcaaatggtc    5820
ttggacagca gacggtcaat tagttttcga tggttctttt tcaggttctg acggaacaac    5880
atggcaagga acatatacgc atacaggaat aggtgttcag aatcctgtac taaatccacc    5940
actaaccccg gatttaacag gaataacagg ttggttatca tctataagtt catggttaac    6000
tagtttgttt gcgtttccaa ctgattttag tttgaattta gacccgttga aaaatctacc    6060
```

```
tatagcaaca aaatttcctt tctgtttgcc atttgattta aaaatagca ttgaatcatt    6120 gcaatctcct gtcgttgtcc cagtttttac gactacttgg aatttaccct tttatcaagg    6180
agatatagag attaatttag cagctatgga acgatttgca caaataacac gttggggaac    6240
gttaattgta tttaatcttg gtttaatact tgttacaagg aaggtgttat catgatatgg    6300
caagcactag catctttttat taatctactt attaaagcat taggaacggt tttaggggca    6360
attatcggat tattaccttc aagtcctttt caaactattt caaattcagc agtaacagaa    6420
tatttaggca tgttgaattg gtttatatcc gtagatgcca tgataactat attaacttac    6480
tggactactg caattataag ttactatgta atatcaactg cgatgagatg gggaaaaaca    6540
attgaatagg gggataatat gataagtttt tatagtggta ctccaggaag tggaaaaagt    6600
cttaatatag ctagatacat atggattaaa gttcgacatg ctaaacaaaa tataatactt    6660
gttaatatga cagttaatag agagtatctt attacatcaa aactgaagca acttgttaat    6720
aaaattagat tgaaattaaa acttaaacct attaatacta agttaaaaga ctatggcaaa    6780
atctattcta taagactcga tcagctgaac acaaaatttc tagaagatta tgctatgaaa    6840
tttcacatgg tgggcattga aggacaatca aaaataataa tagatgaggc acaactgatt    6900
tggtccccaa cggtgatgaa aaataaaaag caggtagacc ctaattatcg tgaacgctgg    6960
atagagttta tgacactcca tagacactta ggttttgaca tgataattat aagtcaattt    7020
gataggttga tagatgcaca aatacgttgt ctatttgaat acaatcatat tcatcggaaa    7080
gtcaataact tttgtatagg ttattggcta aacctattca aaataaaagt atttgcagaa    7140
gtgcaatatt ggtatggagt tagagcaagg attggagtta atttcttcgc tattactcca    7200
tggacttcaa acactatag gaaaatttat aacgcacata aaaggttctc agatttaaag    7260
ggaaagaaaa aagtagcgta gcgttggact tttttcttcc ctttaaatca agaaatataa    7320
tgttcgtaaa aaaatgaatc ctgatgtcat ggatcacgtg gcagcagtca atatttagat    7380
ctaaaaattg aataatatcc aaacaaatag gaggtgtgta aaataaatgt tcgtgattat    7440
atggttaatg ttaagtgctg aggtcaatct atgaaatgcg attaagggcc ggccgaagca    7500
aacttaagag tgtgttgata gtgcagtatc ttaaaatttt gtataatagg aattgaagtt    7560
aaattagatg ctaaaaattt gtaattaaga aggagtgatt acatgaacaa aaatataaaa    7620
tattctcaaa acttttttaac gagtgaaaaa gtactcaacc aaataataaa acaattgaat    7680
ttaaaagaaa ccgataccgt ttacgaaatt ggaacaggta aagggcattt aacgacgaaa    7740
ctggctaaaa taagtaaaca ggtaacgtct attgaattag acagtcatct attcaactta    7800
tcgtcagaaa aattaaaact gaatactcgt gtcactttaa ttcaccaaga tattctacag    7860
tttcaattcc ctaacaaaca gaggtataaa attgttggga gtattcctta ccatttaagc    7920
acacaaatta ttaaaaaagt ggttttttgaa agccatgcgt ctgacatcta tctgattgtt    7980
gaagaaggat tctacaagcg taccttggat attcaccgaa cactagggtt gctcttgcac    8040
actcaagtct cgattcagca attgcttaag ctgccagcgg aatgctttca tcctaaacca    8100
aaagtaaaca gtgtcttaat aaaacttacc cgccatacca cagatgttcc agataaaatat    8160 tggaagctat atacgtactt tgtttcaaaa tgggtcaatc gagaatatcg tcaactgttt    8220
actaaaaatc agtttcatca agcaatgaaa cacgccaaag taaacaattt aagtaccgtt    8280
acttatgagc aagtattgtc tattttttaat agttatctat tatttaacgg gaggaaataa    8340
ttctatgagt cgcttttgta aatttggaaa gttacacgtt actaaaggga atgtgttt    8398
```

<210> SEQ ID NO 16
<211> LENGTH: 4762
<212> TYPE: DNA
<213> ORGANISM: Artificial Sequence
<220> FEATURE:
<223> OTHER INFORMATION: Synthetic Construct

<400> SEQUENCE: 16

```
aaactccttt tgataatct catgaccaaa atcccttaac gtgagttttc gttccactga      60
gcgtcagacc ccgtagaaaa gatcaaagga tcttcttgag atccttttt tctgcgcgta    120
atctgctgct tgcaaacaaa aaaccaccg ctaccagcgg tggtttgttt gccggatcaa    180
gagctaccaa ctcttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat    600
ctttatagtc ctgtcgggtt tcgccacctc tgacttgagc gtcgatttt gtgatgctcg    660
tcagggggg ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggccccctg cttcggggtc    900
attatagcga ttttttcggt atatccatcc tttttcgcac gatatacagg attttgccaa    960
agggttcgtg tagactttcc ttggtgtatc caacggcgtc agccgggcag gataggtgaa   1020
gtaggcccac ccgcgagcgg gtgttccttc ttcactgtcc cttattcgca cctggcggtg   1080
ctcaacggga atcctgctct gcgaggctgg ccggctaccg ccggcgtaac agatgagggc   1140
aagcggatgg ctgatgaaac caagccaacc aggaagggca gcccacctat caaggtgtac   1200
tgccttccag acgaacgaag agcgattgag gaaaaggcgg cggcggccgg catgagcctg   1260
tcggcctacc tgctggccgt cggccagggc tacaaaatca cgggcgtcgt ggactatgag   1320
cacgtccgcg agctggcccg catcaatggc gacctgggcc gctgggcgg cctgctgaaa   1380
ctctggctca ccgacgaccc gcgcacgcg cggttcggtg atgccacgat cctcgccctg   1440
ctggcgaaga tcgaagagaa gcaggacgag cttggcaagg tcatgatggg cgtggtccgc   1500
ccgagggcag agccatgact ttttagccg ctaaaacggc cgggggtgc gcgtgattgc   1560
caagcacgtc cccatgcgct ccatcaagaa gagcgacttc gcggagctgg tgaagtacat   1620
caccgacgag caaggcaaga ccgatcgggc cccctgcagg ataaaaaaat tgtagataaa   1680
ttttataaaa tagtttttatc tacaatttt ttatcaggaa acagctatga ccgcggccgc   1740
cagctatagc agctactctt tggtattatt atcaaaatgc ttaataaaat agatttacaa   1800
aagtgtctat acatgatagt atatattta tgatatatag ggggtgtat agattgttta   1860
caaggaaacc agaaactaaa ataagtcttt tagttcttag aatgacagaa acgcaaaaga   1920
agatacttga gattatggct aatgagagag gtttatcaca atcagaatta attatgatat   1980
tattggagaa tgaattcaag aagcctgtat tagaaataaa gcagcaagat taaacttgcc   2040
gccttggata gcggagcaac ggttttatcc aagcggtaaa caatattcta aacagcggtg   2100
```

```
tttaaaatta tcaactagaa gtgtattaat ggctgcggaa agaaatatta aaccagtact   2160
atcacaattc gcaccttaaa agtaaggttt ttaatgttta attttggcac ggaacttgat   2220
atattacaaa caagtcggct aaaattgaaa ttttaacgtt atcctgaaag gggggcaaaa   2280
tttggatgag aagatactta aagatgtaag ggtttctaaa aatcatttac aatcggttca   2340
taataataat cagtataata agttgattgt aggttattac aatcaataca tagaagattc   2400
tagacctgta aagaagaaaa agactatttt ggattatact agatttactt atgaagatta   2460
ttttgttgaa aaattagaac ataaaagaga taagttagct aattgtaata agaaatggga   2520
agttgaagtt tatgaaaaac ttaaagtaaa agattatgtg tctactttat tatgtaatga   2580
taagttttgt agtaattgta agaaagtaaa gcaagcttca aggatggcga aaaatatgcc   2640
tttgcttgaa cagtataaag ataaattata tcaaatggtt ttaactacac caaatattgt   2700
agatcataca ggggaagaat tgaaaaaaga gattaaaaag caatttaaag cattaactta   2760
tttaacagaa tatttaaaag gtaaaaaaca agtaaagggt ttagattttg atattggata   2820
cttaggtgca ataaggtcgt tggaggtaac ttatagcggt gactattatc atccgcattt   2880
gcatttgata ttagtattgg ataatcaaaa tgaatttata acagataaaa aaaatataaa   2940
taactattct tatgattatt ataaaaaaag accaactaga ttattttcag attttgaaat   3000
attgttacag aaatcttggt atcttttata taatggggaa agattgacta aggaaaatat   3060
agataaactg gaaaaaggtt atagttgcat gatggataag gcaaagaag atgattttt    3120 agaagttttt aaatacatgg tgaagaatga tccggcagag gagaatgtaa aaggtagtaa   3180
caaaatgact tataaaaatt ttagagtatt agaatatgca ttgcatagta aagacagat    3240 acaaggttat ggagtttttt ataatattaa agatatatta atggctgaag aagtaaatga   3300
aatgtatgaa tggataagag agtatttaat caaaaatgaa ggagaagctc ctgcatatcg   3360
tgttgagaag atacagaagc ttctagatga tactgagtat actcttatat caaggaaaaa   3420
aatatttacg tatttaagaa aaatatactc tgaataataa cattatagca taaagagggc   3480
ttaattgctc tcttttttaa tttcttttaa agcttcattt gggtgtatgt ttaatagatt   3540
acagtaaatt cgcctgaaag cccacggttt caatcgtggg atgaaaggcg tttcttttaa   3600
tcttcttgtt gcagttttcag tttaaactga tactataaat attagcgttg gactttttc    3660 ttcccttttaa atcaagaaat ataatgttcg taaaaaaatg aatcctgatg tcatggatca   3720
cgtggcagca gtcaatattt agatctaaaa attgaataat atccaaacaa ataggaggtg   3780
tgtaaaataa atgttcgtga ttatatggtt aatgttaagt gctgaggtca atctatgaaa   3840
tgcgattaag ggccggccga agcaaactta agagtgtgtt gatagtgcag tatcttaaaa   3900
ttttgtataa taggaattga agttaaatta gatgctaaaa atttgtaatt aagaaggagt   3960
gattacatga acaaaaatat aaaatattct caaaactttt taacgagtga aaaagtactc   4020
aaccaaataa taaaacaatt gaatttaaaa gaaaccgata ccgtttacga aattggaaca   4080
ggtaaagggc atttaacgac gaaactggct aaaatagta aacaggtaac gtctattgaa    4140
ttagacagtc atctattcaa cttatcgtca gaaaaattaa aactgaatac tcgtgtcact   4200
ttaattcacc aagatattct acagtttcaa ttccctaaca acagaggta taaaattgtt    4260 gggagtattc cttaccattt aagcacacaa attattaaaa aagtggtttt tgaaagccat   4320
gcgtctgaca tctatctgat tgttgaagaa ggattctaca agcgtacctt ggatattcac   4380
cgaacactag ggttgctctt gcacactcaa gtctcgattc agcaattgct taagctgcca   4440
```

-continued

| | |
|---|---|
| gcggaatgct ttcatcctaa accaaaagta aacagtgtct taataaaact tacccgccat | 4500 |
| accacagatg ttccagataa atattggaag ctatatacgt actttgtttc aaaatgggtc | 4560 |
| aatcgagaat atcgtcaact gtttactaaa aatcagtttc atcaagcaat gaaacacgcc | 4620 |
| aaagtaaaca atttaagtac cgttacttat gagcaagtat tgtctatttt taatagttat | 4680 |
| ctattattta acgggaggaa ataattctat gagtcgcttt tgtaaatttg gaaagttaca | 4740 |
| cgttactaaa gggaatgtgt tt | 4762 |

<210> SEQ ID NO 17
<211> LENGTH: 5254
<212> TYPE: DNA
<213> ORGANISM: Artificial Sequence
<220> FEATURE:
<223> OTHER INFORMATION: Synthetic Construct

<400> SEQUENCE: 17

| | |
|---|---|
| cctgcaggat aaaaaaattg tagataaatt ttataaaata gttttatcta caatttttt | 60 |
| atcaggaaac agctatgacc gcggccgctg tatccatatg accatgatta cgaattcgag | 120 |
| ctcggtaccc ggggatcctc tagagtcgac gtcacgcgtc catggagatc tcgaggcctg | 180 |
| cagacatgca agcttggcac tggccgtcgt tttacaacgt cgtgactggg aaaaccctgg | 240 |
| cgttacccaa cttaatcgcc ttgcagcaca tccccctttc gccagctggc gtaatagcga | 300 |
| agaggcccgc accgatcgcc cttcccaaca gttgcgcagc ctgaatggcg aatggcgcta | 360 |
| gcataaaaat aagaagcctg catttgcagg cttcttattt ttatggcgcg ccgttctgaa | 420 |
| tccttagcta atggttcaac aggtaactat gacgaagata gcaccctgga taagtctgta | 480 |
| atggattcta aggcatttaa tgaagacgtg tatataaaat gtgctaatga aaagaaaat | 540 |
| gcgttaaaag agcctaaaat gagttcaaat ggttttgaaa ttgattggta gtttaattta | 600 |
| atatatttt tctattggct atctcgatac ctatagaatc ttctgttcac ttttgttttt | 660 |
| gaaatataaa aagggctttt ttagccccctt tttttaaaa ctccggagga gtttcttcat | 720 |
| tcttgatact atacgtaact attttcgatt tgacttcatt gtcaattaag ctagtaaaat | 780 |
| caatggttaa aaaacaaaaa acttgcattt ttctacctag taatttataa ttttaagtgt | 840 |
| cgagtttaaa agtataattt accaggaaag gagcaagttt tttaataagg aaaaattttt | 900 |
| ccttttaaaa ttctatttcg ttatatgact aattataatc aaaaaatga aaataaacaa | 960 |
| gaggtaaaaa ctgctttaga gaaatgtact gataaaaaaa gaaaaaatcc tagatttacg | 1020 |
| tcatacatag caccttttaac tactaagaaa aatattgaaa ggacttccac ttgtggagat | 1080 |
| tatttgttta tgttgagtga tgcagactta gaacatttta aattacataa aggtaatttt | 1140 |
| tgcggtaata gattttgtcc aatgtgtagt tggcgacttg cttgtaagga tagtttagaa | 1200 |
| atatctattc ttatggagca tttaagaaaa gaagaaaata aagagtttat atttttaact | 1260 |
| cttacaactc caaatgtaaa aagttatgat cttaattatt ctattaaaca atataataaa | 1320 |
| tcttttaaaa aattaatgga gcgtaaggaa gttaaggata taactaaagg ttatataaga | 1380 |
| aaattagaag taacttacca aaaggaaaaa tacataacaa aggatttatg gaaaataaaa | 1440 |
| aaagattatt atcaaaaaaa aggacttgaa attggtgatt tagaacctaa ttttgatact | 1500 |
| tataatcctc atttcatgt agttattgca gttaataaaa gttattttac agataaaaat | 1560 |
| tattatataa atcgagaaag atggttggaa ttatggaagt ttgctactaa ggatgattct | 1620 |
| ataactcaag ttgatgttag aaaagcaaaa attaatgatt ataaagaggt ttacgaactt | 1680 |
| gcgaaatatt cagctaaaga cactgattat ttaatatcga ggccagtatt tgaaattttt | 1740 |

```
tataaagcat taaaaggcaa gcaggtatta gttttagtg gattttttaa agatgcacac   1800
aaattgtaca agcaaggaaa acttgatgtt tataaaaaga aagatgaaat taaatatgtc   1860
tatatagttt attataattg gtgcaaaaaa caatatgaaa aaactagaat aagggaactt   1920
acggaagatg aaaaagaaga attaaatcaa gatttaatag atgaaataga aatagattaa   1980
agtgtaacta tactttatat atatatgatt aaaaaaataa aaaacaacag cctattaggt   2040
tgttgttttt tattttcttt attaattttt ttaattttta gttttagtt ctttttaaa   2100 ataagtttca gcctcttttt caatattttt taaagaagga gtatttgcat gaattgcctt   2160
ttttctaaca gacttaggaa atattttaac agtatcttct tgcgccggtg attttggaac   2220
ttcataactt actaatttat aattattatt ttcttttta attgtaacag ttgcaaaaga   2280
agctgaacct gttccttcaa ctagtttatc atcttcaata taatattctt gacctatata   2340
gtataaatat attttttatta tattttact tttttctgaa tctattattt tataatcata   2400 aaaagttta ccaccaaaag aaggttgtac tccttctggt ccaacatatt tttttactat   2460
attatctaaa taattttgg gaactggtgt tgtaatttga ttaatcgaac aaccagttat   2520
acttaaagga attataacta taaaatata taggattatc ttttttaaatt tcattattgg   2580 cctcctttt attaaattta tgttaccata aaaaggacat aacgggaata tgtagaatat   2640
ttttaatgta gacaaaattt tacataaata taaagaaagg aagtgtttgt ttaaatttta   2700
tagcaaacta tcaaaaatta gggggataaa aatttatgaa aaaaaggttt tcgatgttat   2760
ttttatgttt aactttaata gtttgtggtt tatttacaaa ttcggccggc cagtgggcaa   2820
gttgaaaaat tcacaaaaat gtggtataat atctttgttc attagagcga taaacttgaa   2880
tttgagaggg aacttagatg gtatttgaaa aaattgataa aaatagttgg aacagaaaag   2940
agtattttga ccactacttt gcaagtgtac cttgtaccta cagcatgacc gttaaagtgg   3000
atatcacaca aataaaggaa aagggaatga aactatatcc tgcaatgctt tattatattg   3060
caatgattgt aaaccgccat tcagagttta ggacggcaat caatcaagat ggtgaattgg   3120
ggatatatga tgagatgata ccaagctata caatatttca caatgatact gaaacatttt   3180
ccagcctttg gactgagtgt aagtctgact ttaaatcatt tttagcagat tatgaaagtg   3240
atacgcaacg gtatggaaac aatcatagaa tggaaggaaa gccaaatgct ccggaaaaca   3300
tttttaatgt atcctatgata ccgtggtcaa ccttcgatgg cttaatctg aatttgcaga   3360 aaggatatga ttatttgatt cctatttta ctatggggaa atattataaa gaagataaca   3420
aaattatact tcctttggca attcaagttc atcacgcagt atgtgacgga ttcacattt   3480 gccgttttgt aaacgaattg caggaattga taaatagtta acttcaggtt tgtctgtaac   3540
taaaaacaag tatttaagca aaaacatcgt agaaatacgg tgttttttgt taccctaagt   3600
ttaaactcct ttttgataat ctcatgacca aaatccctta acgtgagttt tcgttccact   3660
gagcgtcaga ccccgtagaa aagatcaaag gatcttcttg agatcctttt ttctgcgcg   3720 taatctgctg cttgcaaaca aaaaaaccac cgctaccagc ggtggtttgt ttgccggatc   3780
aagagctacc aactcttttt ccgaaggtaa ctggcttcag cagagcgcag ataccaaata   3840
ctgttcttct agtgtagccg tagttaggcc accacttcaa gaactctgta gcaccgccta   3900
catacctcgc tctgctaatc ctgttaccag tggctgctgc cagtggcgat aagtcgtgtc   3960
ttaccgggtt ggactcaaga cgatagttac cggataaggc gcagcggtcg ggctgaacgg   4020
ggggttcgtg cacacagccc agcttggagc gaacgaccta caccgaactg agatacctac   4080
```

```
agcgtgagct atgagaaagc gccacgcttc ccgaagggag aaaggcggac aggtatccgg      4140
taagcggcag ggtcggaaca ggagagcgca cgagggagct tccagggggga aacgcctggt      4200 atctttatag tcctgtcggg tttcgccacc tctgacttga gcgtcgattt ttgtgatgct      4260
cgtcaggggg gcggagccta tggaaaaacg ccagcaacgc ggccttttta cggttcctgg      4320
ccttttgctg gccttttgct cacatgttct ttcctgcgtt atcccctgat tctgtggata      4380
accgtattac cgcctttgag tgagctgata ccgctcgccg cagccgaacg accgagcgca      4440
gcgagtcagt gagcgaggaa gcggaagagc gcccaatacg cagggccccc tgcttcgggg      4500
tcattatagc gattttttcg gtatatccat ccttttccgc acgatataca ggattttgcc      4560
aaagggttcg tgtagacttt ccttggtgta tccaacggcg tcagccgggc aggataggtg      4620
aagtaggccc accgcgagc gggtgttcct tcttcactgt cccttattcg cacctggcgg      4680
tgctcaacgg gaatcctgct ctgcgaggct ggccggctac cgccggcgta acagatgagg      4740
gcaagcggat ggctgatgaa accaagccaa ccaggaaggg cagcccacct atcaaggtgt      4800
actgccttcc agacgaacga agagcgattg aggaaaaggc ggcggcggcc ggcatgagcc      4860
tgtcggccta cctgctggcc gtcggccagg gctacaaaat cacgggcgtc gtggactatg      4920
agcacgtccg cgagctggcc cgcatcaatg gcgacctggg ccgcctgggc ggcctgctga      4980
aactctggct caccgacgac ccgcgcacgg cgcggttcgg tgatgccacg atcctcgccc      5040
tgctggcgaa gatcgaagag aagcaggacg agcttggcaa ggtcatgatg ggcgtggtcc      5100
gcccgagggc agagccatga cttttttagc cgctaaaacg gccggggggt gcgcgtgatt      5160
gccaagcacg tccccatgcg ctccatcaag aagagcgact tcgcggagct ggtgaagtac      5220
atcaccgacg agcaaggcaa gaccgatcgg gccc                                 5254
```

<210> SEQ ID NO 18
<211> LENGTH: 4476
<212> TYPE: DNA
<213> ORGANISM: Artificial Sequence
<220> FEATURE:
<223> OTHER INFORMATION: Synthetic Construct

<400> SEQUENCE: 18

```
ggataaaaaa attgtagata aattttataa aatagtttta tctacaattt ttttatcagg       60
aaacagctat gaccgcggcc gctgtatcca tatgaccatg attacgaatt cgagctcggt      120
acccggggat cctctagagt cgacgtcacg cgtccatgga gatctcgagg cctgcagaca      180
tgcaagcttg gcactggccg tcgttttaca acgtcgtgac tgggaaaacc ctggcgttac      240
ccaacttaat cgccttgcag cacatccccc tttcgccagc tggcgtaata gcgaagaggc      300
ccgcaccgat cgcccttccc aacagttgcg cagcctgaat ggcgaatggc gctagcataa      360
aaataagaag cctgcatttg caggcttctt attttttatgg cgcgccgcca ttattttttt      420
gaacaattga caattcattt cttattttt attaagtgat agtcaaaagg cataacagtg      480
ctgaatagaa agaaatttac agaaaagaaa attatagaat ttagtatgat taattatact      540
catttatgaa tgtttaattg aatacaaaaa aaaatacttg ttatgtattc aattacgggt      600
taaaatatag acaagttgaa aaatttaata aaaaaataag tcctcagctc ttatatatta      660
agctaccaac ttagtatata agccaaaact taaatgtgct accaacacat caagccgtta      720
gagaactcta tctatagcaa tatttcaaat gtaccgacat acaagagaaa cattaactat      780
atatattcaa tttatgagat tatcttaaca gatataaatg taaattgcaa taagtaagat      840
ttagaagttt atagcctttg tgtattggaa gcagtacgca aaggcttttt tatttgataa      900
```

```
aaattagaag tatatttatt ttttcataat taatttatga aaatgaaagg gggtgagcaa    960
agtgacagag gaaagcagta tcttatcaaa taacaaggta ttagcaatat cattattgac   1020
tttagcagta aacattatga cttttatagt gcttgtagct aagtagtacg aaaggggag    1080 cttttaaaaag ctccttggaa tacatagaat tcataaatta atttatgaaa agaagggcgt   1140
atatgaaaac ttgtaaaaat tgcaaagagt ttattaaaga tactgaaata tgcaaaatac   1200
attcgttgat gattcatgat aaaacagtag caacctattg cagtaaatac aatgagtcaa   1260
gatgtttaca taaagggaaa gtccaatgta ttaattgttc aaagatgaac cgatatggat   1320
ggtgtgccat aaaaatgaga tgttttacag aggaagaaca gaaaaaagaa cgtacatgca   1380
ttaaatatta tgcaaggagc tttaaaaaag ctcatgtaaa gaagagtaaa aagaaaaaat   1440
aatttattta ttaatttaat attgagagtg ccgacacagt atgcactaaa aaatatatct   1500
gtggtgtagt gagccgatac aaaaggatag tcactcgcat tttcataata catcttatgt   1560
tatgattatg tgtcggtggg acttcacgac gaaaacccac aataaaaaaa gagttcgggg   1620
tagggttaag catagttgag gcaactaaac aatcaagcta ggatatgcag tagcagaccg   1680
taaggtcgtt gtttaggtgt gttgtaatac atacgctatt aagatgtaaa aatacggata   1740
ccaatgaagg gaaaagtata atttttggat gtagtttgtt tgttcatcta tgggcaaact   1800
acgtccaaag ccgtttccaa atctgctaaa aagtatatcc tttctaaaat caaagtcaag   1860
tatgaaatca taaataaagt ttaattttga agttattatg atattatgtt tttctattaa   1920
aataaattaa gtatatagaa tagttttaata atagtatata cttaatgtga taagtgtctg   1980
acagtgtcac agaaaggatg attgttatgg attataagcg gccggccagt gggcaagttg   2040
aaaaattcac aaaaatgtgg tataatatct ttgttcatta gagcgataaa cttgaatttg   2100
agagggaact tagatggtat ttgaaaaaat tgataaaaat agttggaaca gaaaagagta   2160
ttttgaccac tactttgcaa gtgtaccttg tacctacagc atgaccgtta aagtggatat   2220
cacacaaata aaggaaaagg gaatgaaact atatcctgca atgctttatt atattgcaat   2280
gattgtaaac cgccattcag agtttaggac ggcaatcaat caagatggtg aattggggat   2340
atatgatgag atgataccaa gctatacaat atttcacaat gatactgaaa catttttccag   2400 cctttggact gagtgtaagt ctgactttaa atcatttttta gcagattatg aaagtgatac   2460
gcaacggtat ggaaacaatc atagaatgga aggaaagcca aatgctccgg aaaacatttt   2520
taatgtatct atgataccgt ggtcaacctt cgatggcttt aatctgaatt tgcagaaagg   2580
atatgattat ttgattccta ttttttactat ggggaaatat tataaagaag ataacaaaat   2640
tatacttcct ttggcaattc aagttcatca cgcagtatgt gacggatttc acatttgccg   2700
ttttgtaaac gaattgcagg aattgataaa tagttaactt caggtttgtc tgtaactaaa   2760
aacaagtatt taagcaaaaa catcgtagaa atacggtgtt ttttgttacc ctaagtttaa   2820
actccttttt gataatctca tgaccaaaat cccttaacgt gagttttcgt tccactgagc   2880
gtcagacccc gtagaaaaga tcaaaggatc ttcttgagat ccttttttttc tgcgcgtaat   2940 ctgctgcttg caaacaaaaa aaccaccgct accagcggtg gtttgtttgc cggatcaaga   3000
gctaccaact cttttttccga aggtaactgg cttcagcaga gcgcagatac caaatactgt   3060
ccttctagtg tagccgtagt taggccacca cttcaagaac tctgtagcac cgcctacata   3120
cctcgctctg ctaatcctgt taccagtggc tgctgccagt ggcgataagt cgtgtcttac   3180
cgggttggac tcaagacgat agttaccgga taaggcgcag cggtcgggct gaacggggggg   3240
```

| | |
|---|---|
| ttcgtgcaca cagcccagct tggagcgaac gacctacacc gaactgagat acctacagcg | 3300 |
| tgagcattga gaaagcgcca cgcttcccga agggagaaag gcggacaggt atccggtaag | 3360 |
| cggcagggtc ggaacaggag agcgcacgag ggagcttcca gggggaaacg cctggtatct | 3420 |
| ttatagtcct gtcgggtttc gccacctctg acttgagcgt cgattttgt gatgctcgtc | 3480 |
| aggggggcgg agcctatgga aaaacgccag caacgcggcc ttttacggt tcctggcctt | 3540 |
| ttgctggcct tttgctcaca tgttctttcc tgcgttatcc cctgattctg tggataaccg | 3600 |
| tattaccgcc tttgagtgag ctgataccgc tcgccgcagc cgaacgaccg agcgcagcga | 3660 |
| gtcagtgagc gaggaagcgg aagagcgccc aatacgcagg gccccctgct cggggtcat | 3720 |
| tatagcgatt ttttcggtat atccatcctt tttcgcacga tatacaggat tttgccaaag | 3780 |
| ggttcgtgta gactttcctt ggtgtatcca acggcgtcag ccgggcagga taggtgaagt | 3840 |
| aggcccaccc gcgagcgggt gttccttctt cactgtccct tattcgcacc tggcggtgct | 3900 |
| caacgggaat cctgctctgc gaggctggcc ggctaccgcc ggcgtaacag atgagggcaa | 3960 |
| gcggatggct gatgaaacca agccaaccag gaagggcagc ccacctatca aggtgtactg | 4020 |
| ccttccagac gaacgaagag cgattgagga aaggcggcg gcggccggca tgagcctgtc | 4080 |
| ggcctacctg ctggccgtcg gccagggcta caaaatcacg ggcgtcgtgg actatgagca | 4140 |
| cgtccgcgag ctggcccgca tcaatggcga cctgggccgc ctgggcggcc tgctgaaact | 4200 |
| ctggctcacc gacgacccgc gcacggcgcg gttcggtgat gccacgatcc tcgccctgct | 4260 |
| ggcgaagatc gaagagaagc aggacgagct tggcaaggtc atgatgggcg tggtccgccc | 4320 |
| gagggcagag ccatgacttt tttagccgct aaaacggccg gggggtgcgc gtgattgcca | 4380 |
| agcacgtccc catgcgctcc atcaagaaga gcgacttcgc ggagctggtg aagtacatca | 4440 |
| ccgacgagca aggcaagacc gatcgggccc cctgca | 4476 |

<210> SEQ ID NO 19
<211> LENGTH: 4215
<212> TYPE: DNA
<213> ORGANISM: Artificial Sequence
<220> FEATURE:
<223> OTHER INFORMATION: Synthetic Construct

<400> SEQUENCE: 19

| | |
|---|---|
| cctgcaggat aaaaaattg tagataaatt ttataaaata gttttatcta caattttttt | 60 |
| atcaggaaac agctatgacc gcggccgctg tatccatatg accatgatta cgaattcgag | 120 |
| ctcggtaccc ggggatcctc tagagtcgac gtcacgcgtc catggagatc tcgaggcctg | 180 |
| cagacatgca agcttggcac tggccgtcgt tttacaacgt cgtgactggg aaaaccctgg | 240 |
| cgttacccaa cttaatcgcc ttgcagcaca tcccccttc gccagctggc gtaatagcga | 300 |
| agaggcccgc accgatcgcc cttcccaaca gttgcgcagc ctgaatggcg aatggcgcta | 360 |
| gcataaaaat aagaagcctg catttgcagg cttcttatt tatggcgcg ccgttctgaa | 420 |
| tccttagcta atggttcaac aggtaactat gacgaagata gcaccctgga taagtctgta | 480 |
| atggattcta aggcatttaa tgaagacgtg tatataaaat gtgctaatga aaagaaaat | 540 |
| gcgttaaaag agcctaaaat gagttcaaat ggttttgaaa ttgattggta gtttaattta | 600 |
| atatatttt tctattggct atctcgatac ctatagaatc ttctgttcac ttttgttttt | 660 |
| gaaatataaa aagggctttt tagcccctt tttttaaaa ctccggagga gtttcttcat | 720 |
| tcttgatact atacgtaact atttcgatt tgacttcatt gtcaattaag ctagtaaat | 780 |
| caatggttaa aaaacaaaaa acttgcattt ttctacctag taatttataa ttttaagtgt | 840 |

```
cgagtttaaa agtataattt accaggaaag gagcaagttt tttaataagg aaaaattttt      900
ccttttaaaa ttctatttcg ttatatgact aattataatc aaaaaaatga aaataaacaa      960
gaggtaaaaa ctgctttaga gaaatgtact gataaaaaaa gaaaaaatcc tagatttacg     1020
tcatacatag caccttttaac tactaagaaa aatattgaaa ggacttccac ttgtggagat    1080
tatttgttta tgttgagtga tgcagactta gaacatttta aattacataa aggtaatttt    1140
tgcggtaata gattttgtcc aatgtgtagt tggcgacttg cttgtaagga tagtttagaa    1200
atatctattc ttatggagca tttaagaaaa gaagaaaata aagagtttat attttaact     1260
cttacaactc caaatgtaaa aagttatgat cttaattatt ctattaaaca atataataaa    1320
tcttttaaaa aattaatgga gcgtaaggaa gttaaggata taactaaagg ttatataaga    1380
aaattagaag taacttacca aaaggaaaaa tacataacaa aggatttatg gaaaataaaa    1440
aaagattatt atcaaaaaaa aggacttgaa attggtgatt tagaacctaa ttttgatact    1500
tataatcctc attttcatgt agttattgca gttaataaaa gttattttac agataaaaat    1560
tattatataa atcgagaaag atggttggaa ttatggaagt ttgctactaa ggatgattct    1620
ataactcaag ttgatgttag aaaagcaaaa attaatgatt ataaagaggt ttacgaactt    1680
gcgaaatatt cagctaaaga cactgattat ttaatatcga ggccagtatt tgaaattttt    1740
tataaagcat taaaaggcaa gcaggtatta gttttttagtg gattttttaa agatgcacac   1800
aaattgtaca agcaaggaaa acttgatgtt tataaaaaga aagatgaaat taaatatgtc   1860
tatatagttt attataattg gtgcaaaaaa caatatgaaa aaactagaat aagggaactt   1920
acggaagatg aaaaagaaga attaaatcaa gatttaatag atgaaataga aatagattaa   1980
agtgtaacta tactttatat atatatgatt aaaaaaataa aaaacaacag cctattaggt   2040
tgttgttttt tattttcttt attaattttt ttaattttta gttttttagtt ctttttttaaa 2100
ataagtttca gcctcttttt caatattttt taaagaagga gtatttgcat gaattgcctt   2160
ttttctaaca gacttaggaa atattttaac agtatcttct tgcgccggtg attttggaac   2220
ttcataactt actaatttat aattattatt ttctttttta attgtaacag ttgcaaaaga   2280
agctgaacct gttccttcaa ctagtttatc atcttcaata taatattctt gacctatata   2340
gtataaatat attttttatta tattttttact tttttctgaa tctattattt tataatcata  2400
aaaagtttta ccaccaaaag aaggttgtac tccttctggt ccaacatatt ttttactat    2460
attatctaaa taattttttgg gaactggtgt tgtaatttga ttaatcgaac aaccagttat  2520
acttaaagga attataacta taaaatata taggattatc tttttaaatt tcattattgg   2580
cctccttttt attaaattta tgttaccata aaaaggacat aacgggaata tgtagaatat  2640
ttttaatgta gacaaaattt tacataaata taaagaaagg aagtgtttgt ttaaatttta   2700
tagcaaacta tcaaaaatta gggggataaa aatttatgaa aaaaaggttt tcgatgttat   2760
ttttatgttt aactttaata gtttgtggtt tatttacaaa ttcggccggc cgaagcaaac   2820
ttaagagtgt gttgatagtg cagtatctta aaattttgta taataggaat tgaagttaaa   2880
ttagatgcta aaaatttgta attaagaagg agtgattaca tgaacaaaaa tataaaatat   2940
tctcaaaact ttttaacgag tgaaaagta ctcaaccaaa taataaaaca attgaattta    3000
aaagaaaccg ataccgttta cgaaattgga acaggtaaag ggcatttaac gacgaaactg   3060
gctaaaataa gtaaacaggt aacgtctatt gaattagaca gtcatctatt caacttatcg   3120
tcagaaaaat taaaactgaa tactcgtgtc actttaattc accaagatat tctacagttt   3180
```

```
caattccta  acaaacagag  gtataaaatt  gttgggagta  ttccttacca  tttaagcaca   3240
caaattatta  aaaagtggt   ttttgaaagc  catgcgtctg  acatctatct  gattgttgaa   3300
gaaggattct  acaagcgtac  cttggatatt  caccgaacac  tagggttgct  cttgcacact   3360
caagtctcga  ttcagcaatt  gcttaagctg  ccagcggaat  gctttcatcc  taaaccaaaa   3420
gtaaacagtg  tcttaataaa  acttacccgc  cataccacag  atgttccaga  taaatattgg   3480
aagctatata  cgtactttgt  ttcaaaatgg  gtcaatcgag  aatatcgtca  actgtttact   3540
aaaaatcagt  ttcatcaagc  aatgaaacac  gccaaagtaa  acaatttaag  taccgttact   3600
tatgagcaag  tattgtctat  ttttaatagt  tatctattat  ttaacgggag  gaaataattc   3660
tatgagtcgc  ttttgtaaat  tggaaagtt   acacgttact  aaagggaatg  tgtttaaact   3720
cctttttgat  aatctcatga  ccaaaatccc  ttaacgtgag  ttttcgttcc  actgagcgtc   3780 agacccgta   gaaagatca   aaggatcttc  ttgagatcct  ttttttctgc  gcgtaatctg   3840
ctgcttgcaa  acaaaaaaac  caccgctacc  agcggtggtt  tgtttgccgg  atcaagagct   3900
accaactctt  tttccgaagg  taactggctt  cagcagagcg  cagataccaa  atactgttct   3960
tctagtgtag  ccgtagttag  gccaccactt  caagaactct  gtagcaccgc  ctacatacct   4020
cgctctgcta  atcctgttac  cagtggctgc  tgccagtggc  gataagtcgt  gtcttaccgg   4080
gttggactca  agacgatagt  taccggataa  ggcgcagcgg  tcgggctgaa  cggggggttc   4140
gtgcacacag  cccagcttgg  agcgaacgac  ctacaccgaa  ctgagatacc  tacagcgtga   4200
gctatgagaa  agcgc                                                       4215

<210> SEQ ID NO 20
<211> LENGTH: 4167
<212> TYPE: DNA
<213> ORGANISM: Artificial Sequence
<220> FEATURE:
<223> OTHER INFORMATION: Synthetic Construct

<400> SEQUENCE: 20
cctgcaggat  aaaaaaattg  tagataaatt  ttataaaata  gttttatcta  caattttttt     60
atcaggaaac  agctatgacc  gcggccgctg  tatccatatg  accatgatta  cgaattcgag    120
ctcggtaccc  ggggatcctc  tagagtcgac  gtcacgcgtc  catggagatc  tcgaggcctg    180
cagacatgca  agcttggcac  tggccgtcgt  tttacaacgt  cgtgactggg  aaaaccctgg    240
cgttacccaa  cttaatcgcc  ttgcagcaca  tccccctttc  gccagctggc  gtaatagcga    300
agaggcccgc  accgatcgcc  cttcccaaca  gttgcgcagc  ctgaatggcg  aatggcgcta    360
gcataaaaat  aagaagcctg  catttgcagg  cttcttattt  ttatggcgcg  ccgccattat    420
ttttttgaac  aattgacaat  tcatttctta  tttttttatta  agtgatagtc  aaaaggcata    480
acagtgctga  atagaaagaa  atttacagaa  aagaaaatta  tagaatttag  tatgattaat    540
tatactcatt  tatgaatgtt  taattgaata  caaaaaaaaa  tacttgttat  gtattcaatt    600
acgggttaaa  atatagacaa  gttgaaaaat  ttaataaaaa  aataagtcct  cagctcttat    660
atattaagct  accaacttag  tatataagcc  aaaacttaaa  tgtgctacca  acacatcaag    720
ccgttagaga  actctatcta  tagcaatatt  tcaaatgtac  cgacatacaa  gagaaacatt    780
aactatatat  attcaattta  tgagattatc  ttaacagata  taaatgtaaa  ttgcaataag    840
taagatttag  aagtttatag  cctttgtgta  ttggaagcag  tacgcaaagg  ctttttttatt    900 tgataaaaat  tagaagtata  tttattttt   cataattaat  ttatgaaaat  gaaggggggt    960
gagcaaagtg  acagaggaaa  gcagtatctt  atcaaataac  aaggtattag  caatatcatt   1020
```

| | | | | |
|---|---|---|---|---|
| attgacttta | gcagtaaaca | ttatgacttt | tatagtgctt | gtagctaagt | agtacgaaag | 1080 |
| ggggagcttt | aaaaagctcc | ttggaataca | tagaattcat | aaattaattt | atgaaaagaa | 1140 |
| gggcgtatat | gaaaacttgt | aaaaattgca | aagagtttat | taaagatact | gaaatatgca | 1200 |
| aaatacattc | gttgatgatt | catgataaaa | cagtagcaac | ctattgcagt | aaatacaatg | 1260 |
| agtcaagatg | tttacataaa | gggaaagtcc | aatgtattaa | ttgttcaaag | atgaaccgat | 1320 |
| atggatggtg | tgccataaaa | atgagatgtt | ttacagagga | agaacagaaa | aaagaacgta | 1380 |
| catgcattaa | atattatgca | aggagcttta | aaaaagctca | tgtaaagaag | agtaaaaaga | 1440 |
| aaaaataatt | tatttattaa | tttaatattg | agagtgccga | cacagtatgc | actaaaaaat | 1500 |
| atatctgtgg | tgtagtgagc | cgatacaaaa | ggatagtcac | tcgcattttc | ataatacatc | 1560 |
| ttatgttatg | attatgtgtc | ggtgggactt | cacgacgaaa | acccacaata | aaaaagagt | 1620 |
| tcggggtagg | gttaagcata | gttgaggcaa | ctaaacaatc | aagctaggat | atgcagtagc | 1680 |
| agaccgtaag | gtcgttgttt | aggtgtgttg | taatacatac | gctattaaga | tgtaaaaata | 1740 |
| cggataccaa | tgaagggaaa | agtataattt | ttggatgtag | tttgtttgtt | catctatggg | 1800 |
| caaactacgt | ccaaagccgt | ttccaaatct | gctaaaaagt | atatcctttc | taaaatcaaa | 1860 |
| gtcaagtatg | aaatcataaa | taaagtttaa | ttttgaagtt | attatgatat | tatgttttc | 1920 |
| tattaaaata | aattaagtat | atagaatagt | ttaataatag | tatatactta | atgtgataag | 1980 |
| tgtctgacag | tgtcacagaa | aggatgattg | ttatggatta | taagcggccg | gccgaagcaa | 2040 |
| acttaagagt | gtgttgatag | tgcagtatct | taaaattttg | tataataggga | attgaagtta | 2100 |
| aattagatgc | taaaaatttg | taattaagaa | ggagtgatta | catgaacaaa | aatataaaat | 2160 |
| attctcaaaa | cttttttaacg | agtgaaaaag | tactcaacca | aataataaaa | caattgaatt | 2220 |
| taaagaaac | cgataccgtt | tacgaaattg | gaacaggtaa | agggcattta | acgacgaaac | 2280 |
| tggctaaaat | aagtaaacag | gtaacgtcta | ttgaattaga | cagtcatcta | ttcaacttat | 2340 |
| cgtcagaaaa | attaaaactg | aatactcgtg | tcactttaat | tcaccaagat | attctacagt | 2400 |
| ttcaattccc | taacaaacag | aggtataaaa | ttgttgggag | tattccttac | catttaagca | 2460 |
| cacaaattat | taaaaaagtg | gtttttgaaa | gccatgcgtc | tgacatctat | ctgattgttg | 2520 |
| aagaaggatt | ctacaagcgt | accttggata | ttcaccgaac | actagggttg | ctcttgcaca | 2580 |
| ctcaagtctc | gattcagcaa | ttgcttaagc | tgccagcgga | atgctttcat | cctaaaccaa | 2640 |
| aagtaaacag | tgtcttaata | aaacttaccc | gccataccac | agatgttcca | gataaatatt | 2700 |
| ggaagctata | tacgtacttt | gtttcaaaat | gggtcaatcg | agaatatcgt | caactgttta | 2760 |
| ctaaaaatca | gtttcatcaa | gcaatgaaac | acgccaaagt | aaacaattta | agtaccgtta | 2820 |
| cttatgagca | agtattgtct | atttttaata | gttatctatt | atttaacggg | aggaaataat | 2880 |
| tctatgagtc | gcttttgtaa | atttggaaag | ttacacgtta | ctaaagggaa | tgtgtttaaa | 2940 |
| ctccttttg | ataatctcat | gaccaaaatc | ccttaacgtg | agtttcgtt | ccactgagcg | 3000 |
| tcagaccccg | tagaaaagat | caaaggatct | tcttgagatc | cttttttct | gcgcgtaatc | 3060 |
| tgctgcttgc | aaacaaaaaa | accaccgcta | ccagcggtgg | tttgtttgcc | ggatcaagag | 3120 |
| ctaccaactc | tttttccgaa | ggtaactggc | ttcagcagag | cgcagatacc | aaatactgtt | 3180 |
| cttctagtgt | agccgtagtt | aggccaccac | ttcaagaact | ctgtagcacc | gcctacatac | 3240 |
| ctcgctctgc | taatcctgtt | accagtggct | gctgccagtg | gcgataagtc | gtgtcttacc | 3300 |
| gggttggact | caagacgata | gttaccggat | aaggcgcagc | ggtcgggctg | aacggggggt | 3360 |

| | |
|---|---|
| tcgtgcacac agcccagctt ggagcgaacg acctacaccg aactgagata cctacagcgt | 3420 |
| gagctatgag aaagcgccac gcttcccgaa gggagaaagg cggacaggta tccggtaagc | 3480 |
| ggcagggtcg gaacaggaga gcgcacgagg gagcttccag ggggaaacgc ctggtatctt | 3540 |
| tatagtcctg tcgggtttcg ccacctctga cttgagcgtc gattttttgtg atgctcgtca | 3600 |
| gggggggcgga gcctatggaa aaacgccagc aacgcggcct ttttacggtt cctggccttt | 3660 |
| tgctggcctt ttgctcacat gttctttcct gcgttatccc ctgattctgt ggataaccgt | 3720 |
| attaccgcct ttgagtgagc tgataccgct cgccgcagcc gaacgaccga gcgcagcgag | 3780 |
| tcagtgagcg aggaagcgga agagcgccca atacgcaggg cccctgctt cggggtcatt | 3840 |
| atagcgattt tttcggtata tccatccttt ttcgcacgat atacaggatt ttgccaaagg | 3900 |
| gttcgtgtag actttccttg gtgtatccaa cggcgtcagc cggcaggat aggtgaagta | 3960 |
| ggcccacccg cgagcgggtg ttccttcttc actgtcccett attcgcacct ggcggtgctc | 4020 |
| aacgggaatc ctgctctgcg aggctggccg gctaccgccg gcgtaacaga tgagggcaag | 4080 |
| cggatggctg atgaaaccaa gccaaccagg aagggcagcc cacctatcaa ggtgtactgc | 4140 |
| cttccagacg aacgaagagc gattgag | 4167 |

<210> SEQ ID NO 21
<211> LENGTH: 7571
<212> TYPE: DNA
<213> ORGANISM: Artificial Sequence
<220> FEATURE:
<223> OTHER INFORMATION: Synthetic Construct

<400> SEQUENCE: 21

| | |
|---|---|
| tcattccgct gttatggccg cgtttgtctc attccacgcc tgacactcag ttccgggtag | 60 |
| gcagttcgct ccaagctgga ctgtatgcac gaaccccccg ttcagtccga ccgctgcgcc | 120 |
| ttatccggta actatcgtct tgagtccaac ccggaaagac atgcaaaagc accactggca | 180 |
| gcagccactg gtaattgatt tagaggagtt agtcttgaag tcatgcgccg gttaaggcta | 240 |
| aactgaaagg acaagttttg gtgactgcgc tcctccaagc cagttacctc ggttcaaaga | 300 |
| gttggtagct cagagaacct tcgaaaaacc gccctgcaag gcggtttttt cgttttcaga | 360 |
| gcaagagatt acgcgcagac caaaacgatc tcaagaagat catcttatta atcagataaa | 420 |
| atatttctag atttcagtgc aatttatctc ttcaaatgta gcacctgaag tcagccccat | 480 |
| acgatataag ttgtaattct catgtttgac agcttatcat cgataagctt taatgcggta | 540 |
| gtttatcaca gttaaattgc taacgcagtc aggcaccgtg tatgaaatct aacaatgcgc | 600 |
| tcatcgtcat cctcggcacc gtcaccctgg atgctgtagg cataggcttg gttatgccgg | 660 |
| tactgccggg cctcttgcgg gatatcgtcc attccgacag catcgccagt cactatggcg | 720 |
| tgctgctagc gctatatgcg ttgatgcaat ttctatgcgc acccgttctc ggagcactgt | 780 |
| ccgaccgctt tggccgccgc ccagtcctgc tcgcttcgct acttggagcc actatcgact | 840 |
| acgcgatcat ggcgaccaca cccgtcctgt ggatcctcta cgccggacgc atcgtggccg | 900 |
| gcatcaccgg cgccacaggt gcggttgctg gcgcctatat cgccgacatc accgatgggg | 960 |
| aagatcgggc tcgccacttc gggctcatga gcgcttgttt cggcgtgggt atggtggcag | 1020 |
| gccccgtggc cgggggactg ttgggcgcca tctccttgca tgcaccattc cttgcggcgg | 1080 |
| cggtgctcaa cggcctcaac ctactactgg gctgcttcct aatgcaggag tcgcataagg | 1140 |
| gagagcgtcg acagaaagta taatgagaaa atataaaata taataatttt tctaaaaaac | 1200 |
| ttgacatcat gtgaaaagtt tgttataata taaatgagca cgttaatcat ttaacataga | 1260 |

```
taattaaaata gtaaaaggag gattagtcat gaggtcaaaa attgaggcta atgagtataa    1320
ggattttatt cttggcttta ttttctacaa atatttatct gagaaagagg tggccttttt    1380
tagaaaagaa agattaaccg atgcagatat tgaaaaagtt acagaagatg atgttaagta    1440
cgcatcccat gtaagagaaa atttgggata ttttattgcg tatgaaaatc ttttttcaac    1500
ttggcttaag aaaggtaatg attttgatat atcgaatgtt agggatgcat tatctgcttt    1560
tgatcgtaac attgatgatg tatatagaaa agtgtttgag aaaattttca atacattgca    1620
gacaggctta tctaagcttg gagaaactgc acaagcacaa acaaaggctg taaaaagtct    1680
tcttaaattg ataagaaaaa ttcctatgga tggaaagcaa gattatgatg ttcttgggtt    1740
catttacgaa tatctaatta gtatgttcgc tgccaacgca ggtaaaaaag caggagaatt    1800
ttacactccg catgaagttt ctgttttaat gtcagaaatt attgcagaac atttgaaaaa    1860
tagaaagcaa attaaaatat atgaccctac atctgggtcg ggttcgttgc tgataaatat    1920
tggtaactca gctgcaaaat ttatagatgg agaaaacaag atagattatt acgcacagga    1980
gcttaaggaa aatacttata acctcacaag aatgaacttg gttatgcgtg gcatcagtcc    2040
tgcaaatata aatgtgagaa atggtgacac attagaggat gattggcctt ttttttgagga    2100 taccgacaag gataaaacat ataaatttat accagtagat gccgttgttt ctaatccacc    2160
ttactcacaa aaatgggatc catctgataa agaatttgac ccacgatata agtattatgg    2220
tgttgcacca agagtaaagg ctgattatgc atttttattg catgatttgt atcacctaaa    2280
ggacgatggt atcatgacaa tcgttcttcc ccatggtgta ctttttagag gtggagagga    2340
aggtaaaatc agagagaaac ttatagaaaa aaaccgcata gatgcaatta tcggattacc    2400
accaaatatt ttctttggta caggtattcc tactattata atggtcctta aaagaattcg    2460
ccctacttca gacgtgttga ttatagatgc atctaaaggg tttgagaaag ttggaaagaa    2520
taacaaattg agagcctgtg acattaaaaa aattgctgac actgttaaga gcagagaatc    2580
cattgaaaag tattcgactc ttgtttctaa ggaaaccatc cgagaaaatg gctataacct    2640
taatatccct cgctatgtta attccttaga acctgcagaa agttgggata ttcatgcgac    2700
tatgtttggt ggaataccctg taaaggaagt agaccaacta tttgagtatt gggaggcttt    2760
tcccgaactc aaagatgcaa ttttttcggaa aatttctaat gaatatttag ctgtgaaatg    2820
cgatgatatt aaagcggcta ttacctctca tgagtcattg aaaatctata acaggcatt    2880 ctcaaatgaa tttggtaatt tttatgaaga acttaaaaat gatttgattg aagaaattct    2940
tgatgtatct gctgagcatg agaaagaaaa ggtaagcaag gatattttta taagaataga    3000
aaatgtaaaa cttgctgaca agtataaagc gtaccagata ctttcggata attgggatgt    3060
gatttcaaca gatttggaaa tgattcagtc agaaggtttt gaggttatca atcaagtgga    3120
tcctaacatg attttaaaga agaaagaagc taacgatgat gaggttccag aggtacaaga    3180
tgggtggaag ggtcatatac tgccttttga tttggttcag agagagattc ttactgaaga    3240
tttagaagaa cttcaggcaa tagaaaaaag attaactgaa atcacttctt tgtatggtga    3300
aattattgat tcgcttgatg aagaagaaag agaaagcagt gtgttgaatg aagctaacga    3360
tgcttttgta gcaaaagaag ttaagagttt tgttgcagaa gccctcagcg atgtggaaaa    3420
tgatgaaatt aaagcattaa gaggatatct aagccttttca aagaaaaaag aaaagctaga    3480
ttatgtaaat aaatgtgata tagttttcgtg gaatttaatg gaacaaggtt ctgatggagc    3540
atataagaaa ggttctgtta ttagtagaat aagcgaattg caaaggatgt atgaattccc    3600
```

```
gaaagattcc tttgaacaga aagtgatgac cgtattatct cttatggaag aagaaagcca   3660
ggctaaaaaa gatctaaaac agaaatcgga agccctccat attaagacca agaaaaccat   3720
tgaaaatctg gatgaagacg aatctttgcg tttgttagaa ttaaaatgga taaagccatt   3780
agtagattcc cttttttgcta ttccagatga aatcatcgga gagctgatta acaaagtaat   3840
tcatctacac gataaatatt gcactacatt ttccgatatt gaacatgata tcgaaaacac   3900
aagtgcgaaa ttatcaaata tgattgataa gcttgttggc agtgtggcag atattgaggg   3960
attagaagaa ttgaagaaga ttttgggggt atagtaaaaa taagagttac cttaaatggt   4020
aactcttatt ttttaatat tgtttcatag tatttctttg tcgaccgatg cccttgagag   4080
ccttcaaccc agtcagctcc ttccggtggg cgcggggcat gactatcgtc gccgcactta   4140
tgactgtctt ctttatcatg caactcgtag gacaggtgcc ggcagcgctc tgggtcattt   4200
tcggcgagga ccgctttcgc tggagcgcga cgatgatcgg cctgtcgctt gcggtattcg   4260
gaatcttgca cgccctcgct caagccttcg tcactggtcc cgccaccaaa cgtttcggcg   4320
agaagcaggc cattatcgcc ggcatggcgg ccgacgcgct gggctacgtc ttgctggcgt   4380
tcgcgacgcg aggctggatg ccttcccca ttatgattct tctcgcttcc ggcggcatcg   4440
ggatgcccgc gttgcaggcc atgctgtcca ggcaggtaga tgacgaccat cagggacagc   4500
ttcaaggatc gctcgcggct cttaccagcc taacttcgat cactggaccg ctgatcgtca   4560
cggcgattta tgccgcctcg gcgagcacat ggaacgggtt ggcatggatt gtaggcgccg   4620
ccctatacct tgtctgcctc cccgcgttgc gtcgcggtgc atggagccgg ccacctcga   4680 cctgaatgga agccggcggc acctcgctaa cggattcacc actccaagaa ttggagccaa   4740
tcaattcttg cggagaactg tgaatgcgca aaccaaccct tggcagaaca tatccatcgc   4800
gtccgccatc tccagcagcc gcacgcggcg catctcgggc agcgttgggt cctggccacg   4860
ggtgcgcatg atcgtgctcc tgtcgttgag gacccggcta ggctggcggg gttgccttac   4920
tggttagcag aatgaatcac cgatacgcga gcgaacgtga agcgactgct gctgcaaaac   4980
gtctgcgacc tgagcaacaa catgaatggt cttcggtttc cgtgtttcgt aaagtctgga   5040
aacgcggaag tccctacgt gctgctgaag ttgcccgcaa cagagagtgg aaccaaccgg   5100
tgataccacg atactatgac tgagagtcaa cgccatgagc ggcctcattt cttattctga   5160
gttacaacag tccgcaccgc tgtccggtag ctccttccgg tgggcgcggg gcatgactat   5220
cgtcgccgca cttatgactg tcttctttat catgcaactc gtaggacagg tgccggcagc   5280
gcccaacagt ccccccggcca cggggcctgc caccataccc acgccgaaac aagcgccctg   5340
caccattatg ttccggaacg ggaaacgtct tgctcgagat ctatcgattt tcgttcgtga   5400
atacatgtta taataactat aactaataac gtaacgtgac tggcaagaga tattttttaaa   5460 acaatgaata ggtttacact tactttagtt ttatggaaat gaaagatcat atcatatata   5520
atctagaata aaattaacta aaataattat tatctagata aaaatttag aagccaatga   5580 aatctataaa taaactaaat taagtttatt taattaacaa ctatggatat aaaataggta   5640
ctaatcaaaa tagtgaggag gatatatttg aatacatacg aacaaattaa taaagtgaaa   5700
aaaatacttc ggaaacattt aaaaaataac cttattggta cttacatgtt tggatcagga   5760
gttgagagtg gactaaaacc aaatagtgat cttgactttt tagtcgtcgt atctgaacca   5820
ttgacagatc aaagtaaaga aatacttata caaaaaatta gacctatttc aaaaaaaata   5880
ggagataaaa gcaacttacg atatattgaa ttaacaatta ttattcagca agaaatggta   5940
ccgtggaatc atcctcccaa acaagaattt atttatggag aatggttaca agagctttat   6000
```

```
gaacaaggat acattcctca gaaggaatta aattcagatt taaccataat gctttaccaa    6060
gcaaaacgaa aaaataaaag aatatacgga aattatgact tagaggaatt actacctgat    6120
attccatttt ctgatgtgag aagagccatt atggattcgt cagaggaatt aatagataat    6180
tatcaggatg atgaaaccaa ctctatatta actttatgcc gtatgatttt aactatggac    6240
acgggtaaaa tcataccaaa agatattgcg ggaaatgcag tggctgaatc ttctccatta    6300
gaacataggg agagaatttt gttagcagtt cgtagttatc ttggagagaa tattgaatgg    6360
actaatgaaa atgtaaattt aactataaac tatttaaata acagattaaa aaaattataa    6420
aaaaattgaa aaaatggtgg aaacactttt ttcaattttt ttgttttatt atttaatatt    6480
tgggaaatat tcattctaat tggtaatcag attttagaaa acaataaacc cttgcatatg    6540
atatcgatgt acagatccct ggtatgagtc agcaactccg gatgagcatt catcaggcgg    6600
gcaagaatgt gaataaaggc cggataaaac ttgtgcttat ttttctttac ggtctttaaa    6660
aaggccgtaa tatccagctg aacggtctgg ttataggtac attgagcaac tgactgaaat    6720
gcctcaaaat gttctttacg atgccattgg gatatatcaa cggtggtata ccagtgatt    6780 ttttctcca ttttagcttc cttagctcct gaaaatctcg ataactcaaa aaatacgccc    6840
ggtagtgatc ttatttcatt atggtgaaag ttggaacctc ttacgtgccg atcaacgtct    6900
cattttcgcc aaaagttggc ccagggcttc ccggtatcaa cagggacacc aggatttatt    6960
tattctgcga agtgatcttc cgtcacaggt atttattcgg cgcaaagtgc gtcgggtgat    7020
gctgccaact tactgattta gtgtatgatg gtgtttttga ggtgctccag tggcttctgt    7080
ttctatcagc tgtccctcct gttcagctac tgacggggtg gtgcgtaacg gcaaaagcac    7140
cgccggacat cagcgctagc ggagtgtata ctggcttact atgttggcac tgatgagggt    7200
gtcagtgaag tgcttcatgt ggcaggagaa aaaaggctgc accggtgcgt cagcagaata    7260
tgtgatacag gatatattcc gcttcctcgc tcactgactc gctacgctcg gtcgttcgac    7320
tgcggcgagc ggaaatggct tacgaacggg gcggagattt cctggaagat gccaggaaga    7380
tacttaacag ggaagtgaga gggccgcggc aaagccgttt ttccataggc tccgccccc    7440 tgacaagcat cacgaaatct gacgctcaaa tcagtggtgc gaaacccga caggactata    7500 aagataccag gcgttttccc ctggcggctc cctcgtgcgc tctcctgttc ctgcctttcg    7560
gtttaccggt g                                                        7571
```

<210> SEQ ID NO 22
<211> LENGTH: 5056
<212> TYPE: DNA
<213> ORGANISM: Artificial Sequence
<220> FEATURE:
<223> OTHER INFORMATION: Synthetic Construct

<400> SEQUENCE: 22

```
cttcattttt aatttaaaag gatctaggtg aagatccttt ttgataatct catgaccaaa      60
atcccttaac gtgagttttc gttccactga gcgtcagacc ccgtagaaaa gatcaaagga    120
tcttcttgag atccttttttt ctgcgcgta atctgctgct tgcaaacaaa aaaaccaccg    180
ctaccagcgg tggtttgttt gccggatcaa gagctaccaa ctctttttcc gaaggtaact    240
ggcttcagca gagcgcagat accaaatact gtccttctag tgtagccgta gttaggccac    300
cacttcaaga actctgtagc accgcctaca tacctcgctc tgctaatcct gttaccagtg    360
gctgctgcca gtggcgataa gtcgtgtctt accgggttgg actcaagacg atagttaccg    420
```

```
gataaggcgc agcggtcggg ctgaacgggg ggttcgtgca cacagcccag cttggagcga    480
acgacctaca ccgaactgag atacctacag cgtgagctat gagaaagcgc cacgcttccc    540
gaagggagaa aggcggacag gtatccggta agcggcaggg tcggaacagg agagcgcacg    600
agggagcttc caggggggaaa cgcctggtat ctttatagtc ctgtcgggtt tcgccacctc    660
tgacttgagc gtcgattttt gtgatgctcg tcagggggc ggagcctatg gaaaaacgcc    720
agcaacgcgg cctttttacg gttcctggcc ttttgctggc cttttgctca catgttcttt    780
cctgcgttat cccctgattc tgtggataac cgtattaccg cctttgagtg agctgatacc    840
gctcgccgca gccgaacgac cgagcgcagc gagtcagtga gcgaggaagc ggaagagcgc    900
ctgatgcggt attttctcct tacgcatctg tgcggctcga ggtcgacggt atcgataatc    960
gcatttcata gattgacctc caataacta cgtggtgtta ttgggaggtc aatctatttc    1020
atttgcctct tgctcaaagt tcccaaattc gagtaagagg tattttttgtt tttggtcgtc    1080 gcctctcatt agtagttcag ggtttaacat taatactcca gttttctttt ttataatatt    1140
tccttcttct aagattttaa gtgttgttat tactgtttgt agacttgttc ctgtagcttt    1200
tgctatttct cttgttgtag ctatcattgt attgttactt aagtggacat tatctaggat    1260
atagttaacg attttaagtt ttttccgcc aatcatatct aacatactta ttaattgcac    1320
tatatatgcc tttacgaagt taccagacgt ttgtttacgg tataacttgt ctacctctat    1380
gacttctcca ctttcttcgt ctatgagcct ctgagagcct ttatagactg ttccatatct    1440
ttctttcatc tttttctcac tccttatttt aaactattct aactatatca taactgttct    1500
aaaaaaaaaa gaacatttgt taaagaaat tagaacaaaa tgagtgaaaa attagaacaa    1560
acaaattcct tataaaacctt atcatctcaa cctatattaa gattttaccct agttgaatct    1620 tcttttctat ataaagcgtc ggagcatatc agggggttat ctaacgtaaa tgctacccctt   1680 cggctcgctt tcgctcggca ttgacgtcag atactgcacc ccctgaaccc ccatgctcca    1740
acagcaaaaa ggaaacttttt tgctgctttt ccgacgctta ttcgcttcgc tcatatttat    1800
atagaaaaga agtgaatgcg caaaagacat aatcgattca caaaaaatag gtacacgaaa    1860
aacaagttaa gggatgcagt ttatgcatcc cttaacttac ttattaaata atttatagct    1920
attgaaaaga gataagaatt gttcaaagct aatattgttt aaatcgtcaa ttcctgcatg    1980
ttttaaggaa ttgttaaatt gatttttttgt aaatatttc ttgtattctt tgttaaccca    2040
tttcataacg aaataattat acttctgttt atctttgtgt gatattcttg attttttttct    2100 atttaatctg ataagtgagc tattcacttt aggtttagga tgaaaatatt ctcttggaac    2160
catacttaat atagaaatat caacttctgc cattaaaaat aatgccaatg agcgttttgt    2220
atttaataat cttttagcaa acccgtattc cacgattaaa taaatctcat cagctatact    2280
atcaaaaaca attttgcgta ttatatccgt acttatgtta aaggtatat taccaaatat    2340 tttataggat tggttttag gaaatttaaa ctgcaatata tccttgttta aaacttggaa    2400
attatcgtga tcaacaagtt tattttctgt agttttgcat aatttatggt ctatttcaat    2460
ggcagttacg aaattacacc tctgtactaa ttcaagggta aaatgcccctt ttcctgagcc    2520 gatttcaaag atattatcat gttcatttaa tcttatattt gtcattattt tatctatatt    2580
atgttttgaa gtaataaagt tttgactgtg tttatatttt ttctcgttca ttataaccct    2640
ctttattttt tcctccttat aaaattagta taattatagc acgagctctg ataaatatga    2700
acatgatgag tgatcgttaa atttatattc aataatcgca tcagattgca gtaaaagata    2760
tgagagattt atctagtttc ttttttttaca agaaaaaaga aagttcttaa aggttttata    2820
```

```
cttttggtcg tagagcacac ggtttaacga cttaattacg aagtaaataa gtctagtgtg    2880
ttagacttta atgttttttt aaggcattag tgcatttaag cgtcagagca tggctttatg    2940
ccgagaaaac tattggttgg aatggcgtgt gtgttagcca aagcttgata tcgaattcct    3000
gcagcccgcc catggacgca caccgtggaa acgatgaagc gcacgaaccc agttgacata    3060
agcctgttcg gttcgtaaac tgtaatgcaa gtagcgtatg cgctcacgca actggtccag    3120
aaccttgacc gaacgcagcg gtggtaacgg cgcagtggcg gttttcatgg cttgttatga    3180
ctgttttttt gtacagtcta tgcctcgggc atccaagcag caagcgcgtt acgccgtggg    3240
tcgatgtttg atgttatgga gcagcaacga tgttacgcag cagcaacgat gttacgcagc    3300
agggcagtcg ccctaaaaca aagttaggtg gctcaagtat gggcatcatt cgcacatgta    3360
ggctcggccc tgaccaagtc aaatccatgc gggctgctct tgatcttttc ggtcgtgagt    3420
tcggagacgt agccacctac tcccaacatc agccggactc cgattacctc gggaacttgc    3480
tccgtagtaa gacattcatc gcgcttgctg ccttcgacca agaagcggtt gttggcgctc    3540
tcgcggctta cgttctgccc aagtttgagc agccgcgtag tgagatctat atctatgatc    3600
tcgcagtctc cggagagcac cggaggcagg gcattgccac cgcgctcatc aatctcctca    3660
agcatgaggc caacgcgctt ggtgcttatg tgatctacgt gcaagcagat tacggtgacg    3720
atcccgcagt ggctctctat acaaagttgg gcatacggga agaagtgatg cactttgata    3780
tcgacccaag taccgccacc taacaattcg ttcaagccga gatcggcttc ccggccgcgg    3840
agttgttcgg taaattgtca caacgccgcg ggggatccac tagttctaga gtcggtgaac    3900
gctctcctga gtaggacaaa tccgccggga gcggatttga acgttgcgaa gcaacggccc    3960
ggagggtggc gggcaggacg cccgccataa actgccaggc atcaaattaa gcagaaggcc    4020
atcctgacgg atggcctttt tgcgttttcta caaactcttt tgtttatttt tctaaataca    4080
ttcaaatatg tatccgctca tgagacaata accctgataa atgcttcaat aatattgaaa    4140
aaggaagagt atgagtattc aacatttccg tgtcgccctt attcccttttt ttgcggcatt    4200
ttgccttcct gttttttgctc acccagaaac gctggtgaaa gtaaaagatg ctgaagatca    4260
gttgggtgca cgagtgggtt acatcgaact ggatctcaac agcggtaaga tccttgagag    4320
ttttcgcccc gaagaacgtt ttccaatgat gagcactttt aaagttctgc tatgtggcgc    4380
ggtattatcc cgtgttgacg ccgggcaaga gcaactcggt cgccgcatac actattctca    4440
gaatgacttg gttgagtact caccagtcac agaaaagcat cttacggatg gcatgacagt    4500
aagagaatta tgcagtgctg ccataaccat gagtgataac actgcggcca acttacttct    4560
gacaacgatc ggaggaccga aggagctaac cgcttttttg cacaacatgg gggatcatgt    4620
aactcgcctt gatcgttggg aaccggagct gaatgaagcc ataccaaacg acgagcgtga    4680
caccacgatg cctgtagcaa tggcaacaac gttgcgcaaa ctattaactg gcgaactact    4740
tactctagct tcccggcaac aattaataga ctggatggag gcggataaag ttgcaggacc    4800
acttctgcgc tcggcccttc cggctggctg gtttattgct gataaatctg gagccggtga    4860
gcgtgggtct cgcggtatca ttgcagcact ggggccagat ggtaagccct cccgtatcgt    4920
agttatctac acgacgggga gtcaggcaac tatggatgaa cgaaatagac agatcgctga    4980
gataggtgcc tcactgatta agcattggta actgtcagac caagtttact catatatact    5040
ttagattgat ttaaaa                                                    5056
```

<210> SEQ ID NO 23

<211> LENGTH: 6334
<212> TYPE: DNA
<213> ORGANISM: Artificial Sequence
<220> FEATURE:
<223> OTHER INFORMATION: Synthetic Construct

<400> SEQUENCE: 23

| | | | | | |
|---|---|---|---|---|---|
| tcattccgct | gttatggccg | cgtttgtctc | attccacgcc | tgacactcag | ttccgggtag | 60 |
| gcagttcgct | ccaagctgga | ctgtatgcac | gaaccccccg | ttcagtccga | ccgctgcgcc | 120 |
| ttatccggta | actatcgtct | tgagtccaac | ccggaaagac | atgcaaaagc | accactggca | 180 |
| gcagccactg | gtaattgatt | tagaggagtt | agtcttgaag | tcatgcgccg | gttaaggcta | 240 |
| aactgaaagg | acaagttttg | gtgactgcgc | tcctccaagc | cagttacctc | ggttcaaaga | 300 |
| gttggtagct | cagagaacct | tcgaaaaacc | gccctgcaag | gcggttttttt | cgttttcaga | 360 |
| gcaagagatt | acgcgcagac | caaaacgatc | tcaagaagat | catcttatta | atcagataaa | 420 |
| atatttctag | atttcagtgc | aatttatctc | ttcaaatgta | gcacctgaag | tcagccccat | 480 |
| acgatataag | ttgtaattct | catgtttgac | agcttatcat | cgataagctt | taatgcggta | 540 |
| gtttatcaca | gttaaattgc | taacgcagtc | aggcaccgtg | tatgaaatct | aacaatgcgc | 600 |
| tcatcgtcat | cctcggcacc | gtcacccfgg | atgctgtagg | cataggcttg | gttatgccgg | 660 |
| tactgccggg | cctcttgcgg | gatatcgtcc | attccgacag | catcgccagt | cactatggcg | 720 |
| tgctgctagc | gctatatgcg | ttgatgcaat | ttctatgcgc | acccgttctc | ggagcactgt | 780 |
| ccgaccgctt | tggccgccgc | ccagtcctgc | tcgcttcgct | acttggagcc | actatcgact | 840 |
| acgcgatcat | ggcgaccaca | cccgtcctgt | ggatcctcta | cgccggacgc | atcgtggccg | 900 |
| gcatcaccgg | cgccacaggt | gcggttgctg | gcgcctatat | cgccgacatc | accgatgggg | 960 |
| aagatcgggc | tcgccacttc | gggctcatga | gcgcttgttt | cggcgtgggt | atggtggcag | 1020 |
| gccccgtggc | cgggggactg | ttgggcgcca | tctccttgca | tgcaccattc | cttgcggcgg | 1080 |
| cggtgctcaa | cggcctcaac | ctactactgg | gctgcttcct | aatgcaggag | tcgcataagg | 1140 |
| gagagcgtcg | acagaaagta | taatgagaaa | atataaaata | taataatttt | tctaaaaaac | 1200 |
| ttgcatcat | gtgaaaagtt | tgttataata | taaatgagca | cgttaatcat | ttaacataga | 1260 |
| taattaaata | gtaaaaggag | gattagtcat | gaggtcaaaa | attgaggcta | atgagtataa | 1320 |
| ggattttatt | cttggcttta | ttttctacaa | atatttatct | gagaaagagg | tggccttttt | 1380 |
| tagaaaagaa | agattaaccg | atgcagatat | tgaaaaagtt | acagaagatg | atgttaagta | 1440 |
| cgcatcccat | gtaagagaaa | atttgggata | ttttattgcg | tatgaaaatc | ttttttcaac | 1500 |
| ttggcttaag | aaaggtaatg | attttgatat | atcgaatgtt | agggatgcat | tatctgcttt | 1560 |
| tgatcgtaac | attgatgatg | tatatagaaa | agtgtttgag | aaaattttca | atacattgca | 1620 |
| gacaggctta | tctaagcttg | gagaaactgc | acaagcacaa | acaaaggctg | taaaaagtct | 1680 |
| tcttaaattg | ataagaaaaa | ttcctatgga | tggaaagcaa | gattatgatg | ttcttgggtt | 1740 |
| catttacgaa | tatctaatta | gtatgttcgc | tgccaacgca | ggtaaaaaag | caggagaatt | 1800 |
| ttacactccg | catgaagttt | ctgttttaat | gtcagaaatt | attgcagaac | atttgaaaaa | 1860 |
| tagaaagcaa | attaaaatat | atgaccctac | atctgggtcg | ggttcgttgc | tgataaatat | 1920 |
| tggtaactca | gctgcaaaat | ttatagatgg | agaaaacaag | atagattatt | acgcacagga | 1980 |
| gcttaaggaa | aatacttata | acctcacaag | aatgaacttg | ttatgcgtg | gcatcagtcc | 2040 |
| tgcaaatata | aatgtgagaa | atggtgacac | attagaggat | gattggcctt | ttttggagga | 2100 |
| taccgacaag | gataaaacat | ataaatttat | accagtagat | gccgttgttt | ctaatccacc | 2160 |

```
ttactcacaa aaatgggatc catctgataa agaatttgac ccacgatata agtattatgg   2220
tgttgcacca aagagtaagg ctgattatgc atttttattg catgatttgt atcacctaaa   2280
ggacgatggt atcatgacaa tcgttcttcc ccatggtgta cttttagag gtggagagga    2340 aggtaaaatc agagagaaac ttatagaaaa aaaccgcata gatgcaatta tcggattacc   2400
accaaatatt ttctttggta caggtattcc tactattata atggtcctta aaagaattcg   2460
ccctacttca gacgtgttga ttatagatgc atctaaaggg tttgagaaag ttggaaagaa   2520
taacaaattg agagcctgtg acattaaaaa aattgctgac actgttaaga gcagagaatc   2580
cattgaaaag tattcgactc ttgtttctaa ggaaaccatc cgagaaaatg gctataacct   2640
taatatccct cgctatgtta attccttaga acctgcagaa agttgggata ttcatgcgac   2700
tatgtttggt ggaatacctg taaggaagt agaccaacta tttgagtatt gggaggcttt    2760
tcccgaactc aaagatgcaa ttttttcggaa aatttctaat gaatatttag ctgtgaaatg   2820
cgatgatatt aaagcggcta ttacctctca tgagtcattg aaaatctata acaggcatt    2880 ctcaaatgaa tttggtaatt tttatgaaga acttaaaaat gatttgattg aagaaattct   2940
tgatgtatct gctgagcatg agaaagaaaa ggtaagcaag gatatttta taagaataga    3000 aaatgtaaaa cttgctgaca agtataaagc gtaccagata ctttcggata attgggatgt   3060
gatttcaaca gatttggaaa tgattcagtc agaaggtttt gaggttatca atcaagtgga   3120
tcctaacatg atttttaaga agaagaagc taacgatgat gaggttccag aggtacaaga    3180
tgggtggaag ggtcatatac tgccttttga tttggttcag agagagattc ttactgaaga   3240
tttagaagaa cttcaggcaa tagaaaaaag attaactgaa atcacttctt tgtatggtga   3300
aattattgat tcgcttgatg aagaagaaag agaaagcagt gtgttgaatg aagctaacga   3360
tgcttttgta gcaaaagaag ttaagagttt tgttgcagaa gccctcagcg atgtggaaaa   3420
tgatgaaatt aaagcattaa gaggatatct aagcctttca aagaaaaaag aaaagctaga   3480
ttatgtaaat aaatgtgata tagtttcgtg gaatttaatg gaacaaggtt ctgatggagc   3540
atataagaaa ggttctgtta ttagtagaat aagcgaattg caaaggatgt atgaattccc   3600
gaaagattcc tttgaacaga aagtgatgac cgtattatct cttatggaag aagaaagcca   3660
ggctaaaaaa gatctaaaac agaaatcgga agccctccat attaagacca agaaaccat    3720 tgaaaatctg gatgaagacg aatctttgcg tttgttagaa ttaaaatgga taagccatt    3780 agtagattcc cttttttgcta ttccagatga aatcatcgga gagctgatta acaaagtaat   3840
tcatctacac gataaatatt gcactacatt ttccgatatt gaacatgata tcgaaaacac   3900
aagtgcgaaa ttatcaaata tgattgataa gcttgttggc agtgtggcag atattgaggg   3960
attagaagaa ttgaagaaga ttttgggggt atagtaaaaa taagagttac cttaaatggt   4020
aactcttatt tttttaatat tgtttcatag tatttctttg tcgaccgatg cccttgagag   4080
ccttcaaccc agtcagctcc ttccggtggg cgcggggcat gactatcgtc gccgcactta   4140
tgactgtctt ctttatcatg caactcgtag gacaggtgcc ggcagcgctc tgggtcattt   4200
tcggcgagga ccgctttcgc tggagcgcga cgatgatcgg cctgtcgctt gcggtattcg   4260
gaatcttgca cgccctcgct caagccttcg tcactggtcc cgccaccaaa cgtttcggcg   4320
agaagcaggc cattatcgcc ggcatggcgg ccgacgcgct gggctacgtc ttgctggcgt   4380
tcgcgacgcg aggctggatg gccttcccca ttatgattct tctcgcttcc ggcggcatcg   4440
ggatgcccgc gttgcaggcc atgctgtcca ggcaggtaga tgacgaccat cagggacagc   4500
```

```
tagttctaga gtcggtgaac gctctcctga gtaggacaaa tccgccggga gcggatttga   4560
acgttgcgaa gcaacggccc ggagggtggc gggcaggacg cccgcccataa actgccaggc  4620 atcaaattaa gcagaaggcc atcctgacgg atggcctttt tgcgtttcta caaactcttt   4680
tgtttatttt tctaaataca ttcaaatatg tatccgctca tgagacaata accctgataa   4740
atgcttcaat aatattgaaa aaggaagagt atgagtattc aacatttccg tgtcgccctt   4800 attcccttt ttgcggcatt tgccttcct gtttttgctc acccagaaac gctggtgaaa    4860
gtaaaagatg ctgaagatca gttgggtgca cgagtgggtt acatcgaact ggatctcaac  4920
agcggtaaga tccttgagag ttttcgcccc gaagaacgtt ttccaatgat gagcactttt   4980
aaagttctgc tatgtggcgc ggtattatcc cgtgttgacg ccgggcaaga gcaactcggt   5040
cgccgcatac actattctca gaatgacttg gttgagtact caccagtcac agaaaagcat   5100
cttacggatg gcatgacagt aagagaatta tgcagtgctg ccataaccat gagtgataac   5160
actgcggcca acttacttct gacaacgatc ggaggaccga aggagctaac cgcttttttg   5220
cacaacatgg gggatcatgt aactcgcctt gatcgttggg aaccggagct gaatgaagcc   5280
ataccaaacg acgagcgtga caccacgatg cctgtagcaa tggcaacaac gttgcgcaaa   5340
ctattaactg gcgaactact tactctagct tcccggcaac aattaataga ctggatggag   5400
gcggataaag ttgcaggacc acttctgcgc tcggcccttc cggctggctg gtttattgct   5460
gataaatctg gagccggtga gcgtgggtct cgcggtatca ttgcagcact ggggccagat   5520
ggtaagccct cccgtatcgt agttatctac acgacgggga gtcaggcaac tatggatgaa   5580
cgaaatagac agatcgctga gataggtgcc tcactgatta gcattggta actgtcagac   5640 caagtttact catatatact ttagattgat ttaaaaagtt ggcccagggc ttcccggtat   5700 caacaggggac accaggattt atttattctg cgaagtgatc ttccgtcaca ggtatttatt   5760
cggcgcaaag tgcgtcgggt gatgctgcca acttactgat ttagtgtatg atggtgtttt   5820
tgaggtgctc cagtggcttc tgtttctatc agctgtccct cctgttcagc tactgacggg   5880
gtggtgcgta acggcaaaag caccgccgga catcagcgct agcggagtgt atactggctt   5940
actatgttgg cactgatgag ggtgtcagtg aagtgcttca tgtggcagga gaaaaaaggc   6000
tgcaccggtg cgtcagcaga atatgtgata caggatatat tccgcttcct cgctcactga   6060
ctcgctacgc tcggtcgttc gactgcggcg agcggaaatg gcttacgaac ggggcggaga   6120
tttcctggaa gatgccagga agatacttaa cagggaagtg agagggccgc ggcaaagccg   6180
tttttccata ggctccgccc ccctgacaag catcacgaaa tctgacgctc aaatcagtgg   6240
tggcgaaacc cgacaggact ataaagatac caggcgtttc ccctggcgg ctccctcgtg    6300 cgctctcctg ttcctgcctt tcggtttacc ggtg                               6334
```

<210> SEQ ID NO 24
<211> LENGTH: 25
<212> TYPE: DNA
<213> ORGANISM: Artificial Sequence
<220> FEATURE:
<223> OTHER INFORMATION: Synthetic Construct

<400> SEQUENCE: 24
gaaaaccctg acgttaccca actta                                         25

<210> SEQ ID NO 25
<211> LENGTH: 23
<212> TYPE: DNA
<213> ORGANISM: Artificial Sequence
<220> FEATURE:
<223> OTHER INFORMATION: Synthetic Construct

<400> SEQUENCE: 25
tgggtaacgt cagggttttc cca                                              23

<210> SEQ ID NO 26
<211> LENGTH: 26
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11
<223> OTHER INFORMATION: n = A,T,C or G

<400> SEQUENCE: 26
gaaacgcctg ntatctttat agtcct                                           26

<210> SEQ ID NO 27
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 18
<223> OTHER INFORMATION: n = A,T,C or G

<400> SEQUENCE: 27
acaggactat aaagatanca ggcgt                                            25

<210> SEQ ID NO 28
<211> LENGTH: 25
<212> TYPE: DNA
<213> ORGANISM: Artificial Sequence
<220> FEATURE:
<223> OTHER INFORMATION: Synthetic Construct

<400> SEQUENCE: 28
acggttcctg accttttgct ggcct                                            25

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
ggccagcaaa aggtcaggaa ccgta                                            25

<210> SEQ ID NO 30
<211> LENGTH: 44
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 10, 26
<223> OTHER INFORMATION: n = A,T,C or G

<400> SEQUENCE: 30
ataaagatan caggcgtttc cccctngaag ctccctcgtg cgct                        44

<210> SEQ ID NO 31
<211> LENGTH: 44
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 10, 23, 24, 25
<223> OTHER INFORMATION: n = A,T,C or G

<400> SEQUENCE: 31
ataaagatan caggcgtttc ccnnnggaag ctccctcgtg cgct                44

<210> SEQ ID NO 32
<211> LENGTH: 44
<212> TYPE: DNA
<213> ORGANISM: Artificial Sequence
<220> FEATURE:
<223> OTHER INFORMATION: Synthetic Construct

<400> SEQUENCE: 32
ataaagataa caggcgtttc cccctagaag ctccctcgtg cgct                44

<210> SEQ ID NO 33
<211> LENGTH: 51
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 23, 24
<223> OTHER INFORMATION: n = A,T,C or G

<400> SEQUENCE: 33
ataaagataa caggcgtttc ccnntggaag ctccctcgtg cgctctcctg t         51

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct

<400> SEQUENCE: 34
gaaacgcctg ttatctttat agtcct                                    26

<210> SEQ ID NO 35
<211> LENGTH: 18
<212> TYPE: DNA
<213> ORGANISM: Artificial Sequence
<220> FEATURE:
<223> OTHER INFORMATION: Synthetic Construct

<400> SEQUENCE: 35
caggaaacag ctatgacc                                             18

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
ctcattagta gttcagggtt taaca                                     25

<210> SEQ ID NO 37
<211> LENGTH: 44
<212> TYPE: DNA
<213> ORGANISM: Artificial Sequence
<220> FEATURE:
<223> OTHER INFORMATION: Synthetic Construct

<400> SEQUENCE: 37
tacccgggga ggaataataa atggccgtac tccgcaatat tgat            44

<210> SEQ ID NO 38
<211> LENGTH: 38
<212> TYPE: DNA
<213> ORGANISM: Artificial Sequence
<220> FEATURE:
<223> OTHER INFORMATION: Synthetic Construct

<400> SEQUENCE: 38
ttattattcc tccccgggta ccgagctcga attcgcta                   38

<210> SEQ ID NO 39
<211> LENGTH: 39
<212> TYPE: DNA
<213> ORGANISM: Artificial Sequence
<220> FEATURE:
<223> OTHER INFORMATION: Synthetic Construct

<400> SEQUENCE: 39
caaagatcgt tgaggctgtt ttggcggatg agagaagat                  39

<210> SEQ ID NO 40
<211> LENGTH: 46
<212> TYPE: DNA
<213> ORGANISM: Artificial Sequence
<220> FEATURE:
<223> OTHER INFORMATION: Synthetic Construct

<400> SEQUENCE: 40
aacagcctca acgatctttg cgcagcacga cgatgtgctc gttcgt          46

<210> SEQ ID NO 41
<211> LENGTH: 36
<212> TYPE: DNA
<213> ORGANISM: Artificial Sequence
<220> FEATURE:
<223> OTHER INFORMATION: Synthetic Construct

<400> SEQUENCE: 41
agggacagct agttctagag tcggtgaacg ctctcc                     36

<210> SEQ ID NO 42
<211> LENGTH: 49
<212> TYPE: DNA
<213> ORGANISM: Artificial Sequence
<220> FEATURE:
<223> OTHER INFORMATION: Synthetic Construct

<400> SEQUENCE: 42 ccaactttt aaatcaatct aaagtatata tgagtaaact tggtctgac        49

<210> SEQ ID NO 43
<211> LENGTH: 30
<212> TYPE: DNA
<213> ORGANISM: Artificial Sequence
<220> FEATURE:

<223> OTHER INFORMATION: Synthetic Construct

<400> SEQUENCE: 43
gatttaaaaa gttggcccag ggcttcccgg                    30

<210> SEQ ID NO 44
<211> LENGTH: 31
<212> TYPE: DNA
<213> ORGANISM: Artificial Sequence
<220> FEATURE:
<223> OTHER INFORMATION: Synthetic Construct

<400> SEQUENCE: 44
gaactagctg tccctgatgg tcgtcatcta c                  31

<210> SEQ ID NO 45
<211> LENGTH: 32
<212> TYPE: DNA
<213> ORGANISM: Artificial Sequence
<220> FEATURE:
<223> OTHER INFORMATION: Synthetic Construct

<400> SEQUENCE: 45
cagcacttaa cattaaccat ataatcacga ac                 32

<210> SEQ ID NO 46
<211> LENGTH: 39
<212> TYPE: DNA
<213> ORGANISM: Artificial Sequence
<220> FEATURE:
<223> OTHER INFORMATION: Synthetic Construct

<400> SEQUENCE: 46
cagctatagc agctactctt tggtattatt atcaaaatg          39

<210> SEQ ID NO 47
<211> LENGTH: 25
<212> TYPE: DNA
<213> ORGANISM: Artificial Sequence
<220> FEATURE:
<223> OTHER INFORMATION: Synthetic Construct

<400> SEQUENCE: 47
ggtagaccct aattatcgtg aacgc                         25

<210> SEQ ID NO 48
<211> LENGTH: 37
<212> TYPE: DNA
<213> ORGANISM: Artificial Sequence
<220> FEATURE:
<223> OTHER INFORMATION: Synthetic Construct

<400> SEQUENCE: 48
tgattattat tatgaaccga ttgtaaatga tttttag            37

<210> SEQ ID NO 49
<211> LENGTH: 31
<212> TYPE: DNA
<213> ORGANISM: Artificial Sequence
<220> FEATURE:
<223> OTHER INFORMATION: Synthetic Construct

<400> SEQUENCE: 49
ttggatgaga agatacttaa agatgtaagg g                  31

```
<210> SEQ ID NO 50
<211> LENGTH: 40
<212> TYPE: DNA
<213> ORGANISM: Artificial Sequence
<220> FEATURE:
<223> OTHER INFORMATION: Synthetic Construct

<400> SEQUENCE: 50
ttcagagtat attttcttta aatacgtaaa tattttttc                              40

<210> SEQ ID NO 51
<211> LENGTH: 38
<212> TYPE: DNA
<213> ORGANISM: Artificial Sequence
<220> FEATURE:
<223> OTHER INFORMATION: Synthetic Construct

<400> SEQUENCE: 51
atgaacaaaa atataaaata ttctcaaaac tttttaac                               38

<210> SEQ ID NO 52
<211> LENGTH: 34
<212> TYPE: DNA
<213> ORGANISM: Artificial Sequence
<220> FEATURE:
<223> OTHER INFORMATION: Synthetic Construct

<400> SEQUENCE: 52
ttatttcctc ccgttaaata atagataact atta                                   34

<210> SEQ ID NO 53
<211> LENGTH: 41
<212> TYPE: DNA
<213> ORGANISM: Artificial Sequence
<220> FEATURE:
<223> OTHER INFORMATION: Synthetic Construct

<400> SEQUENCE: 53
ctataaatat tagcgttgga ctttttttctt ccctttaaat c                          41

<210> SEQ ID NO 54
<211> LENGTH: 46
<212> TYPE: DNA
<213> ORGANISM: Artificial Sequence
<220> FEATURE:
<223> OTHER INFORMATION: Synthetic Construct

<400> SEQUENCE: 54
tccaacgcta atatttatag tatcagtttt aaactgaaac tgcaac                      46

<210> SEQ ID NO 55
<211> LENGTH: 31
<212> TYPE: DNA
<213> ORGANISM: Artificial Sequence
<220> FEATURE:
<223> OTHER INFORMATION: Synthetic Construct

<400> SEQUENCE: 55
ccgcggccgc cattatagca taaagagggc t                                      31

<210> SEQ ID NO 56
<211> LENGTH: 34
<212> TYPE: DNA
<213> ORGANISM: Artificial Sequence
<220> FEATURE:
<223> OTHER INFORMATION: Synthetic Construct
```

<400> SEQUENCE: 56
agattgacct ttattattca gagtatattt ttct                      34

<210> SEQ ID NO 57
<211> LENGTH: 31
<212> TYPE: DNA
<213> ORGANISM: Artificial Sequence
<220> FEATURE:
<223> OTHER INFORMATION: Synthetic Construct

<400> SEQUENCE: 57
tgaataataa aggtcaatct atgaaatgcg a                         31

<210> SEQ ID NO 58
<211> LENGTH: 31
<212> TYPE: DNA
<213> ORGANISM: Artificial Sequence
<220> FEATURE:
<223> OTHER INFORMATION: Synthetic Construct

<400> SEQUENCE: 58
tgctataatg gcggccgcgg tcatagctgt t                         31

<210> SEQ ID NO 59
<211> LENGTH: 30
<212> TYPE: DNA
<213> ORGANISM: Artificial Sequence
<220> FEATURE:
<223> OTHER INFORMATION: Synthetic Construct

<400> SEQUENCE: 59
ccgcggccgc cagctatagc agctactctt                           30

<210> SEQ ID NO 60
<211> LENGTH: 30
<212> TYPE: DNA
<213> ORGANISM: Artificial Sequence
<220> FEATURE:
<223> OTHER INFORMATION: Synthetic Construct

<400> SEQUENCE: 60
agattgacct cagcacttaa cattaaccat                           30

<210> SEQ ID NO 61
<211> LENGTH: 31
<212> TYPE: DNA
<213> ORGANISM: Artificial Sequence
<220> FEATURE:
<223> OTHER INFORMATION: Synthetic Construct

<400> SEQUENCE: 61
ttaagtgctg aggtcaatct atgaaatgcg a                         31

<210> SEQ ID NO 62
<211> LENGTH: 31
<212> TYPE: DNA
<213> ORGANISM: Artificial Sequence
<220> FEATURE:
<223> OTHER INFORMATION: Synthetic Construct

<400> SEQUENCE: 62
gctatagctg gcggccgcgg tcatagctgt t                         31